(12) United States Patent
Abreu

(10) Patent No.: US 10,448,890 B2
(45) Date of Patent: *Oct. 22, 2019

(54) APPARATUS AND METHOD FOR MEASURING BIOLOGIC PARAMETERS

(71) Applicant: GEELUX HOLDINGS, LTD., Tortola (VG)

(72) Inventor: Marcio Marc Abreu, Bridgeport, CT (US)

(73) Assignee: Geelux Holdings, Ltd., Tortola (VG)

( * ) Notice: Subject to any disclaimer, the term of this patent is extended or adjusted under 35 U.S.C. 154(b) by 560 days.

This patent is subject to a terminal disclaimer.

(21) Appl. No.: 15/234,471

(22) Filed: Aug. 11, 2016

(65) Prior Publication Data

US 2017/0095205 A1    Apr. 6, 2017

Related U.S. Application Data

(63) Continuation of application No. 14/801,394, filed on Jul. 16, 2015, now Pat. No. 9,445,767, which is a
(Continued)

(51) Int. Cl.
*A61B 5/00* (2006.01)
*A61B 5/01* (2006.01)
(Continued)

(52) U.S. Cl.
CPC .......... *A61B 5/6803* (2013.01); *A61B 5/0002* (2013.01); *A61B 5/0008* (2013.01);
(Continued)

(58) Field of Classification Search
CPC ....... A61B 5/0002; A61B 5/0008; A61B 5/01; A61B 5/6803; A61B 5/6814;
(Continued)

(56) References Cited

U.S. PATENT DOCUMENTS 3,463,885 A    8/1969  Upton
3,531,642 A    9/1970  Barnes et al.
(Continued)

FOREIGN PATENT DOCUMENTS

CN    2398565 Y    9/2000
CN    2446955 Y    9/2001
(Continued)

OTHER PUBLICATIONS

RCA Technical Notes, Contact Lens Tonometer by Robert E. Morey, RCA TN No. 602, dated Dec. 1964, 2 pages.
(Continued)

*Primary Examiner* — Adam J Eiseman
(74) *Attorney, Agent, or Firm* — Studebaker & Brackett PC

(57) ABSTRACT

Support structures for positioning sensors on a physiologic tunnel for measuring physical, chemical and biological parameters of the body and to produce an action according to the measured value of the parameters. The support structure includes a sensor fitted on the support structures using a special geometry for acquiring continuous and undisturbed data on the physiology of the body. Signals are transmitted to a remote station by wireless transmission such as by electromagnetic waves, radio waves, infrared, sound and the like or by being reported locally by audio or visual transmission. The physical and chemical parameters include brain function, metabolic function, hydrodynamic function, hydration status, levels of chemical compounds in the blood, and the like. The support structure includes patches, clips, eyeglasses, head mounted gear and the like, containing passive or active sensors positioned at the end of the tunnel with sensing systems positioned on and accessing a physiologic tunnel.

24 Claims, 86 Drawing Sheets

Related U.S. Application Data continuation of application No. 13/465,444, filed on May 7, 2012, now Pat. No. 9,119,530, which is a continuation of application No. 11/585,357, filed on Oct. 24, 2006, now Pat. No. 8,172,459.

(60) Provisional application No. 60/729,232, filed on Oct. 24, 2005, provisional application No. 60/802,503, filed on May 23, 2006.

(51) Int. Cl.
*G01K 13/00* (2006.01)
*A61B 8/08* (2006.01)

(52) U.S. Cl.
CPC .............. *A61B 5/01* (2013.01); *A61B 5/4064* (2013.01); *A61B 5/6814* (2013.01); *A61B 5/6821* (2013.01); *A61B 5/6833* (2013.01); *A61B 5/6887* (2013.01); *A61B 8/0808* (2013.01); *G01K 13/002* (2013.01); *A61B 2560/0418* (2013.01); *A61B 2562/0271* (2013.01)

(58) Field of Classification Search
CPC ................ A61B 5/6821; A61B 5/6833; A61B 2562/0271; G01K 13/002; G01K 13/004
See application file for complete search history.

(56) References Cited

U.S. PATENT DOCUMENTS

| | | |
|---|---|---|
| 3,545,260 A | 12/1970 | Lichtenstein et al. |
| 3,585,849 A | 6/1971 | Grolman |
| 3,626,757 A | 12/1971 | Benzinger |
| 3,724,263 A | 4/1973 | Rose et al. |
| 3,769,961 A | 11/1973 | Fatt et al. |
| 3,897,272 A | 7/1975 | Medlar |
| 3,897,790 A | 8/1975 | Magilton et al. |
| 3,963,019 A | 6/1976 | Quandt |
| 4,186,184 A | 1/1980 | Zaffaroni |
| 4,231,052 A | 10/1980 | Day et al. |
| 4,297,685 A | 10/1981 | Brainard, II |
| 4,305,399 A | 12/1981 | Beale |
| 4,312,358 A | 1/1982 | Barney |
| 4,321,261 A | 3/1982 | Ellis et al. |
| 4,330,299 A | 5/1982 | Cerami |
| 4,331,161 A | 8/1982 | Patel |
| 4,344,315 A | 8/1982 | Moxon et al. |
| 4,344,438 A | 8/1982 | Schultz |
| 4,386,831 A | 6/1983 | Grounauer |
| 4,444,990 A | 4/1984 | Viillar |
| 4,485,820 A | 12/1984 | Flower |
| 4,488,558 A | 12/1984 | Simbruner et al. |
| 4,595,020 A | 6/1986 | Palti |
| 4,597,392 A | 7/1986 | Opitz et al. |
| 4,628,938 A | 12/1986 | Lee |
| 4,629,424 A | 12/1986 | Lauks et al. |
| 4,771,792 A | 9/1988 | Seale |
| 4,784,149 A | 11/1988 | Berman et al. |
| 4,830,014 A | 5/1989 | Goodman et al. |
| 4,846,196 A | 7/1989 | Wiksell et al. |
| 4,860,755 A | 8/1989 | Erath |
| 4,922,913 A | 5/1990 | Waters, Jr. et al. |
| 4,944,303 A | 7/1990 | Katsuragi |
| 4,947,849 A | 8/1990 | Takahashi et al. |
| 4,951,671 A | 8/1990 | Coan |
| 4,979,831 A | 12/1990 | Schertz et al. |
| 5,005,577 A | 4/1991 | Frenkel |
| 5,046,482 A | 9/1991 | Everest |
| 5,062,432 A | 11/1991 | James et al. |
| 5,076,274 A | 12/1991 | Matsumoto |
| 5,109,852 A | 5/1992 | Kaye et al. |
| 5,115,815 A | 5/1992 | Hansen |
| 5,148,807 A | 9/1992 | Hsu |
| 5,165,409 A | 11/1992 | Coan |
| 5,179,953 A | 1/1993 | Kursar |
| 5,183,044 A | 2/1993 | Nishio et al. |
| 5,190,039 A | 3/1993 | Takeuchi et al. |
| 5,209,231 A | 5/1993 | Cote et al. |
| 5,217,015 A | 6/1993 | Kaye et al. |
| 5,222,495 A | 6/1993 | Clarke et al. |
| 5,222,809 A | 6/1993 | Ehrenkranz |
| 5,246,867 A | 9/1993 | Lakowicz et al. |
| 5,251,627 A | 10/1993 | Morris |
| 5,255,979 A | 10/1993 | Ferrari |
| 5,295,495 A | 3/1994 | Maddess |
| 5,297,554 A | 3/1994 | Glynn et al. |
| 5,341,805 A | 8/1994 | Stavridi et al. |
| 5,342,283 A | 8/1994 | Good |
| 5,342,789 A | 8/1994 | Chick et al. |
| 5,352,411 A | 10/1994 | Khuri |
| 5,356,780 A | 10/1994 | Robinson et al. |
| 5,375,595 A | 12/1994 | Sinha et al. |
| 5,383,452 A | 1/1995 | Buchert |
| 5,433,197 A | 7/1995 | Stark |
| 5,435,307 A | 7/1995 | Friauf et al. |
| 5,441,476 A | 8/1995 | Kitado et al. |
| 5,503,770 A | 4/1996 | James et al. |
| 5,522,662 A | 6/1996 | Shiokawa |
| 5,636,635 A | 6/1997 | Massie et al. |
| 5,653,239 A | 8/1997 | Pompei et al. |
| 5,664,578 A | 9/1997 | Boczan |
| 5,673,692 A | 10/1997 | Schulze et al. |
| 5,711,915 A | 1/1998 | Siegmund et al. |
| 5,796,341 A | 8/1998 | Stratiotis |
| 5,813,982 A | 9/1998 | Baratta |
| 5,817,008 A | 10/1998 | Rafert et al. |
| 5,820,557 A | 10/1998 | Hattori et al. |
| 5,830,139 A | 11/1998 | Abreu |
| 5,833,633 A | 11/1998 | Sarvazyan |
| 5,854,078 A | 12/1998 | Asher et al. |
| 5,860,934 A | 1/1999 | Sarvazyan |
| 5,862,803 A | 1/1999 | Besson et al. |
| 5,898,004 A | 4/1999 | Asher et al. |
| 5,984,880 A | 11/1999 | Lander et al. |
| 5,994,701 A | 11/1999 | Tsuchimoto et al. |
| 6,011,984 A | 1/2000 | Van Antwerp et al. |
| 6,028,323 A | 2/2000 | Liu |
| 6,040,194 A | 3/2000 | Chick et al. |
| 6,042,266 A | 3/2000 | Cheslock et al. |
| 6,047,203 A | 4/2000 | Sackner et al. |
| 6,072,180 A | 6/2000 | Kramer et al. |
| 6,113,237 A | 9/2000 | Ober et al. |
| 6,120,460 A | 9/2000 | Abreu |
| 6,123,668 A | 9/2000 | Abreu |
| 6,126,595 A | 10/2000 | Amano et al. |
| 6,135,968 A | 10/2000 | Brounstein |
| 6,152,875 A | 11/2000 | Hakamata |
| 6,178,346 B1 | 1/2001 | Amundson et al. |
| 6,181,957 B1 | 1/2001 | Lambert et al. |
| 6,187,599 B1 | 2/2001 | Asher et al. |
| 6,196,714 B1 | 3/2001 | Bellifemine et al. |
| 6,197,534 B1 | 3/2001 | Lakowicz et al. |
| 6,197,928 B1 | 3/2001 | Tsien et al. |
| 6,203,193 B1 | 3/2001 | Egawa |
| 6,213,943 B1 | 4/2001 | Abreu |
| 6,256,522 B1 | 7/2001 | Schultz |
| 6,290,658 B1 | 9/2001 | Kolich |
| 6,292,685 B1 | 9/2001 | Pompei |
| 6,300,871 B1 | 10/2001 | Irwin et al. |
| 6,312,393 B1 | 11/2001 | Abreu |
| 6,319,540 B1 | 11/2001 | Van Antwerp et al. |
| 6,385,473 B1 | 5/2002 | Haines et al. |
| 6,385,474 B1 | 5/2002 | Rather et al. |
| 6,423,001 B1 | 7/2002 | Abreu |
| 6,432,050 B1 | 8/2002 | Porat et al. |
| 6,470,893 B1 | 10/2002 | Boesen |
| 6,529,617 B1 | 3/2003 | Prokoski |
| 6,536,945 B2 | 3/2003 | Rolston |
| 6,542,081 B2 | 4/2003 | Torch |
| 6,543,933 B2 | 4/2003 | Stergiopoulos et al. |
| 6,544,193 B2 | 4/2003 | Abreu |
| 6,681,127 B2 | 1/2004 | March |

(56) References Cited

U.S. PATENT DOCUMENTS

| | | | |
|---|---|---|---|
| 6,731,976 B2 | 5/2004 | Penn et al. | |
| 6,789,901 B1 | 9/2004 | Kormos | |
| 6,791,087 B1 | 9/2004 | Okumura | |
| 6,846,106 B1 | 1/2005 | Chen et al. | |
| 7,187,960 B2 | 3/2007 | Abreu | |
| 7,340,293 B2 | 3/2008 | McQuilkin | |
| 7,346,386 B2 | 3/2008 | Pompei | |
| 7,515,054 B2 | 4/2009 | Torch | |
| 7,597,668 B2 | 10/2009 | Yarden | |
| 7,621,877 B2 | 11/2009 | Schnall | |
| 7,689,437 B1 | 3/2010 | Teller et al. | |
| 7,756,559 B2 | 7/2010 | Abreu | |
| 7,787,938 B2 | 8/2010 | Pompei | |
| 7,837,623 B2 | 11/2010 | Aubry et al. | |
| 8,103,071 B2 | 1/2012 | Schnell et al. | |
| 8,172,459 B2 * | 5/2012 | Abreu | A61B 5/0002 374/208 |
| 8,328,420 B2 | 12/2012 | Abreu | |
| 8,500,271 B2 | 8/2013 | Howell et al. | |
| 8,527,022 B1 | 9/2013 | Lash et al. | |
| 8,721,562 B2 | 5/2014 | Abreu | |
| 8,834,020 B2 | 9/2014 | Abreu | |
| 8,849,379 B2 | 9/2014 | Abreu | |
| 9,007,220 B2 | 4/2015 | Johns et al. | |
| 9,119,530 B2 * | 9/2015 | Abreu | A61B 5/0002 |
| 9,445,767 B2 * | 9/2016 | Abreu | A61B 5/0002 |
| 2001/0028309 A1 | 10/2001 | Torch | |
| 2002/0026119 A1 | 2/2002 | Pompei | |
| 2002/0035340 A1 | 3/2002 | Fraden et al. | |
| 2002/0049374 A1 | 4/2002 | Abreu | |
| 2002/0049389 A1 | 4/2002 | Abreu | |
| 2002/0068876 A1 | 6/2002 | Pompei et al. | |
| 2002/0111657 A1 | 8/2002 | Dae et al. | |
| 2002/0126731 A1 | 9/2002 | Stergiopoulos et al. | |
| 2003/0055473 A1 | 3/2003 | Ramsden et al. | |
| 2003/0060863 A1 | 3/2003 | Dobak, III | |
| 2003/0067958 A1 | 4/2003 | Jang | |
| 2003/0108223 A1 | 6/2003 | Prokoski | |
| 2003/0111605 A1 | 6/2003 | Sato et al. | |
| 2003/0179094 A1 | 9/2003 | Abreu | |
| 2003/0210146 A1 | 11/2003 | Tseng | |
| 2003/0212340 A1 | 11/2003 | Lussier et al. | |
| 2004/0039298 A1 | 2/2004 | Abreu | |
| 2004/0059212 A1 | 3/2004 | Abreu | |
| 2004/0076316 A1 | 4/2004 | Fauci | |
| 2004/0082862 A1 | 4/2004 | Chance | |
| 2004/0125996 A1 | 7/2004 | Eddowes et al. | |
| 2004/0152991 A1 | 8/2004 | Pompei | |
| 2004/0154550 A1 | 8/2004 | McQuilkin | |
| 2004/0170216 A1 | 9/2004 | Russak et al. | |
| 2004/0210159 A1 | 10/2004 | Kibar | |
| 2004/0246548 A1 | 12/2004 | Papuchon et al. | |
| 2005/0250996 A1 | 11/2005 | Shirai et al. | |
| 2006/0122473 A1 | 6/2006 | Kill et al. | |
| 2006/0215728 A1 | 9/2006 | Jang | |
| 2006/0264726 A1 | 11/2006 | Manheimer et al. | |
| 2007/0055171 A1 | 3/2007 | Fraden | |
| 2007/0219434 A1 | 9/2007 | Abreu | |
| 2008/0043809 A1 | 2/2008 | Herbert | |
| 2008/0200830 A1 | 8/2008 | Pompei | |
| 2008/0214949 A1 | 9/2008 | Stivoric et al. | |
| 2009/0105605 A1 | 4/2009 | Abreu | |
| 2009/0157056 A1 | 6/2009 | Ferren et al. | |
| 2010/0022909 A1 | 1/2010 | Padiy | |
| 2010/0113894 A1 | 5/2010 | Padiy | |
| 2010/0204765 A1 | 8/2010 | Hall et al. | |
| 2011/0024626 A1 | 2/2011 | O'Donnell et al. | |
| 2011/0040161 A1 | 2/2011 | Abreu | |
| 2011/0077546 A1 | 3/2011 | Fabian | |
| 2011/0092822 A1 | 4/2011 | Pompei | |
| 2012/0031405 A1 | 2/2012 | Geist et al. | |
| 2012/0136285 A1 | 5/2012 | Korb et al. | |
| 2013/0124039 A1 | 5/2013 | Abreu | |
| 2013/0215928 A1 | 8/2013 | Bellifemine | |
| 2013/0292571 A1 | 11/2013 | Mukherjee et al. | |

FOREIGN PATENT DOCUMENTS

| | | | |
|---|---|---|---|
| CN | 1328432 | A | 12/2001 |
| DE | 4433104 | C1 | 5/1996 |
| EP | 0236028 | A2 | 9/1987 |
| EP | 0411121 | A1 | 2/1991 |
| EP | 2 120 681 | B1 | 7/2011 |
| EP | 1 951 110 | B1 | 10/2012 |
| GB | 2396421 | A | 6/2004 |
| JP | S61-48369 | A | 3/1986 |
| JP | H10-075934 | A | 3/1998 |
| JP | H10-239158 | A | 9/1998 |
| JP | H11-164826 | A | 6/1999 |
| JP | 2001-500394 | A | 1/2001 |
| JP | 2001/031151 | A | 2/2001 |
| JP | 2002-525132 | A | 8/2002 |
| JP | 3885024 | B2 | 2/2007 |
| WO | 93/01745 | A1 | 2/1993 |
| WO | 97/19188 | A1 | 5/1997 |
| WO | 98/22820 | A1 | 5/1998 |
| WO | 99/51142 | A2 | 10/1999 |
| WO | 00/10007 | A2 | 2/2000 |
| WO | 00/13580 | A1 | 3/2000 |
| WO | 00/16051 | A1 | 3/2000 |
| WO | 00/16099 | A1 | 3/2000 |
| WO | 00/18237 | A1 | 4/2000 |
| WO | 20000025662 | A1 | 5/2000 |
| WO | 00/64492 | A1 | 11/2000 |
| WO | 02/03855 | A1 | 1/2002 |
| WO | 02/28271 | A2 | 4/2002 |
| WO | 02/067688 | A1 | 9/2002 |
| WO | 2005/015163 | A2 | 2/2005 |
| WO | 2010-042738 | A2 | 4/2010 |

OTHER PUBLICATIONS

Ophthal. Physiol. Opt., 1989, vol. 9, April, Research Note, Multiple Applications of the NCT: An Assessment of Instrument's Effect on IOP by G.E. Russell and J.P.G. Bergmanson, pp. 212-214.

Arch Ophthalmol—vol. 97, Mar. 1979, The Pneumatonograph—A Laboratory Study, by Robert A. Moses, M.D. and Walter J. Grodzki Jr., D.D.S., pp. 547-552.

IEEE Transactions on bio-Medical Engineering, vol. BME-14, No. 2, Apr. 1967, Miniature Passive Pressure Transensor for Implanting in the Eye, by C.C. Collins, pp. 74-83.

Trans. Amer. Acad. of O. & O., Jan.-Feb. 1957, Tonometer Calibration, An Attempt to Remove Discrepancies Found in the 1954 Calibration Scale for Schiotz Tonometers by Jonas S. Friedenwald, M.D., pp. 108-123.

Investigative Ophthalmology, Feb. 1962, The Relationship Between Pressure and Volume Changes in Living and Dead Rabbit Eyes, by John E. Eisenlohr and Maurice E. Langham, pp. 63-77.

Investigative Ophthalmology, Sep. 1971, vol. 10, No. 9, Theory and Calibration of the Schiotz Tonometer VII. Experimental Results of Tonometric Measurements: Scale Reading Versus Indentation Volume, by Robert A. Moses and Walter J. Grodzki, pp. 716-723.

The British Journal of Ophthalmology, Jun. 1920, Communications—Tonometry, by HJ. Schiötz, pp. 249-261.

American Journal of Opthalmology, vol. 20, No. 10, Oct. 1937, Contribution to the Theory and Practice of Tonometry by Jonas S. Friedenwald, M.D., pp. 985-1024.

Ophthalmologica vol. 150, No. 5, (1965), Rheology of the Human Sclera, Unifying Formulation of Ocular Rigidity, by W.K. McEwen and Roger St. Helen, pp. 321-346.

A.M.A. Archives of Ophthalmology, vol. 57, Apr. 1957, Tonometer Calibration, by Earle H. McBain, M.D., pp. 520-531.

The Photonics Dictionary, 1996 Book 4, 42nd Edition, pp. D-24, D153.

Manual of Skin Diseases, Fifth Edition, Gordon C. Sauer, MD., 1985, pp. 204, 373.

FM-2 Fluorotron™ Master Ocular Fluorophotometer, 1994 OcuMetrics, Inc.

Textbook of Biochemistry With Clinical Correlations, Second Edition, Thomas M. Devlin, Ph.D., 1986, pp. 118, 139.

(56) References Cited

OTHER PUBLICATIONS

Physical Optics, Third Revised Edition, Robert W. Wood, 1961, pp. 650-651.
An Examiner's First Report; issued by the Australian Government, IP Australia dated Dec. 18, 2008, which corresponds to Australian Patent Application No. 2004263812.
An Examiner's First Report; issued by the Australian Government, IP Australia dated Mar. 10, 2010, which corresponds to Australian Patent Application No. 2009212808.
An Examiner's First Report; issued by the Australian Government, IP Australia dated Feb. 19, 2010, which corresponds to Australian Patent Application No. 2009212861.
An Examiner's First Report; issued by the Australian Government, IP Australia dated Nov. 4, 2013, which corresponds to Australian Patent Application No. 2012247045.
An Office Action issued by the Canadian Intellectual Property Office dated May 3, 2012, which corresponds to Canadian Patent Application No. 2,517,869.
English translation of a First Office Action and Search Report; issued by the State Intellectual Property Office of the People's Republic of China dated Jul. 21, 2014, which corresponds to Chinese Patent Application No. 201310097177.3.
English translation of a First Office Action and Search Report; issued by the State Intellectual Property Office of the People's Republic of China dated Jul. 22, 2014, which corresponds to Chinese Patent Application No. 201310097142.X.
A supplementary European Search Report; issued by the European Patent Office dated Oct. 17, 2008, which corresponds to European Patent Application No. 04785841.0-1265.
A "Communication pursuant to Article 94(3) EPC," issued by the European Patent Office dated Jan. 27, 2009, which corresponds to European Patent Application No. 04785841.0-1265.
A "Communication pursuant to Article 94(3) EPC," issued by the European Patent Office dated Sep. 12, 2013, which corresponds to European Patent Application No. 04785841.0-1657.
English Translation of Relevant Portion of Office Action; issued by the State of Israel Department of Justice, Patent Office dated Jul. 3, 2013, which corresponds to Israeli Patent Application No. 1704896.
English translation of Notification of Reasons for Refusal; issued by the Japanese Patent Office dated Jun. 11, 2009, which corresponds to Japanese Patent Application No. 2006-508817.
English translation of Notification of Reasons for Refusal; issued by the Japanese Patent Office dated Jan. 12, 2010, which corresponds to Japanese Patent Application No. 2006-508817.
A Summarized English Translation of Office Action; issued by the Instituto Mexicano de la Propiedad Industrial dated Jul. 4, 2008, which corresponds to Mexican National Phase Patent Application No. PA/a/2005/009159.
An Office Action; issued by the Instituto Mexicano de la Propiedad Industrial dated Sep. 25, 2009, which corresponds to Mexican National Phase Patent Application No. PA/a/2005/009159.
International Search Report & Written Opinion; PCT/US2004/005496; dated May 6, 2005.
English translation of an Office Action; issued by the Japanese Patent Office dated Jan. 22, 2009, which corresponds to Japanese Patent Application No. 2004-515642.
English translation of an Office Action; issued by the National Institute of Industrial Property dated Jul. 1, 2013, which corresponds to Brazilian Patent Application PI0309578-9.
English translation of an Office Action; issued by the National Institute of Industrial Property, which corresponds to Brazilian Patent Application PI0309578-9.
English translation of the "First Office Action," and "Search Report," issued by the State Intellectual Property Office of the People's Republic of China dated Jun. 4, 2014, which corresponds to Chinese Application No. 201210361917.5.
A "Communication pursuant to Article 94(3) EPC," issued by the European Patent Office dated Jan. 27, 2009, which corresponds to European Patent Application No. 03 754 363.4-1265.

A second "Communication pursuant to Article 94(3) EPC," issued by the European Patent Office dated Sep. 13, 2013, which corresponds to European Patent Application No. 03 754 363.4-1657.
A third "Communication pursuant to Article 94(3) EPC," issued by the European Patent Office dated Mar. 4, 2014, which corresponds to European Patent Application No. 03 754 363.4-1657.
A fourth "Communication pursuant to Article 94(3) EPC," issued by the European Patent Office dated Sep. 24, 2014, which corresponds to European Patent Application No. 03 754 363.4-1657.
English translation of an Office Action; issued by the State of Israel Department of Justice, Patent Office dated Nov. 26, 2008, which corresponds to Israeli Patent Application No. 164685.
English translation of an Office Action; issued by the Korean Intellectual Property Office dated Dec. 26, 2011, which corresponds to Korean Patent Application No. 10-2010-7018173.
International Search Report; PCT/US03/12382; dated May 13, 2005.
International Search Report; PCT/US2006/041238; dated Aug. 31, 2007.
An Office Action issued by the Canadian Intellectual Property Office dated Aug. 2, 2011, which corresponds to Canadian Patent Application No. 2,627,278.
A Second Office Action issued by the Canadian Intellectual Property Office dated Mar. 14, 2012, which corresponds to Canadian Patent Application No. 2,627,278.
A "Communication pursuant to Particle 94(3) EPC," issued by the European Patent Office dated May 13, 2011, which corresponds to European Patent Application No. 06 826 452.2-2319.
English translation of an Office Action; issued by the State of Israel Department of Justice, Patent Office dated Jun. 23, 2011, which corresponds to Israeli Patent Application No. 191039.
An Examiner's First Report; issued by the Australian Government, IP Australia dated Jan. 13, 2012, which corresponds to Australian Patent Application No. 2011202015.
Patent Examination Report No. 1; issued by the Australian Government, IP Australia dated Dec. 13, 2013, which corresponds to Australian Patent Application No. 2012203667.
An Examiner's First Report; issued by the Australian Government, IP Australia dated Apr. 21, 2009, which corresponds to Australian Patent Application No. 2006306422.
An Examiner's Report No. 2; issued by the Australian Government, IP Australia dated Nov. 10, 2010, which corresponds to Australian Patent Application No. 2006306422.
English translation of an Office Action; issued by the Korean Intellectual Property Office dated Jun. 21, 2013, which corresponds to Korean Patent Application No. 10-2008-7012335.
English translation of an Office Action; issued by the Japanese Patent Office dated Nov. 17, 2011, which corresponds to Japanese Patent Application No. 2008-537828.
English translation of a Second Office Action; issued by the Japanese Patent Office dated Nov. 13, 2012, which corresponds to Japanese Patent Application No. 2008-537828.
English translation of a Third Office Action; issued by the Japanese Patent Office dated Nov. 26, 2013, which corresponds to Japanese Patent Application No. 2008-537828.
Overton, Staci. "Brain Temperature Tunnel Discovered." Medical Breakthroughs Reported by Ivanhoe, Jun. 2, 2003.
International Search Report; PCT/US2014/060199; dated Jan. 8, 2015.
International Search Report; PCT/US2014/060201; dated Mar. 3, 2015.
Dittmar, A. et al., A Non Invasive Wearable Sensor for the Measurement of Brain Temperature. Proceedings of the 28th IEEE EMBS Annual International Conference. Aug. 30-Sep. 3, 2006. pp. 900-902, New York City, USA.
An Office Action and Examination Search Report issued by the Canadian Intellectual Property Office dated Mar. 26, 2015, which corresponds to Canadian Patent Application No. 2,627,278.
International Search Report; PCTUS2015/010873; dated Apr. 10, 2015.
English translation of an Unfavorable Technical Opinion; issued by the National Institute of Industrial Property, which corresponds to Brazilian Patent Application BR122013001249-4.

(56) References Cited

OTHER PUBLICATIONS

International Search Report; PCT/US15/10938; dated Jun. 12, 2015.
Written Opinion of the International Searching Authority; PCT/US15/10938; dated Jun. 12, 2015.
Examination report issued in corresponding Australian application No. 2016247223 dated Mar. 2, 2018; 5pp.
First Examination Report issued by the Australian Patent Office dated May 10, 2018 in corresponding Australian Patent Application No. 2016201025; 6pp.

* cited by examiner

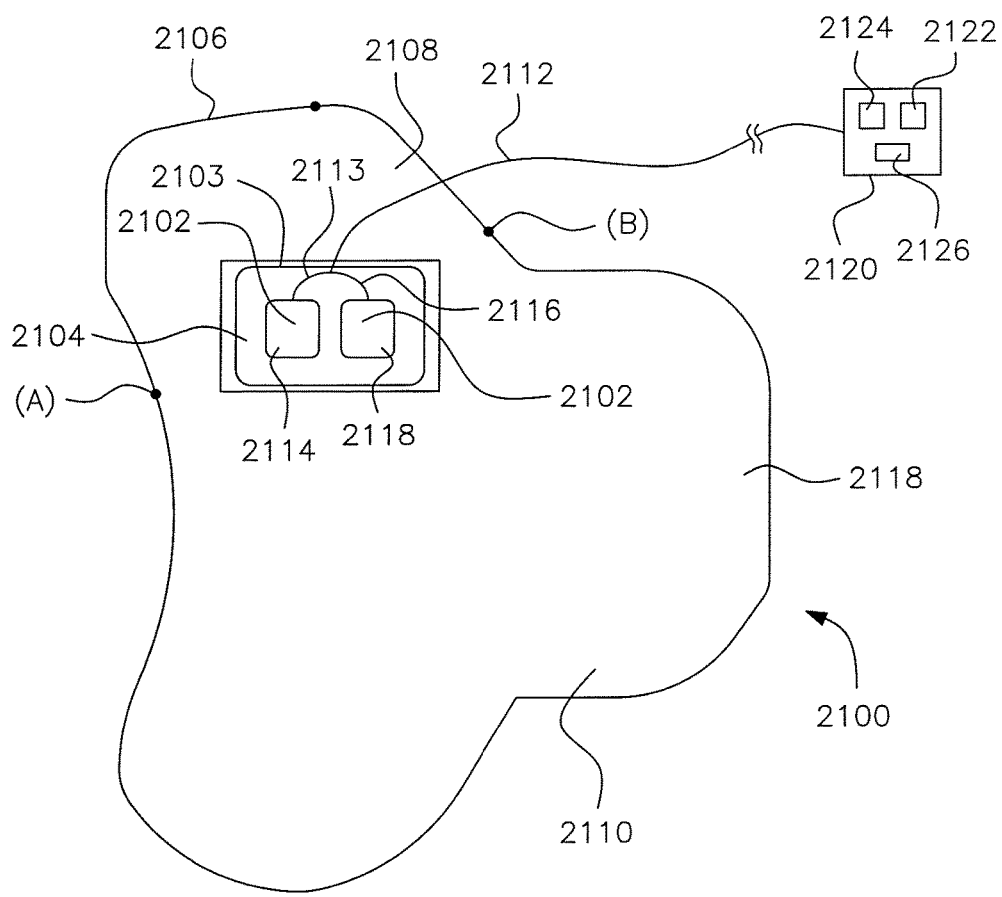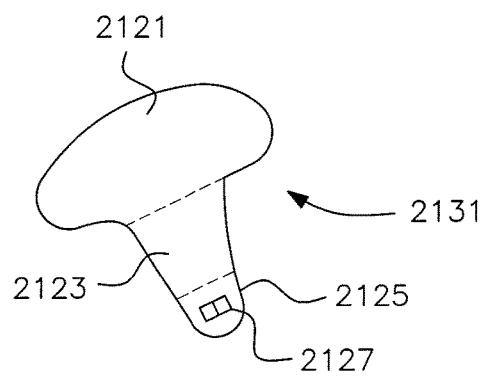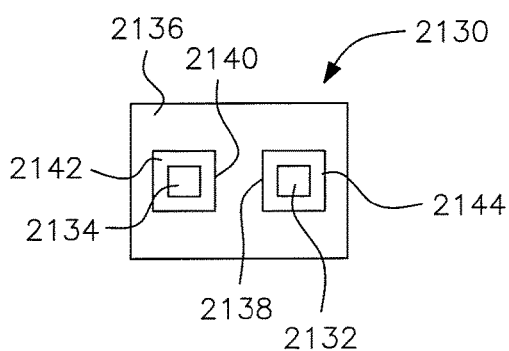

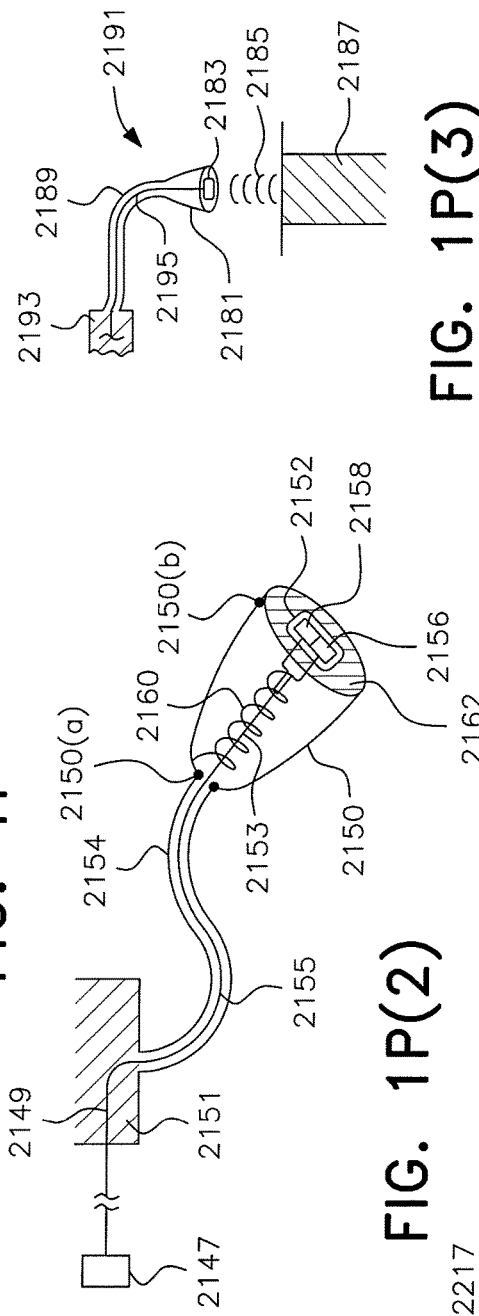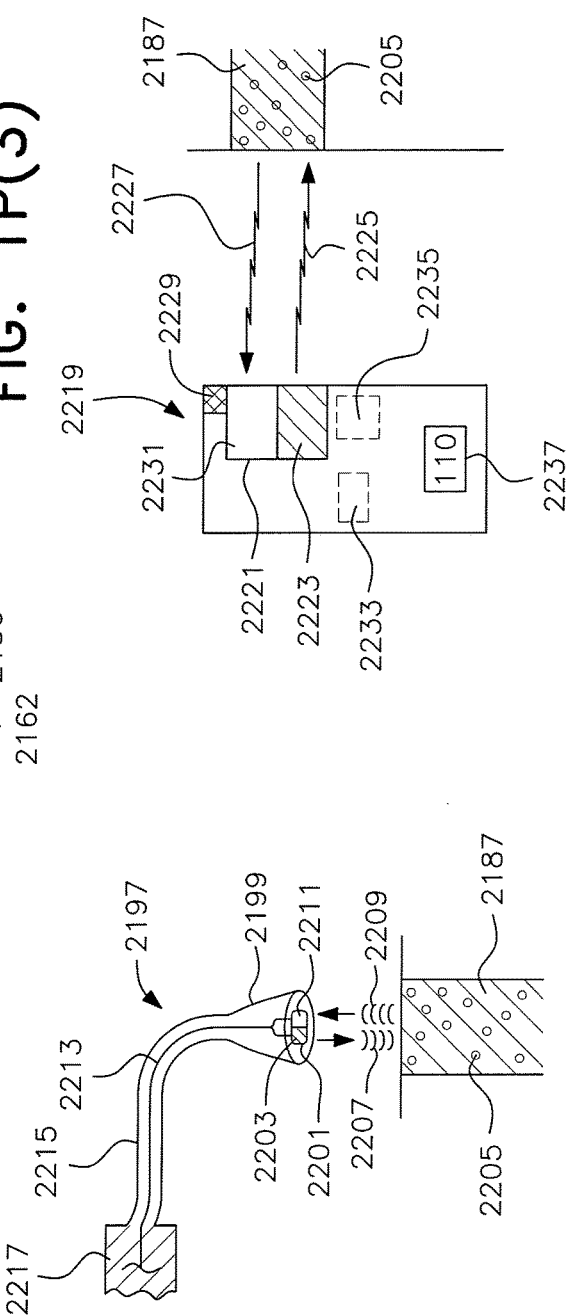

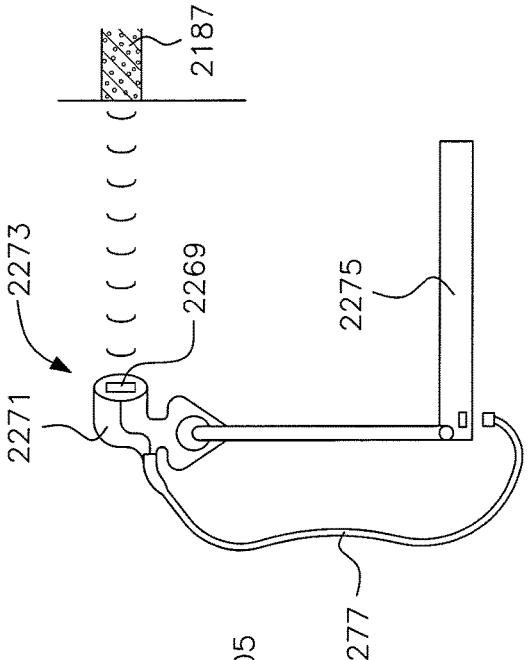
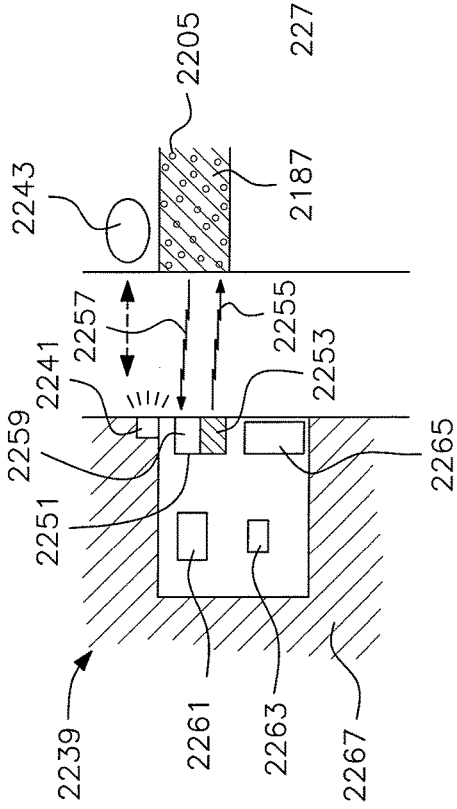
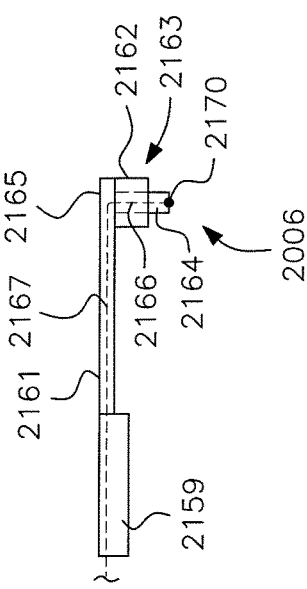

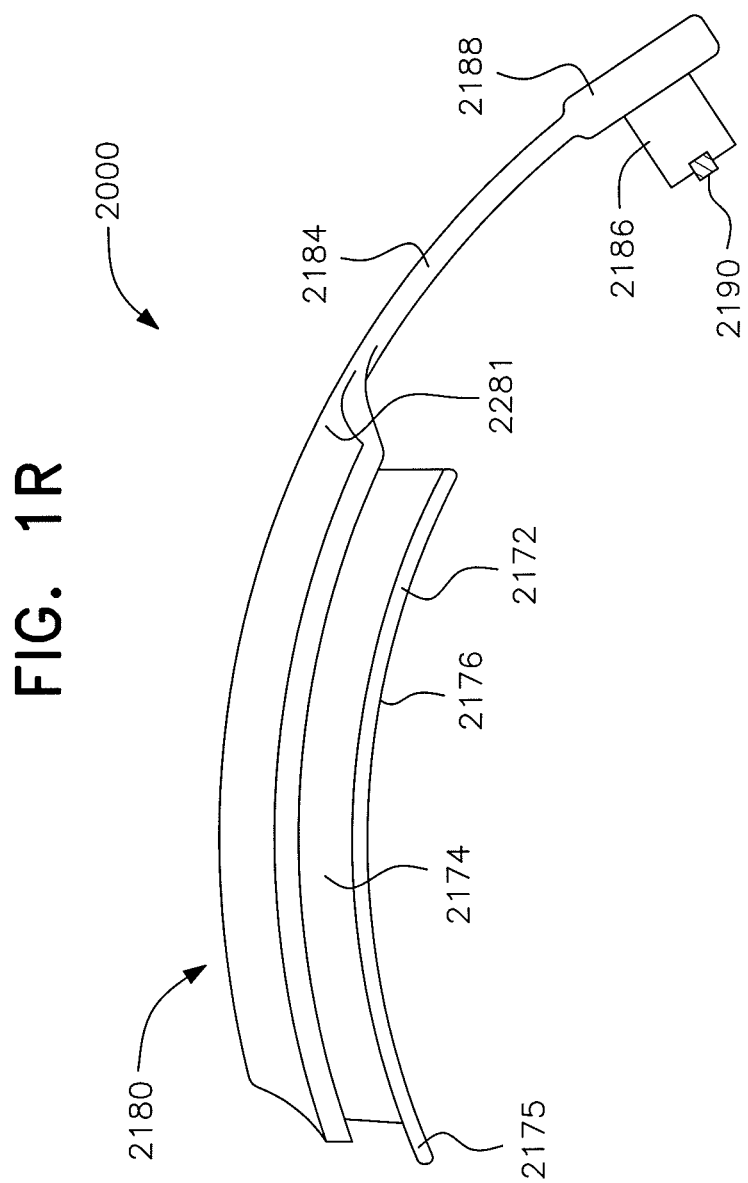

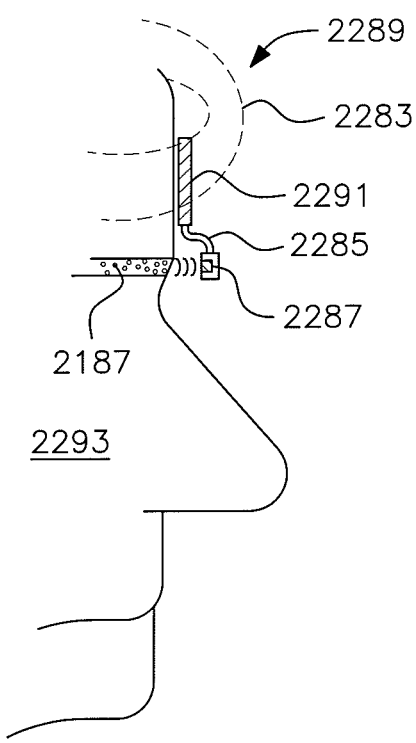
FIG. 1R(1)
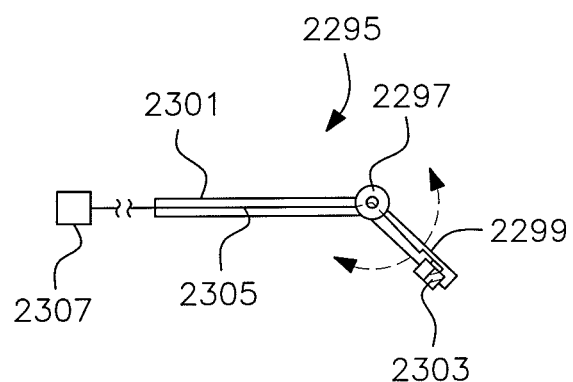
FIG. 1R(2)
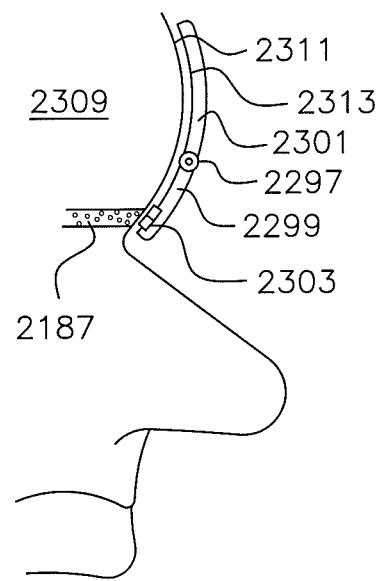
FIG. 1R(3)

FIG. 1S(1)
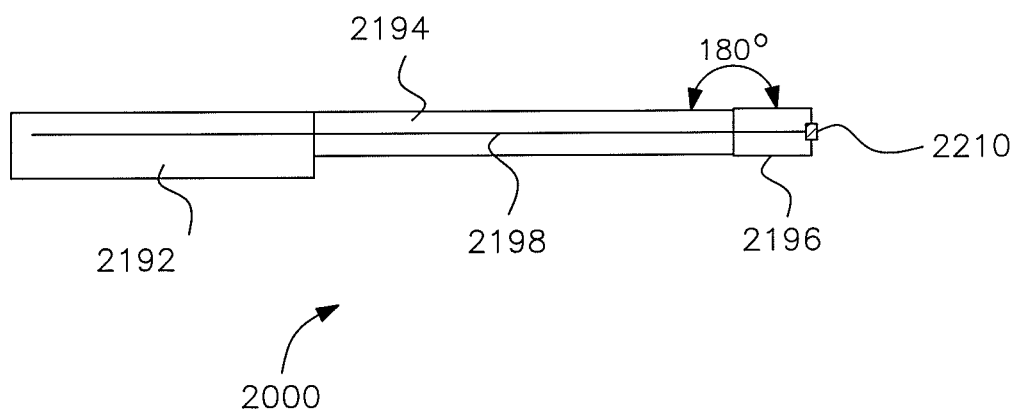
FIG. 1S(2)
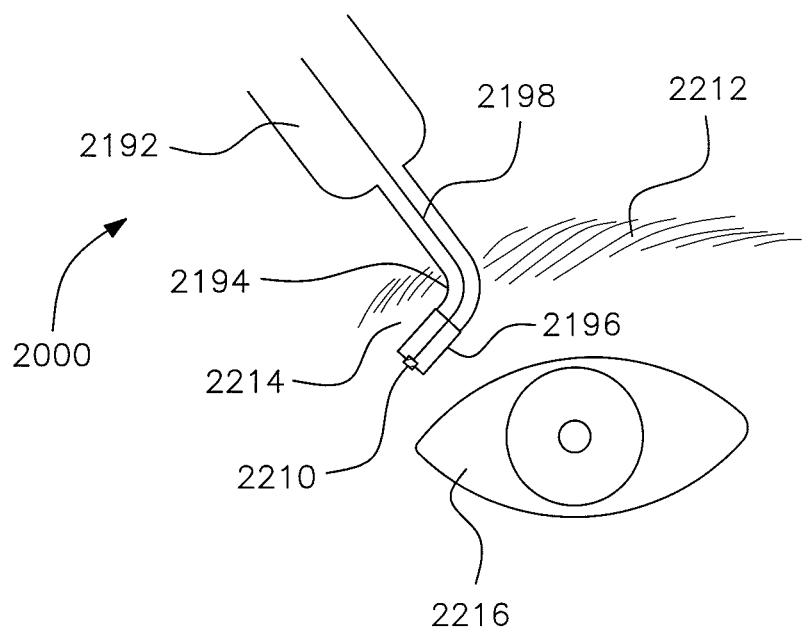

FIG. 1T(1)
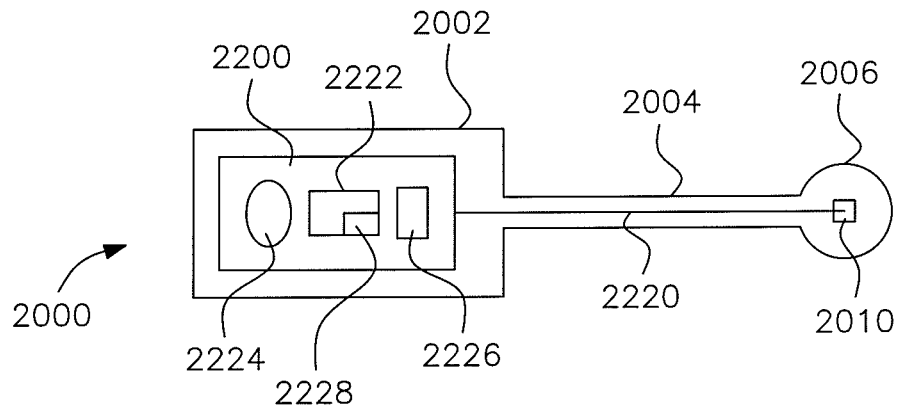
FIG. 1T(2)
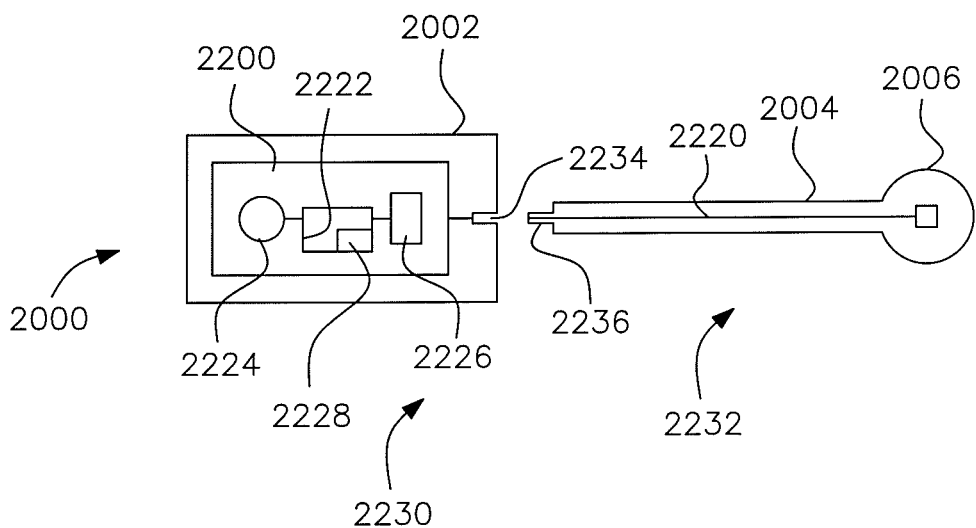
FIG. 1T(3)
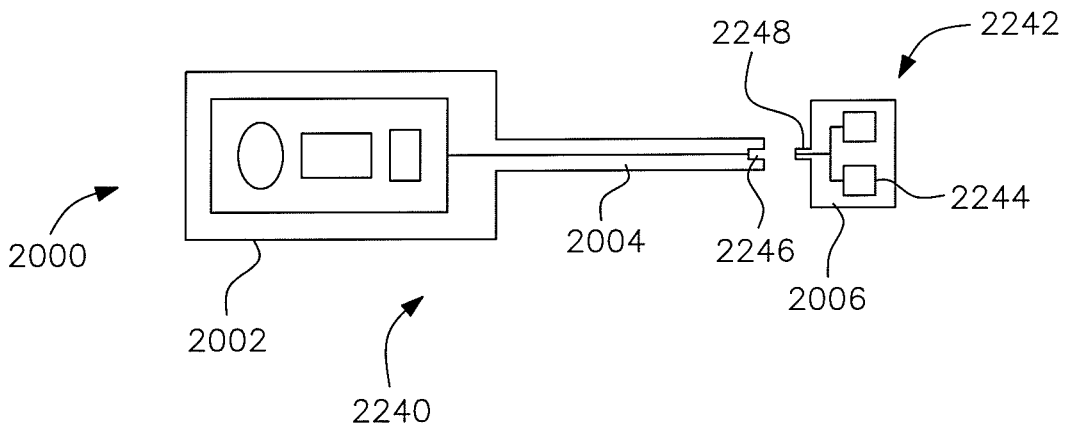

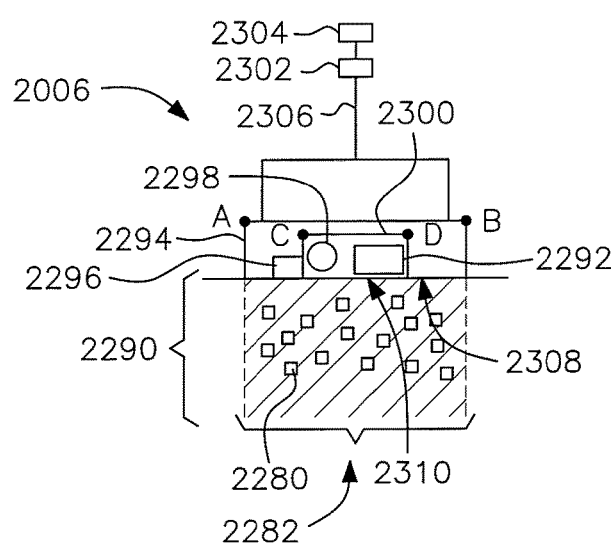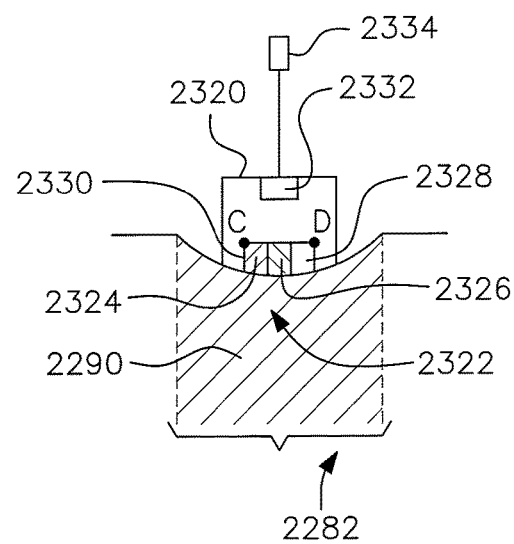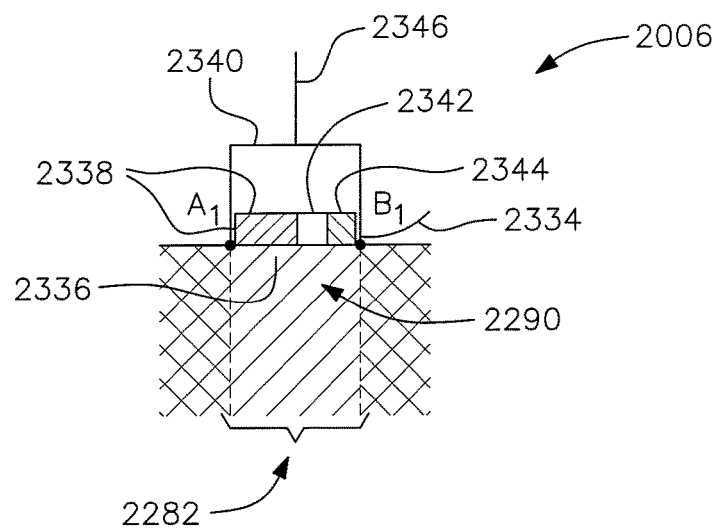

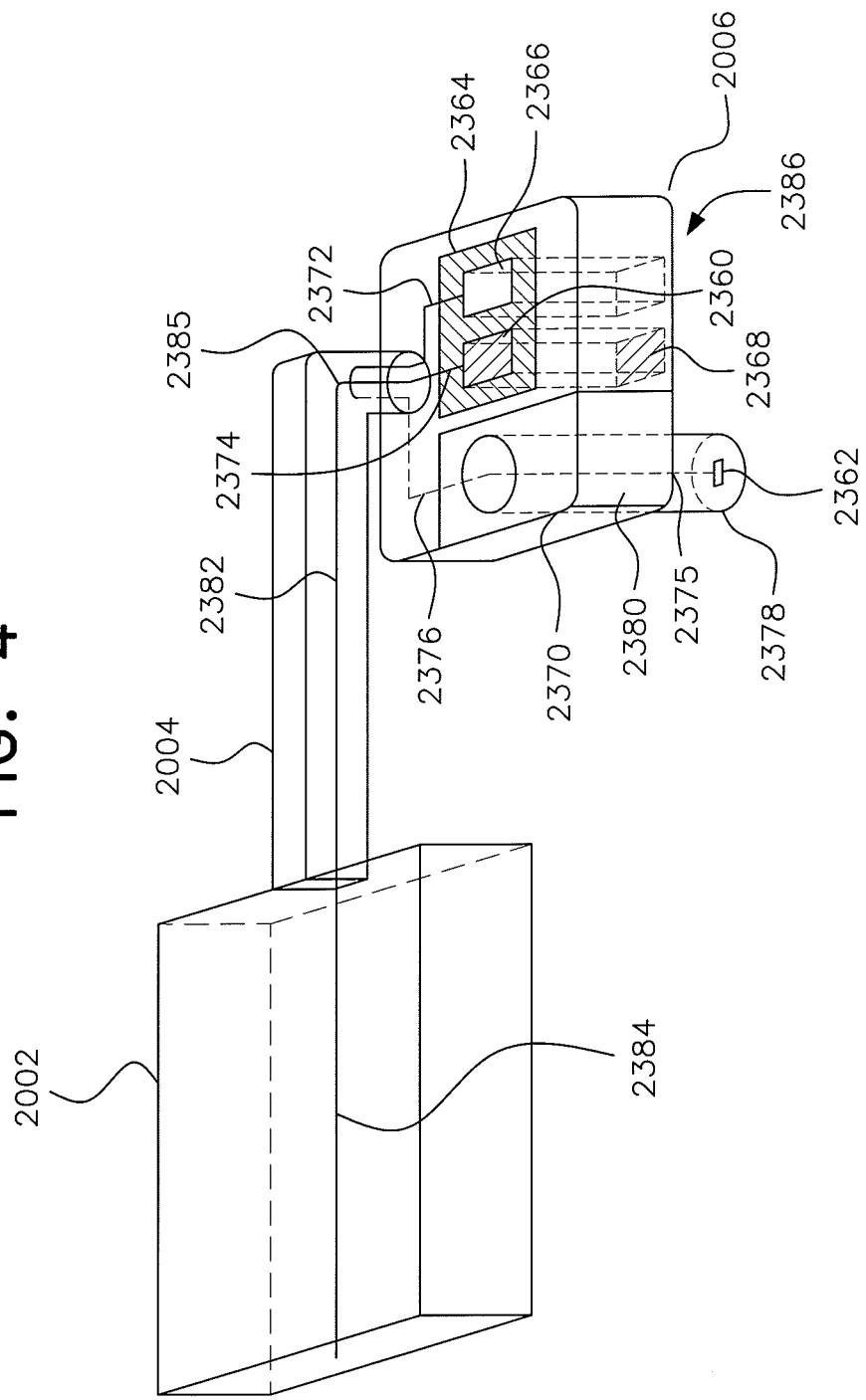

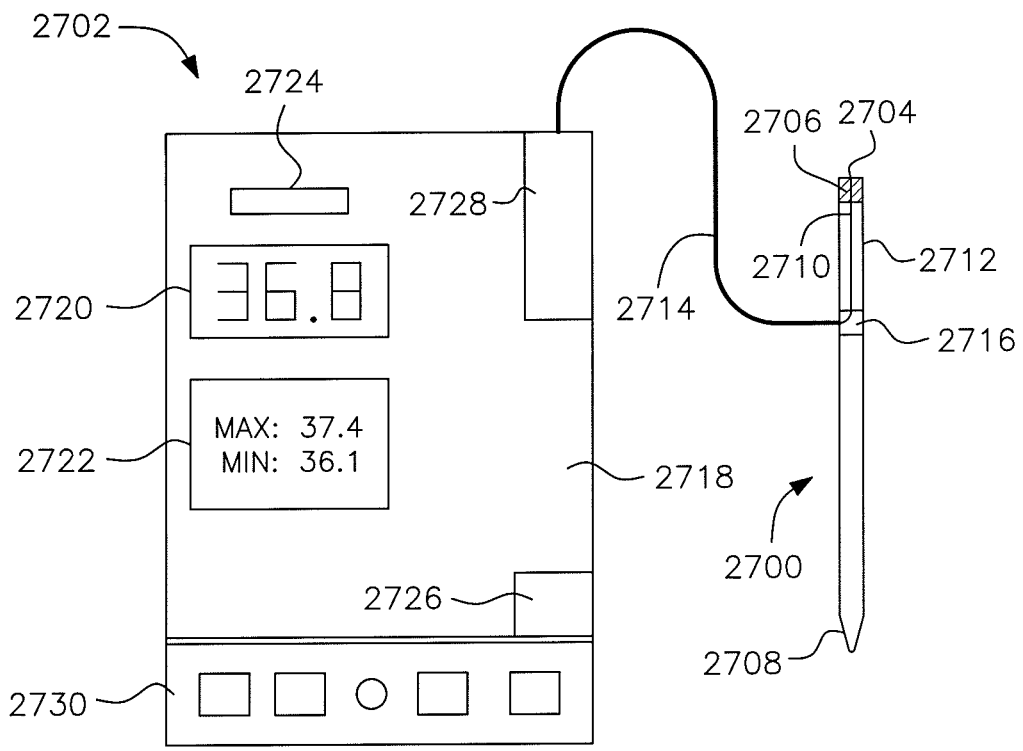
FIG. 11
FIG. 11A
(PRIOR ART)
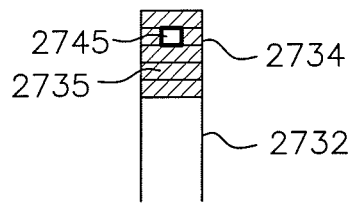
FIG. 11B
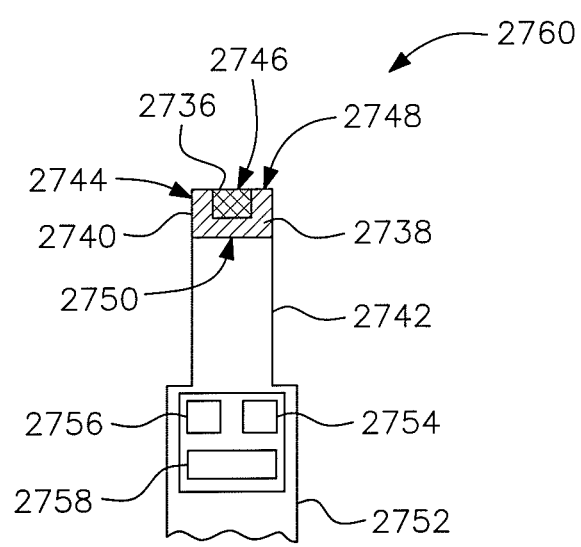

FIG. 11C
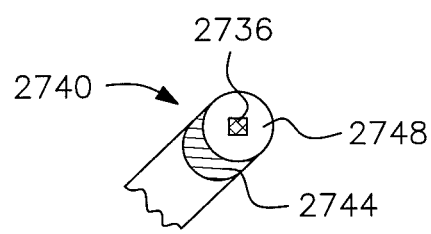
FIG. 11D
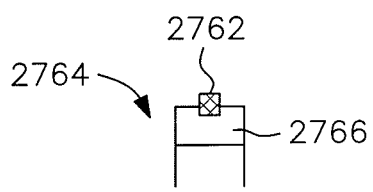
FIG. 11E
(PRIOR ART)
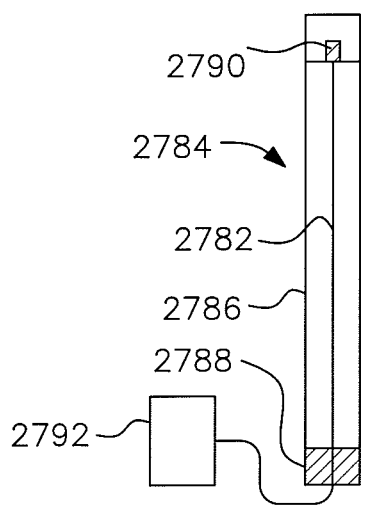
FIG. 11F
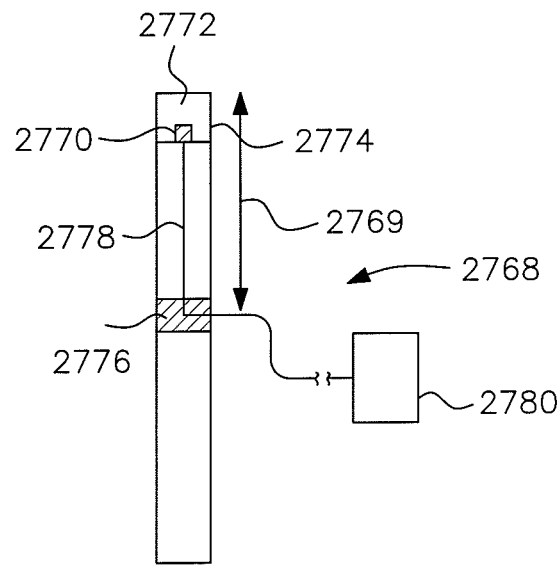
FIG. 11-G1
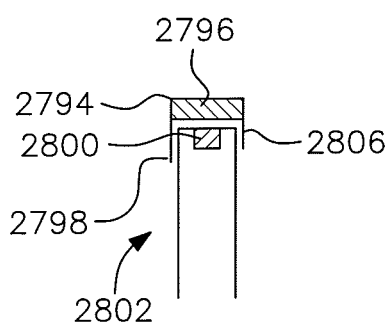
FIG. 11-G2
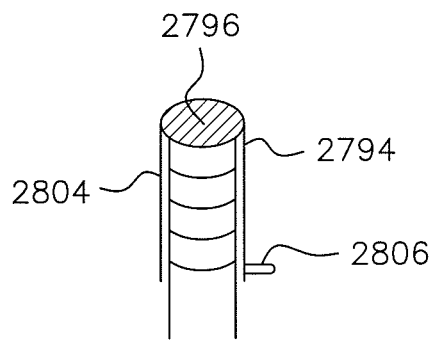

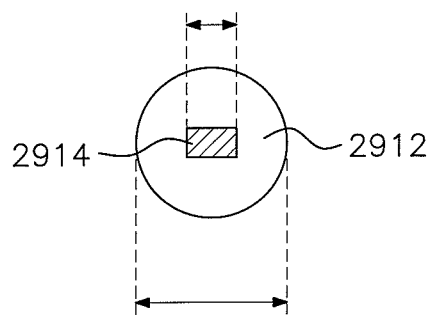
FIG. 11-Q1
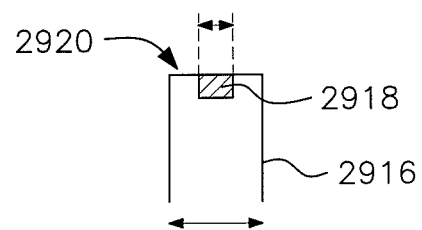
FIG. 11-Q2
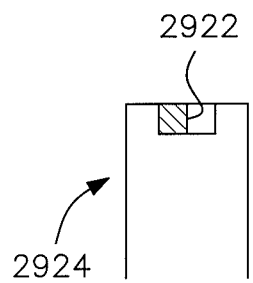
FIG. 11-Q3
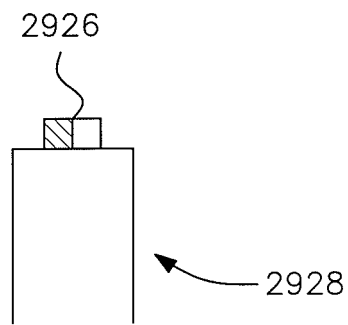
FIG. 11-Q4

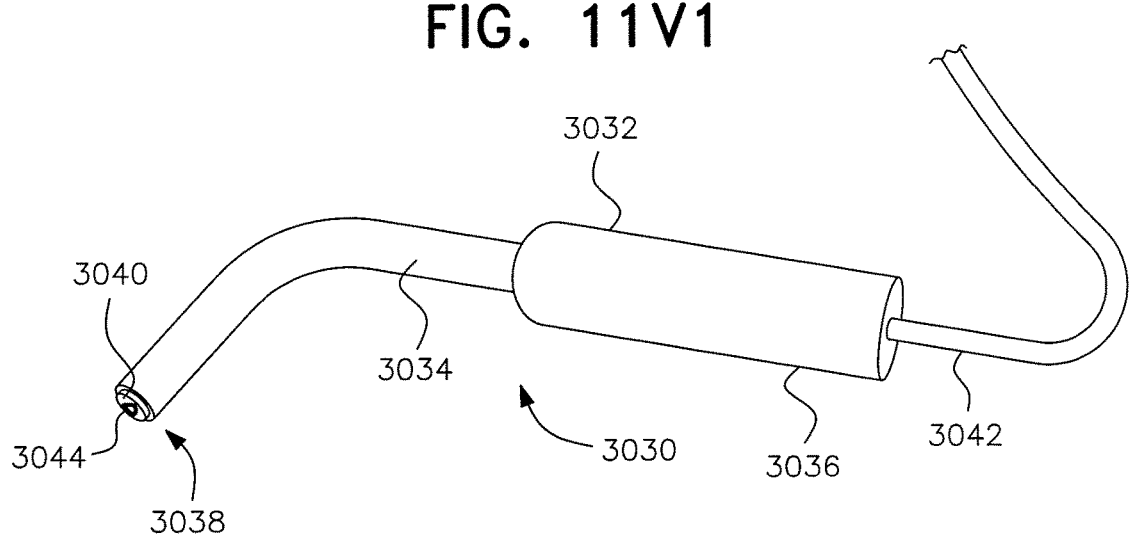
FIG. 11V1
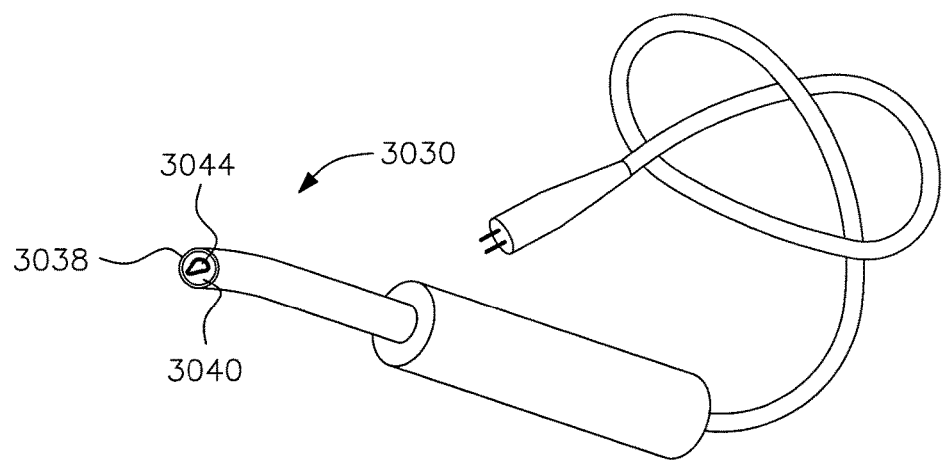
FIG. 11V2

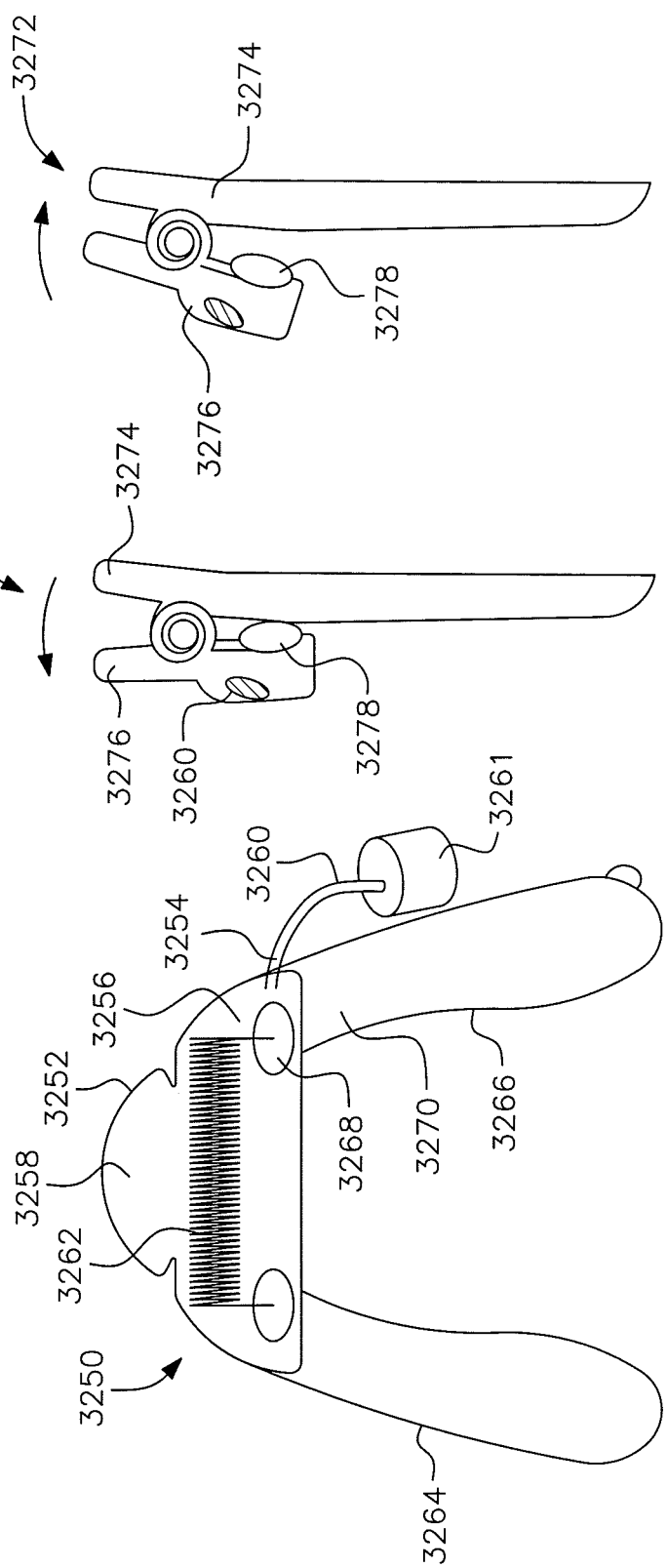

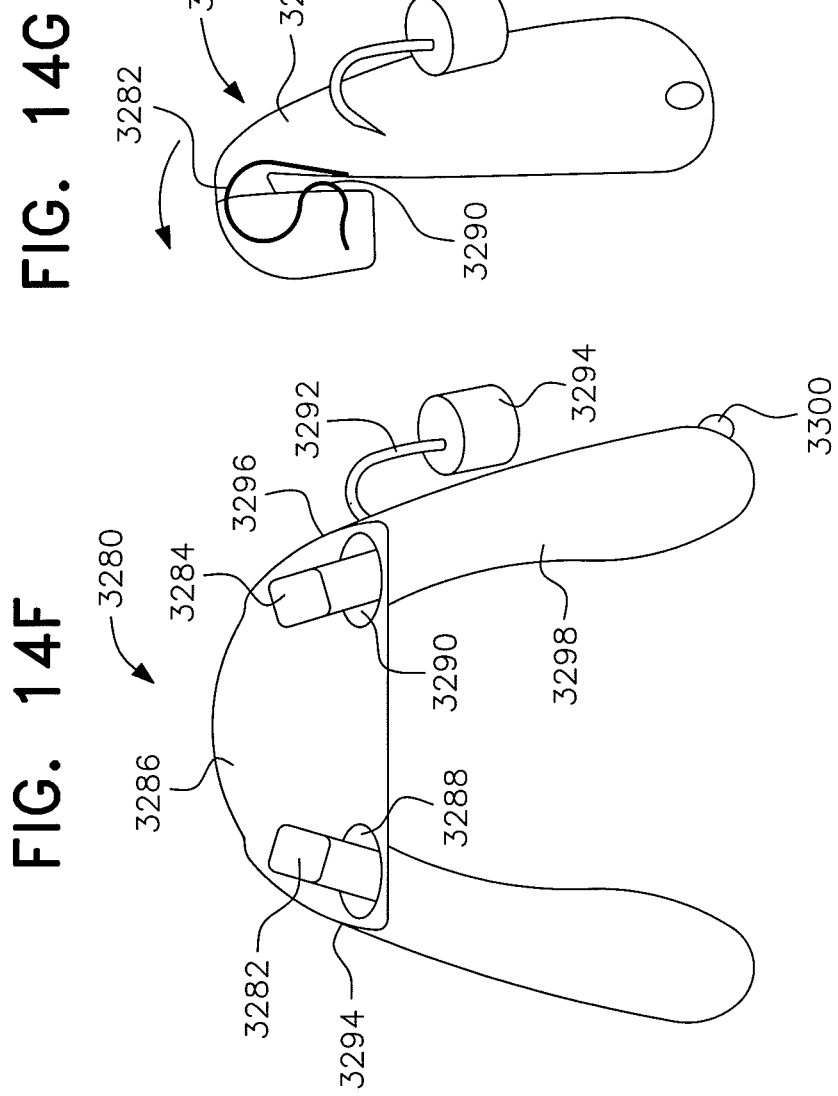

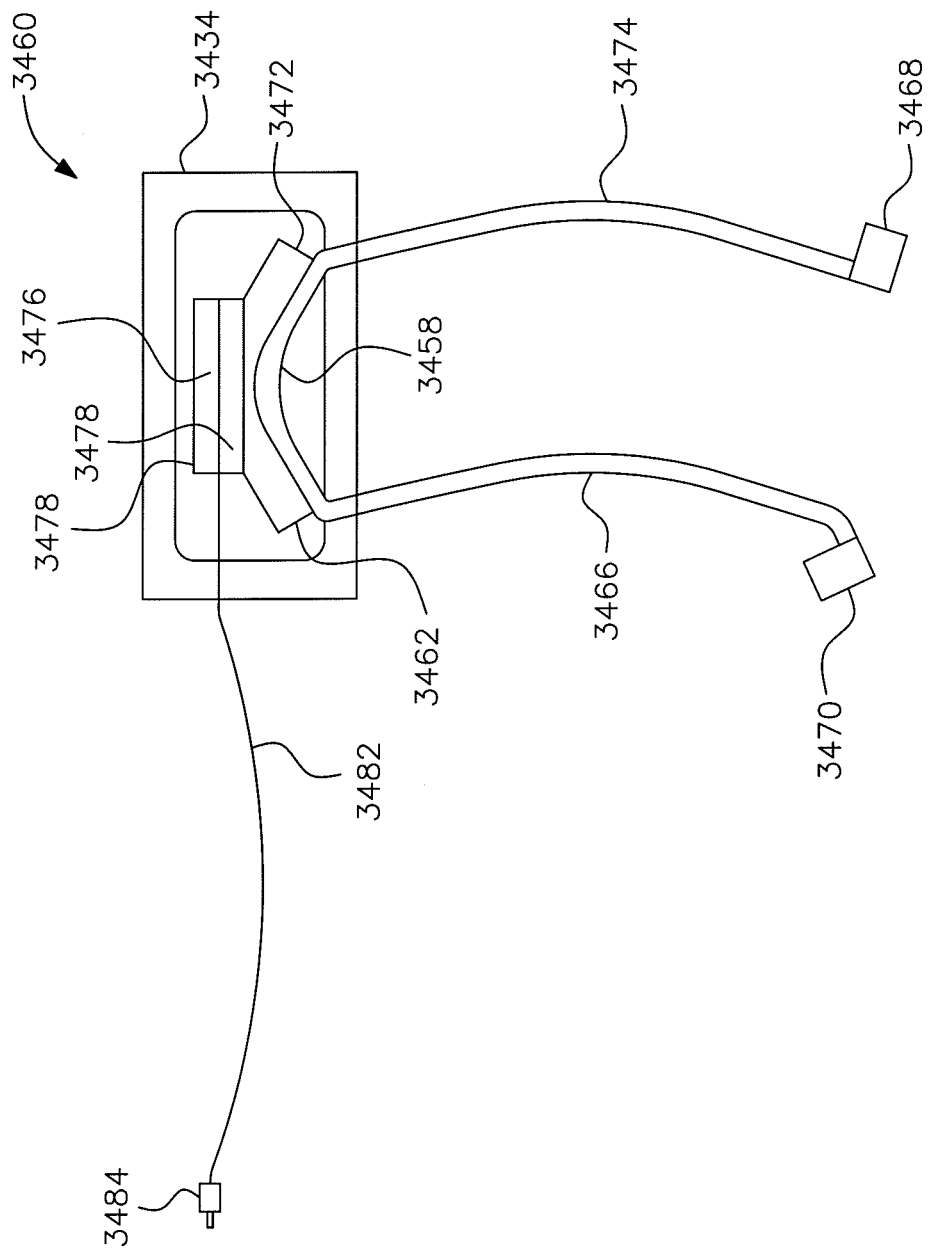

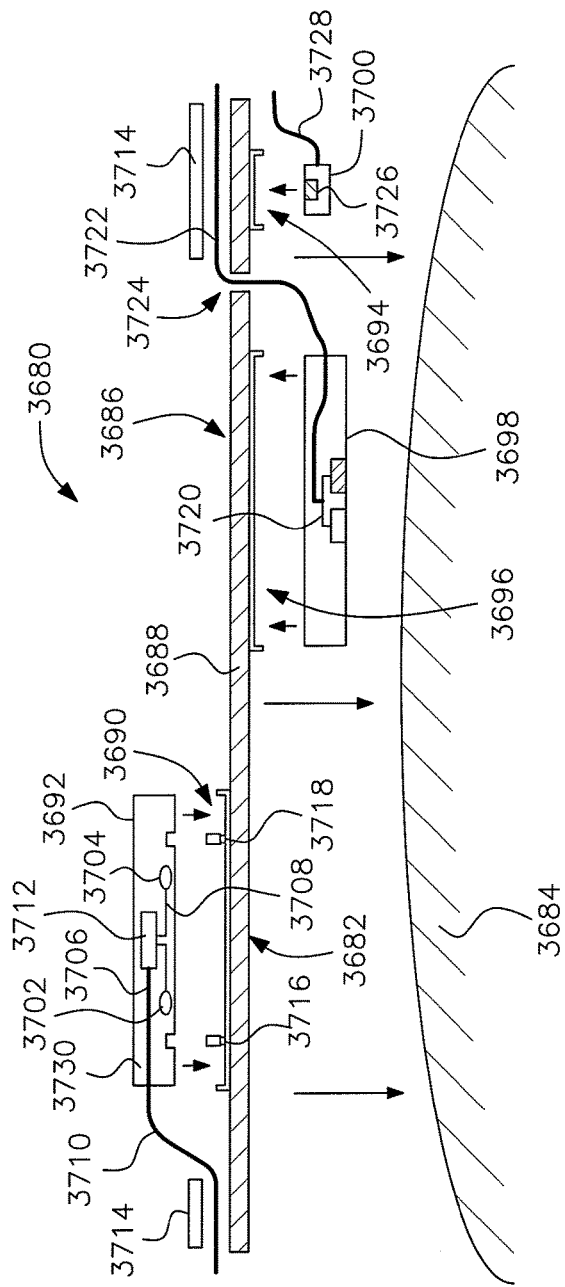
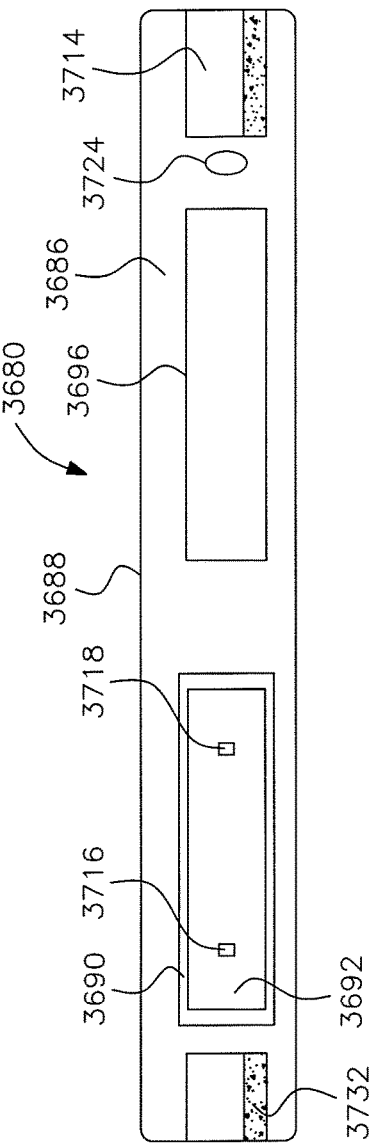

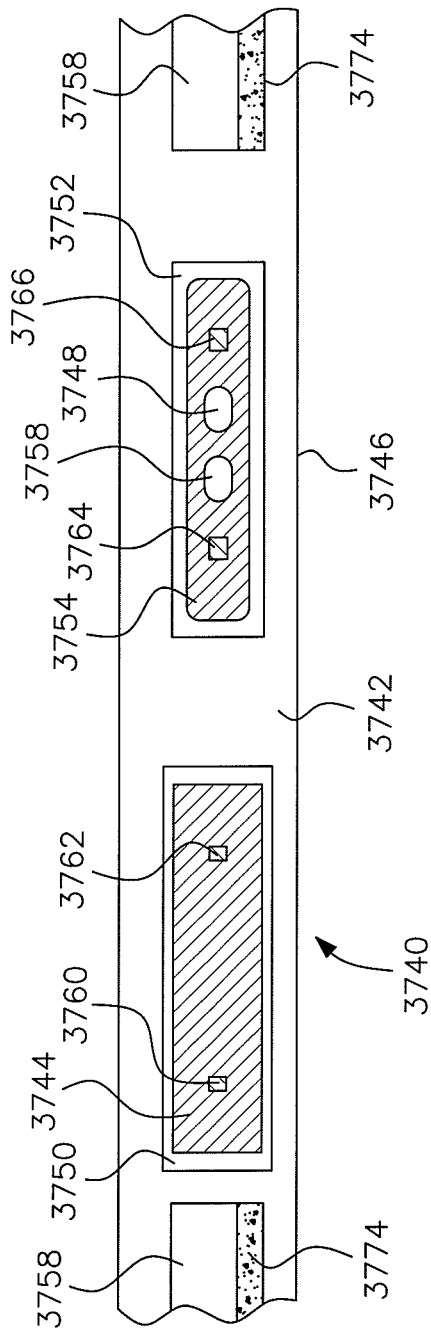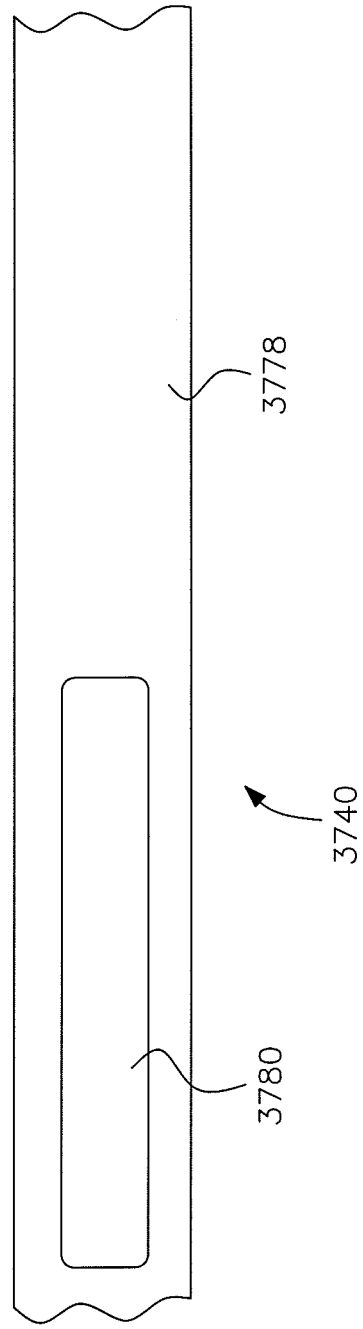

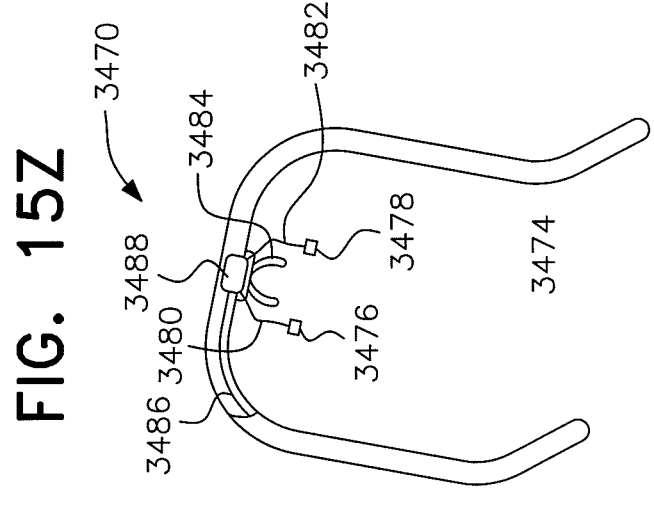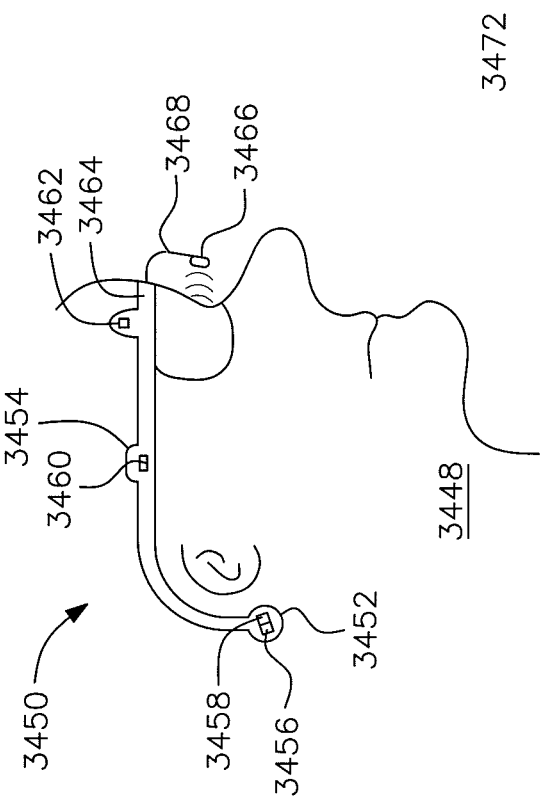

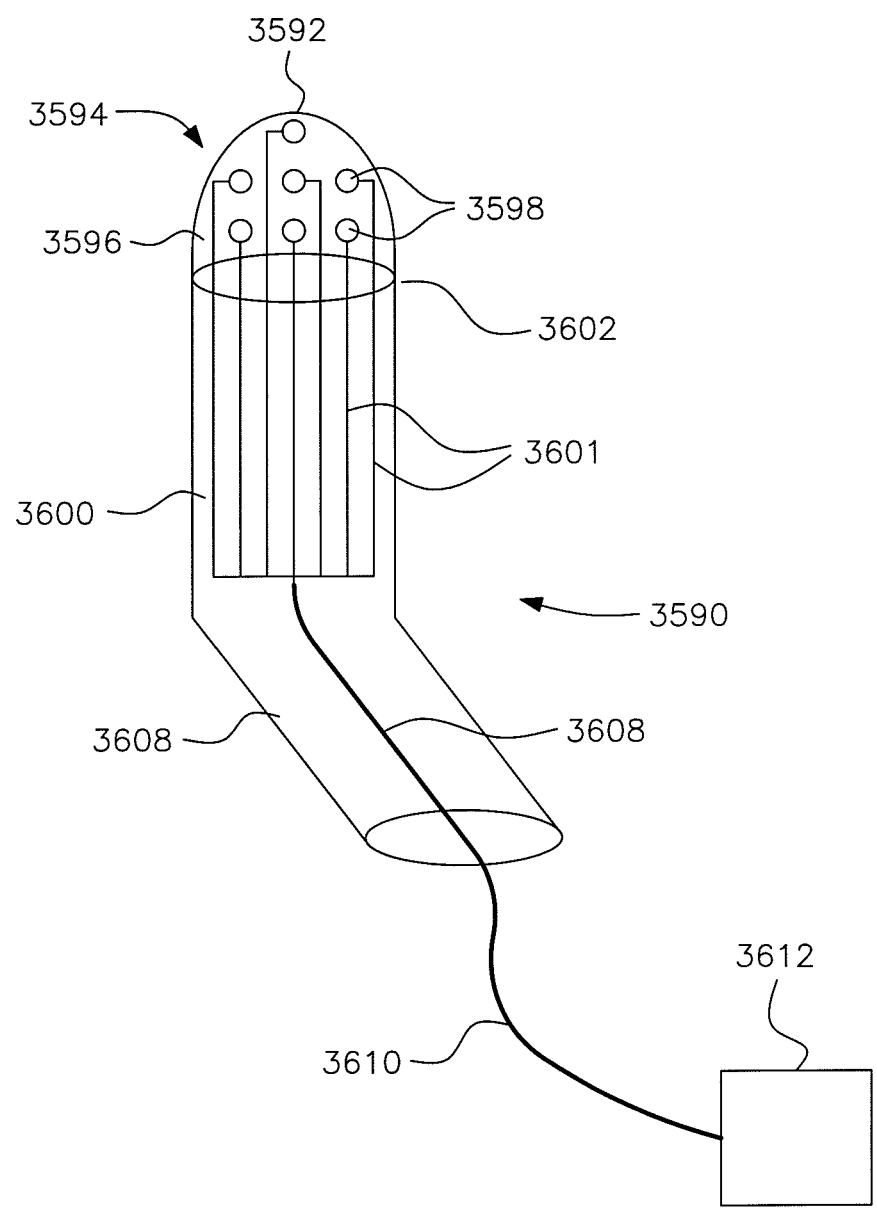
FIG. 19-A

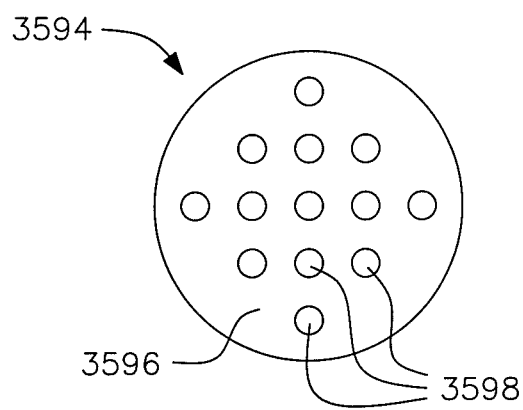
FIG. 19-B

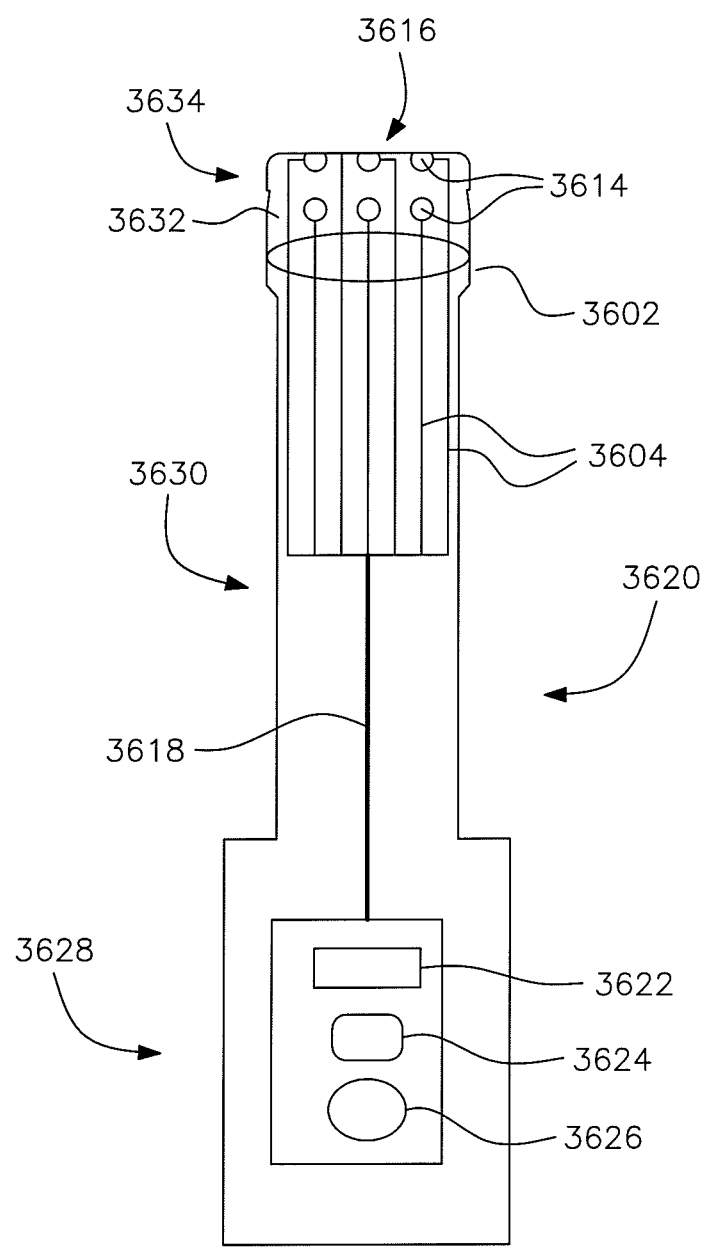
FIG. 19-C

FIG. 19-D
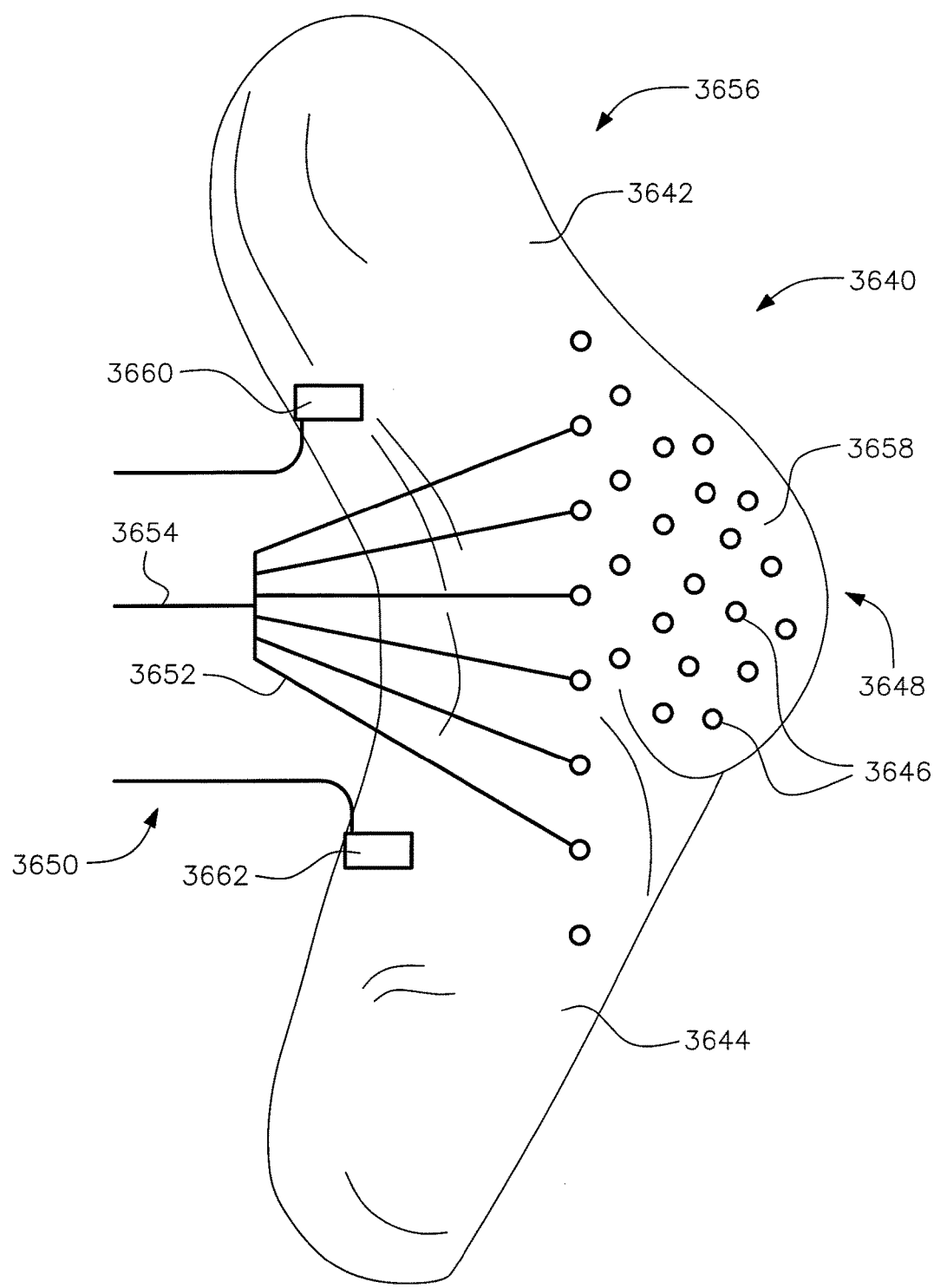

FIG. 19-E
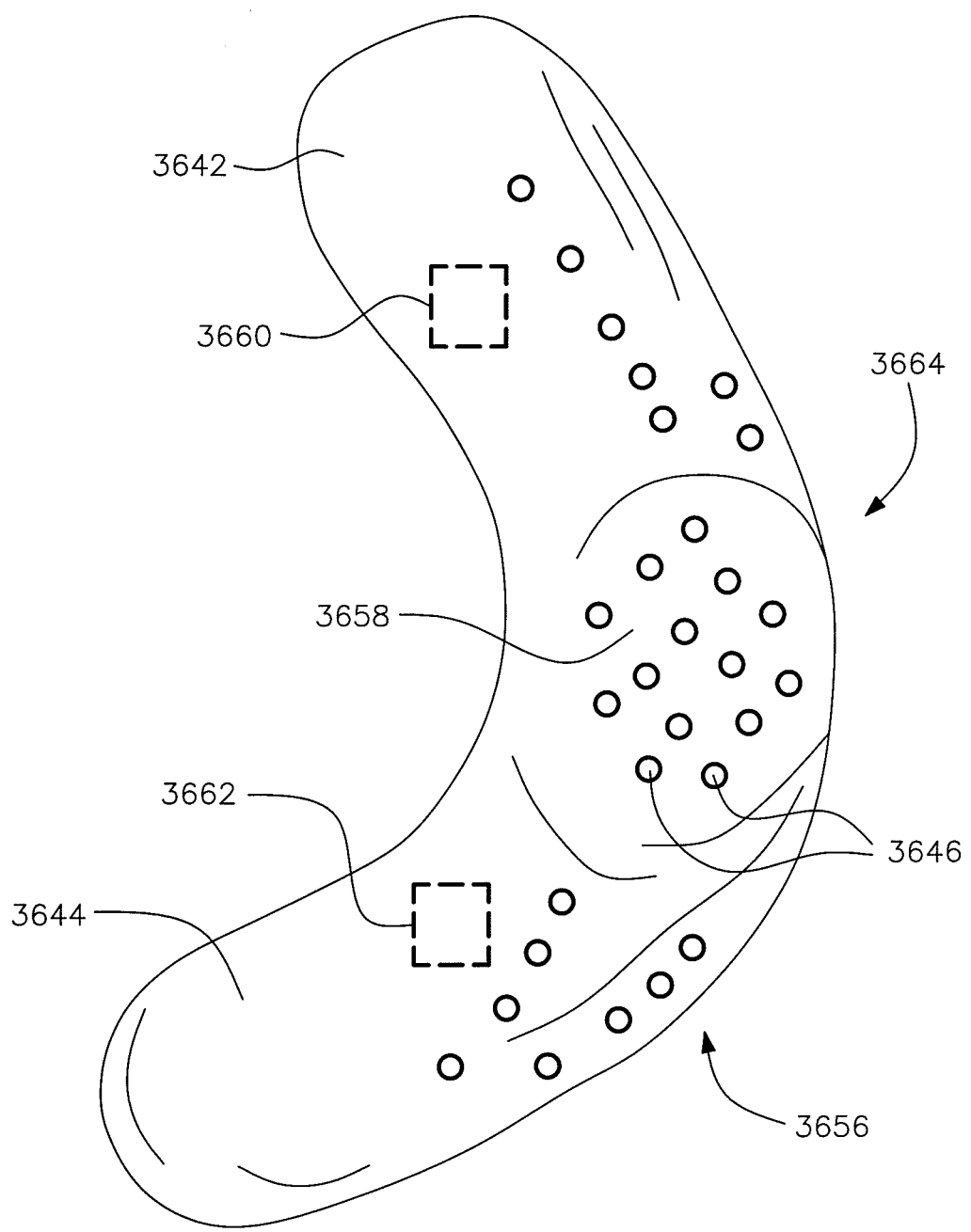

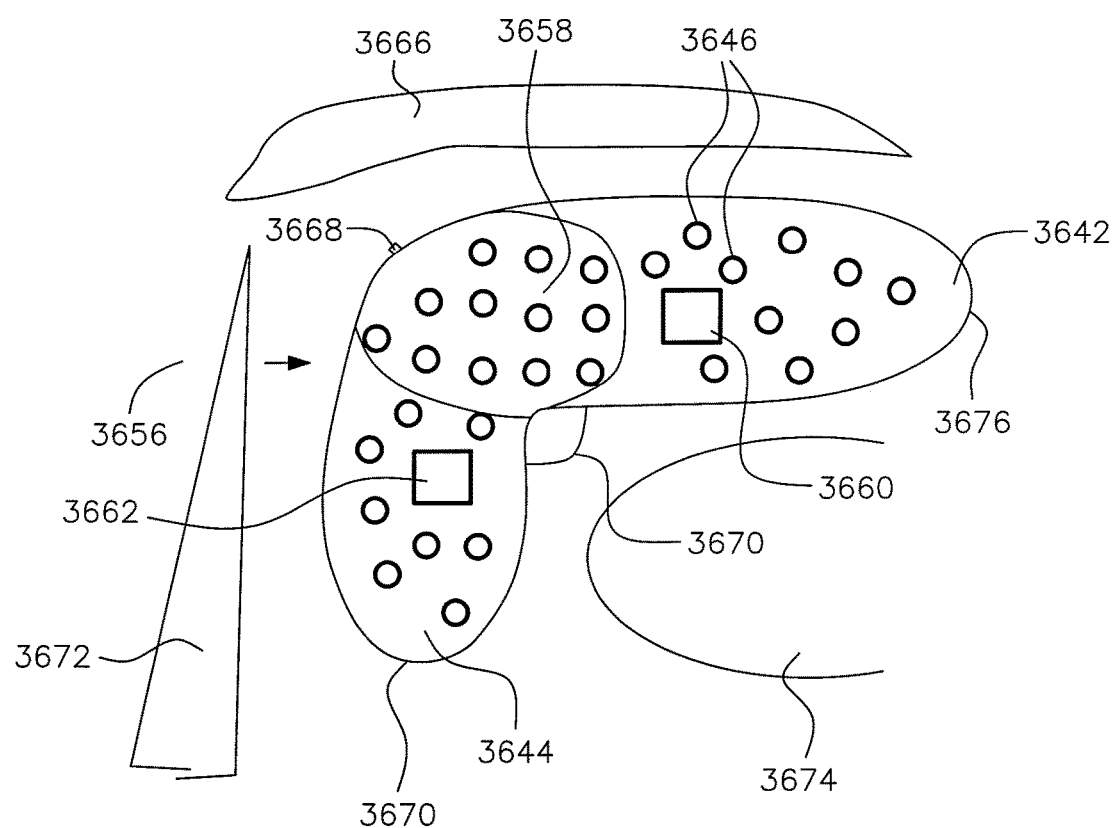
FIG. 19-F

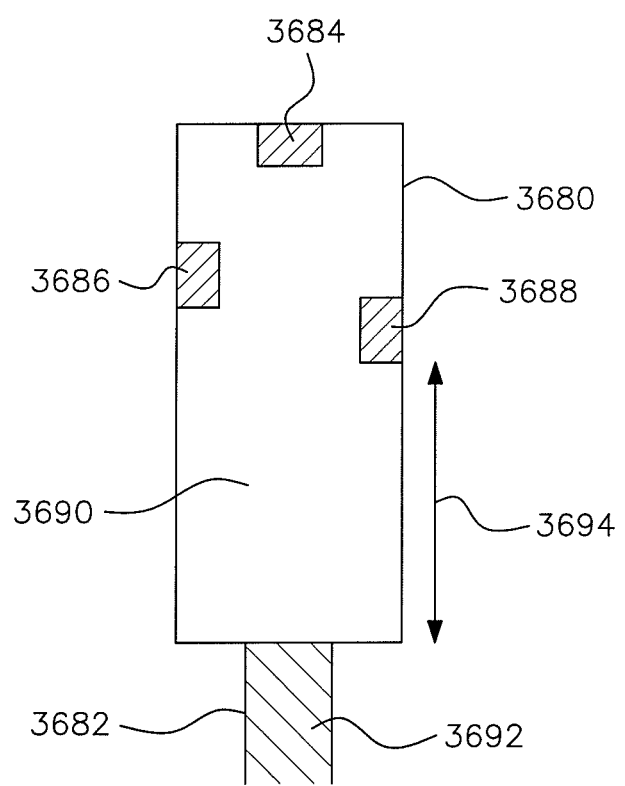
FIG. 19-G

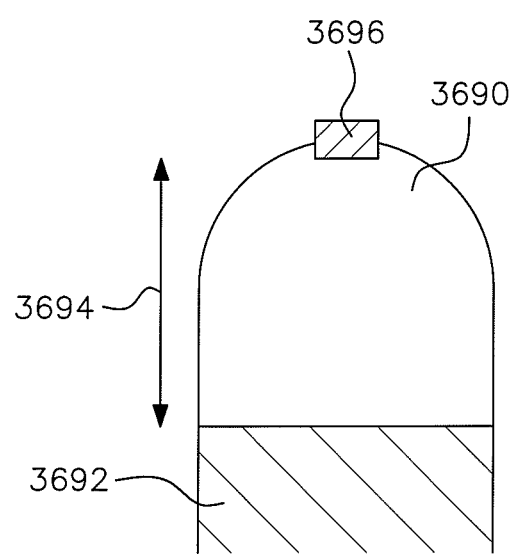
FIG. 19-H

APPARATUS AND METHOD FOR MEASURING BIOLOGIC PARAMETERS

APPARATUS AND METHOD FOR MEASURING BIOLOGIC PARAMETERS

This application is a Continuation of U.S. patent application Ser. No. 14/801,394, filed on Jul. 16, 2015, which is a Continuation of U.S. patent application Ser. No. 13/465,444, filed on May 7, 2012 which is a Continuation of U.S. patent application Ser. No. 11/585,357, filed on Oct. 24, 2006, which is a complete application of U.S. Provisional Application No. 60/729,232, filed on Oct. 24, 2005 and U.S. Provisional Application No. 60/802,503, filed on May 23, 2006, herein incorporated in their entirety by reference.

FIELD OF THE INVENTION

The present invention includes support and sensing structures positioned in a physiologic tunnel for measuring bodily functions and to manage abnormal conditions indicated by the measurements.

BACKGROUND OF THE INVENTION interfering constituents and variables can introduce significant source of errors that prevent measured biologic parameters from being of clinical value. In order to bypass said interfering constituents and achieve undisturbed signals, invasive and semi-invasive techniques have been used. Such techniques have many drawbacks including difficulties in providing continuous monitoring for long periods of time. Non-invasive techniques also failed to deliver the clinical usefulness needed. The placement of a sensor on the skin characterized by the presence of interfering constituents do not allow obtaining clinically useful nor accurate signals due to the presence of said interfering constituents and background noise which greatly exceeds the signal related to the physiologic parameter being measured.

The most precise, accurate, and clinically useful way of evaluating thermal status of the body in humans and animals is by measuring brain temperature. Brain temperature measurement is the key and universal indicator of both disease and health equally, and is the only vital sign that cannot be artificially changed by emotional states. The other vital signs (heart rate, blood pressure, and respiratory rate) all can be influenced and artificially changed by emotional states or voluntary effort.

Body temperature is determined by the temperature of blood, which emits heat as far-infrared radiation. Adipose tissue (fat tissue) absorbs far-infrared and the body is virtually completely protected with a layer of adipose tissue adherent to the skin. Thus measurement of temperature using the skin did not achieve precision nor accuracy because previous techniques used sensors placed on skin characterized by the presence of adipose tissue.

Because it appeared to be impossible with current technology to non-invasively measure brain temperature, attempts were made to determine internal body temperature, also referred to as core temperature. An invasive, artificial, inconvenient, and costly process is currently used to measure internal (core) temperature consisting of inserting a catheter with a temperature sensor in the urinary canal, rectum or esophagus. But such methodology is not suitable for routine measurement, it is painful, and has potential fatal complications.

Semi-invasive techniques have also being tried. Abreu disclosed in U.S. Pat. No. 6,120,460 apparatus and methods for measuring core temperature continuously using a contact lens in the eyelid pocket, but the contact lens is a semi-invasive device which requires prescription by a physician and sometimes it is not easy to place the contact lens in the eye of an infant or even in adults and many people are afraid of touching their eyes.

There are several drawbacks and limitations in the prior art for continuous and/or core measurement of temperature.

Measurement of temperature today is non-continuous, non-core and nurse dependent. Nurses have to stick a thermometer in the patient's mouth, rectum or ear. To get core temperature nurses invasively place a tube inside the body which can cause infection and costly complications.

Measurement of core temperature on a routine basis in the hospital and/or continuously is very difficult and risky because it requires an invasive procedure with insertion of tubes inside the body or by ingesting a thermometer pill. The thermometer pill can cause diarrhea, measure temperature of the fluid/food ingested and not body temperature, and have fatal complications if the pill obstructs the pancreas or liver ducts. Placement of sensors on the skin do not provide clinically useful measurements because of the presence of many interfering constituents including fat tissue.

It is not possible to acquire precise and clinically useful measurements of not only brain temperature, but also metabolic parameters, physical parameters, chemical parameters, and the like by simply placing a sensor on the skin. One key element is the presence of fat tissue. Fat varies from person to person, fat varies with aging, fat content varies from time to time in the same person, fat attenuates a signal coming from a blood vessel, fat absorbs heat, fat prevents delivery of undisturbed far-infrared radiation, fat increases the distance traveled by the element being measured inside the body and an external sensor placed on the surface of the skin.

There is a need to identify a method and apparatus that can non-invasively, conveniently and continuously monitor brain temperature in a painless, simple, external and safe manner with sensors placed on the skin.

There is further a need to identify a method and apparatus that can conveniently, non-invasively, safely and precisely monitor biological parameters including metabolic parameters, physical parameters, chemical parameters, and the like.

There is a need to identify an apparatus and method capable of measuring biological parameters by positioning a sensor on a physiologic tunnel for the acquisition of undisturbed and continuous biological signals.

SUMMARY OF THE INVENTION

The present invention provides methods, apparatus and systems that effectively address the needs of the prior art.

In general, the invention provides a set of sensing systems and reporting means which may be used individually or in combination, which are designed to access a physiologic tunnel to measure biological, physical and chemical parameters. Anatomically and physiologically speaking, the tunnel discovered by the present invention is an anatomic path which conveys undisturbed physiologic signals to the exterior. The tunnel consists of a direct and undisturbed connection between the source of the function (signal) within the body and an external point at the end of the tunnel located on the skin. A physiologic tunnel conveys continuous and integral data on the physiology of the body. An undisturbed signal from within the body is delivered to an external point at the end of the tunnel. A sensor placed on the skin at the end of the tunnel allows optimal signal acquisition without interfering constituents and sources of error.

Included in the present invention are support structures for positioning a sensor on the skin at the end of the tunnel. The present invention discloses devices directed at measuring brain temperature, brain function, metabolic function, hydrodynamic function, hydration status, hemodynamic function, body chemistry and the like. The components include devices and methods for evaluating biological parameters using patches, clips, eyeglasses, head mounted gear and the like with sensing systems adapted to access physiologic tunnels to provide precise and clinically useful information about the physiologic status of the wearer and for enhancing the safety and performance of said wearer, and helping to enhance and preserve the life of said wearer by providing adequate reporting means and alert means relating to the biological parameter being monitored. Other components provide for producing direct or indirect actions, acting on another device, or adjusting another device or article of manufacture based on the biological parameter measured.

The search for a better way to measure biological parameters has resulted in long and careful research, which included the discovery of a Brain Temperature Tunnel (BTT) and other physiologic tunnels in humans and animals. The present invention was the first to recognize the physiologic tunnel in the body. The present invention was yet the first to recognize the end of the tunnel on the skin surface in which an optimal signal is acquired and measurements can be done without the presence of interfering constituents and background noise that exceeds the signal being measured. The present invention was also the first to recognize and precisely map the special geometry and location of the tunnel including the main entry point. The present invention was yet first to recognize the precise positioning of sensing systems at the main entry point for optimal signal acquisition. Careful studies have been undertaken including software development for characterizing infrared radiation to precisely determine the different aspects of the tunnel. This research has determined that the measurement of brain (core) temperature and other body parameters can be accomplished in a non-invasive and continuous manner in humans and animals with sensors positioned in a confined area of the skin at the end of a physiologic tunnel.

The key function and critical factor for life preservation and human performance is brain temperature. Brain tissue is the tissue in the body most susceptible to thermal damage, by both high and low temperature. Brain temperature is the most clinically relevant parameter to determine the thermal status of the body and the human brain is responsible for 18 to 20% of the heat produced in the body, which is an extraordinary fact considering that the brain represents only 2% of the body weight. The great amount of thermal energy generated in the brain is kept in a confined space and the scalp, skull, fat and CSF (cerebral spinal fluid) form an insulating layer. The recognition of the BTT by the present invention bypasses the insulating barriers and provides a direct connection to inside the brain physiology and physics.

Anatomically and physiologically speaking, a Brain Temperature Tunnel consists of a continuous, direct, and undisturbed connection between the heat source within the brain and an external point at the end of the tunnel. The physical and physiological events at one end of the tunnel inside the brain are reproduced at the opposite end on the skin. A BTT enables the integral and direct heat transfer through the tunnel without interference by heat absorbing elements, i.e., elements that can absorb far-infrared radiation transmitted as heat by blood within the brain. There are six characteristics needed to define a BTT. These characteristics are:

1) area without heat absorbing elements, i.e., the area must not contain adipose tissue (fat tissue). This is a key and needed characteristic for defining a temperature tunnel,
2) area must have a terminal branch of a vessel in order to deliver the integral amount of heat,
3) terminal branch has to be a direct branch of a blood vessel from the brain,
4) terminal branch has to be superficially located to avoid heat absorption by deep structures such as muscles,
5) area must have a thin and negligible interface between a sensor and the source of thermal energy to achieve high heat flow, and
6) area must not have thermoregulatory arteriovenous shunts.

All six characteristics are present on the skin on the medial canthal area adjacent to the medial corner of the eye above the medial canthal tendon and in the medial third of the upper eyelid. In more detail the end of BTT area on the skin measures about 11 mm in diameter measured from the medial corner of the eye at the medial canthal tendon and extends superiorly for about 6 mm and then extends into the upper eyelid in a horn like projection for another 22 mm.

The BTT area is the only area in the body without adipose tissue, which is in addition supplied by a terminal branch, which has a superficial blood vessel coming from the brain vasculature, and which has a thin interface and no thermoregulatory shunts. The BTT area is supplied by a terminal branch of the superior ophthalmic vein which is a direct connection to the cavernous sinus, said cavernous sinus being an endothelium-lined system of venous channels inside the brain which collects and stores thermal energy. The blood vessel supplying the BTT area is void of thermoregulatory arteriovenous shunts and it ends on the skin adjacent to the medial corner of the eye and in the superior aspect of the medial canthal area right at the beginning of the upper eyelid. The blood vessels deliver undisturbed heat to the skin on the medial canthal area and upper eyelid as can be seen in the color as well as black and white photos of infrared images.

The undisturbed thermal radiation from the brain is delivered to the surface of the skin at the end of the tunnel. The heat is delivered to an area of skin without fat located at the end of the tunnel. The blood vessel delivering heat is located just below the skin and thus there is no absorption of infrared radiation by deep structures.

If the blood vessel is located deep, other tissues and chemical substances would absorb the heat, and that can invalidate the clinical usefulness of the measurement. There is direct heat transfer and the skin in the BTT area is the thinnest skin in the body and is void of thermoregulatory arteriovenous shunts. A very important aspect for optimal measurement of temperature is no interference by fat tissue and direct heat transfer.

The absence of fat tissue in this particular and unique area in the body at the end of the tunnel allows the undisturbed acquisition of the signal. The combination of those six elements allows the undisturbed and integral emission of infrared radiation from the brain in the form of direct heat transfer at the BTT area location, which can be seen in the infrared image photographs.

The BTT and physiologic tunnels are also referred in this description as the "Target Area".

From a physical standpoint, the BTT is the equivalent of a Brain Thermal Energy tunnel with high total radiant power and high heat flow. The temperature of the brain is determined by the balance between thermal energy produced due to metabolic rate plus the thermal energy delivered by the arterial supply to the brain minus the heat that is removed by cerebral blood flow. Convection of heat between tissue and capillaries is high and the temperature of the cerebral venous blood is in equilibrium with cerebral tissue. Accordingly, parenchymal temperature and thermal energy of the brain can be evaluated by measuring the temperature and thermal energy of the cerebral venous blood. The superior ophthalmic vein has a direct and undisturbed connection to the cavernous sinus and carries cerebral venous blood with a thermal energy capacity of 3.6 $J \cdot ml^{-1} \cdot (° C.)^{-1}$ at hematocrit of 45%. Cerebral thermodynamic response, thermal energy, and brain temperature can be evaluated by placing a sensor to capture thermal energy conveyed by the cerebral venous blood at the end of the BTT.

The research concerning BTT and physiologic tunnels involved various activities and studies including: 1) In-vitro histologic analysis of mucosal and superficial body areas; 2) In-vivo studies with temperature evaluation of external areas in humans and animals; 3) In-vivo functional angiographic evaluation of heat source; 4) Morphologic studies of the histomorphometric features of the BTT area; 5) In-vivo evaluation of temperature in the BTT area using: thermocouples, thermistors, and far-infrared; 6) Comparison of the BTT area measurements with the internal eye anatomy and current standard most used (oral) for temperature measurement; 7) Cold and heat challenge to determine temperature stability of BTT; and 8) Infrared imaging and isotherm determination. Software for evaluating geometry of tunnel was also developed and used. Simultaneous measurement of a reference temperature and temperature in the BTT area were done using pre-equally calibrated thermistors. A specific circuit with multiple channels was designed for the experiments and data collection.

The measurement of temperature in the BTT area showed almost identical temperature signal between the BTT area and the internal conjunctival anatomy of the eye, which is a continuation of the central nervous system. Measurement of the temperature in the internal conjunctival anatomy of eye as used in the experiment was described by Abreu in U.S. Pat. Nos. 6,120,460 and 6,312,393. The averaged temperature levels for BTT and internal eye were within 0.1° C. (0.18° F.) with an average normothermia value equivalent of 37.1° C. (98.8° F.) for the BTT and 37° C. (98.6° F.) for the internal eye. Comparison with the standard most used, oral temperature, was also performed. The temperature voltage signal of the BTT area showed an average higher temperature level in the BTT area of an equivalent of 0.3° C. (0.5° F.) when compared to oral.

Subjects underwent cold challenge and heat challenge through exercising and heat room. The lowering and rising of temperature in the BTT area was proportional to the lowering and rising in the oral cavity. However, the rate of temperature change was faster in the BTT area than for oral by about 1.2 minutes, and temperature at the BTT site was 0.5° C. (0.9° F.) higher on few occasions. Subjects of different race, gender, and age were evaluated to determine the precise location of the BTT area across a different population and identify any anatomic variation. The location of the BTT was present at the same location in all subjects with no significant anatomic variation, which can be seen in a sample of infrared imaging of different subjects.

The tunnel is located in a crowded anatomic area and thus the positioning of the sensor requires special geometry for optimal alignment with the end of the tunnel. The clinical usefulness of the tunnel can only be achieved with the special positioning of the sensor in relation to anatomic landmarks and the support structure. The tunnel is located in a unique position with distinctive anatomic landmarks that help define the external geometry and location of the end of the tunnel. The main entry point of the tunnel, which is the preferred location for positioning the sensor, requires the sensor to be preferably placed in the outer edge of a support structure. The preferred embodiment for the measurement of biological parameters by accessing a physiologic tunnel includes sensors positioned in a particular geometric position on the support structure.

The support structure includes patches containing sensors. For the purpose of the description any structure containing an adhesive as means to secure said structure to the skin at the end of the tunnel is referred to as a patch including strips with adhesive surfaces such as a "BAND-AID" adhesive bandage. It is understood that a variety of attachment means can be used including adhesives, designs incorporating spring tension pressure attachment, and designs based on other attachment methods such as elastic, rubber, jelly-pads and the like.

The patches are adapted to position sensors at the end of the tunnel for optimal acquisition of the signal. The patch is preferably secured to the area by having an adhesive backing which lays against the skin, although a combination of adhesive and other means for creating a stable apposition of the sensor to the tunnel can be used such as fastening or pressure.

Support structures also include clips or structures that are positioned at the end of the tunnel with or without adhesive and which are secured to the area by pressure means. Any structure that uses pressure means to secure said structure to the skin at the end of the tunnel is referred as a clip.

Head-mounted structures are structures mounted on the head or neck for positioning sensors on the end of the tunnel and include head bands with accessories that are adjacent to the tunnel, visors, helmets, headphone, structures wrapping around the ear and the like. For the purpose of this description TempAlert is referred herein as a system that measures temperature in the BTT area and has means to report the measured value and that can incorporate alarm devices that are activated when certain levels are reached. Support structures yet include any article that has sensing devices in which said sensing devices are positioned at the end of the tunnel.

Support structures further include medial canthal pieces of eyeglasses. A medial canthal piece is also referred to herein as a medial canthal pad and includes a pad or a piece which positions sensing devices on the skin at the medial canthal area on top of a tunnel, with said medial canthal piece being permanently attached to or mounted to an eyeglass. Any sensing devices incorporated in an eyeglass (fixed or removable) for accessing a tunnel are referred to herein as EyEXT including devices for sensing physical and chemical parameters. Any article of manufacture that has visual function, or ocular protection, or face protection with a part in contact with the tunnel is referred herein as eyeglasses and includes conventional eyeglasses, prescription eyeglasses, reading glasses, sunglasses, goggles of any type, masks (including gas masks, surgical masks, cloth masks, diving masks, eyemask for sleeping and the like) safety glasses, and the like.

For brain temperature evaluation the tunnel area consists of the medial canthal area and the superior aspect of the medial corner of the eye. For brain function evaluation the tunnel area consists of primarily the upper eyelid area. For metabolic function evaluation the tunnel area consists of an area adjacent to the medial corner of the eye and both the upper and lower eyelids.

The measurement of metabolic function, brain function, immunogenic function, physical parameters, physicochemical parameters and the like includes a variety of support structures with sensors accessing the physiologic tunnels. The sensors are placed in apposition to the skin immediately adjacent to the medial corner of the eye preferably in the superior aspect of the medial canthal area. The sensor can also be positioned in the medial third of the upper eyelid. The sensor is most preferably located at the main entry point of the tunnel which is located on the skin 2.5 mm medial to the corner of the eye and about 3 mm above the medial corner of the eye. The diameter of the main entry point is about 6 to 7 mm. The positioning of the sensor at the main entry point of the tunnel provides the optimum site for measuring physical and chemical parameters of the body.

Besides a sensor that makes contact with the skin at the Target Area, it is understood that sensors which do not make contact with the skin can be equally used. For instance an infrared-based temperature measuring system can be used. The measurement is based on the Stefan-Boltzman law of physics in which the total radiation is proportional to the fourth power of the absolute temperature, and the Wien Displacement law in which the product of the peak wavelength and the temperature are constant. The field of view of the non-contact infrared apparatus of the invention is adapted to match the size and geometry of the BTT area on the skin.

A variety of lenses known in the art can be used for achieving the field of view needed for the application. For example, but not by way of limitation, a thermopile can be adapted and positioned in a manner to have a field of view aimed at the main entry point of the BTT area on the skin. The signal is then amplified, converted into a voltage output and digitized by a MCU (microcontroller).

This infrared-based system can be integrated into a support structure that is in contact with the body such as any of the support structures of the present invention. In addition, it is understood that the infrared-based system of the present invention can be integrated as a portable or hand-held unit completely disconnected from the body. The apparatus of the present invention can be held by an operator that aims said apparatus at the BTT area to perform the measurement. The apparatus further includes an extension shaped to be comfortably positioned at the BTT site for measuring biological parameters without discomfort to the subject. The extension in contact with the skin at the BTT is shaped in accordance with the anatomic landmarks and the geometry and size of the BTT site. The infrared radiation sensor is positioned in the extension in contact with the skin for receiving radiation emitted from the BTT site.

The present invention provides a method for measuring biological parameters including the steps of positioning a sensing device means on the skin area at the end of a tunnel, producing a signal corresponding to the biological parameter measured and reporting the value of the parameter measured.

It is also includes a method to measure biological parameters by non-contact infrared thermometry comprising the steps of positioning an infrared detector at the BTT site with a field of view that encompasses the BTT site and producing a signal corresponding to the measured infrared radiation. The biological parameters include temperature, blood chemistry, metabolic function and the like.

Temperature and ability to do chemical analysis of blood components is proportional to blood perfusion. The present invention recognizes that the tunnel area, herein also referred as a Target Area, has the highest superficial blood perfusion in the head and has a direct communication with the brain, and that the blood vessels are direct branches of the cerebral vasculature and void of thermoregulatory arteriovenous shunts. It was also recognized that the Target Area has the highest temperature in the surface of the body as can be seen in the photographs of experiments measuring infrared emission from the body and the eye.

The Target Area discovered not only has the thinnest and most homogeneous skin in the whole body but is the only skin area without a fat layer. Since fat absorbs significant amounts of radiation, there is a significant reduction of signal. Furthermore other skin areas only provide imprecise and inaccurate signals because of the large variation of adipose tissue from person to person and also great variability of fat tissue according to age. This interference by a fat layer does not occur in the Target Area. Furthermore, the combined characteristics of the Target Area, contrary to the skin in the rest of the body, enable the acquisition of accurate signals and a good signal to noise ratio which far exceeds background noise. In addition, body temperature such as is found in the surface of the skin in other parts of the body is variable according to the environment.

Another important discovery of the present invention was the demonstration that the Target Area is not affected by changes in the environment (experiments included cold and heat challenge). The Target Area provides an optimum location for temperature measurement which has a stable temperature and which is resistant to ambient conditions. The Target Area discovered has a direct connection to the brain, is not affected by the environment and provides a natural, complete thermal seal and stable core temperature. The apparatus and methods of the present invention achieve precision and clinical usefulness needed with the non-invasive placement of a temperature sensor on the skin in direct contact with the heat source from the brain without the interference of heat absorbing elements.

The Target Area is extremely vascularized and is the only skin area in which a direct branch of the cerebral vasculature is superficially located and covered by a thin skin without a fat layer. The main trunk of the terminal branch of the ophthalmic vein is located right at the BTT area and just above the medial canthal tendon supplied by the medial palpebral artery and medial orbital vein. The BTT area on the skin supplied by a terminal and superficial blood vessel ending in a particular area without fat and void of thermoregulatory arteriovenous shunts provides a superficial source of undisturbed biological signals including brain temperature, metabolic function, physical signals, and body chemistry such as glucose level, and the like.

Infrared spectroscopy is a technique based on the absorption of infrared radiation by substances with the identification of said substances according to its unique molecular oscillatory pattern depicted as specific resonance absorption peaks in the infrared region of the electromagnetic spectrum. Each chemical substance absorbs infrared radiation in a unique manner and has its own unique absorption spectra depending on its atomic and molecular arrangement and vibrational and rotational oscillatory pattern. This unique absorption spectra allows each chemical substance to basically have its own infrared spectrum, also referred to as fingerprint or signature which can be used to identify each of such substances. Radiation containing various infrared wavelengths is emitted at the substance to be measured and the amount of absorption of radiation is dependent upon the concentration of said chemical substance being measured according to Beer-Lambert's Law.

Interfering constituents and variables such as fat, bone, muscle, ligaments and cartilage introduce significant source of errors which are particularly critical since the background noise greatly exceeds the signal of the substance of interest. Since those interfering constituents are not present on the skin at the BTT area, the sensing systems positioned at said BTT area can acquire optimal signal with minimal noise including spectroscopic-based measurements.

Spectroscopic devices integrated into support structures disclosed in the present invention can precisely non-invasively measure blood components since the main sources of variation and error, such as fat tissue, are not present in the Target Area. In addition, other key constituents which interfere with electromagnetic energy emission such as muscle, cartilage and bones, are not present in the Target Area either. The blood vessels delivering the infrared radiation are superficially located and the infrared radiation is delivered at the end of the tunnel without interacting with other structures. The only structure to be traversed by the infrared radiation is a very thin skin, which does not absorb the infrared wavelength. The present invention includes infrared spectroscopy means to provide a clinically useful measurement with the precise and accurate determination of the concentration of the blood components at the end of the tunnel.

In addition to spectroscopy in which electromagnetic energy is delivered to the Target Area, the present invention also discloses apparatus and methods for measuring substances of interest through far infrared thermal emission from the Target Area. Yet, besides near-infrared spectroscopy and thermal emission, other devices are disclosed for measurement of substances of interest at the Target Area including electroosmosis as a flux enhancement by iontophoresis or reverse iontophoresis with increased passage of fluid through the skin through application of electrical energy. Yet, transcutaneous optical devices can also be integrated into support structures including medial canthal pieces, modified nose pads, and the frame of eyeglasses, with said devices positioned to access the tunnel.

It is understood that application of current, ultrasonic waves as well as chemical enhancers of flow, electroporation and other devices can be used to increase permeation at the tunnel site such as for example increased flow of glucose with the use of alkali salts. In addition creating micro holes in the target area with a laser, or other means that penetrate the skin can be done with the subsequent placement of sensing devices on the BTT site, with said devices capable of measuring chemical compounds. Furthermore, reservoirs mounted on or disposed within support structures, such as the frame and pads of eyeglasses, can deliver substances transdermally at the BTT site by various devices including iontophoresis, sonophoresis, electrocompression, electroporation, chemical or physical permeation enhancers, hydrostatic pressure and the like.

In addition to measure the actual amount of oxygen in blood, the present invention also discloses devices to measure oxygen saturation and the amount of oxygenated hemoglobin. In this embodiment the medial canthal piece of a support structure or the modified nose pads of eyeglasses contain LEDs emitting at two wave lengths around 940 and 660 nanometers. As the blood oxygenation changes, the ratio of the light transmitted by the two frequencies changes indicating the oxygen saturation. Since the blood level is measured at the end of a physiologic brain tunnel, the amount of oxygenated hemoglobin in the arterial blood of the brain is measured, which is the most valuable and key parameter for athletic purposes and health monitoring.

The present invention also provides a method for measuring biological parameters with said method including the steps of directing electromagnetic radiation at the BTT area on the skin, producing a signal corresponding to the resulting radiation and converting the signal into a value of the biological parameter measured.

Besides using passive radio transmission or communication by cable; active radio transmission with active transmitters containing a microminiature battery mounted in the support structure can also be used. Passive transmitters act from energy supplied to it from an external source. The transensor transmits signals to remote locations using different frequencies indicative of the levels of biological parameters. Ultrasonic micro-circuits can also be mounted in the support structure and modulated by sensors which are capable of detecting chemical and physical changes at the Target Area. The signal may be transmitted using modulated sound signals particularly under water because sound is less attenuated by water than are radio waves.

One preferred embodiment comprises a support structure including a patch adapted to be worn on or attached with adhesives to the tunnel and includes structural support, a sensor for measuring biological parameters, power source, microcontroller and transmitter. The parts can be incorporated into one system or work as individual units. The sensor is located preferably within 7 mm from the outer edge of the patch. The apparatus of the invention can include a temperature sensor located in the outer edge of the patch for sensing temperature. The transmitter, power source and other components can be of any size and can be placed in any part of the patch or can be connected to the patch as long as the sensing part is placed on the edge of the patch in accordance with the principles of the invention. The sensor in the patch is positioned on the skin adjacent to the medial canthal area (medial corner of the eye) and located about 2 mm from the medial canthal tendon. The sensor can preferably include electrically-based sensors, but non-electrical systems can be used such as chemicals that respond to changes in temperature including mylar.

Besides patches, another preferred embodiment for measuring biological parameters at the physiologic tunnel includes a medial canthal pad. The medial canthal piece is a specialized structure containing sensors for accessing the tunnel and adapted to be worn on or attached to eyeglasses in apposition to the tunnel and includes structural support, a sensor for measuring biological parameters, power source, microcontroller and transmitter. The parts can be incorporated into one system or work as individual units. The sensors are positioned on the BTT area. The transmitter, power source, and other components can be placed in the medial canthal pad or in any part of the eyeglasses. A medial canthal piece or extension of nose pads of eyeglasses allow accessing the physiologic tunnel with sensing devices laying in apposition to the BTT area.

The apparatus of the invention include a temperature sensor located in the medial canthal pad. For temperature measurement the sensing system is located on a skin area that includes the medial canthal corner of the eye and upper eyelid. The sensor in the medial canthal pad is preferably positioned on the skin adjacent to the medial canthal area (medial corner of the eye). Although one of the preferred embodiments for measurement of brain temperature consists of medial canthal pads, it is understood that also included in the scope of the invention are nose pads of a geometry and size that reach the tunnel and that are equipped with temperature sensors preferably in the outer edge of said nose pads for measuring brain temperature and other functions. An oversized and modified nose pad containing sensors using a special geometry for adequate positioning at the BTT area is also included in the invention.

With the disclosure of the present invention and by using anatomic landmarks in accordance with the invention the sensor can be precisely positioned on the skin at the end of the tunnel. However, since there is no external visible indication on the skin relating to the size or geometry of the tunnel, accessory means can be used to visualize, map or measure the end of the tunnel on the skin. These accessory means may be particularly useful for fitting medial canthal pads or modified nose pads of eyeglasses.

Accordingly, an infrared detector using thermocouple or thermopiles can be used as an accessory for identifying the point of maximum thermal emission and to map the area. An infrared imaging system or thermography system may be preferably used. In this instance, an optical store selling the eyeglasses can have a thermal imaging system. The optician, technician and the like take an infrared image picture or film the area, and in real time localize the tunnel of the particular user. The medial canthal pads or modified nose pads can then be adjusted to fit the particular user based on the thermal infrared imaging. The eyeglasses are fitted based on the thermal image created. This will allow customized fitting according to the individual needs of the user. Any thermography-based system can be used including some with great visual impact and resolution as a tri-dimensional color thermal wave imaging.

It is also a feature of the invention to provide a method to be used for example in optical stores for locating the tunnel including the steps of measuring thermal infrared emission, producing an image based on the infrared emission, and detecting the area with the highest amount of infrared emission. Another step that can be included is adjusting sensors in support structures to match the area of highest infrared emission.

One of said support structures includes the medial canthal pieces or nose pads of eyeglasses. The thermal imaging method can be used for fitting a patch, but said patch can be positioned at the tunnel by having an external indicator for lining up said indicator with a permanent anatomic landmark such as the medial corner of the eye. Although medial canthal pieces of eyeglasses can have an external indicator for precise positioning, since opticians are used to fit eyeglasses according to the anatomy of the user, the thermal imaging method can be a better fit for eyeglasses than an external indicator on the medial canthal pieces or modified nose pads of eyeglasses.

BRIEF DESCRIPTION OF THE DRAWINGS

FIG. 1M illustrates a cloverleaf shaped adhesive patch embodiment.

FIG. 1M(1) illustrates a rear view of an adhesive patch.

FIG. 1N illustrates the details of a light emitter-detector pair.

FIG. 1P illustrates an alternate embodiment of a sensor assembly.

FIG. 1P(1) diagrammatically illustrates the noncontact measurement of the brain tunnel.

FIG. 1P(2) schematically illustrates a light source directing radiation at the brain tunnel and measurement of reflected radiation.

FIG. 1P(3) diagrammatically illustrates a handheld sensing device for noncontact measurement at the brain tunnel.

FIG. 1P(4) illustrates a noncontact measurement at the brain tunnel.

FIG. 1P(5) illustrates a sensing device and a sensor mounted on a web-camera for measurement of radiation from the brain tunnel.

FIG. 1Q is a sectional view of a sensing device shown in detail.

FIG. 1Q(1) is a perspective diagrammatic view of a measuring portion of a sensor assembly.

FIG. 1R illustrates a perspective view of a sensing device mounted on a support structure.

FIG. 1R(1) illustrates a sensing device worn by a user.

FIG. 1R(2) illustrates a sensing device having a swivel mechanism at the junction of an arm and a body.

FIG. 1R(3) illustrates the swivel assembly of a sensing device and support structure worn by a user.

FIG. 1S(1) is a side view of a sensing device having a straight extending wire.

FIG. 1S(2) shows a sensing device worn by a user with an arm bent into position.

FIG. 1T(1) illustrates a sensing device including an arm, measuring portion and plate.

FIG. 1T(2) shows a sensing device and support structure formed of separable pieces.

FIG. 1T(3) shows an alternate embodiment of a sensing device and support structure with different separable pieces from FIG. 1T(2).

FIG. 2A illustrates the advantageous use of a small heating element.

FIG. 2B illustrates a convex sensing surface for a sensing system.

FIG. 2C illustrates a specialized two-plane surface including a convex surface and a flat central surface.

FIG. 4 is a diagrammatic perspective view of a sensor assembly measuring portion mounted on a support structure.

FIG. 10B-2 is an enlarged view of an alert device worn by a user.

FIG. 10C-1 schematically illustrates an algorithm for heart monitoring.

FIG. 10C-2 schematically illustrates an algorithm for body temperature monitoring.

FIG. 11 illustrates an apparatus for measuring biological parameters.

FIG. 11A illustrates a known contact sensing tip of a rod.

FIG. 11B illustrates a specialized temperature measuring device of the present invention.

FIG. 11C is a schematic perspective view of the tip of the rod.

FIG. 11D illustrates an alternate embodiment of a rod having a sensor.

FIG. 11E is a known thermometer.

FIG. 11F illustrates a sensor housed in an end of a stylus.

FIG. 11-G1 illustrates a glucose sensing device.

FIG. 11-G2 illustrates a specialized cap of a sensing device.

FIG. 11Q-1 is a planar view of a rod-like sensing device.

FIG. 11Q-2 is a side view of the rod-like structure.

FIG. 11Q-3 illustrates a pair of light emitter-light detector sensors at the end of the rod.

FIG. 11Q-4 illustrates a projecting light emitter-light detector pair.

FIG. 11R-1 illustrates a spring based measuring portion of a sensing rod.

FIG. 11R-2 is a planar view of the spring based measuring portion.

FIG. 11S-1 illustrates a measuring portion having a convex cap.

FIG. 11S-2 illustrates a measuring portion and a sensor arrangement.

FIG. 11S-3 illustrates a flat cap measuring portion.

FIG. 11S-4 illustrates a solid metal cap sensing portion.

FIG. 11T-1 illustrates a sensor arrangement.

FIG. 11T-2 illustrates a detailed view of a wire portion pressing on a spring in the measuring portion.

FIG. 11V-1 illustrates a handheld device for measuring biological parameters.

FIG. 11V-2 is an alternate perspective view of the handheld device

FIG. 11V-3 illustrates a handheld probe including a sensing tip.

FIG. 11V-4 illustrates a handheld probe including a barrier to infrared light.

FIG. 11V-5 illustrates a J-shape configuration of the probe.

FIG. 12K-1 illustrates a wire adjacent to a support structure of a sensing assembly.

FIG. 12K-2 illustrates the manufacturing step of attaching a wire to the support structure.

FIG. 12M-1 illustrates a perforated plate for receiving a measuring portion of a measuring assembly.

FIG. 12M-2 illustrates a measuring portion of a sensing assembly.

FIG. 14F illustrates a tension bar in a rest position.

FIG. 14G is a side view of the sensing device shown in FIG. 14F.

FIG. 14H is a side view of the tension bar in an open position.

FIG. 14J illustrates a sensing device to be secured to the frame of eyeglasses.

FIG. 14K illustrates a sensing device mounted on a pair of eyeglasses.

FIG. 14L illustrates a sensing device clipped to a pair of eyeglasses.

FIG. 14M illustrates a sensing device secured to the frame of a pair of eyeglasses.

FIG. 14N-1 is a side view of a sensing device.

FIG. 14N-2 is a front view of the sensing clip device of FIG. 14N-1.

FIG. 14N-3 illustrates the mounting of the sensing clip device on a pair of eyeglasses.

FIG. 14P is a front view of a dual sensing clip and its interaction with a plurality of devices.

FIG. 15A illustrates a headband receiving a housing removably attached to the headband.

FIG. 15B illustrates a detailed view of a brain temperature tunnel temperature module.

Figure 15A:
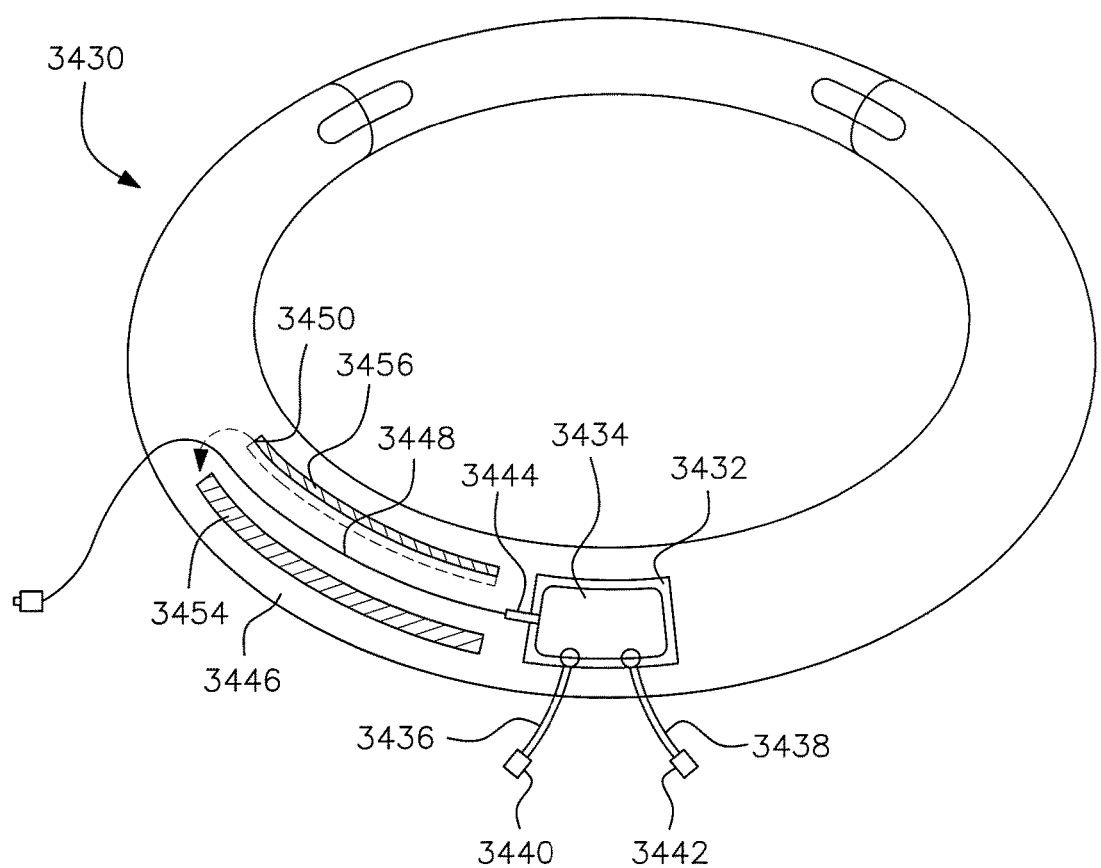
Figure 15C:
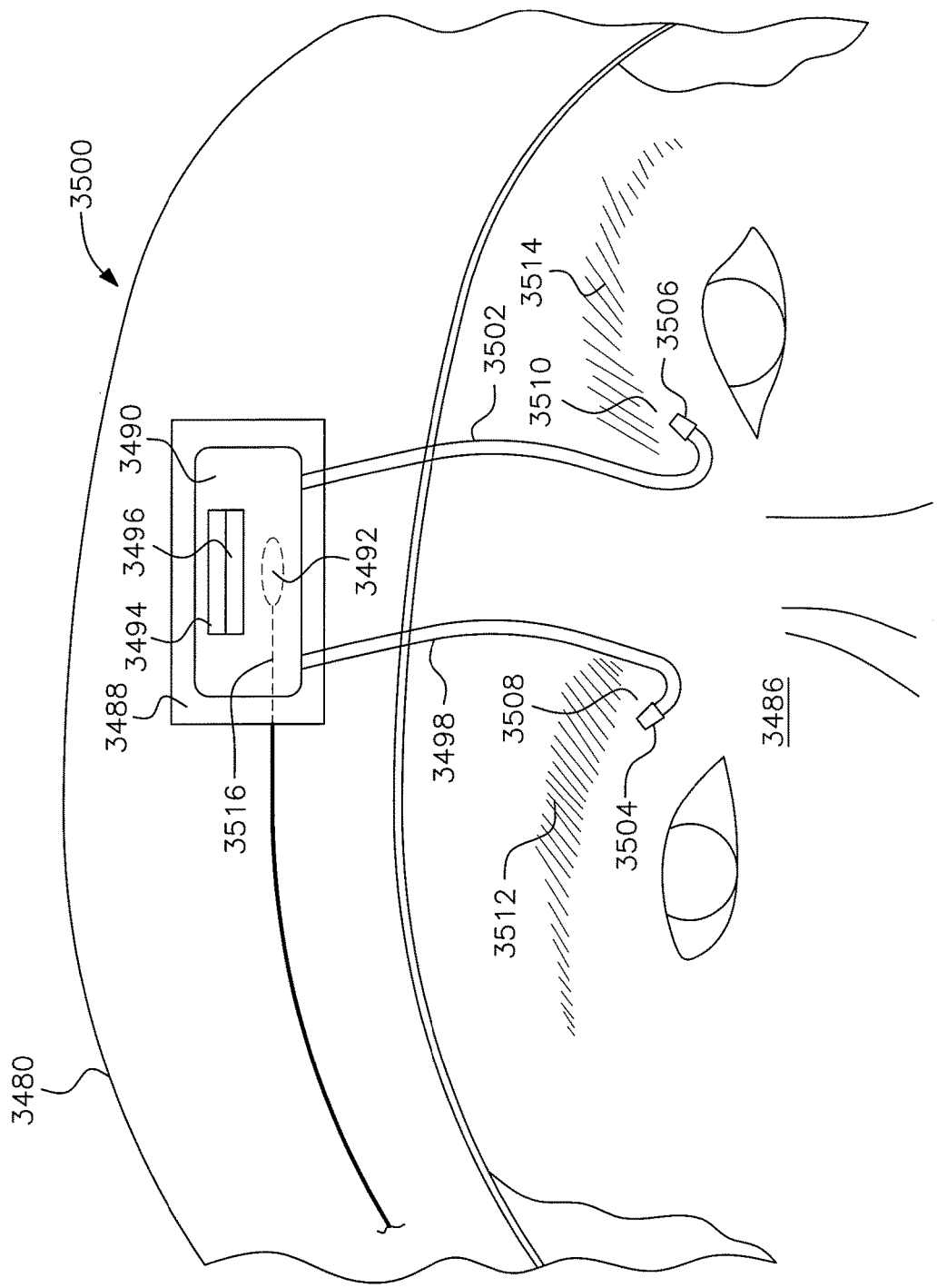

FIG. 15C illustrates the wearing of a sensing modular headband.

Figure 15D:
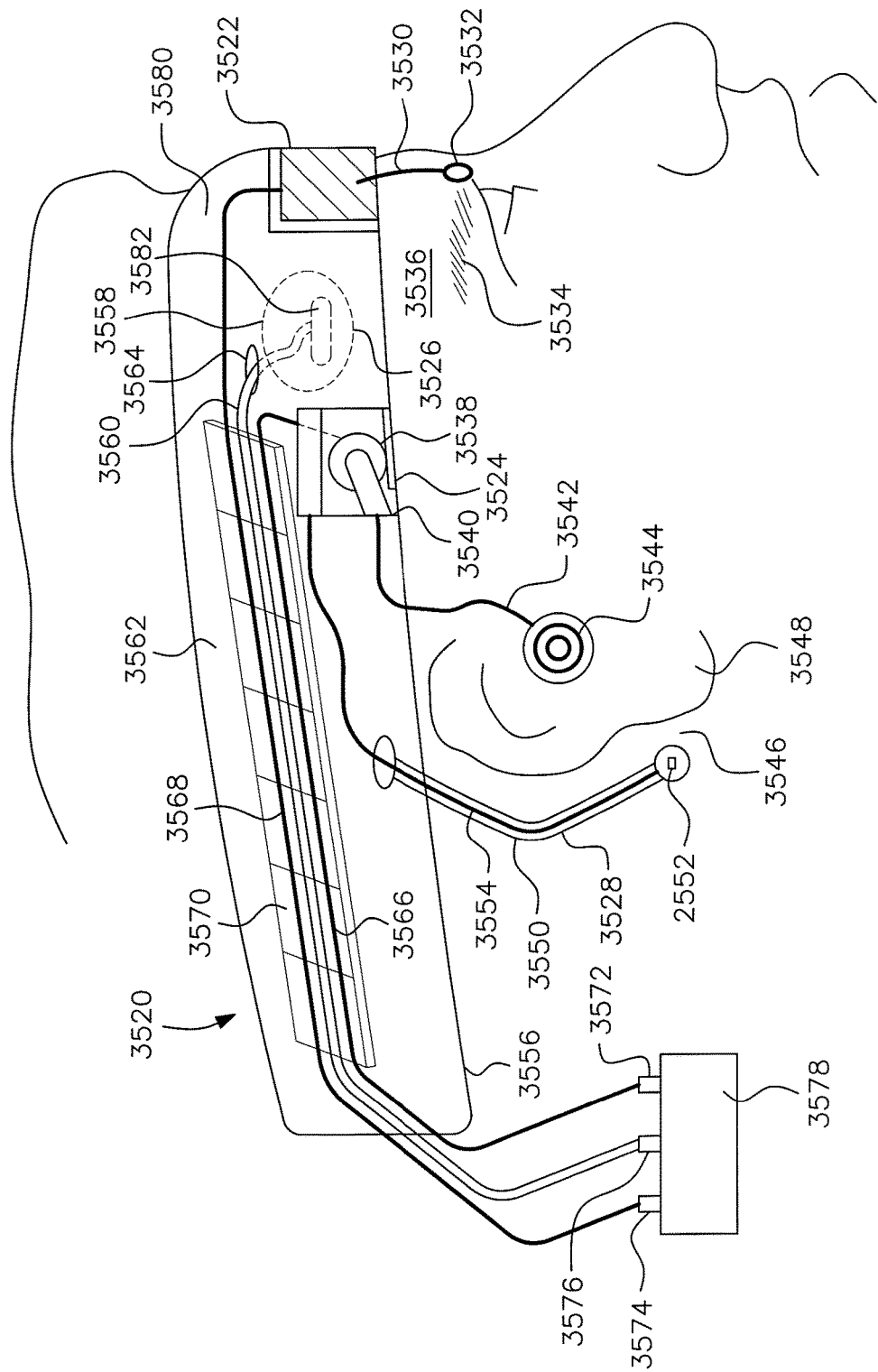

FIG. 15D illustrates an alternate embodiment of a sensing modular headband.

Figure 15E:
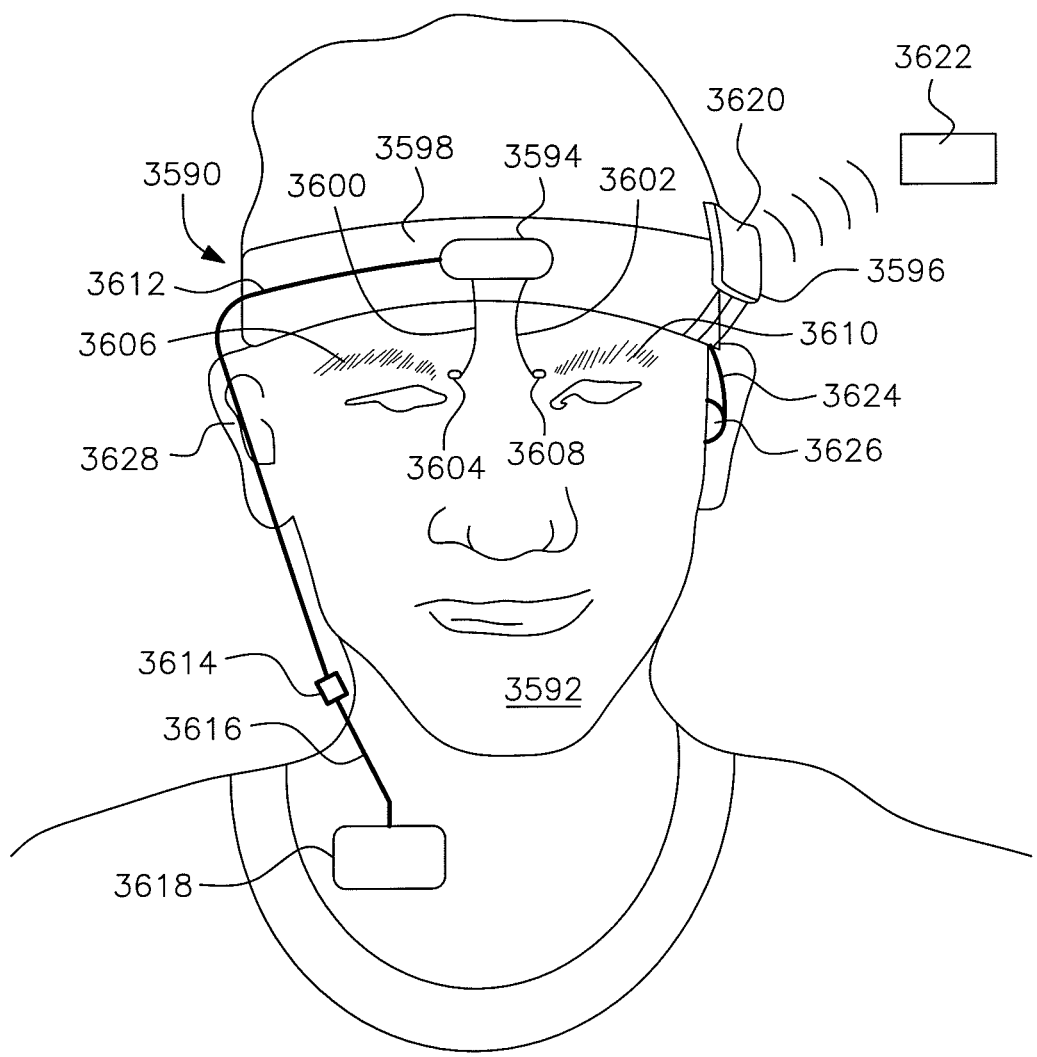

FIG. 15E illustrates another embodiment of a sensing modular headband.

Figure 15F:
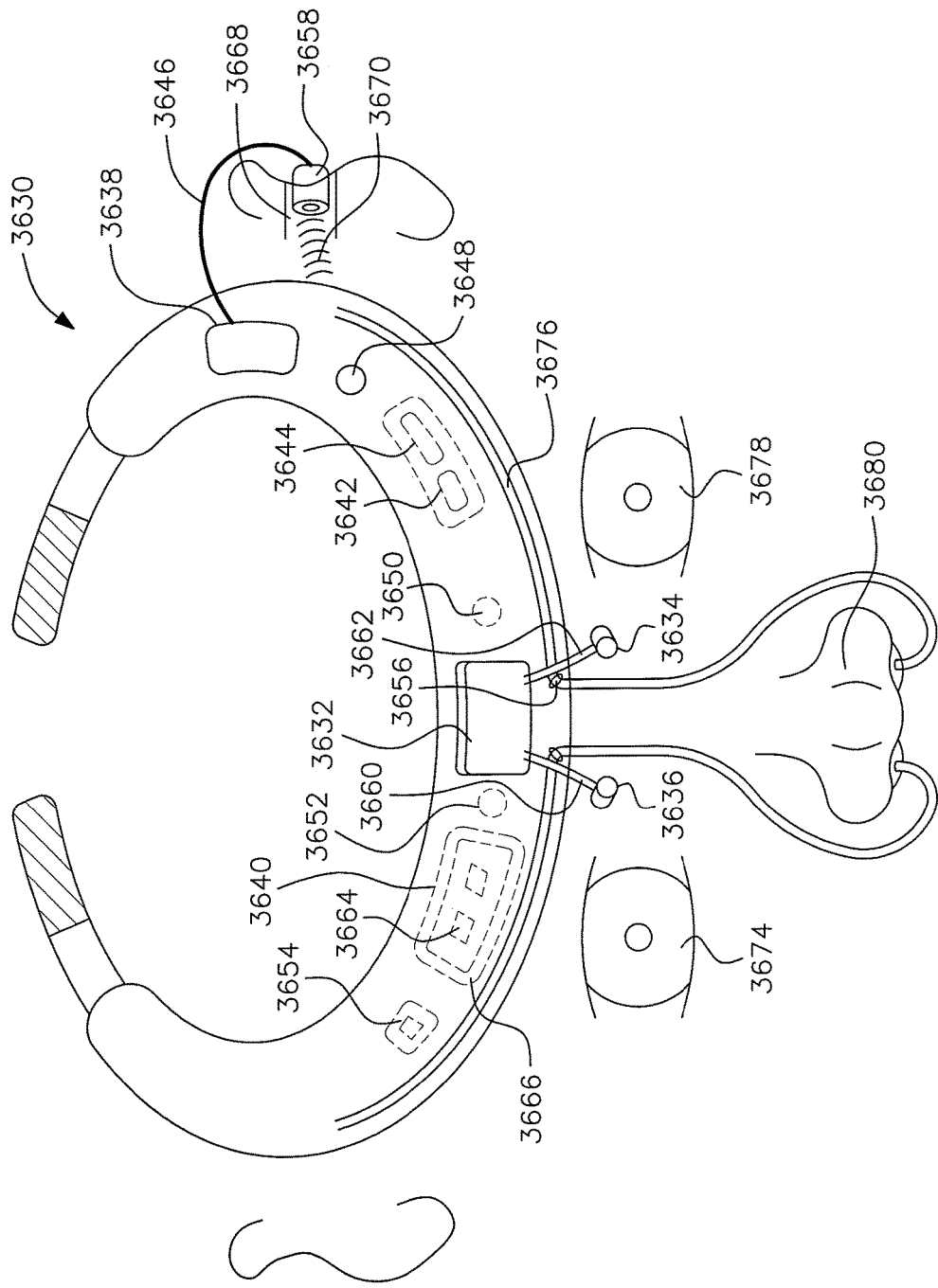

FIG. 15F illustrates a sensing modular headband having eight biologic parameter modules.

FIG. 15G is a sectional view of a sensing modular headband.

FIG. 15H is a planar view of a sensing modular headband.

Figure 15J:
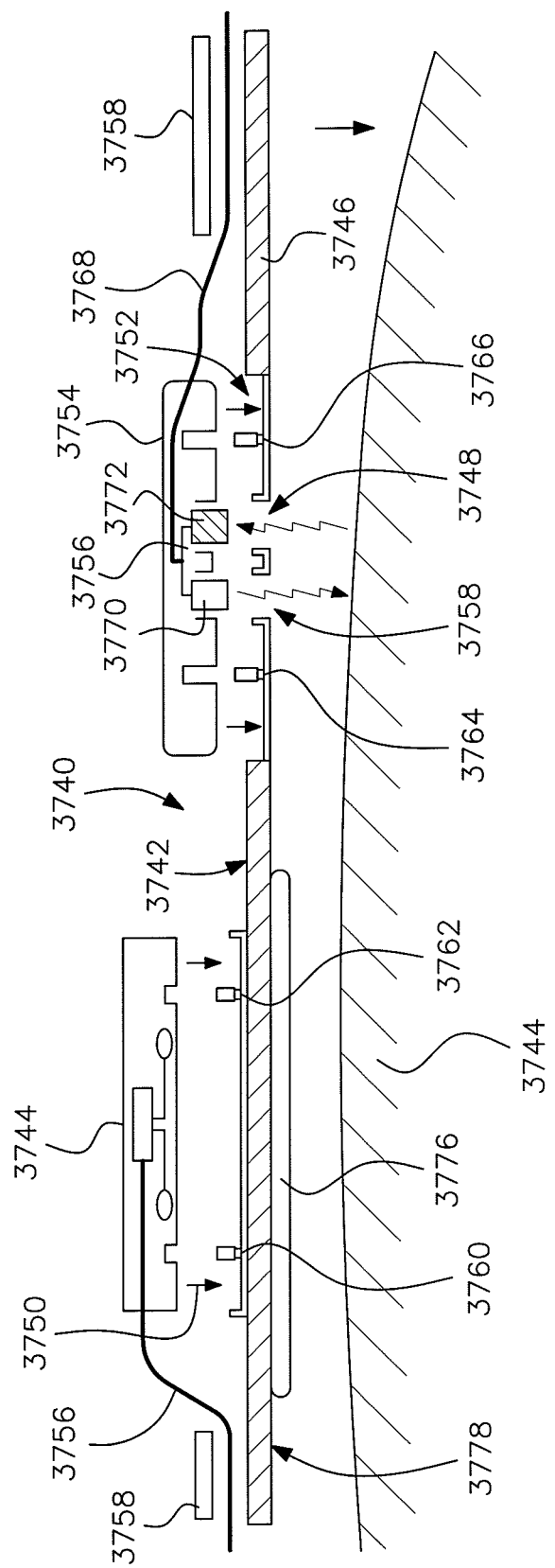

FIG. 15J illustrates the disposition of modules on an external surface of a sensing modular headband.

FIG. 15K is an external view of a sensing modular headband.

FIG. 15L illustrates an adhesive surface of an internal area of a sensing modular headband.

Figure 15M:
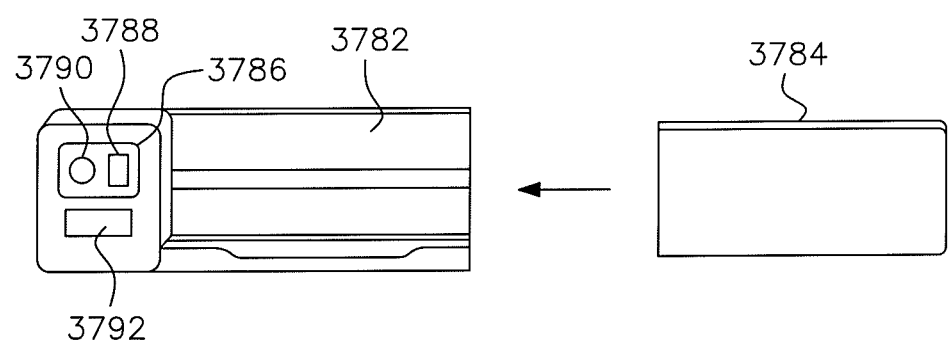

FIG. 15M illustrates a cavity for receiving a module in a sensing modular headband.

Figure 15N:
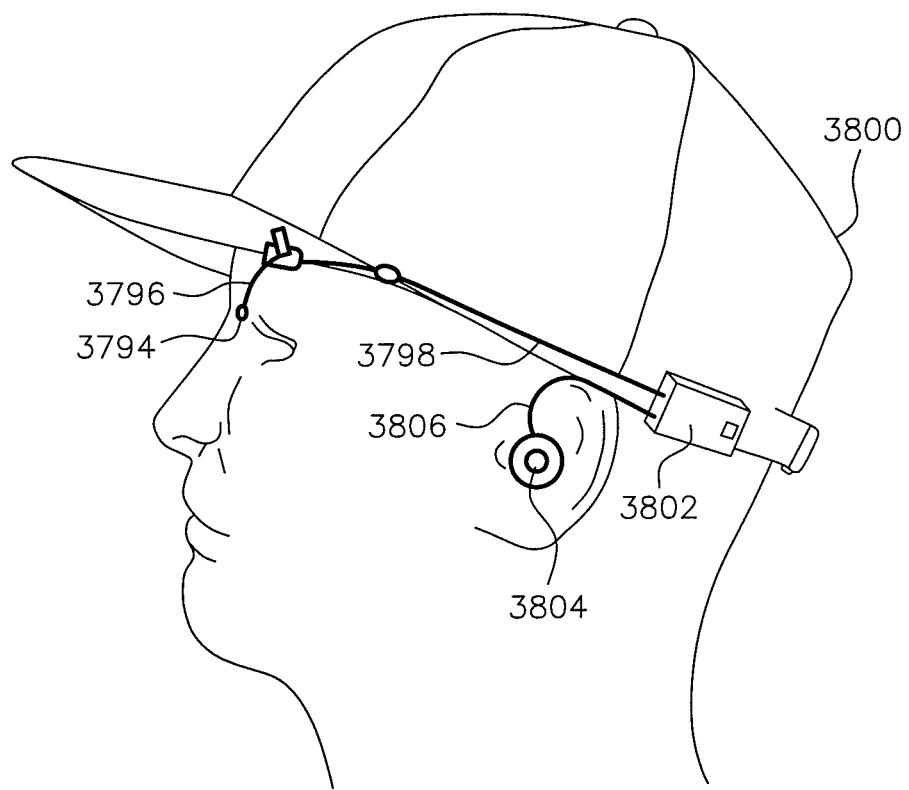

FIG. 15N illustrates a cap worn by a user including a sensing assembly.

Figure 15P:
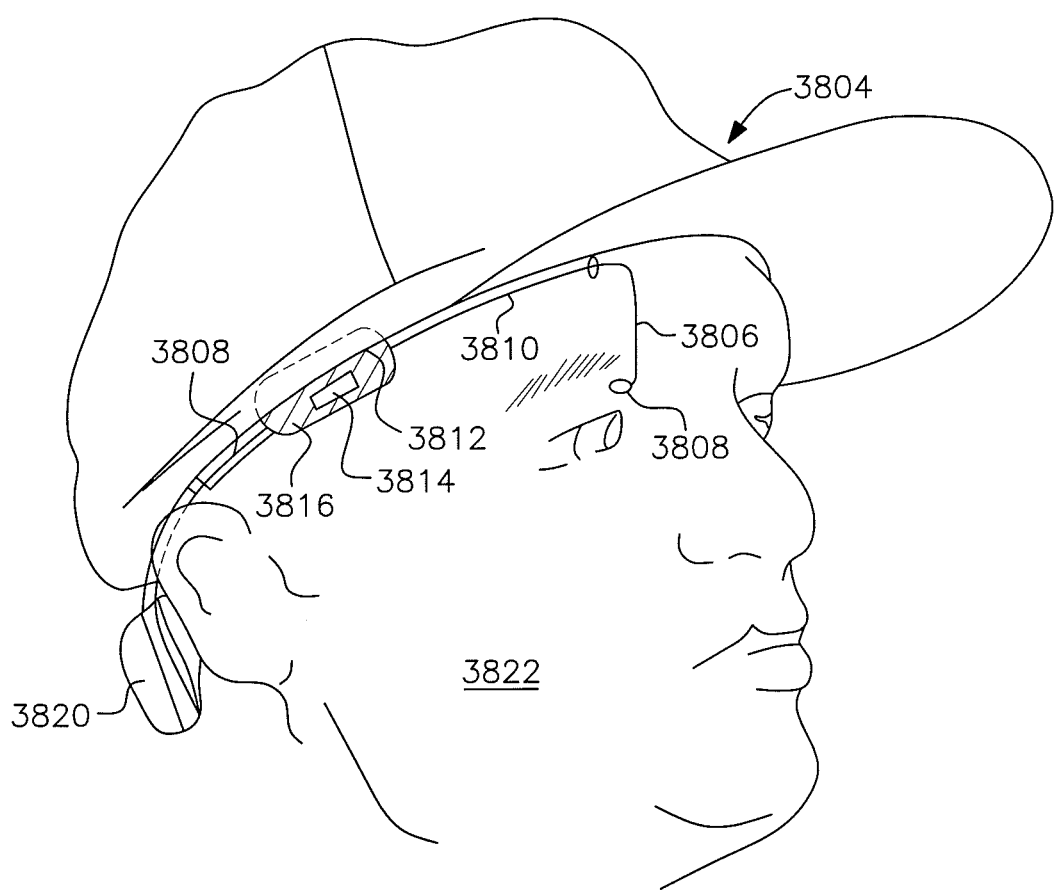

FIG. 15P illustrates a cap worn by a user including a sensing assembly.

Figure 15Q:
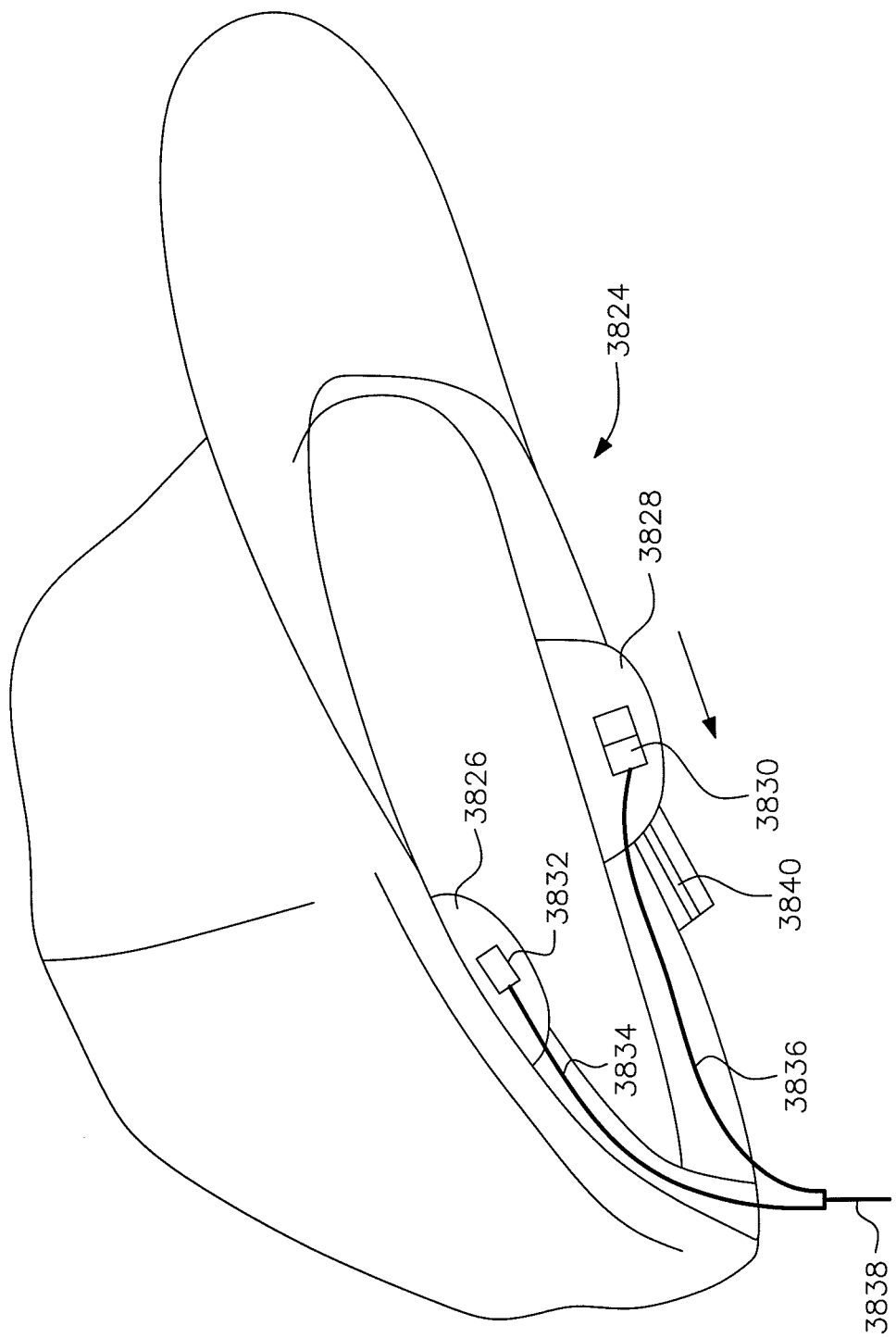

FIG. 15Q illustrates a cap worn by a user including a sensing assembly.

Figure 15R:
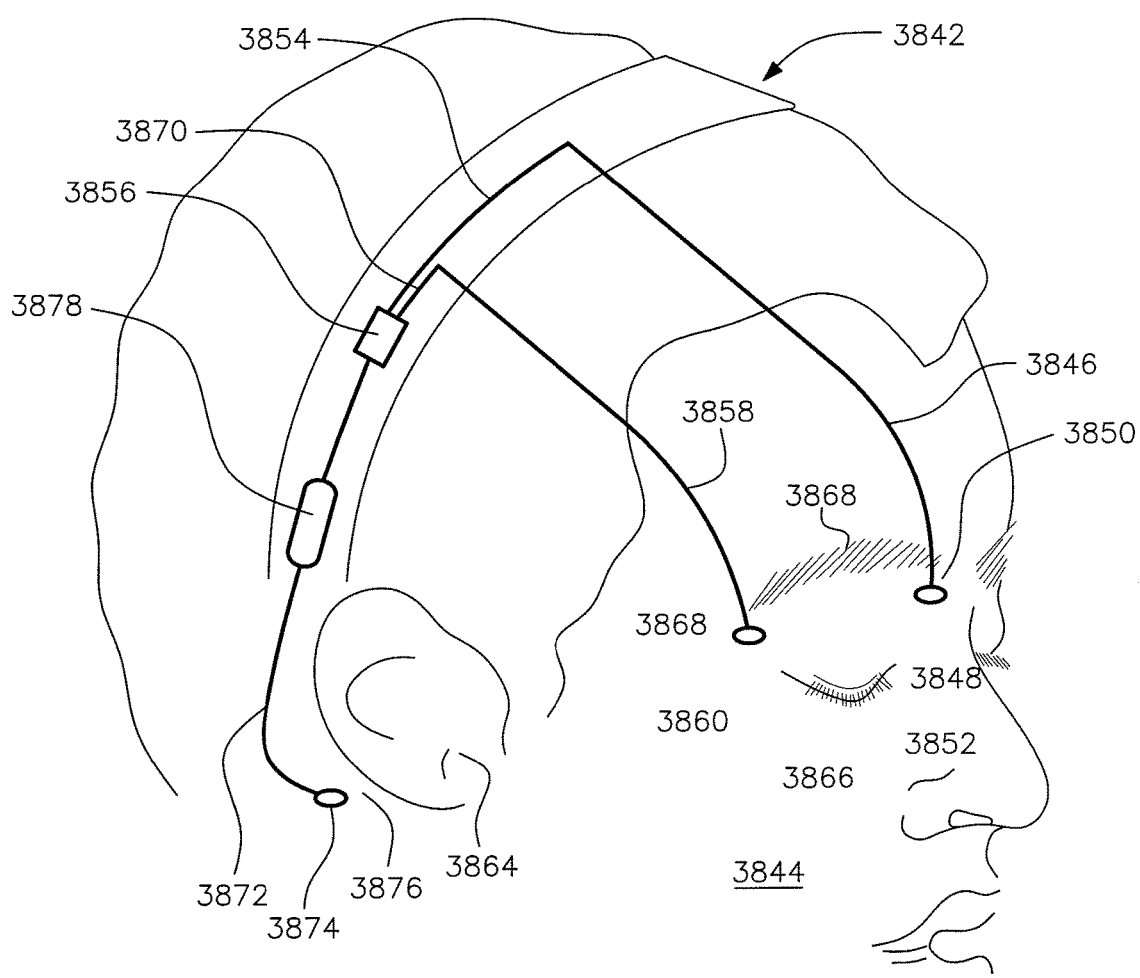

FIG. 15R illustrates head mounted gear including a sensing assembly.

Figure 15S:
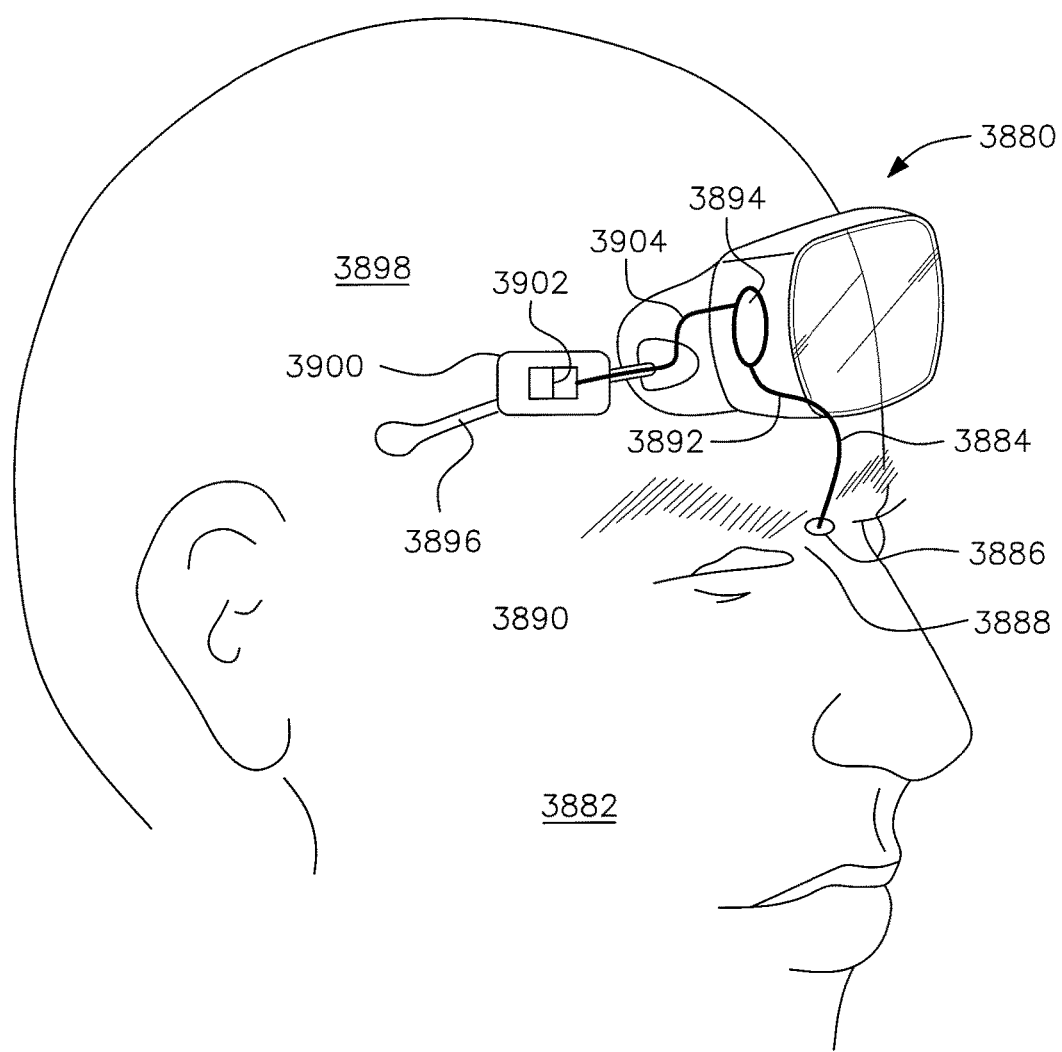

FIG. 15S illustrates head mounted gear having a light source and a sensing assembly.

Figure 15T:
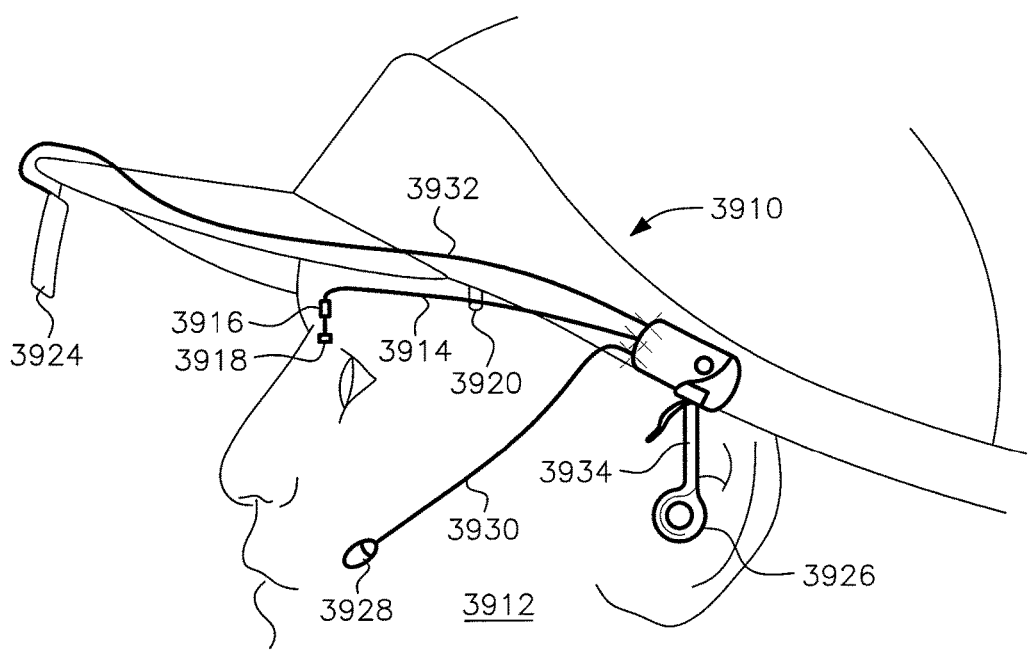

FIG. 15T illustrates head mounted gear having a sensing visor worn by a user.

Figure 15U:
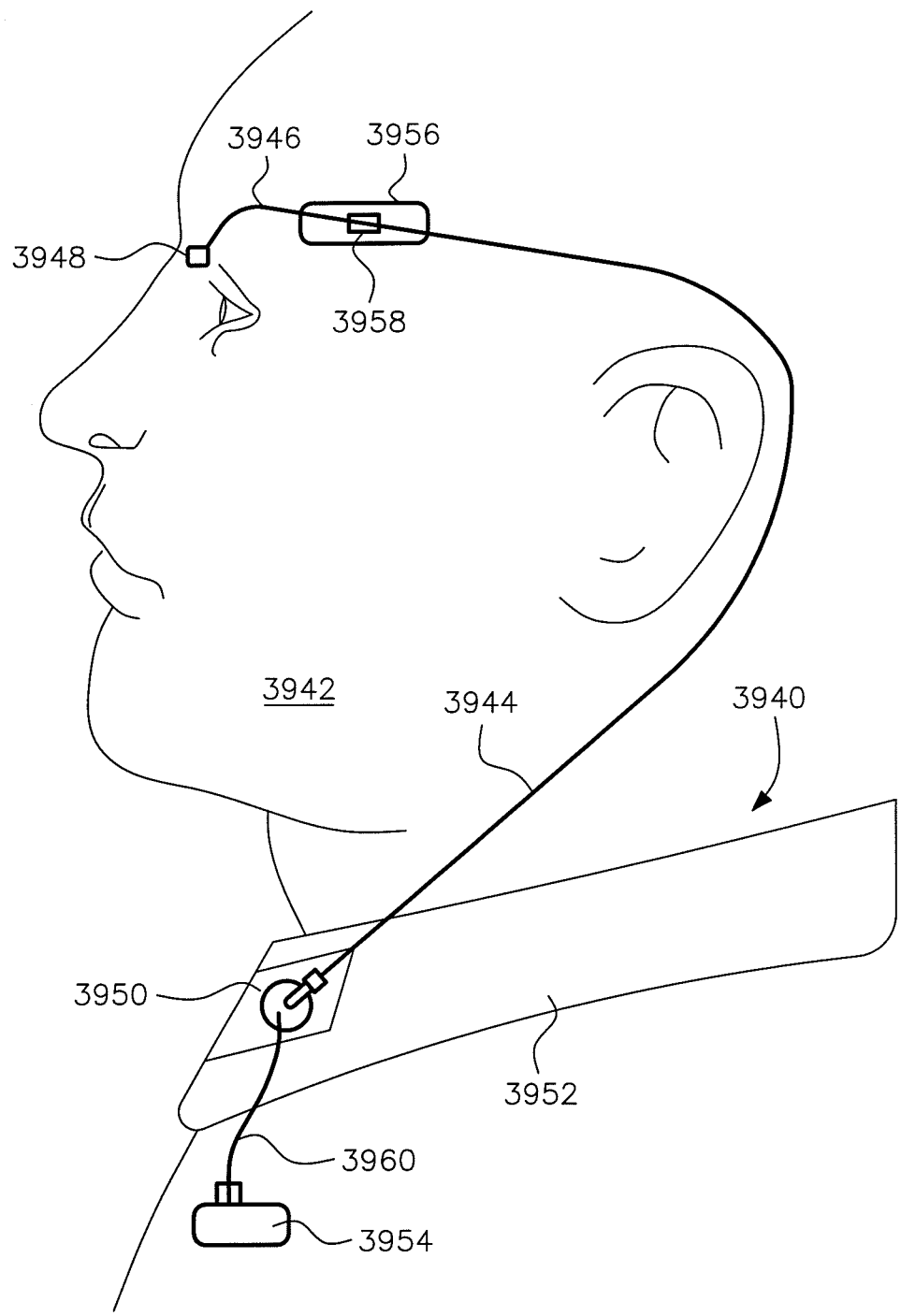

FIG. 15U illustrates a sensing enabled shirt.

Figure 15V:
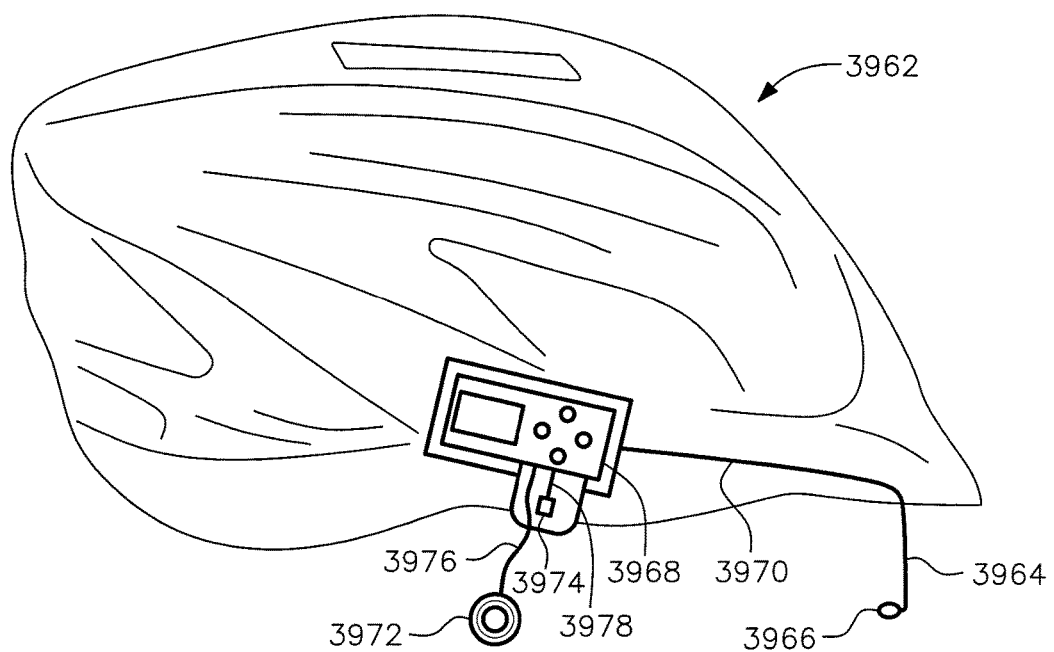

FIG. 15V illustrates a helmet including a temperature sensor.

Figure 15X:
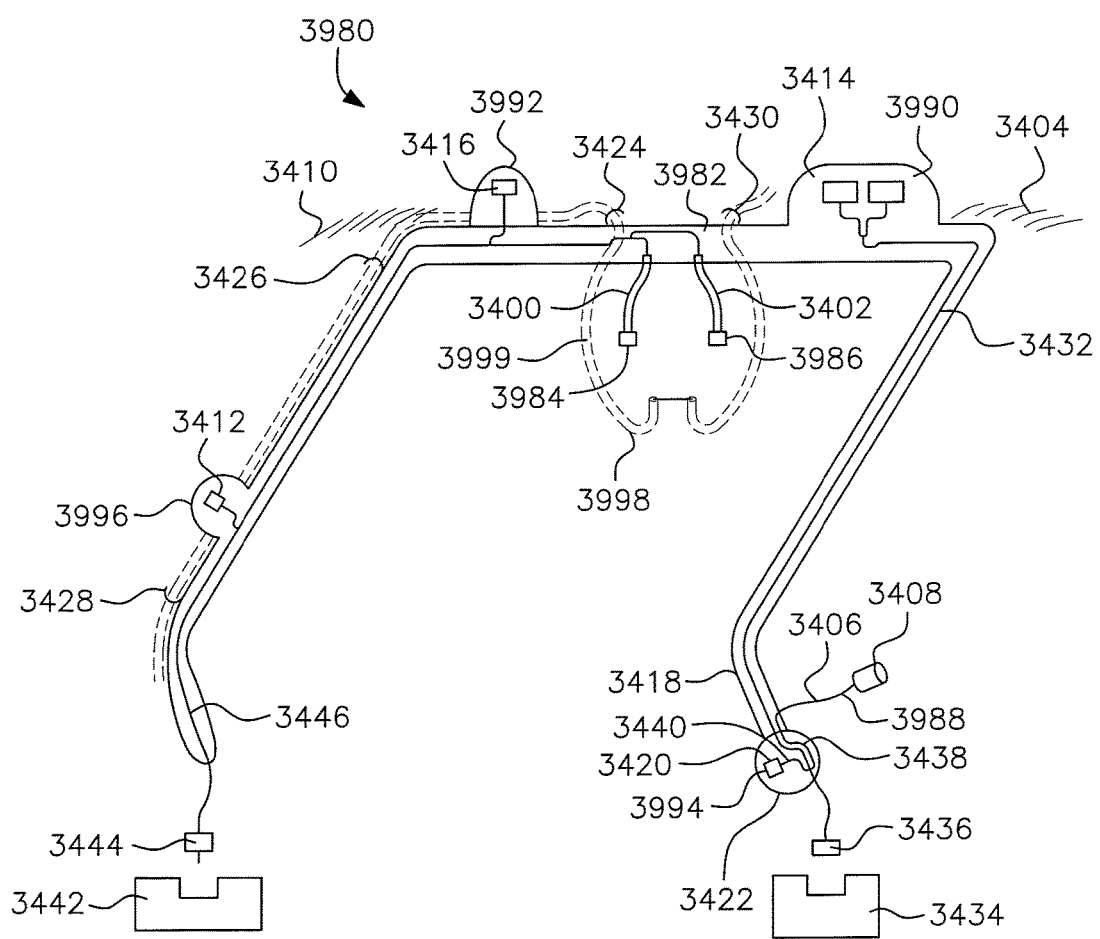

FIG. 15X is a sensing frame including seven biologic parameter modules.

FIG. 15Y illustrates a sensing frame worn by a user.

FIG. 15Z illustrates a sensing frame having temples.

Figure 16:
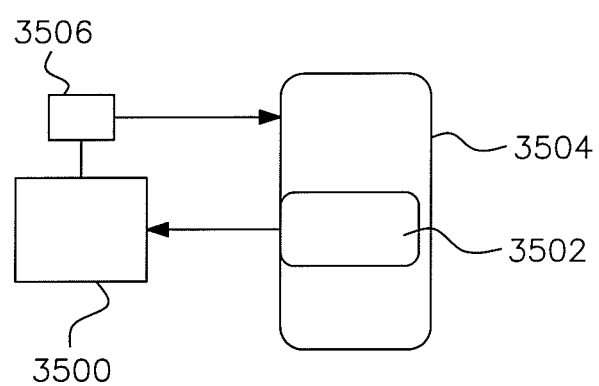

FIG. 16 illustrates an infusion pump connected to a temperature monitoring system.

Figure 17:
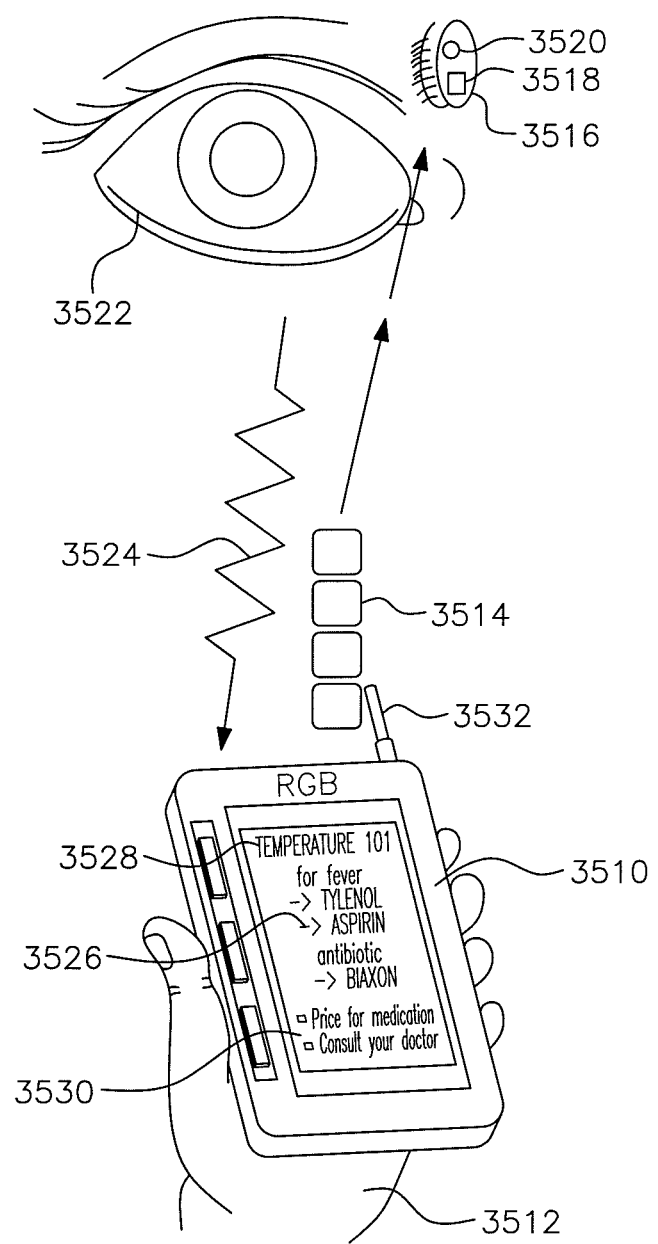

FIG. 17 illustrates a portable powering device coupled to a passive sensing device.

Figure 18A:
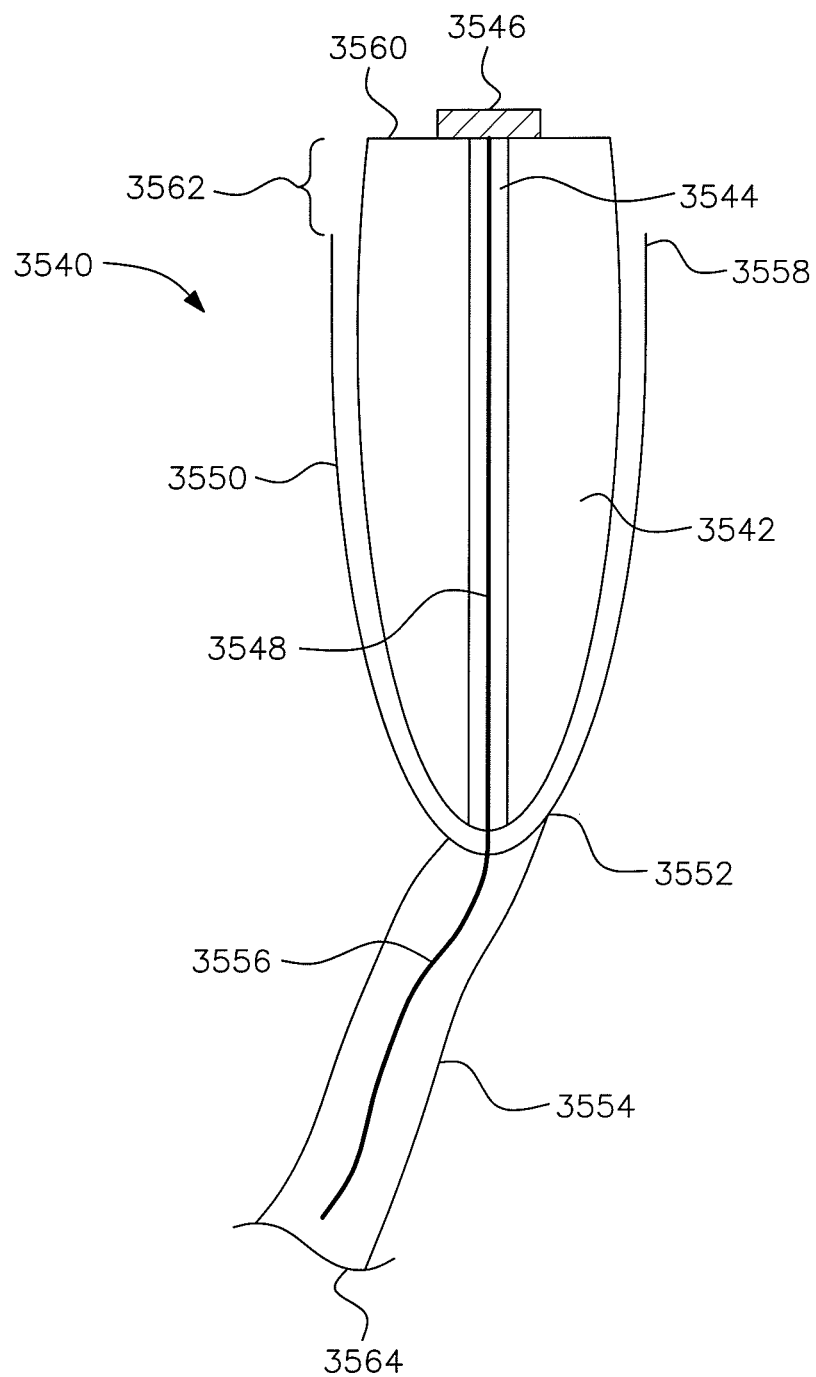

FIG. 18A illustrates a sensing device including a measuring portion and an arm.

Figure 18B:
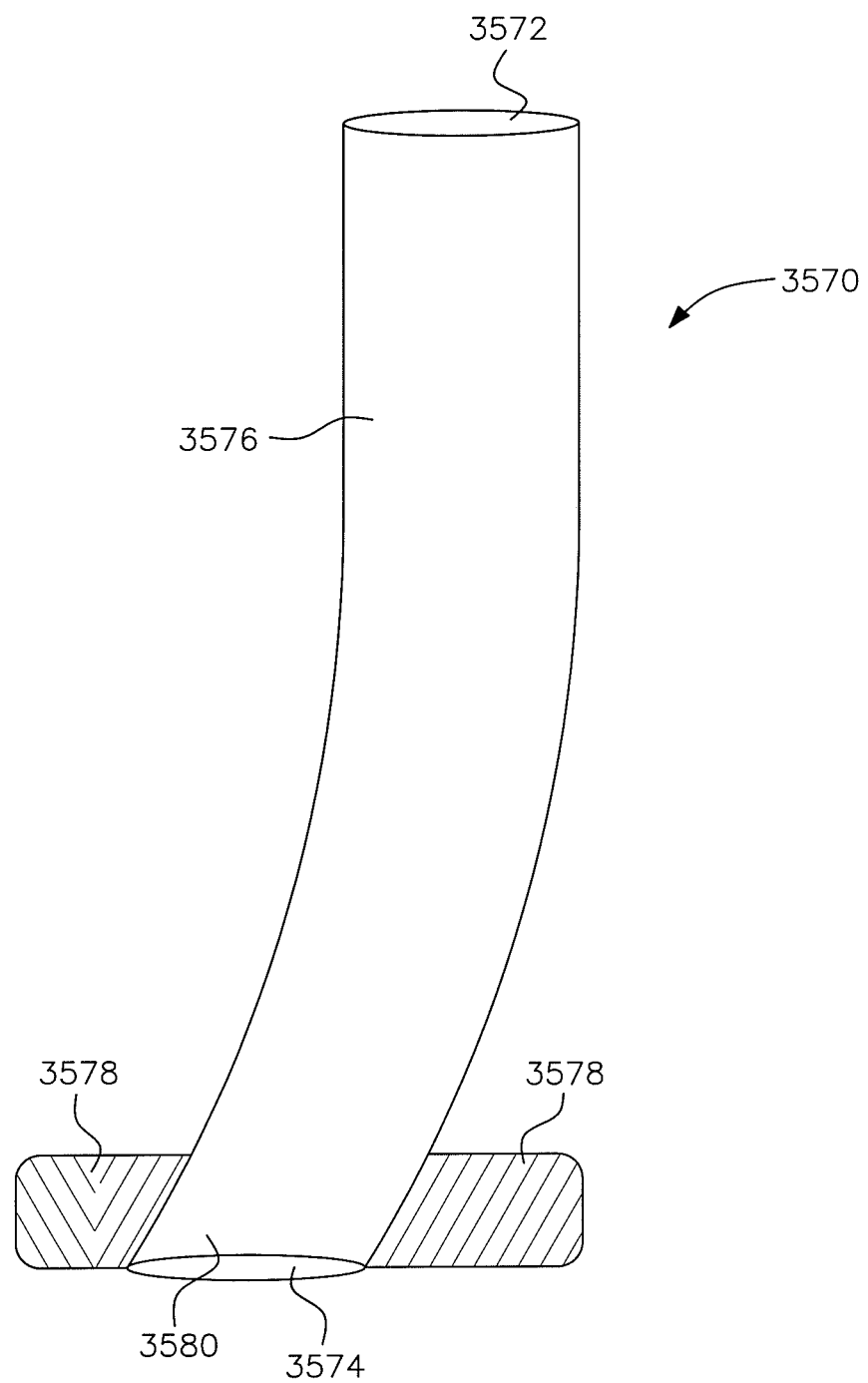

FIG. 18B illustrates a probe covering for a measuring portion of a sensing device.

FIG. 19-A illustrates a non-invasive internal surface measurement probe.

FIG. 19-B is a planar view of a sensor head.

FIG. 19-C illustrates a handheld portable sensing probe.

FIG. 19-D illustrates a boomerang shaped sensor probe.

FIG. 19-E illustrates the boomerang shaped sensor probe showing the sensor surface of the sensor head.

FIG. 19-F illustrates the boomerang shaped sensor head and its relationship to anatomic structures.

FIG. 19-G illustrates a sensor head and handle.

FIG. 19-H illustrates a bulging sensor on the surface of an insulating material.

Figure 20:
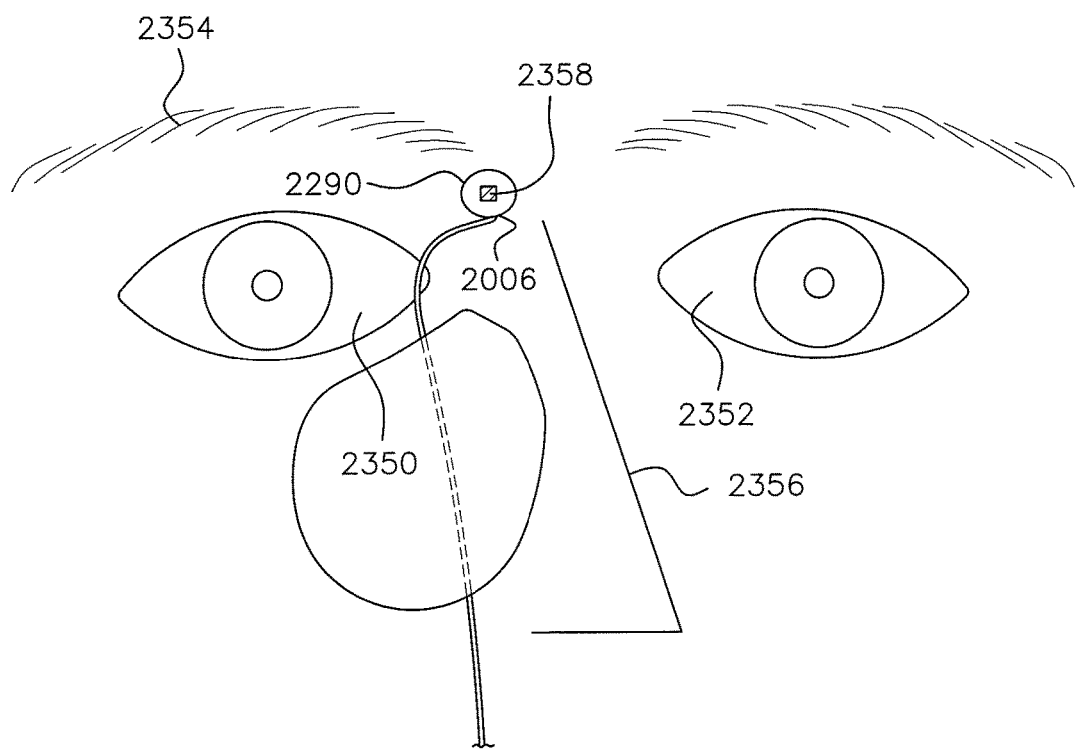

FIG. 20 illustrates an alternate embodiment of placement of a sensing assembly by securing a support structure to a cheek of the user.

DETAILED DESCRIPTION OF THE PREFERRED EMBODIMENTS

Figure 1A:
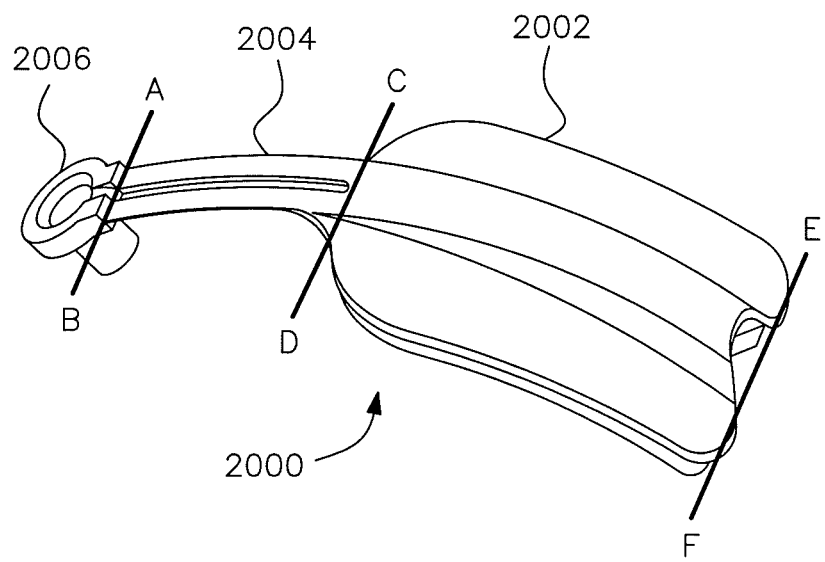
FIG. 1A is a perspective view of a support structure for the brain temperature tunnel sensor assembly of the present invention.
Figure 1B:
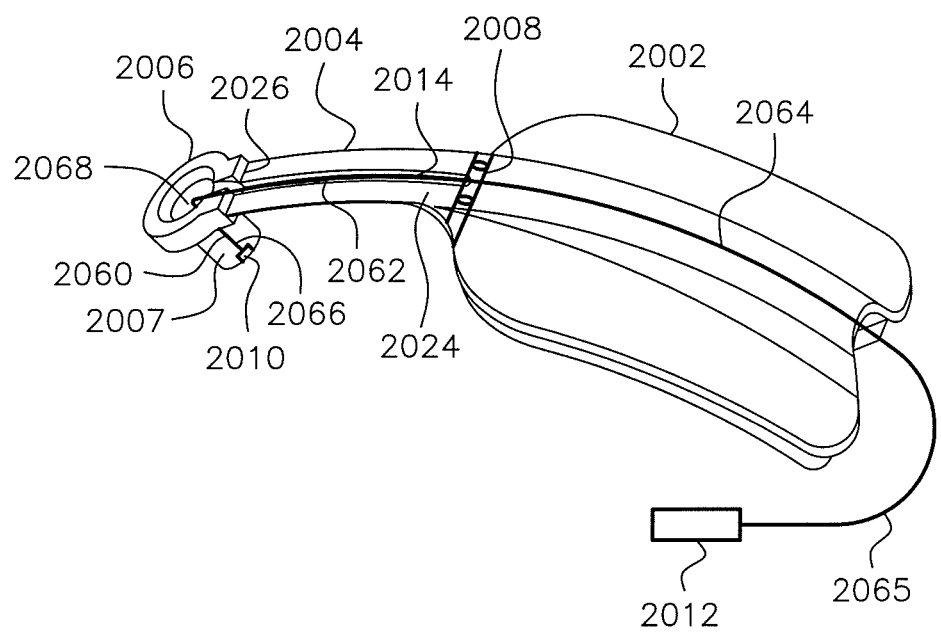
FIG. 1B illustrates an alternate embodiment with a pivotable support arm of the support structure.
Figure 1C:
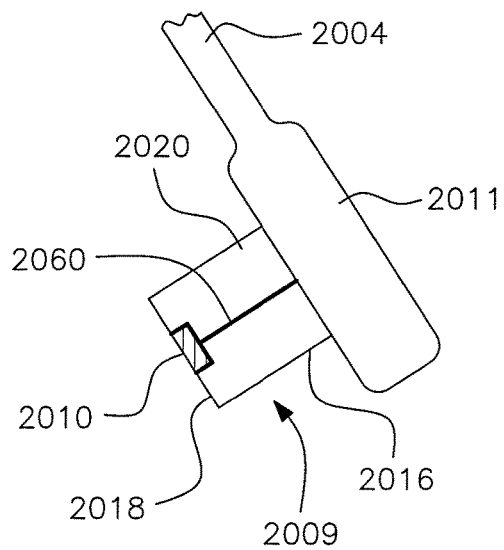
FIG. 1C is a detailed view of a sensor at one end of the support structure.
Figure 1D:
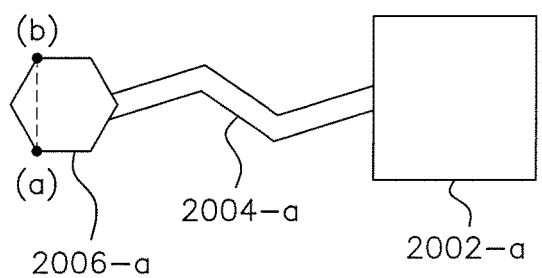
FIG. 1D is a planar diagrammatic view of an alternate embodiment of the support structure and sensor assembly.
Figure 1E:
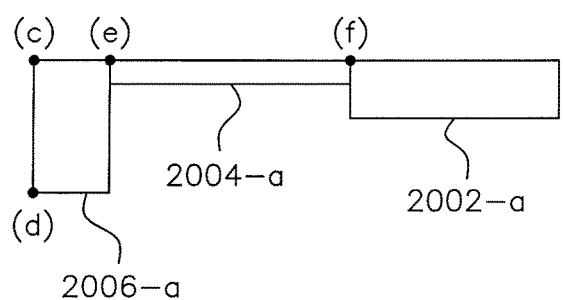
FIG. 1E is a diagrammatic side view of the embodiment of FIG. 1D.
Figure 1F:
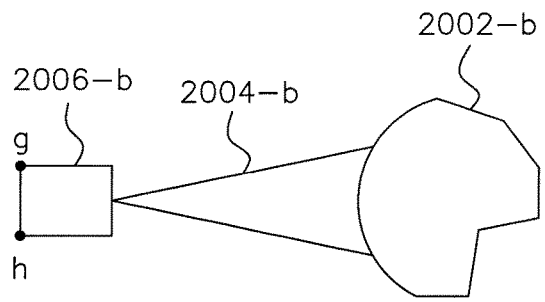
FIG. 1F illustrates an irregular geometric shape of a body portion supported by a triangular shaped arm.
Figure 1G:
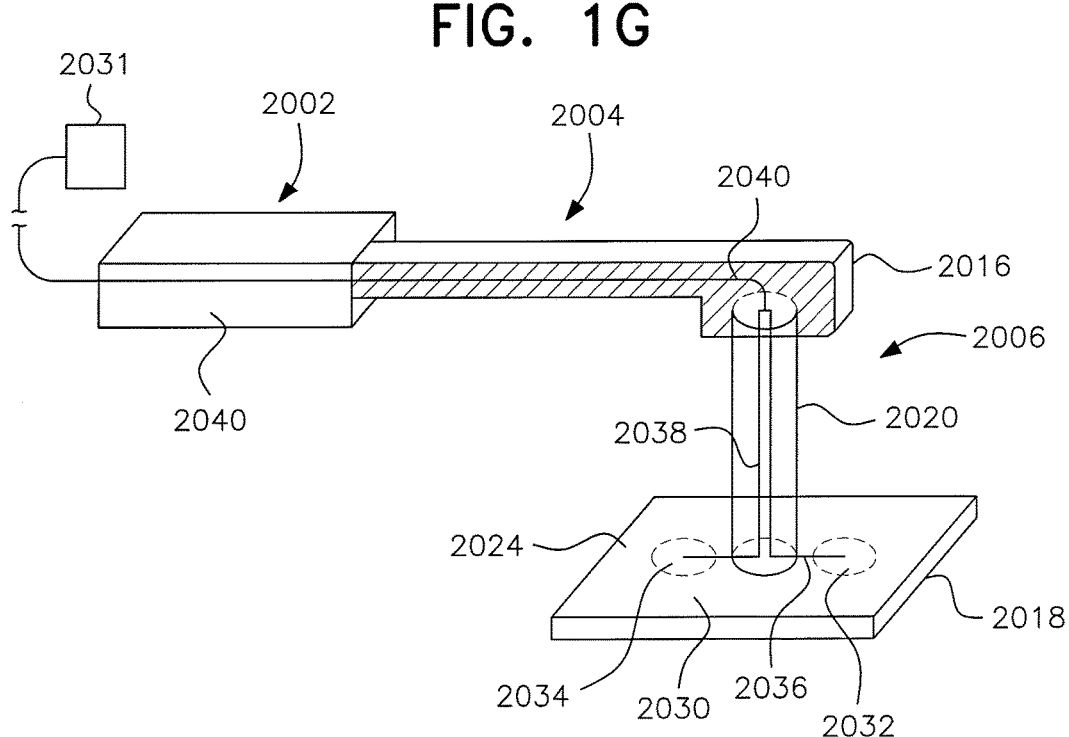
FIG. 1G is a diagrammatic perspective view of an alternate embodiment of a support structure and sensor assembly.
Figure 1H:
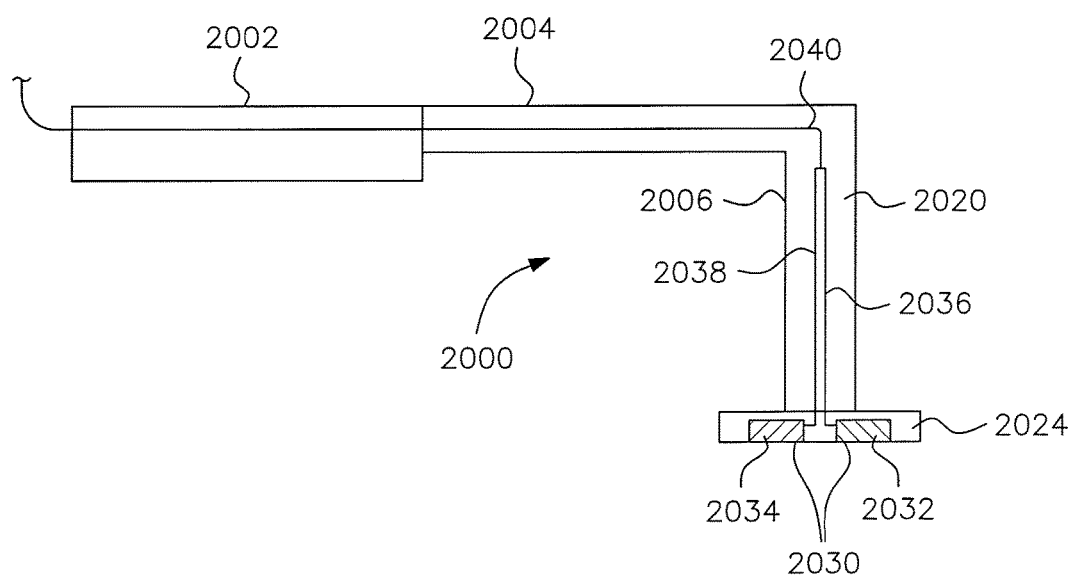
FIG. 1H is a sectional view of the embodiment shown in FIG. 1G.
Figure 1I:
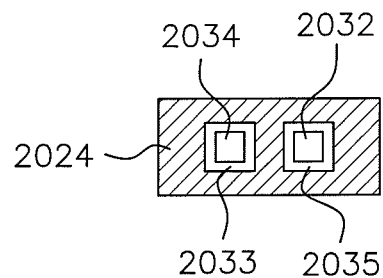
FIG. 1I is a bottom planar view of the sensor assembly illustrating the housing light emitter and light detector.
Figure 1J:
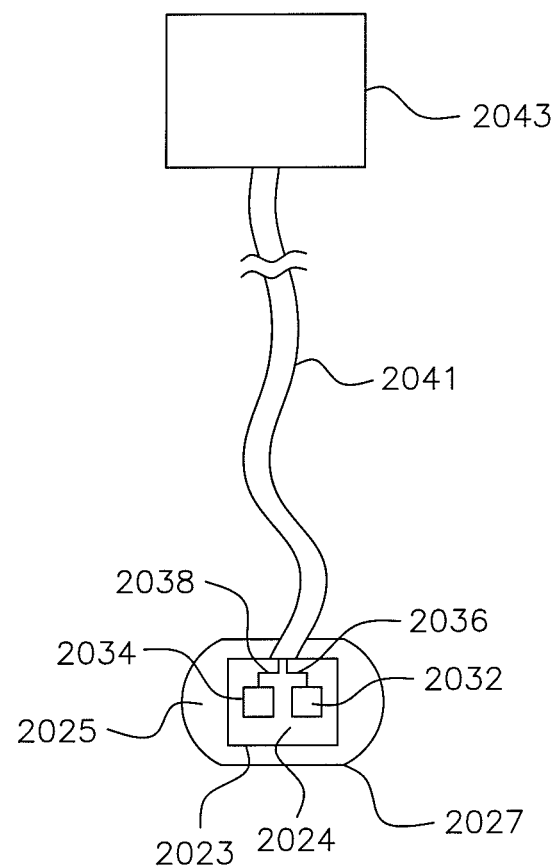
FIG. 1J is a diagrammatic planar view of an alternate embodiment of the support structure and sensor assembly.
Figure 1K:
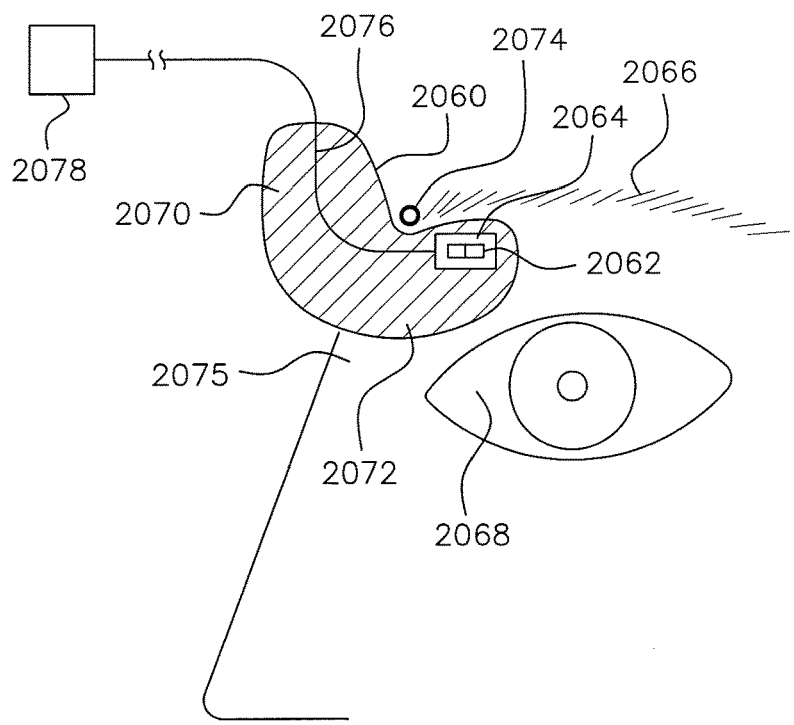
FIG. 1K illustrates an embodiment worn by a user including an adhesive patch and a light emitter-light detector pair located adjacent to the edge of the adhesive patch.
Figure 1L:
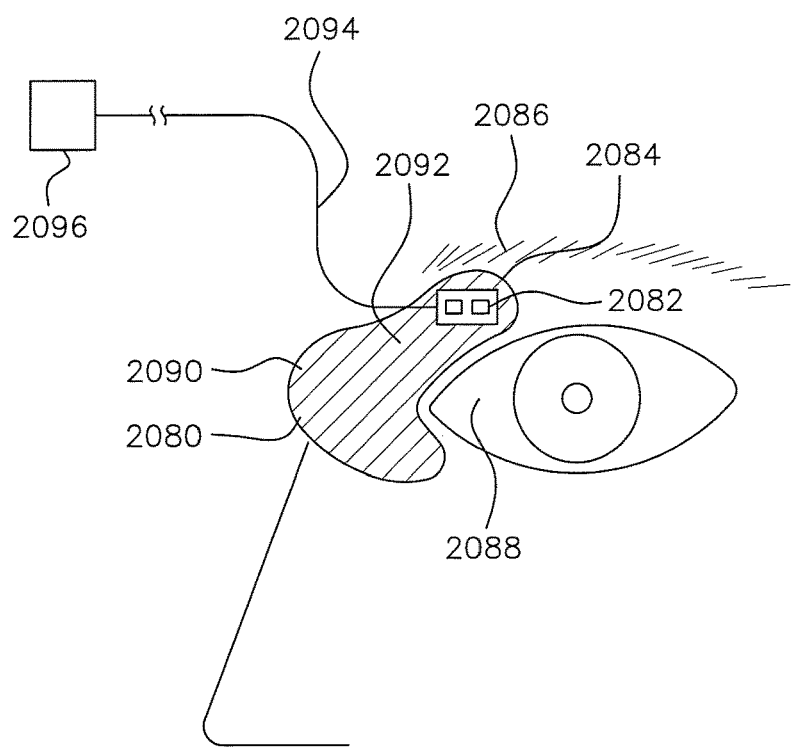
FIG. 1L illustrates an alternate embodiment of the adhesive patch.
Figure 1U:
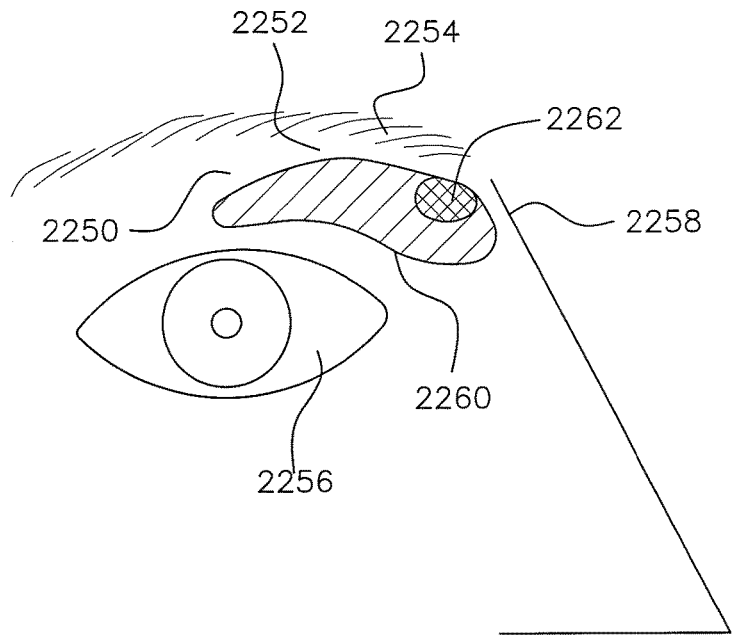
FIG. 1U illustrates the specialized skin area of the brain tunnel with a patch worn over the brain tunnel area.

FIGS. 1A to 1U show preferred embodiments for the sensing and detecting system of the present invention. It is important to note that due to the specialized anatomic and physical configuration of the Brain Temperature Tunnel (BTT) as described in U.S. patent application Ser. No. 10/786,623, hereby incorporated by reference in its entirety, special dimensions and configurations of a sensing device are required, and will be reflected by the specialized dimensions and structure of the present invention disclosed herein. Accordingly, FIG. 1A shows the specialized support structure 2000, referred herein as sensing device 2000 which includes a specialized body 2002, which includes an essentially flexible substrate, an arm 2004, and a sensing portion such as a measuring portion 2006.

Sensing device 2000, for purposes of illustration, is shown as comprised of three parts, body 2002, arm 2004, and measuring portion 2006. Body 2002 is demarcated by line EF and line CD. Arm 2004 is demarcated by line CD and line AB. Measuring portion 2006 is demarcated by line AB, and works as the free end of sensing device 2000. Arm 2004 is connected to measuring portion 2006 and to body 2002. Body 2002 of the sensor system 2000 can preferably comprise a plate configuration, said plate preferably having essentially flexible characteristics so as to be molded and/or to conform to a body part of a human or animal. Plate 2002 can be preferably secured to a body part by adhesive or attachment means. Body part for the purpose of the description includes the body of any living creature including humans and animals of any type as well as birds and other species such as insects. Body 2002 can also include an adhesive surface or any other fastening means, clipping means, and the like which is used to secure body 2002 to an area adjacent to the BTT or on the BTT.

The present invention includes a support structure 2000 removably securable to a body part and having a sensor for measuring biological parameters from a brain tunnel. Any sensor, detector, sensing structure, molecule, moiety, element, radiation detector, a pair of light emitter-detector, fluorescent element, and the like, which can sense, analyze and/or measure an analyte or tissue can be used and disposed in or on measuring portion 2006 or at the end of arm 2004, including contact as well as non-contact detector configurations, and all fall within the scope of the invention. The sensors and/or detectors preferably are positioned on or adjacent to the upper or lower eyelid, and most preferably on or adjacent to the upper eyelid, and even more preferably on or adjacent to an area between the eye and the eyebrow.

Sensing device 2000 preferably comprises: body 2002, which has an inner surface for disposition towards the body part and preferably includes an adhesive surface to securely attach and conform the body 2002 to a body part, and an outer surface for disposition away from the body part; arm 2004 connected to body 2002, said arm 2004 being adjustably positionable and adapted to position sensor 2010 adjacent, on, or firmly against the brain tunnel; and a measuring portion 2006 connected to arm 2004, said measuring portion housing a sensor 2010. Body 2002 is physically conformable to the body part, and preferably includes an outer layer and an inner layer, the inner layer comprised of essentially soft material and including an adhesive surface, said inner layer being attached to an outer layer, said outer layer including a flexible substrate, such as a thin metal sheet, to conform to the body part and to provide stable attachment. A wire is preferably disposed on the outer layer or between the inner layer and the outer layer.

Although sensing device 2000, for purposes of illustration is shown as three parts, it is understood that sensing device 2000 can comprise an integral device fabricated as one piece. Sensing device 2000 can also comprise an integral one-piece device that is fabricated as one piece, but having three different portions. In addition, for example, arm 2004 and measuring portion 2006 can be considered as one piece. Any combination of the parts, namely body, arm, and measuring portion, described herein can be used as the support structure for a sensor, molecule, or detector.

FIG. 1B shows in more detail the sensing system 2000 of FIG. 1A including the specialized body 2002, the arm 2004, and the measuring portion 2006, said measuring portion 2006 housing a sensor 2010. Sensor system 2000 comprises preferably a plate 2002 for securing the device 2000 to a body part, and further comprises an arm 2004, said arm 2004 connecting supporting plate 2002 to a measuring portion 2006. Arm 2004 is preferably an adjustably positionable arm, which is movable in relation to plate 2002. Arm 2004 preferably comprises a shape memory alloy or any material, including plastics and polymers that have memory. Preferably, arm 2004 is deformable and has a memory. The end 2026 of arm 2004 terminates in the measuring portion 2006. Although arm 2004 comprises preferably an adjustably positionable arm, arm 2004 can also include a rigid arm. Preferred materials for the arm 2004 include a thin sheet of metal such as stainless steel, aluminum, and the like or polymers and plastics of various kinds. The material can also include rubber, silicone or other material. Sensor 2010 at the end of arm 2004 is connected to a reading and processing circuit 2012, referred to also herein as a biological parameter monitor, through wire portion 2065. Sensor 2010 is electrically coupled to the biological parameter monitor, which receives a signal from sensor 2010, and determines the value of the biological parameter, and reports the value including by visual display and audio reporting.

The present invention can employ a cantilever for sensing system 2000, in which arm 2004 is supported rigidly at plate 2002 to carry a load, such as measuring portion 2006, said measuring portion 2006 being disposed along the free end 2026 of said arm 2004. The arm 2004 is fixed at a base of body 2002, with said body 2002 being a support structure exemplarily described in embodiments as a plate; a housing secured to a head mounted gear including a headband, frame of eyewear, hats, helmets, visors, burettes for holding hair; the frame of eyewear or of a head mounted gear, clothing of any type including a shirt, a rigid structure secured to an article of manufacturing such as apparel; and the like. The free end 2026 of arm 2004 is connected to measuring portion 2006 which houses sensor 2010. Accordingly, the sensing device 2000 of the invention has an arm 2004 that distributes force and that can apply force to a body part. One of ways arm 2004 can be positioned and/or apply pressure to a body part is by virtue of a memory shape material of said arm 2004. Any means to apply pressure to a body part can be used in sensing system 2000 including a spring loaded system, in which the spring can be located at the junction 2024 of body 2002 and the arm 2004, or the spring is located at the free end 2026 of arm 2004. It is contemplated that any material with springing capabilities and any other compressible materials and materials with spring and/or compressible capabilities such as foams, sponges, gels, tension rings, high-carbon spring steels, alloy spring steels, stainless steels, copper-base alloys, nickel-base alloys, and the like can be used in sensing device 2000 to apply pressure for better apposition of measuring portion 2006 to the body part. The invention teaches apparatus and methods for creating better apposition and/or applying pressure to a body part or article by any sensor, device, detector, machine, equipment, and the like. Sensor 2010 housed in measuring portion 2006 can therefore apply pressure to a body part, such as the brain temperature tunnel area at the roof of the orbit.

The end of arm 2004 preferably terminates as a bulging part, such as measuring portion 2006, which houses sensor 2010. Arm 2004 can move in relation to plate 2002, thus allowing movement of sensor 2010 housed at the free end 2026 of arm 2004. Although the sensing system 2000 is described for a body part, it is understood that the sensing device 2000 can be applied in an industrial setting or any other setting in which a measurement of an object or article is needed. By way of illustration, sensor 2010 can include a temperature and pressure sensor while the plate 2006 is affixed to a support structure, such as a beam or wall of a machine, and the sensor 2010 is applied against a balloon or a surface, thus providing continuous measurement of the pressure and temperature inside the balloon or surface. Outside surface of body 2002 can include an adhesive surface for securing said body 2002 to a second surface such as a body part or the surface of a machine or any article of manufacturing.

In order to fit with the specialized anatomy and physical configuration of the brain tunnel, specialized sensing devices with special dimensions and configurations are necessary. The preferred dimensions and configurations described herein can be applied to any embodiments of this invention including embodiments described from FIG. 1 to FIG. 19. The preferred configuration of sensing device 2000 comprises a body 2002 that has a larger width than arm 2004. The width of body 2002 is of larger dimension than the width of arm 2004. Preferably the width of body 2002 is at least twice the width of arm 2004. Most preferably, arm 2004 has a width which is preferably one third or less than the width of body 2002. Even more preferably, arm 2004 has a width which is preferably one fourth or less than the width of body 2002.

The sensing device 2000, as exemplarily illustrated, includes an essentially curved end portion of arm 2004 and an essentially flat remaining portion of arm 2004 said flat portion connected to body 2002. During use arm 2004 is positioned in a curved configuration to fit around the bone of the eyebrow. Arm 2004 has two end portions, namely end portion 2024 which terminates in body 2002 and a free end portion 2026 which terminates in the measuring portion 2006. The preferred length of arm 2004 is equal to or no greater than 15 cm, and preferably equal to or no greater than 8 cm in length, and most preferably equal to or no greater than 5 cm in length. Depending on the size of the person other dimensions of arm 2004 are contemplated, with even more preferable length being equal to or no greater than 4 cm, and for children length equal to or no greater than 3 cm, and for babies or small children the preferred length of arm 2004 is equal to or no greater than 2 cm. Depending on the size of an animal or the support structure being used such as a burette of FIG. 15R, cap of FIG. 15P, or the visor of FIG. 15T other dimensions are contemplated, such as length of arm 2004 equal to or no greater than 40 cm.

The preferred width or diameter of arm 2004 is equal to or no greater than 6 cm, and preferably equal to or no greater than 3 cm, and most preferably equal to or no greater than 1.0 cm. Depending on the size of the person other dimensions for arm 2004 are contemplated, with an even more preferable width or diameter being equal to or no greater than 0.5 cm, and for children width or diameter equal to or no greater than 0.3 cm, and for babies or small children the preferred equal to or no greater than 0.2 cm. Depending on the size of a large person or size of an animal or support structure being used other dimensions for arm 2004 are contemplated, such as width or diameter equal to or no greater than 12 cm.

The preferred height (or thickness) of arm 2004 is equal to or no greater than 2.5 cm, and preferably equal to or no greater than 1.0 cm in thickness, and most preferably equal to or no greater than 0.5 cm in thickness. Depending on the size of the person other dimensions for arm 2004 are contemplated, with even more preferable thickness being equal to or no greater than 0.3 cm, and for children thickness equal to or no greater than 0.2 cm, and for babies or small children the preferred thickness is equal to or no greater than 0.1 cm. Depending on the size of a large person or size of an animal other dimensions for arm 2004 are contemplated, such as thickness equal to or no greater than 3.0 cm.

For devices, in which the preferred configuration of arm 2004 is a cylinder, the preferred diameter of arm 2004 is equal to or no greater than 2.0 cm, and preferably equal to or no greater than 1.0 cm in thickness, and most preferably equal to or no greater than 0.5 cm in thickness. Depending on the size of the person other dimensions for arm 2004 are contemplated, with even more preferable diameter being equal to or no greater than 0.25 cm, and most preferably being equal to or no greater than 0.15 cm, and for children thickness equal to or no greater than 0.2 cm, and for babies or small children the preferred thickness is equal to or no greater than 0.1 cm. Depending on the size of a large person or size of an animal or the structure being used, other dimensions for arm 2004 are contemplated, such as diameter equal to or no greater than 3.0 cm.

The preferred largest dimension of arm 2004 is equal to or no greater than 30 cm, and preferably equal to or no greater than 20 cm, and most preferably equal to or no greater than 10 cm. Preferred dimensions are based on the size of the person or animal and structure being used such as burette, visors, or cap. The preferred length of arm 2004 is no greater than 40 cm, and preferably equal to or no greater than 20 cm, and most preferably equal to or no greater than 10 cm in length. Depending on the size of the person other preferred dimensions for arm 2004 are contemplated, with an even more preferable length being equal to or no greater than 8 cm, and most preferably equal to or no greater than 6 cm, and for adults of small size length equal to or no greater than 5 cm, and for children length equal to or no greater than 4 cm and for babies or small children the preferred length is equal to or no greater than 2 cm. Arm 2004 is preferably curved at its free end 2026 for fitting with the anatomy of the brain tunnel and the facial bone.

The preferred general dimensions for human use by a person of average size for arm 2004 are: height (or thickness or diameter) equal to or less than 0.4 cm, length equal to or less than 6 cm, and width equal to or less than 0.5 cm. The preferred height (or thickness or diameter) of arm 2004 ranges between equal to or more than 0.1 cm and equal to or less than 0.5 cm. The preferred length of arm 2004 ranges between equal to or more than 1.0 cm and equal to or less than 8 cm. The preferred width of arm 2004 ranges between equal to or more than 0.1 cm and equal to or less than 1 cm.

It should be noted that for small animals such as rats, mice, chicken, birds, and other animals using the brain tunnel smaller size and different configurations are contemplated.

In one embodiment the end portions of arm 2004 terminate in plate 2002 and measuring portion 2006. Preferably, arm 2004 is made of a stainless steel type material or aluminum; however, other materials are contemplated, including other metals, plastics, polymers, rubber, wood, ceramic, and the like. The arm 2004 should be sufficiently flexible such that the relative distance between sensor 2010 and a body part may be enlarged or reduced as needed in accordance to the measurement being performed including measurement in which sensor 2010 touches the body part and measurements in which sensor 2010 is spaced away from the body part and does not touch the body part during measurement. An exemplary sensor which does not touch a body part during measurement is a thermopile. Accordingly, measuring portion 2006 can include said thermopile or any radiation detector.

Although FIG. 1B shows arm 2004 being of different size as compared to plate 2002, it is understood that arm 2004 can have the same size of plate 2002 or have larger size than plate 2002. The preferred largest dimension of end portion 2026 of arm 2004 is equal to or no greater than 3 cm, and preferably equal to or no greater than 2 cm, and most preferably equal to or no greater than 1 cm. Depending on the size of the person, it is also contemplated that end portion 2026 has an even more preferable size equal to or no greater than 0.8 cm, and even most preferably equal to or no greater 0.6 cm. For some adults of small size the end portion 2026 has an even more preferable size equal to or no greater than 0.5 cm, and for children, it is also contemplated that end portion 2026 of arm 2004 has a size equal to or no greater than 0.4 cm. and for babies the contemplated size is equal to or no greater than 0.2 cm As nanotechnology, MEMS (microelectromechanical systems), and NEMS (nanoelectromechanical systems) progresses other configurations, dimensions, and applications of the present invention are contemplated.

Although FIG. 1B shows arm 2004 being of different width (or diameter) as compared to measuring portion 2006, it is understood that arm 2004 can have the same width (or diameter) of measuring portion 2006 or have a larger width (or diameter) than measuring portion 2006. Preferably the width (or diameter) of arm 2004 is of smaller size than the dimension (or diameter) of the measuring portion 2006. Preferably the part of measuring portion 2006 connected to arm 2004 is of larger dimension than the width of arm 2004.

For the purpose of the description thickness and height are used interchangeably. The preferred configuration of sensing device 2000 comprises a body 2002 (including the body of any embodiment from FIGS. 1 to 19, and in particular the body corresponding to a housing or structure securing sensors/detector described in all figures, from FIG. 14A to FIG. 15Z) that is thicker than arm 2004. The height or thickness of body 2002 is preferably of larger size than the thickness (or height or diameter) of arm 2004. Arm 2004 has thickness (or height or diameter) which is preferably of lesser size than the thickness (or height) of body 2002. Arm 2004 has thickness (or height) which is preferably half or less than the thickness (or height) of body 2002. Arm 2004 has thickness (or height) which is most preferably one third or less than the thickness (or height) of body 2002.

The preferred configuration of sensing device 2000 comprises a measuring portion 2006 that is thicker than arm 2004. The measuring portion 2006 preferably comprises a bulging portion which is thicker than arm 2004. Arm 2004 is thinner than measuring portion 2006. Arm 2004 has thickness (or height or diameter) which is preferably half or less than the thickness (or height or diameter) of measuring portion 2006. Arm 2004 has thickness (or height or diameter) which is most preferably one third or less than the thickness (or height or diameter) of measuring portion 2006. Even more preferably arm 2004 has thickness (or height or diameter) which is one sixth or less than the thickness (or height or diameter) of measuring portion 2006. It is yet contemplated that for proper functioning in accordance with the size of the user and the principles of the invention, measuring portion 2006 has thickness (or height or diameter) which is 3 times or more larger than the thickness (or height or diameter) of arm 2004.

The preferred configuration of sensing device 2000 comprises an arm 2004 that is longer than the height (or thickness or diameter) of measuring portion 2006. The length of arm 2004 is preferably of larger dimension than the largest dimension of measuring portion 2006. In the exemplary embodiment, measuring portion 2006 is essentially cylindrical, and thus includes a circle, said circle having a diameter. For the purposes of the description, an embodiment in which the circle is replaced by a rectangle, square or other shape, the length of said rectangle, square, or other shape is considered an "equivalent dimension" to the diameter. Accordingly, measuring portion 2006 has diameter (or "equivalent dimension"), which is preferably half or less than the length of arm 2004. Measuring portion 2006 has diameter (or "equivalent dimension"), which is preferably one third or less than the length of arm 2004. It is yet contemplated that for proper functioning in accordance with the principles of the invention, arm 2004 has an even more preferred length, which is 5 times or more greater than the diameter (or "equivalent dimension") of measuring portion 2006.

The preferred configuration of sensing device 2000 comprises a measuring portion 2006, which is thicker than the body 2002, as illustrated in FIG. 1B. It is understood that in embodiments of FIG. 15A to FIG. 15Z the body as represented by the headband and housing for electronics are contemplated to be thicker than measuring portion 2006. The thickness (or height) of measuring portion 2006 is preferably of larger dimension than the thickness or height of body 2002. Body 2002 has thickness (or height) which is preferably half or less than the thickness (or height) of measuring portion 2006. Body 2002 has thickness (or height) which is preferably one third or less than the thickness (or height) of measuring portion 2006. It is yet contemplated that for proper functioning in accordance with the principles of the invention, measuring portion 2006 has thickness (or height) which is 4 times or more greater than the thickness (or height) of body 2002. When the embodiment includes body 2002 housing a wireless transmitter and/or other electronic circuit, then body 2002 can preferably have a thickness (or height) equal to or of larger dimension than thickness (or height) of measuring portion 2006.

The length of body 2002 is preferably of larger dimension than the largest dimension of measuring portion 2006. Preferably, the configuration of sensing device 2000 comprises a body 2002 which has a longer length than the length of measuring portion 2006. When measuring portion 2006 includes a circular configuration, then preferably body 2002 has larger length than the diameter of measuring portion 2006. Measuring portion 2006 has length (or diameter) which is preferably half or less than the length (or diameter) of body 2002. Measuring portion 2006 has length (or diameter) which is preferably one third or less than the length (or diameter) of body 2002. It is yet contemplated that for proper functioning in accordance to the principles of the invention, body 2002 has length (or diameter) which is 4 times or more the length (or diameter) of measuring portion 2006.

The preferred configuration of sensing device 2000 comprises an arm 2004, in which the largest dimension of said arm 2004 is larger than the largest dimension of measuring portion 2006. The preferred configuration of sensing device 2000 comprises a body 2002, in which the largest dimension of said body 2002 is larger than the largest dimension of measuring portion 2006. The preferred configuration of sensing device 2000 comprises an arm 2004, in which the smallest dimension of said arm 2004 is equal to or smaller than the smallest dimension of measuring portion 2006. The preferred configuration of sensing device 2000 comprises a body 2002, illustrated in FIG. 1B, in which the smallest dimension of said body 2002 is equal to or smaller than the smallest dimension of measuring portion 2006. The preferred configuration of sensing device 2000 comprises an arm 2004, in which the thickness of said arm 2004 has a smaller dimension than the thickness of measuring portion 2006.

It is contemplated that other geometric configurations, besides square, circle, and rectangles, can be used, such as a star, pentagon, octagon, irregular shape, or any geometric shape, and in those embodiments the largest dimension or smallest dimension of the plate 2002 (e.g., body) of sensing device 2000 is measured against the largest dimension or smallest dimension of the other part, such as arm 2004 or measuring portion 2006. The same apply when fabricating sensing device 2000 and the reference is the arm 2004, but now compared to body 2000 and/or measuring portion 2006. Yet the same apply when fabricating sensing device 2000 and the reference is the measuring portion 2006, which is now compared to body 2002 and/or arm 2004. The largest dimension of one part is compared to the largest dimension of the other part. The smallest dimension of one part is compared to the smallest dimension of the other part.

Still in reference to FIG. 1B, the end 2024 of arm 2004 connected to plate 2002 can further include a swivel or rotating mechanism 2008, allowing rotation of arm 2004, and/or the up and down movement of measuring portion 2006. The swivel or rotating mechanism 2008 can include a lock for locking arm 2004 in different angles. The different angles and positions can be based on predetermined amount of pressure by said arm 2004 applied to a body part. In addition, arm 2004 can operate as a movable arm sliding in a groove in body 2002. According to this arrangement, the movable arm 2004 works as a slidable shaft housing a measuring portion 2006 in its free end. This embodiment can comprise a larger plate 2002 which is secured to the cheek or nose, and the sliding mechanism is used to position sensor 2010 of measuring portion 2006 against the skin of the brain tunnel (BT) underneath the eyebrow, with body 2002 positioned below the eye or at the eye level. This embodiment can comprise embodiments of FIG. 5 to FIG. 15Z, including embodiments in which the arm 2004 is secured to the forehead such as using a headband, and the sliding mechanism is used to position sensor 2010 of measuring portion 2006 against the skin of the brain tunnel (BT) underneath the eyebrow, with body of the sensing device positioned above the eye or at the forehead. Other embodiments are contemplated including the slidable mechanism and swivel mechanism used as part of a headband and embodiments described in FIG. 14 to FIG. 15Z. Furthermore, another embodiment can include a dial mechanism in which the arm 2004 moves from right to left as in the hands of a clock facing the plane of the face. In this embodiment the right brain tunnel area for example of a subject with a wide nose bridge can be reached by moving the dial to the 7 o'clock or 8 o'clock position, said illustrative clock being observed from an external viewer standpoint.

Sensor 2010 at the end of measuring portion 2006 is connected to processing and display unit 2012 through wire 2014. Wire 2014 has three portions 2060, 2062, 2064. Accordingly, there is seen in FIG. 1B wire portion 2060 secured to measuring portion 2006 with the free end 2066 of said wire portion 2060 terminating in sensor 2010 and the opposite end 2068 of said wire portion 2060 terminating in arm 2004. End 2068 of wire portion 2060 preferably terminates in a 90 degree angle between the measuring portion 2006 and arm 2004. Second wire portion 2062 is secured to arm 2004 and terminates in body 2002 preferably in an essentially 180 degree angle while the opposite end of wire 2062 forms the 90 degree angle with wire portion 2068. In addition, in embodiments of FIG. 14 to FIG. 15Z, wire portion 2062 secured to arm 2004 may terminate in a housing and/or printed circuit board secured for example to a headband or any head mounted gear. Third wire portion 2064 is secured to body 2002 and remains essentially flat in body 2002. Wire portion 2064 terminates in reading and processing unit 2012 through a fourth wire portion 2065. Wire portion 2065 connects body 2002 to processing circuit and display 2012 which provides processing of the signal and may display the result. Although a 90 degree angle between measuring portion 2006 and arm 2004 comprises the preferred embodiment, it is understood that any angle including a 180 degree angle between measuring portion 2006 and arm 2004 can be used. In an alternative embodiment, the axis of measuring portion 2006 can be parallel to arm 2004 and body 2002, and all three wire portions 2060, 2062 and 2064 of wire 2014 can be disposed within the same plane of sensing device 2000. Thus wire 2014 does not need to have the 90 degree bent for functioning in this alternative embodiment.

Sensor 2010 at the end 2026 of arm 2004 comprises any sensor or detector, or any element, molecule, moiety, or element capable of measuring a substance or analyzing an analyte or tissue. Exemplary sensor 2010 includes electrochemical, optical, fluorescent, infrared, temperature, glucose sensor, chemical sensor, ultrasound sensing, acoustic sensing, radio sensing, photoacoustic, electrical, biochemical, opto-electronic, or a combination thereof in addition to a light source and detector pair, and the like, all of which for the purpose of the description will be referred herein as sensor 2010.

The preferred largest dimension of sensor 2010 is equal to or no greater than 3 cm, and preferably equal to or no greater than 1.5 cm, and most preferably equal to or no greater than 0.5 cm. Preferred dimensions are based on the size of the person or animal. Depending on the size of the person other dimensions of sensor 2010 are contemplated, such as largest dimension equal to or no greater than 0.3 cm, and for adults of small size dimension equal to or no greater than 0.0.2 cm, and for small children dimension equal to or no greater than 0.1 cm and for babies preferred dimension is equal to or no greater than 0.05 cm. If more than one sensor is used the dimensions are larger, and if a molecule or moiety are used as sensing element the dimensions are very small and much smaller than any of the above dimensions.

When sensor 2010 comprises a temperature sensor the preferred largest dimension of the sensor is equal to or less than 5 mm, and preferably equal to or less than 4 mm, and most preferably equal to or less than 3 mm, and even more preferably equal to or less than 2 mm. When the temperature sensor has a rectangular configuration, a preferred width is equal to or less than 1 mm, and preferably equal to or less than 500 microns. Those specialized small dimensions are necessary for proper fitting of the sensor with the thermal structure of the tunnel and the entry point of the BTT.

Sensor 2010 can also comprise a radiation source and radiation detector pair, such as a reflectance measuring system, a transmission measuring system, and/or an opto-electronic sensor. Preferably the distance from the outer edge of radiation source (e.g. light emitter) to the outer edge of detector is equal to or less than 3.5 cm, and more preferably equal to or less than 2.0 cm, and most preferably equal to or less than 1.7 cm, and even most preferably equal to or less than 1.2 cm.

In one embodiment sensor system 2010 can further comprise a temperature sensor and include a heating or a cooling element. It is understood that a variety of sensing systems such as optical sensing, fluorescent sensing, electrical sensing, electrochemical sensing, chemical sensing, enzymatic sensing and the like can be housed at the end of arm 2004 or in measuring portion 2006 in accordance to the present invention. Exemplarily, but not by way of limitation, an analyte sensing system such as a glucose sensing system and/or a pulse oximetry sensor comprised of light emitter (also referred to as light source) and light detector can be housed at the end of arm 2004 and operate as sensor system 2010. Likewise a combination light emitter and photodetector diametrically opposed and housed at the end of arm 2004 to detect oxygen saturation, glucose levels, or cholesterol levels by optical means and the like can be used and are within the scope of the present invention. Furthermore, a radiation detector can be housed at the end of arm 2004 for detecting radiation emitted naturally from the brain tunnel and/or the skin area at the brain tunnel between the eye and the eyebrow or at the roof of the orbit.

Sensor 2010 can be a contact or non-contact sensor. In the embodiment pertaining to a contact sensor, exemplarily illustrated as a thermistor, then arm 2004 is positioned in a manner such that sensor 2010 is laying against the skin at the BTT and touching the skin during measurement. When a non-contact sensor is used, two embodiments are disclosed:

Embodiment No. 1: measuring portion 2006 is spaced away from the skin and does not touch the skin, and both measuring portion 2006 and sensor 2010 housed in the measuring portion 2006 do not touch the skin during measurement. This embodiment is exemplarily illustrated as an infrared detector. This infrared detector is adapted for receiving infrared radiation naturally emitted form the brain tunnel, between the eye and the eyebrow. Exemplarily infrared radiation emitted includes near-infrared radiation, mid-infrared radiation, and far-infrared radiation. The emitted infrared can contain spectral information and/or radiation signature of analytes, said infrared radiation signature being used for noninvasive measurement of analytes, such as glucose. Alternatively, infrared radiation source, including but not limited to, near-infrared or mid-infrared can be used and the near infrared radiation and/or mid-infrared radiation directed at the brain tunnel generates a reflected radiation from the brain tunnel, which is used for non-invasive measurement of an analyte. In addition, any emitted electromagnetic radiation can contain spectral information and/or radiation signature of analytes, said infrared radiation signature being used for noninvasive measurement of analytes, such as glucose, or analyze of tissue.

Embodiment No. 2: sensor 2010 does not touch the skin but walls of a measuring portion 2006, which houses the sensor 2010, touch the skin. In this embodiment, there is a gap or space inside measuring portion 2006 and the skin at the BTT, allowing thus the sensor 2010, which is spaced away from the skin, not to be exposed to air or ambient temperature while still not touching the skin. Accordingly, the sensor 2010 is housed in a confined environment formed by essentially the walls of two structures: the wall of the measuring portion 2006 and the wall formed by the skin at the BTT. This embodiment is exemplarily illustrated as an infrared detector. This infrared detector is adapted for receiving infrared radiation naturally emitted form the brain tunnel. Exemplarily infrared radiation emitted includes near-infrared radiation, mid-infrared radiation, and far-infrared radiation. The emitted infrared can contain the radiation signature of analytes, said infrared radiation signature being used for noninvasive measurement of analytes, such as for example glucose, cholesterol, or ethanol. Alternatively, an infrared radiation source such as near-infrared, mid-infrared, and far-infrared in addition to fluorescent light can be used with said radiation directed at the brain tunnel, which generates a reflected radiation from the brain tunnel, with said reflected radiation containing a radiation signature of an analyte and being used for non-invasive measurement of an analyte. In addition, any source of electromagnetic radiation, any sound generating device, and the like can be housed in a measuring portion.

Sensor 2010 can be covered with epoxi, metal sheet, or other material, and in those embodiments the dimensions in accordance with the invention are the dimension of the material covering sensor 2010.

The preferred largest dimensions for body 2002, illustratively represented by a rectangular plate in FIG. 1B, is equal to or no greater than 18 cm, and preferably equal to or no greater than 10 cm, and most preferably equal to or no greater than 6 cm. The preferred dimensions for plate 2002 for human use are equal to or less than 8 cm in length, equal to or less than 6 cm in width, and equal to or less than 2 cm in thickness. The most preferred dimensions for plate 2002 for human use are equal to or less than 6 cm in length, equal to or less than 4 cm in width, and equal to or less than 1 cm in thickness. Most preferably, the dimensions for plate 2002 are equal to or less than 4 cm in length, equal to or less than 2 cm in width, and equal to or less than 0.5 cm in thickness. Although plate 2002 is shown in a rectangular shape, any other shape or configuration can be used including circular, oval, square, oblong, irregular, and the like. It is also contemplated that dimensions of a housing, such as a box, as described for a headband and in the embodiments of FIGS. 14 to 15Z may have different dimensions. For those embodiments the electronics can be spread along the headband making it very thin. Alternatively if a large number of components is used including Bluetooth transmitters, which are commonly of larger size, larger dimensions are contemplated.

It is understood that plate 2002 can preferably house electronics, microchips, wires, circuits, memory, processors, wireless transmitting systems, light source, buzzer, vibrator, accelerometer, LED, and any other hardware and power source necessary to perform functions according to the present invention. It is also understood that arm 2004 can also house the same hardware as does plate 2002, and preferably houses a LED or lights that are within the field of view of the user, so as to alert the user when necessary. Sensing device 2000 can be powered by a power source housed in the plate 2002. It is understood that sensing device 2000 can be powered by an external power source and that wire 2014 can be connected to said external power source. The external power source can preferably include processing circuit and display.

It is also understood that any support structure, head mounted gear, frame of eyeglasses, headband, and the like can be employed as body 2002, or be coupled to measuring portion 2006, or be connected to arm 2004. When arm 2004 and its sensor 2010 at the end of said arm 2004 is coupled to another support structure, such as frame of eyeglasses, helmet, and the like, the frame of said eyeglasses or said helmet operates as the body 2002, and it is used as the connecting point for arm 2004.

Now in reference to FIG. 1C, the measuring portion 2006, as exemplarily illustrated in FIG. 1C, comprises an essentially cylindrical shape. Measuring portion 2006 preferably comprises a body 2020 and a connecting portion 2011, which connects measuring portion 2006 to arm 2004. Body 2020 has preferably two end portions, namely top end 2016 and a bottom end 2018, said top end 2016 being connected with connecting portion 2011 and arm 2004 and said bottom end 2018 housing sensor 2010. The body 2020 houses wire 2060 for connecting sensor 2010 to a transmitting and/or processing circuit and/or display (not shown). In an embodiment for measuring temperature body 2020 includes a soft portion 2009 which is preferably made with insulating material and said body 2020 has insulating properties. The bottom end 2018 has insulating properties and is void of heat conducting elements such as metal, heat conducting ceramic, and heat conducting gel, heat conducting polymers, and the like. Contrary to the prior art which uses heat conductive material to encapsulate around a temperature sensor in order to increase heat transfer from the article or body being measured, the probe of this invention is void of heat conductive materials.

Body 2020 and connecting portion 2011 can also house electronics, chips, and/or processing circuits. In one embodiment body 2020 includes a soft portion and connecting portion 2011 comprises a hard portion.

For temperature measurement and for monitoring certain biological parameters, measuring portion 2006 preferably includes a non-metallic body 2020, said non-metallic body housing wire portion 2060. In one embodiment for measuring temperature sensor 2010 comprises a temperature sensor and body 2020 preferably comprises insulating material, said insulating material preferably being a soft material and having compressible characteristics. Although compressible characteristics are preferred, it is understood that body 2020 can also comprise rigid characteristics or a combination of rigid and soft portions. Most preferably body 2020 comprises a combination of a rigid part and a soft part, said soft part being located at the free end of body 2020, and which is in contact with a body part, such as of a mammal.

In one embodiment sensor 2010 comprises a pressure sensor or piezoelectric element and operates as a pulse and/or pressure measuring portion. In another embodiment sensor 2010 comprises an electrochemical sensor for measurement of analytes such as glucose. In another embodiment sensor 2010 comprises an ultrasound sensing system. In another embodiment sensor 2010 comprises a photoacoustic sensing system for measurement of chemical substances such as glucose. In another embodiment, sensor 2010 comprises a fluorescent element or fluorescein molecule for evaluating temperature, pressure, pulse, and chemical substances including analytes such as glucose. In another embodiment, sensor 2010 comprises an infrared detector for measuring temperature and/or concentration of chemical substances in blood from radiation naturally emitted from the brain tunnel.

The preferred diameter of measuring portion 2006, illustrated as the diameter of the body 2020, housing a temperature sensor is equal to or no greater than 4 cm, and preferably equal to or no greater than 3 cm, and most preferably equal to or no greater than 2 cm. Depending on the size of the person other even more preferable dimensions for measuring portion 2006 are contemplated, such as diameter equal to or no greater than 1.2 cm, and much more preferably equal to or less than 0.8 cm. For children preferred diameter is equal to or no greater than 0.6 cm, and for babies or small children the preferred diameter is no greater than 0.4 cm. Depending on the size of an animal or person other dimensions for measuring portion 2006 are contemplated, such as diameter equal to or no greater than 5 cm.

When a cylindrical shape is used, the preferred diameter of measuring portion 2006 for chemical or certain physical measurement is no greater than 4 cm, and preferably no greater than 3 cm, and most preferably no greater than 2 cm. The same dimensions apply to a non-cylindrical shape, such as a rectangle, and the preferred length of the rectangle is no greater than 4 cm, and preferably no greater than 3 cm, and most preferably no greater than 2 cm. Depending on the size of the person other even more preferable dimensions for measuring portion 2006 are contemplated, such as a diameter equal to or no greater than 1.2 cm, and much more preferably equal to or no greater than 0.8 cm. For children a preferred diameter is equal to or no greater than 0.7 cm, and for babies or small children the preferred diameter is equal to or no greater than 0.5 cm. Depending on the size of an animal or person other dimensions for measuring portion 2006 are contemplated, such as diameter equal to or no greater than 6 cm.

When a non-cylindrical shape is used, such as a rectangle, the preferred width of measuring portion 2006 is equal to or no greater than 2 cm, and preferably equal to or no greater than 1.5 cm, and most preferably equal to or no greater than 1 cm. Depending on the size of the person other dimensions for measuring portion 2006 are contemplated, such as width equal to or no greater than 0.8 cm and more preferably equal to or no greater than 0.5 cm, and for children width equal to or no greater than 0.4 cm, and for babies or small children the preferred width is equal to or no greater than 0.3 cm. Depending on the size of an animal or person other dimensions for measuring portion 2006 are contemplated, such as width equal to or no greater than 5 cm.

The preferred height (or thickness) of measuring portion 2006, considering a cylindrical shape, is equal to or no greater than 4 cm, and preferably equal to or no greater than 2.0 cm in thickness (or height), and most preferably equal to or no greater than 1.5 cm in thickness (or height), and much more preferably equal to or no greater than 1.3 cm. Depending on the size of the person other dimensions of measuring portion 2006 are contemplated, such as height (or thickness) equal to or no greater than 1.0 cm, and for children thickness (or height), equal to or no greater than 0.8 cm, and for babies or small children equal to or no greater than 0.5 cm. Depending on the size of an animal other dimensions of measuring portion 2006 are contemplated, such as thickness (or height) equal to or no greater than 5 cm. In the case of a measuring portion having a rectangular shape, the thickness or height referred to herein, is replaced by the length of the rectangle, and the above dimensions then are applicable.

The following preferred dimensions in this paragraph pertain to a single sensor, such as a temperature sensor or a pulse sensor or a chemical sensor. In this embodiment the preferred largest dimension of measuring portion 2006 is equal to or no greater than 6 cm, and preferably equal to or no greater than 3 cm, and most preferably equal to or no greater than 1.5 cm. The preferred general dimensions for human use for measuring portion 2006 having a cylindrical shape are height (or thickness) equal to or less than 1.2 cm and diameter equal to or less than 0.8 cm, and most preferably height equal to or less than 1.0 cm and diameter equal to or less than 0.6 cm Preferred length of a non-cylindrical measuring portion 2006 is equal to or less than 1.2 cm and width equal to or less than 0.8 cm, and most preferably length equal to or less than 1.0 cm and width equal to or less than 0.6 cm. The preferred height (or thickness) of measuring portion 2006 ranges between equal to or more than 0.4 cm and equal to or less than 2.0 cm. The preferred diameter of measuring portion 2006 ranges between equal to or more than 0.4 cm and equal to or less than 2.0 cm. Although a temperature sensor was illustrated, it is understood that any sensor can be used. For a pair sensor-detector, a pair light emitter-detector, an infrared sensor, or a sensor and combination with other elements such as a heating element other dimensions can be preferably used, and will be described below.

Measuring portion 2006 can be formed integral with arm 2004 creating a single part consisting of an arm and a measuring portion. Preferably, at least a portion of the material used for measuring portion 2006 is different from the material used for arm 2004. Arm 2004 and measuring portion 2006 preferably comprise two separate parts. In one embodiment for measuring temperature the arm 2004 is made in its majority with an adjustably positionable material such as deformable metal while measuring portion 2006 includes a portion of non-metal materials such as polymers, plastics, and/or compressible materials. The metal portion of arm 2004 can be preferably covered with rubber for comfort. Preferred materials for measuring portion 2006 include foams, rubber, polypropylene, polyurethane, plastics, polymers of all kinds, and the like. Preferably, measuring portion 2006 housing a temperature sensor comprises an insulating material, and includes a compressible material and/or a soft material. Measuring portion 2006 can include any compressible material. Measuring portion 2006 can further include a spring housed in the body 2020. Any other material with spring capabilities can be housed in body 2020 of measuring portion 2006.

Preferably, the end portion 2018 of measuring portion 2006 comprises an insulating material. Preferably the end portion 2018 comprises a non-heat conducting material including non-metallic material or non-metal material. Preferably, the end portion 2018 comprises a soft material including polymers such as polyurethane, polypropylene, Thinsulate, and the like in addition to foam, sponge, rubber, and the like.

The largest dimension of end portion 2018 of measuring portion 2006 is preferably equal to or less than 4 cm, and most preferably equal to or less than 2 cm, and even more preferably equal to or less than 1.5 cm. Accordingly, the dimensions of sensor 2010 preferably follow those dimensions of end portion 2018, said sensor 2010 being of smaller dimension than the dimension of end portion 2018. For the embodiment for measurement of temperature, the largest dimension of end portion 2018 is preferably equal to or less than 1 cm, and most preferably equal to or less than 0.8 cm, and even most preferably equal to or less than 0.6 cm.

Methods and apparatus include measuring portion 2006 touching the body part during measurements or measuring portion 2006 being spaced away from the body part and not touching the body during measurement.

In one preferred embodiment the end portion 2018 of measuring portion 2006 does not have an adhesive surface and the surface around sensor 2010 is also adhesive free. In the prior art, sensors are secured in place by adhesive surfaces, with said adhesive surrounding the sensor. Contrary to the prior art, sensors of the present invention do not have adhesive surrounding said sensors, and said sensors of the present invention are secured in place at the measuring site in the body of a mammal by another structure, such as arm 2004, with the adhesive surface being located away from the sensor surface. Accordingly, in one preferred embodiment of the present invention, the surface of the sensor and the surface of the surrounding material around the sensor is adhesive free.

Now in reference to FIG. 1D, by way of an example, FIG. 1D shows a planar diagrammatic view of an embodiment that includes a body 2002-$a$ shaped as a square, an arm 2004-$a$ shaped in a zig-zag configuration and a measuring portion 2006-$a$ shape as a hexagon. In this embodiment, the height (or thickness) of the measuring portion 2006 (represented herein by the height or thickness of the hexagon 2006-$a$) is of larger dimension than the height or thickness of the arm 2004 (represented herein by the thickness of the zig-zag arm 2004-$a$). The thickness of square body 2002-$a$ is the smallest dimension of said square body 2002-$a$, which is compared to the smallest dimension of the hexagon 2006-$a$, which is the length of said hexagon 2006-$a$ from point (a) to (b). Accordingly, thickness of the square 2002-$a$ (body) is smaller than the length of hexagon 2006-$a$, said hexagon 2006-$a$ representing a measuring portion. The length of arm 2004-$a$ is the largest dimension of arm 2004-$a$, which is compared to the largest dimension of hexagon 2006-$a$, which is the height or thickness of said hexagon 2006-$a$, from point (c) to point (d), as seen in FIG. 1E.

FIG. 1E is a diagrammatic side view of the embodiment of FIG. 1D and illustrates the thickness (or height) of the embodiment of FIG. 1D. Accordingly, as per the principles of the invention, length of the zig-zag arm 2004-$a$, represented by point (e) to (f), is of greater dimension than the thickness of hexagon 2006-$a$, represented by point (c) to (d).

To further illustrate the principles of the invention, FIG. 1F shows an embodiment that includes a body 2002-$b$ shaped as an irregular geometric shape, an arm 2004-$b$ shaped in a triangular configuration and a measuring portion 2006-$b$ shape as a rectangle. The thickness of arm 2004-$b$ is the smallest dimension of arm 2004-$b$, which is compared to the smallest dimension of rectangle 2006-$b$, which is the width of said rectangle 2006-$b$ from point (g) to point (h). Accordingly, as per the principles of the invention, the thickness of the arm 2004-$b$ is equal to or smaller than the width of rectangle 2006-$b$, with said rectangle 2006-$b$ representing a measuring portion.

FIG. 1G is a diagrammatic perspective view of another preferred embodiment showing end portion 2018 of measuring portion 2006 having a light emitter-light detector pair assembly 2030, also referred to as radiation source-radiation detector pair. The end portion 2018 of measuring portion 2006 in this embodiment has preferably a larger dimension than the diameter (or dimension) of body 2020 of said measuring portion 2006. The radiation source-detector pair 2030 is preferably housed in a substantially rigid substrate 2024, such as a plastic plate. Although substrate 2024 can have any shape, exemplarily and preferably substrate 2024 has an essentially rectangular shape. Rectangular plate 2024 houses at least one light emitter 2032 in one side and at least one light detector 2034 on the opposite side. Light emitter 2032 is connected to at least one wire 2036 secured to the body 2020 of measuring portion 2006. Detector 2034 is connected to at least one wire 2038 secured to the body 2020 of measuring portion 2006. Wire 2036, 2038 start at the light-emitter-light detector pair 2030 in plate 2024 and run along the body 2020. Wire 2036 and wire 2038 preferably form a single multi-strand wire 2040 which exit body 2020 at the upper portion 2016 of measuring portion 2006, said wire 2040 being disposed on or within arm 2004, and further disposed on or within body 2002 for connecting light emitter-detector pair assembly 2030 to a processing circuit and display and/or a transmitter 2031. The body 2020 of measuring portion 2006 can preferably comprise a rigid material. The light emitter 2032 and detector 2034 are centrically located in plate 2024 in this illustrative embodiment. It is understood that light emitter 2032 and detector 2034 can be eccentrically located in plate 2024 depending on the anatomic configuration of the subject being measured.

FIG. 1H is a diagrammatic cross-sectional view of a preferred embodiment, and depicts a sensing device 2000 including body 2020 of measuring portion 2006 having on its free end the light source-light detector pair 2030, with light detector 2034 being adjacent to light source 2032. The radiation source-detector pair assembly 2030 is preferably mounted on a substantially rigid holder, such as plate 2024. Plate 2024 can preferably comprise a rigid or semi rigid material to allow stable reflectance measurements. Detector 2034 includes a photodetector adapted to detected radiation, including infrared radiation, received from light source 2032 and can include a printed circuit board. Light source assembly 2032 is adapted to emit radiation, including infrared radiation, directed at the brain tunnel and can include a printed circuit board. Plate 2024 can house a single or a plurality of light sources and a single or a plurality of light detectors. For example, in a pulse oximetry sensor the light source assembly may include a plurality of light sources, such as a red light emitting diode and an infrared light emitting diode. Illustratively plate 2024 is shown housing one light source 2032 in one side and one detector 2034 on the opposite side. Light emitter 2032 is connected to at least one wire 2036 secure to the body 2020 of measuring portion 2006. Detector 2034 is connected to at least one wire 2038 secured to the body 2020 of measuring portion 2006. Body 2020 is shown as an integral part with arm 2004. In this embodiment body 2020 of measuring portion 2006 forms one piece with arm 2004. Wires 2036, 2038 start at the light source-light detector pair assembly 2030 in plate 2024 and run on or within the body 2020. Wire 2036 and wire 2038 preferably form a single multi-strand wire 2040 which exits body 2020 and runs along arm 2004, and is further disposed on or within body 2002. Electric signals are carried to and from the light source and light detector assembly 2030 preferably by the multi-strand electric cable 2040, which terminates at an electrical connector for connection to a processing circuit and display and/or a transmitter (not shown). Wires 2036, 2038, and 2040 can be disposed on or within the measuring portion 2006, arm 2004, or body 2002. Plate 2024 can preferably be adapted to provide protection against light from the environment reaching emitter-detector pair 2030.

Figure 10A:
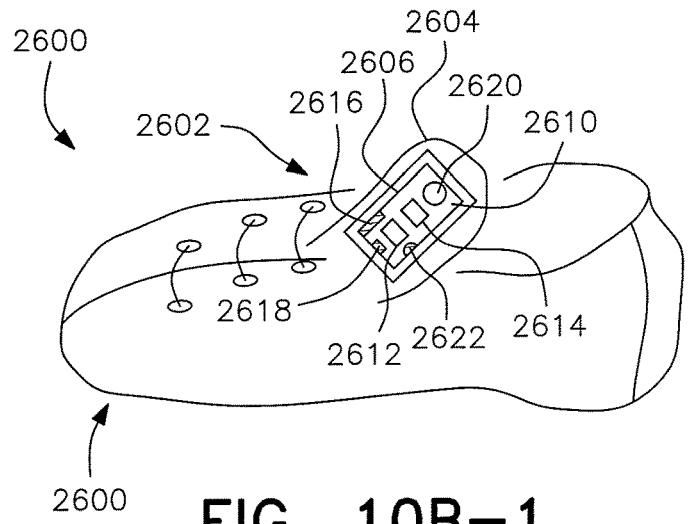
FIG. 10A illustrates a mounting of an alert device on a shoe of a user.
Figures 1, 10B:
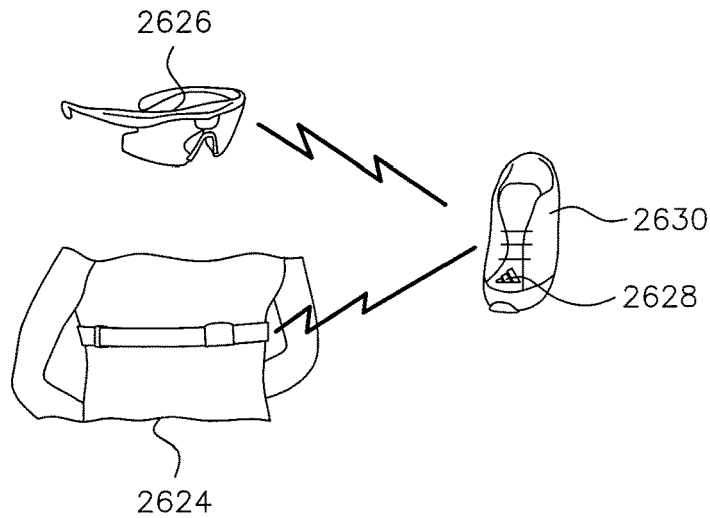
FIG. 10B-1 illustrates the transmission of signals to devices worn by a user.
Figures 2, 10B:
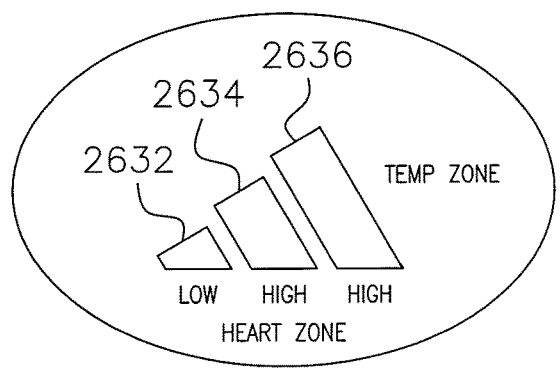

FIG. 1-I is a planar bottom view of plate 2024 showing an exemplary embodiment of said plate 2024. Plate 2024 has preferably two openings 2035, 2033 for respectively housing light emitter 2032 and light detector 2034. Light emitter 2032 and light detector 2034 are preferably disposed adjacent to each other, and in the center of plate 2024. The light source 2032 and light detector 2034 may be encased by a protective transparent material such as silicone.

Although the preferred, embodiment includes an arm 2004 for support structure which works as a sensing device 2000, it is understood that arm 2004 can be replaced by a wire or cord. Accordingly, FIG. 1J shows a diagrammatic planar view of an alternative embodiment comprising an adhesive patch 2025 securing plate 2024, said adhesive patch being connected through cord 2041 to a reading and display unit 2043. The measuring portion in this embodiment comprises an adhesive patch housing a sensor assembly, said adhesive patch connected through a cord to a display unit. Illustratively the sensor or sensing portion in this embodiment is represented by light source-light detector pair 2030. Plate 2024 includes emitter 2032 and detector 2034, respectively connected to wire 2036 and wire 2038. Wire 2036 and 2038 terminates in cord 2041. Cord 2041 houses the wires 2036, 2038, and is preferably flexible in nature. In order to fit the tunnel, and in accordance with the present invention specialized dimensions are needed for functioning. The preferred longest distance between the edge of plate 2024 and adhesive patch 2025 is equal to or less than 12 mm, and preferably equal to or less than 6 mm, and most preferably equal to or less than 3 mm. The largest dimension of patch 2025 is preferably equal to or less than 3 cm and most preferably equal to or less than 2 cm, and even most preferably equal to or less than 1.5 cm. Preferably plate 2024 is located in an eccentric position on adhesive patch 2025.

FIG. 1J shows by way of illustration edge 2023 of plate 2024 and edge 2027 of patch 2025, both located at the free end of the patch 2025 opposite to the cord 2041. Edge 2023 is located preferably equal to or less than 8 mm from the edge 2027 of adhesive patch 2025, and most preferably equal to or less than 5 mm from edge 2027 of adhesive patch 2025, and even more preferably equal to or less than 3 mm from edge 2027 of adhesive patch 2025. Preferred dimensions of the plate 2024 are described in FIG. 1N. A preferred dimension of adhesive patch 2025 includes a width or diameter equal to or less than 25 mm, and preferably equal to or less than 20 mm, and most preferably equal to or less than 15 mm, and even more preferably equal to or less than 10 mm. Those dimensions are preferably used for a centrically placed single sensor, multiple sensors, light emitter-light detector pair, or for an eccentrically placed sensor. The preferred configuration of the adhesive patch is rectangular or oblong, or any configuration in which the sides of the geometric figure are not equal in size. In this embodiment there is no body for the support structure as in the embodiments of FIG. 1H and FIG. 1G. The support structure in this embodiment is comprised of a specialized adhesive patch 2025 connected to a cord 2041, said cord 2041 terminating in a processing circuit and display unit 2043. It is also contemplated that cord 2041 can exit patch 2025 from any of its sides FIG. 1K shows another embodiment when worn by a user comprised of an adhesive patch 2060 housing a light emitter-light detector pair 2062, which is housed in a holder such as plate 2064, said plate 2064 being adjacent to the edge of said adhesive patch 2060. At least one portion of adhesive patch 2060 and the light emitter-light detector pair 2062 is located between the eyebrow 2066 and eye 2068. At least a sensor such as light emitter-light detector pair 2062 is located between the eye 2066 and the eyebrow 2068. Adhesive patch 2062 can include a forehead portion 2070 located on the forehead and an upper eyelid portion 2072 located on the upper eyelid. Any sensor including a pair light emitter-light detector is preferably positioned adjacent to the junction 2074, said junction representing a junction of the end of the eyebrow 2066 with the upper portion of the nose 2075, said junction 2074 represented as a dark circle in FIG. 1K. A sensor housed in the adhesive patch is preferably located in the roof of the orbit area, right below the eyebrow. Adhesive patch 2060 further includes wire 2076 which terminates in a processing circuit and display unit 2078.

FIG. 1L shows another embodiment when worn by a user comprised of an adhesive patch 2080 housing light emitter-light detector pair 2082, said emitter and detector 2082 being located apart from each other, and adjacent to edge 2084 of said adhesive patch 2080. At least one portion of adhesive patch 2080 and a sensor such as the light emitter-light detector pair 2082 is located between the eyebrow 2086 and eye 2088. At least light emitter-light detector pair 2082 is located between the eye 2086 and the eyebrow 2088. Adhesive patch 2080 comprises a nose portion 2090 located on the nose and an upper eyelid portion 2092. Any sensor including a pair light emitter-light detector is preferably positioned adjacent to the eyebrow 2086. The sensor housed in the adhesive patch is preferably located above the eye 2088 and just below the eyebrow 2086. Adhesive patch 2080 further includes wire 2094 which terminates in a processing circuit and display unit 2096, which processes the signal in a conventional manner to detect oxygen saturation and/or concentration of analytes.

FIG. 1M shows another embodiment comprised of a clover-leaf adhesive patch 2100 housing light emitter-light detector pair 2102 housed in plate 2104, and preferably adjacent to edge 2106 of said adhesive patch 2100. Adhesive patch 2100 comprises a sensing portion 2108 housing plate 2104 and a supporting portion 2110 that includes an adhesive surface. Emitter-detector pair 2102 is preferably eccentrically positioned on patch 2100 and further includes wire 2113 from light emitter 2114 and wire 2116 from detector 2118. Wires 2113 and 2116 join at the edge of plate 2104 to form cord 2112 which terminates in unit 2120 which houses processing circuit 2124, memory 2126, and display 2122.

Light emitter 2114 preferably emits at least one infrared wavelength and a detector 2118 is adapted to receive and detect at least one infrared wavelength. Light emitter-detector pair 2102 is preferably eccentrically positioned in adhesive patch 2100, said light emitter-detector pair 2102 being located at the edge of patch 2100. Imaginary line from point (A) to point B going across plate 2104 on adhesive patch 2100 housing light emitter-detector pair 2102 measures equal to or less than 3.0 cm, and preferably measures equal to or less than 2.0 cm, and most preferably equal to or less than 1.5 cm. The preferred distance of external edge 2103 of light emitter-detector pair 2102 to the edge 2105 of patch 2100 is less than 14 mm, and preferably less than 10 mm and most preferably less than 5 mm.

Another embodiment includes an adhesive patch housing a sensor comprised of an adhesive surface intersected by a non-adhesive surface. Accordingly, 1M(1) shows the back side of adhesive patch 2131, said side being disposed toward the skin and in contact with the skin, and comprised of a first adhesive surface 2121, a second non-adhesive surface 2123, and a third adhesive surface 2125 which houses the sensor 2127. The adhesive surface is intersected by a non-adhesive surface. The non-adhesive surface 2123 is adapted to go over the eyebrow, preventing the adhesive from attaching to hair of the eyebrow.

FIG. 1N is another embodiment showing the configuration and dimensions of light emitter-detector pair 2130 and plate 2136. Light emitter 2132 and detector 2134 are disposed preferably as a pair and are positioned side-by-side for reflectance measurements. The preferred dimension of light emitter 2132 is no greater than 1.5 cm in its largest dimension and preferably no greater than 0.7 cm, and most preferably no greater than 0.5 cm, and even most preferably equal to or less than 0.4 cm. The preferred dimension of detector 2034 is equal to or no greater than 1.5 cm in its largest dimension and preferably equal to or no greater than 0.7 cm, and most preferably equal to and no greater than 0.5 cm, and even most preferably equal to or less than 0.4 cm. The preferred distance between inner edge 2138 of light emitter 2132 and the inner edge 2140 of detector 2134 is equal to or less than 0.7 cm, and preferably equal to or no greater than 0.5 cm, and most preferably equal to or no greater than 0.25 cm. It is understood that to better fit the anatomic configuration of the brain tunnel for a vast part of the population, light emitter 2132 and detector 2134 are preferably disposed side-by-side and the distance between the inner edge 2138 of light emitter 2132 and inner edge 2140 of detector 2134 is preferably equal to or no greater than 0.1 cm.

Although a pair radiation emitter-detector has been described, it is understood that another embodiment includes only a radiation detector and the measuring portion 2006 is comprised of a radiation detector for detecting radiation naturally emitted by the brain tunnel. This embodiment can include a infrared detector and is suitable for non-invasive measurement of analytes including glucose as well as temperature, with detector adapted to contact the skin or adapted as non-contact detectors, not contacting skin during measurement.

FIG. 1P shows another embodiment comprised of an essentially cylindrical measuring and sensing portion 2150. Cylindrical structure 2150 operates as the measuring portion and houses a emitter-detector pair 2152 and a wire portion 2153, with said measuring portion 2150 being connected to arm 2154. Arm 2154 comprises an adjustably positionable arm which houses wire portion 2155. Arm 2154 is preferably cylindrical contrary to arm 2004 which has preferably a flat configuration. Arm 2154 connects measuring portion 2150 to supporting portion 2151 which includes adhesive and/or attachment means. Light emitter 2156 and light detector 2158 are preferably positioned adjacent to each other within the holder 2150, represented by cone structure. Light emitter-detector pair 2152 can preferably have a bulging portion, which goes beyond the plane of the edge 2162 of cylindrical measuring portion 2150. Cylindrical measuring portion 2150 can also include a spring 2160, or any other compressible material or material with spring-like characteristics, said spring 2160 or compressible material being disposed along wire portion 2153. Light emitter-detector pair 2152 is disposed at the free end of said spring 2160. It is understood that any sensor, molecule, detector, chemical sensors, and the like can be disposed at the free end of spring 2160. Wire portion 2155 terminates in wire portion 2149 disposed on or within body 2151. Body 2151 can include any support structure, preferably a plate such as shown in FIG. 1A, as well as the frame of eyewear, a headband, the structure of a helmet, the structure of a hat, or any head mounted gear. Wire 2149 can be further connected to a processing circuit and display 2147.

Preferred diameter at the free end of measuring portion 2150 is equal to or no greater than 3.5 cm, and preferably equal to or no greater than 2.0 cm, and most preferably equal to or no greater than 1.5 cm, and even most preferably equal to or no greater than 1.0 cm. Depending on size of a subject and the type of sensor such as temperature, pressure, and the like the preferred diameter at the free end of measuring portion 2150 is equal to or no greater than 0.8 cm and preferably equal to or no greater than 0.6 cm, and more preferably equal to or no greater than 0.4 cm. Preferred length from point 2150(*a*) to point 2150(*b*) of measuring portion 2150 is equal to or no greater than 3 cm, and preferably equal to or no greater than 1.5 cm, and most preferably equal to or no greater than 1 cm. Depending on size of a subject the preferred length from point 2150(*a*) to point 2150(*b*) of cone structure 2150 is equal to or no greater than 0.8 cm and preferably equal to or no greater than 0.6 cm, and more preferably equal to or no greater than 0.4 cm. Measuring portion 2150 can include a contact sensor in which the sensor contacts the skin at the brain tunnel or a non-contact sensor in which the sensor does not contact the skin at the brain tunnel during measurement.

FIG. 1P(1) is an exemplary sensing device 2191 for non-contact measurements at the brain tunnel 2187 and shows sensing portion 2181 housing a sensor illustrated as an infrared sensor 2183 to detect infrared radiation 2185 coming from the brain tunnel 2187. Sensing portion 2181 housing sensor 2183 is connected to body 2193 through adjustably positionable arm 2189. Wire 2195 connects sensor 2183 to body 2193. Sensor 2183 can include any infrared detector, and is adapted to receive and detect infrared radiation from the brain tunnel 2187 for determining temperature, concentration of substances including glucose, and any other measurement of analytes or tissue. Sensor 2183 can also work as a fluorescent sensor, and may include a fluorescent light source or fluorescein molecules. Furthermore, sensor 2183 can include enzymatic sensors or optical sensors.

FIG. 1P(2) is an exemplary sensing device 2197 for non-contact measurements at the brain tunnel 2187 and shows sensing portion 2199 housing a light source-light detector pair assembly 2201, such as an infrared sensor or a fluorescent element. It is contemplated that any electromagnetic radiation including radio waves can be directed at the brain tunnel for determining concentration of analytes and/or presence of analytes and/or absence of analytes and/or evaluating tissue. Light source 2203 directs radiation 2207 such as mid-infrared and/or near-infrared radiation at the brain tunnel 2187 which contains molecules 2205 (including analytes such as glucose), said radiation 2207 generating a reflected radiation that contains the radiation signature of the analyte being measured after said radiation 2207 interacts with the analyte being measured. The reflected radiation 2209 is then detected by detector 2211. The electrical signal generated by the detector 2211 is then fed to a processing circuit (not shown) housed in body 2217 through wire 2213 housed in arm 2215. Sensing portion 2199 housing pair assembly 2201 is preferably connected to body 2217 through an adjustably positionable arm. Detector 2211 can include any infrared detector, and is adapted to receive and detect infrared radiation from the brain tunnel 2187 for determining temperature, concentration of substances including glucose, and any other measurement of analytes or tissue. Detector 2211 can also work as a fluorescent detector for detecting fluorescent light generated.

FIG. 1P(3) is an exemplary hand-held sensing device 2219 for non-contact measurements at the brain tunnel 2187 and shows a light source-light detector pair assembly 2221. Light source 2223 directs radiation 2225 at the brain tunnel 2187 which contains molecules 2205 (including analytes such as glucose), said radiation 2225 generating a reflected radiation 2227 that contains the radiation signature of the analyte being measured after said radiation 2225 interacts with the analyte being measured. The reflected radiation 2227 is then detected by detector 2231. The electrical signal generated by the detector 2231 is then fed to a processing circuit 2233 which calculates the concentration of an analyte based on a calibration reference stored in memory 2235, and display said concentration on display 2237. It is understood that instead of a pair light source-light detector, a stand alone detector for detecting infrared radiation naturally emitted from the brain tunnel can also be used. It is also understood that sensing device 2219 can preferably include a mirror 2229, so as to allow the user to proper position the pair assembly 2221 in line with the skin of the BTT 2187 at the eyelid area. It is contemplated that sensing device 2219 can comprise a mirror in which electronics, display, and pair assembly 2221 are mounted in said mirror, allowing thus measurement of temperature and concentration of analytes being performed any time the user look at the mirror. It is understood that any of the embodiments of the present invention can include a mirror for accurate measurements and proper alignment of a sensor with the BTT.

FIG. 1P(4) is an exemplary sensing device 2239 for non-contact measurements at the brain tunnel 2187, said sensing device 2239 mounted on a support structure 2267, such as a wall or on an article of manufacture or an electronic device including a refrigerator, a television, a microwave, an oven, a cellular phone, a photo camera, video camera, and the like. In this embodiment just performing routine activities such as opening a refrigerator door allows the user to check core temperature, measure glucose, check for cancer markers, and the like. The spectral information contained in the radiation from the brain tunnel is captured by a sensor slidably located on those electronic devices and articles to align with different height individuals. To better align the brain tunnel area 2187 with the sensing device 2239, a light source 2241, such as LED or other confined light source is used. When the eye 2243 of the user is aligned with the light 2241 projecting from a tube or other light path confining or constricting device, the BTT area is aligned with the light source-light detector pair 2251 located at a predetermined distance from the eye. Light source 2253 directs radiation 2255 at the brain tunnel 2187 which contains molecules 2205 (including analytes such as glucose, cholesterol, ethanol, and the like), said radiation 2255 generating a reflected radiation 2257 that contains the radiation signature of the analyte being measured. The reflected radiation 2257 is then detected by detector 2259. The electrical signal generated by the detector 2259 is then fed to a processing circuit 2261 which is operatively coupled with memory 2263, and display 2265. It is understood that an iris scanner, a retinal scanner, or the like or any biometric device such as finger print detectors or camera-like device can be coupled with sensing device 2239. In this embodiment, the pair light source-light detector is preferably replaced by a detector such as for example a thermopile or array of thermopile as previously described in the present invention. Accordingly, light source 2241 can include or be replaced by an iris scanner which identifies a person while measuring the person's core body temperature. This embodiment can be useful at port of entries such as airports in order to prevent entry of people with undetected fever which could lead to entry of fatal disorders such as SARS, bird flu, influenza, and others. The temperature of the person, measured by the sensor aimed at the BTT, is coupled to the identity of the person acquired through the iris scanning, with said data temperature-iris scan being stored in a memory. The system may include a digital camera, allowing a picture of the person being coupled with the body core temperature and the iris scan. A processor identifies whether the temperature is out of range, and activates an alarm when fever is detected. The system allows measurement of temperature and concentration of analytes being performed any time the user look at the iris scanner.

It is understood that a sensor for detecting radiation or capturing a signal from the brain tunnel can be mounted on any device or article of manufacturing. Accordingly and by way of further illustration, FIG. 1P (5) shows a sensing device 2273 including a sensor 2269 mounted on a web-camera 2271 which is secured to a computer 2275 for measurements of radiation from the brain tunnel 2187, said sensing device 2273 having a cord 2277 which is connected to computer 2275 and carries an electrical signal generated detector 2269, with the electrical signal being fed into the computer 2275. In this embodiment, the processor, display and other electronics are housed in the computer. Any time a user looks at the web-camera, measurement of body temperature and/or determination of concentration of analyte can be accomplished.

FIG. 1Q is a side cross-sectional view of sensing device 2000 showing in detail measuring portion 2006. Measuring portion 2006, as illustrated, includes two portions, external part 2162 and internal part 2164, said parts 2162, 2164 having different diameters. Measuring portion 2006 is comprised preferably of a two level (or two height structure) 2163. The external part 2162 has a larger diameter as compared to the internal part 2164. The height (or thickness) of internal part 2164 is of greater dimension than the height (or thickness) of external part 2162. Each part, external part 2162 and internal part 2164, has preferably a different thickness (or height). External part 2162 and internal part 2164 connect to free end 2165 of arm 2161, said arm 2161 terminating in body 2159.

Measuring portion 2006 has an essentially circular configuration and has a wire portion 2166 disposed in the internal part 2164. External part 2162 can comprise a washer or ring around internal part 2164. Internal part 2164 has preferably a cylindrical shape and houses wire portion 2166 inside its structure and houses sensor 2170 at its free end. Wire portion 2166 terminates in wire portion 2167 secured to arm 2161. Although a circular configuration is shown, any other shape or combination of shapes is contemplated.

FIG. 1Q(1) is a perspective diagrammatic view of measuring portion 2006 of FIG. 1Q showing two tiered external part 2162 and internal part 2164, said internal part 2164 housing wire 2166 which terminates in sensor 2170. In order to fit the brain tunnel, specialized geometry and dimensions are necessary. The preferred diameter (or length incase of a non-circular shape) of part 2162 is equal to or no greater than 3.0 cm, and preferably equal to or no greater than 1.5 cm in diameter or length, and most preferably equal to or no greater than 1.0 cm in diameter or length. For a non-circular configuration that includes a width, the preferred width of part 2162 is equal to or no greater than 3.0 cm, and preferably equal to or no greater than 2.0 cm in width, and most preferably equal to or no greater than 1.0 cm in width. The preferred height (or thickness) of part 2162 is equal to or no greater than 3.5 cm, and preferably equal to or no greater than 2.5 cm in thickness, and most preferably equal to or no greater than 1.5 cm in thickness, and much more preferably equal to or no greater than 0.5 cm in thickness. The preferred largest dimension of part 2162 is no greater than 3.5 cm, and preferably no greater than 2.0 cm, and most preferably no greater than 1.5 cm.

Part 2164 has preferably an essentially cylindrical configuration, although any other configuration or geometry is contemplated and can be used in accordance with the invention. The preferred diameter of part 2164 is equal to or no greater than 3.0 cm, and preferably equal to or no greater than 2.0 cm in diameter or length, and most preferably equal to or no greater than 1.0 cm. For a non-circular configuration that includes a width, the preferred width of part 2164 is equal to or no greater than 3.0 cm, and preferably equal to or no greater than 1.5 cm in width, and most preferably equal to or no greater than 1.0 cm in width. The preferred height (or thickness) of part 2164 is equal to or no greater than 3.5 cm, and preferably equal to or no greater than 2.5 cm, and most preferably equal to or no greater than 1.0 cm, and much more preferably equal to or no greater than 0.7 cm. The preferred largest dimension of part 2164 is no greater than 3.5 cm, and preferably no greater than 2.0 cm in diameter or length, and most preferably no greater than 1.5 cm.

For temperature monitoring, preferably, part 2162 and part 2164 are made with an insulating material such as polyurethane, polypropylene, thinsulate, and the like, however, other materials are contemplated, including other polymers, foams, and the like. Part 2162 and part 2164 preferably comprise a compressible material for certain applications.

FIG. 1R shows a diagrammatic perspective view of sensing device 2000 including plate 2180, said plate 2180 having preferably a soft and flexible portion 2172, such as a pad, for cushion, said pad including foam, silicone, polyurethane, or the like, with said soft portion 2172 having an adhesive surface 2174 which is covered by a peel back cover 2176. When in use the cover 2176 is removed by pulling tab 2175, and the adhesive surface 2174 is applied to the skin, preferably on the skin of the forehead or any other part of the face and head, but any other body part is suitable and can be used to secure securing plate 2180. Plate 2180 further comprises preferably an essentially semi-rigid portion 2281, said semi-rigid portion 2281 being connected to soft portion 2172. Semi-rigid portion 2281 can preferably comprise a thin metal sheet such as a metal with memory shape as steel. Semi-rigid portion 2281 can also include plastics and polymers. It is understood that preferably said semi-rigid portion 2281 has flexible characteristics to conform to a body part. Although semi-rigid portion 2281 is disclosed as a preferred embodiment, alternatively, plate 2180 can function only with soft portion 2172.

Rigid portion 2281 of plate 2180 continues as arm 2184, said arm 2184 having a free end 2188 which connects to measuring portion 2186. Measuring portion 2186 includes sensor 2190, said sensor 2190 is preferably disposed as a bulging portion. During use the method includes the steps of, applying plate 2180 to the skin, bending arm 2184 to fit with the particular anatomy of the user and for positioning the sensor 2190 on or adjacent to the skin of the BTT or other tunnels of the invention. Other steps include measuring an analyte or analyzing a tissue, producing a signal corresponding to the measurement and analysis, and reporting the results. Further steps can include processing the signal and displaying the result in alphanumerical format, audible format, a combination thereof and the like. A further step can include transmitting the signal to another device using a wireless or wired transmitter. The step of chemical measuring an analyte can be replaced by measuring a physical parameter such as temperature, pulse, or pressure.

FIG. 1R(1) shows a schematic view of sensing device 2289 when worn by a user 2293 and including a headband 2283 around the forehead, said headband 2283 attached to plate 2291, said plate 2291 having arm 2285 and a sensor 2287 which receives radiation from the brain tunnel 2187.

FIG. 1R(2) shows a schematic view of sensing device 2295 having a swivel mechanism 2297 at the junction of arm 2299 and body 2301, said swivel mechanism allowing rotation and motion of arm 2299 (represented by broken arrows) for positioning sensor 2303 on or adjacent to a brain tunnel. Sensor 2303 is illustrated as a light source-detector pair, with wire 2305 connecting said sensor 2303 to a processing and display unit 2307.

FIG. 1R(3) shows the embodiment of FIG. 1R(2) when worn by a user 2309, and depicting light source-detector pair 2303 positioned on the brain tunnel 2187. Body 2301 is secured to the forehead 2311 preferably by adhesive means 2313 disposed at the inner surface of body 2301, said body 2301 connected to arm 2299 by swivel mechanism 2297, which is preferably positioned over the eyebrow.

FIG. 1S(1) shows a side view of sensing device 2000 including wire 2198 which is disposed flat and without any bending, and runs from sensor 2210 in measuring portion 2196 to body 2192. Measuring portion 2196 is aligned with arm 2194 and body 2192. In this embodiment, the axis of measuring portion 2196 is in line with arm 2194, and forms a 180 degree angle. During fabrication the 180 degree angle configuration and flat shape is obtained. During use, in accordance with the method of the invention, the arm 2194 is bent. Since arm 2194 is flexible and adjustably positionable, during use arm 2194 is bent for positioning measuring portion 2196 in line with the brain tunnel.

Accordingly, FIG. 1S(2) shows sensing device 2000 worn by a user with arm 2194 bent in order to position sensor 2210 of measuring portion 2196 on or adjacent to brain tunnel area 2214 between the eyebrow 2212 and eye 2216. Wire 2198 connects sensor 2210 to body 2192, said body 2192 being preferably secured to the forehead.

Sensing device 2000 can be powered by active power including batteries secured to body 2002, solar power, or by wires connecting sensing device 2000 to a processing unit. It is also understood that any of the sensors housed in an adhesive patch or housed in support structure 2000 can operate on a passive basis, in which no power source is housed in said sensor system. In the case of passive systems, power can be provided remotely by electromagnetic waves. An exemplary embodiment includes Radio Frequency ID methodology, in which a nurse activates remotely the patch or sensor system 2000 of the present invention which then reports back the identification of the patient with the temperature being measured at the time of activation. The sensor system can also include a transponder which is powered remotely by a second device, which emits a radio signal or any suitable electromagnetic wave to power the sensor system. Besides temperature, any other biological parameter can be measured such as pulse, blood pressure, levels of chemical substances such as glucose, cholesterol, and the like in addition to blood gases, oxygen levels, oxygen saturation, and the like.

It is yet understood that arm 2004 connected to measuring portion 2006 can be detachably connected to plate 2002, with said arm 2004 and measuring portion 2006 becoming a disposable part while plate 2002, which preferably houses expensive wireless transmitter and other electronics and power source, works as the durable part of the device 2000. It is also understood that measuring portion 2006 can be detachably connected to arm 2004, said measuring portion 2006 being disposable. It is yet understood that the free end of measuring portion 2006 can be connected to a wire inside body 2020 of measuring portion 2006, said free end housing sensor 2010 being the disposable part. It is also contemplated that the present invention is directed to a method and apparatus in which the disposable part is the body 2002 and the durable reusable part is the measuring portion 2006 and arm 2004. In this embodiment an expensive sensor such as an infrared detector can be disposed in the measuring portion 2006, and is detachably connected to plate 2002, said sensor being the reusable part while the body 2002 being the disposable part. Accordingly, FIG. 1T(1) shows sensing device 2000 including arm 2004, measuring portion 2006 with sensor 2010, and plate 2002, said plate 2002 housing a circuit board 2200 including a processor 2222 operatively coupled to a memory 2228, power source 2224, and transmitter 2226. Wire 2220 connects sensor 2010 to circuit board 2200.

FIG. 1T(2) shows an exemplary embodiment of sensing device 2000 comprised of two separable pieces including a durable part 2230, represent by the body, and a disposable part 2232, represented by the arm and measuring portion. It is understood that sensing device can comprise one or more parts and a combination of durable and disposable parts. Accordingly, in FIG. 1T(2) there is seen durable part 2230 represented by plate 2002, said plate 2002 having a circuit board 2200 including processor 2222 operatively coupled to a memory 2228, power source 2224, and transmitter 2226. Disposable part 2232 comprises arm 2204 and measuring portion 2006. Plate 2002 has an electrical connector 2234 which is electrically and detachably connected to an electrical connector 2236 of arm 2004, preferably creating a male-female interface for electrical connection in which wire 2220 of arm 2004 ends as a male connector 2236 adapted to connect to a female connector 2234 of plate 2002.

FIG. 1T(3) shows an exemplary embodiment of sensing device 2000 comprised of two separable pieces including a durable part 2240 further comprised of arm 2004 and plate 2002 and a disposable part 2242 comprised of measuring portion 2006, said measuring portion 2006 including a light emitter-light detector pair 2244. Arm 2004 has an electrical connector 2246 which is electrically and detachably connected to an electrical connector 2248 of measuring portion 2006.

It is contemplated that durable part represented by plate 2002 can comprise power source and a LED for alerting changes in the biological parameter being measured or to identify that the useful life of the device has expired. Plate 2002 can also house a power source and a wireless transmitter, or a power source and a display for numerical display, or/and a combination thereof. Alternatively plate 2002 works as a passive device and comprises an antenna and other parts for electromagnetic interaction with a remote power source. Another embodiment includes a passive device or an active device comprised of a patch having a sensor and a LED, said LED being activated when certain values are detected by the sensor, allowing a nurse to identify for example a patient with fever by observing a patch in which the LED is on or flashing.

Any biological parameter and tissue can be measured and/or analyzed at the brain tunnel including temperature, concentration of chemical substances, blood pressure, pulse, and the like. Exemplarily a blood gas analyzer and a chemical analyzer will be described. The embodiment relates to a device for the transcutaneous electrochemical or optical determination of the partial pressure of oxygen and/or analytes in the blood of humans or animals at the Brain Temperature Tunnel (BTT) site, also referred to as brain tunnel (BT). The invention comprises a measuring portion 2006 which includes a measuring cell having electrodes, said cell having a surface which is to be disposed in contact with the skin at the BTT. The cell in measuring portion 2006 can include a heating or a cooling element for changing the temperature of the brain tunnel. Preferably the measuring portion 2006 includes an electrical heating element. Besides contacting the skin, the measuring surface of measuring portion 2006 can be spaced away from the skin at the brain tunnel for measuring analytes and the partial pressure of oxygen.

For measurement of oxygen the measuring portion 2006 preferably includes a Clark type sensor, but it is understood that any electrochemical or optical system can be used in accordance with the present invention and fall within the scope of the present invention. Various sensors, electrodes, devices including polarygraphic sensors, enzymatic sensors, fluorescent sensors, optical sensors, molecular imprint, radiation detectors, photodetectors, and the like can be used.

In one preferred embodiment, the measuring portion 2006 includes an element to increase blood flow, such as by way of illustration, a heating element, a suctioning element, or fluid that increases permeability of skin. Preferably a heating element is provided, whereby the sensing surface (or measuring surface) of the measuring portion 2006 is adapted to increase the temperature of the skin at the brain tunnel. This heating element increases blood flow to the entrance of the BT and accelerates the oxygen diffusion through the skin at the BT. The measuring portion 2006 is preferably located in apposition to the BT zone associated with the arterial supply and the orbital artery or any of the arterial branches located in the BT area, in order to achieve ideal measurement of the arterial oxygen and the arterial partial oxygen pressure. The transcutaneously measured oxygen pressure on the skin at the entrance of the BT is obtained by placing a specialized measuring portion 2006 of special geometry and dimensions on the skin at the BTT, in accordance with the present invention and the specialized dimensions and shape of the sensor and support structures as described herein.

In arterial blood an equilibrium exists between the percentage of oxidized hemoglobin and the partial oxygen pressure. When the blood is heated, this equilibrium is shifted so that the partial oxygen pressure increases. Therefore, when the BT method is used, the partial oxygen pressure in the peripheral blood vessels in the BT is higher than in the arteries. The oxygen coming from the arterial region of the BT diffuses through the skin at the BTT.

With exception of the skin at the BT, the skin cells in the whole body consume oxygen during diffusion of oxygen through the skin, because said skin is thick and has a thick underlying layer of subcutaneous tissue (fat tissue). Thus, the oxygen pressure at the area of the epidermis in all areas of the body, with exception of the BT area, is much lower than the actual oxygen pressure in the peripheral blood vessels. However, in the specialized skin areas of the BT the oxygen levels remain stable since the skin at the BT is the thinnest skin in the whole body and free of adipose (fat) tissue.

The specialized skin area of the BT between the eyebrow and the eye, at the roof of the orbit shown in FIG. 1U has stable levels of chemical substances including oxygen, glucose, blood gases, drugs and analytes in general. In FIG. 1U there is seen the BT area 2260 which includes the upper eyelid area 2250 and the roof of the orbit area 2252 located right below the eyebrow 2254, and above the eye 2256. The BT area 2260 is located below the eyebrow 2254, and between the eyebrow 2254 and the eye 2256, with the nose 2258 forming another boundary of the BT area. Accordingly, FIG. 1U shows a first boundary formed by the eyebrow 2254, a second boundary formed by the eye 2256, and a third boundary formed by the nose 2258, with the main entry point 2262 of the BT located at the roof of the orbit, in the junction between the nose 2258 and the eyebrow 2254. A second physiologic tunnel is located in the area adjacent to the lower eyelid extending 10 mm below from the edge of the lower eyelid, however, the most stable area for measuring biological parameters comprises the BT area 2260 with the main entry point 2262 at the roof of the orbit 2252 below the eyebrow 2254. In the BT area the blood gas, such as oxygen, and other molecules including glucose remains stable.

Since consumption of oxygen is proportional to the thickness of the skin and of subcutaneous tissue (which contains the fat tissue), and further considering that the BT, as described above and surrounding physio-anatomic tunnels disclosed in the present invention have very thin skin and no subcutaneous tissue, the amount of oxygen at the epidermis (skin) at the entrance of said tunnels is not reduced, and remains proportional to the amount present in the peripheral blood vessels. Thus, the amount of gases such as oxygen, carbon dioxide, and other gases as well as analytes present in the skin of the BTT is proportional to the amount present in blood.

Another advantage of the present invention is that the heating element does not need to reach high levels of temperature, such as 44 degrees C., since the tunnel area is extremely vascularized and associated with a unique blood vessel which is terminal (which means that the total amount of blood is delivered to the site) in addition to having the thinnest skin interface in the whole body, thereby allowing a lower temperature of a heating element to be used for increasing blood flow to the area. The preferred temperature of the heating element is equal to or less than 44 degrees Celsius, and preferably equal to or less than 41 degrees Celsius, and most preferably equal to or less than 39 degrees Celsius, and even most preferably equal to or less than 38 degrees Celsius.

The electrochemical sensor of the measuring portion 2006 for blood gas and glucose analysis has the same specialized dimensions and shape described for the other sensors of the invention, in accordance with the present invention and specialized anatomy of the BT and other surrounding tunnels. The device includes a measuring portion 2006 having a sensor, said sensor preferably being an electrochemical or optical sensor, and an associated heating element of specialized dimensions, with said measuring portion 2006 located adjacent to the BT or on the skin at the BT or other described tunnels of the invention. One of the objects of the invention includes providing a device of the described kind to be used at the BT for measurement of the arterial oxygen pressure and other blood gases such as carbon dioxide, carbon monoxide, anesthetic gases, and the like.

Figure 2:
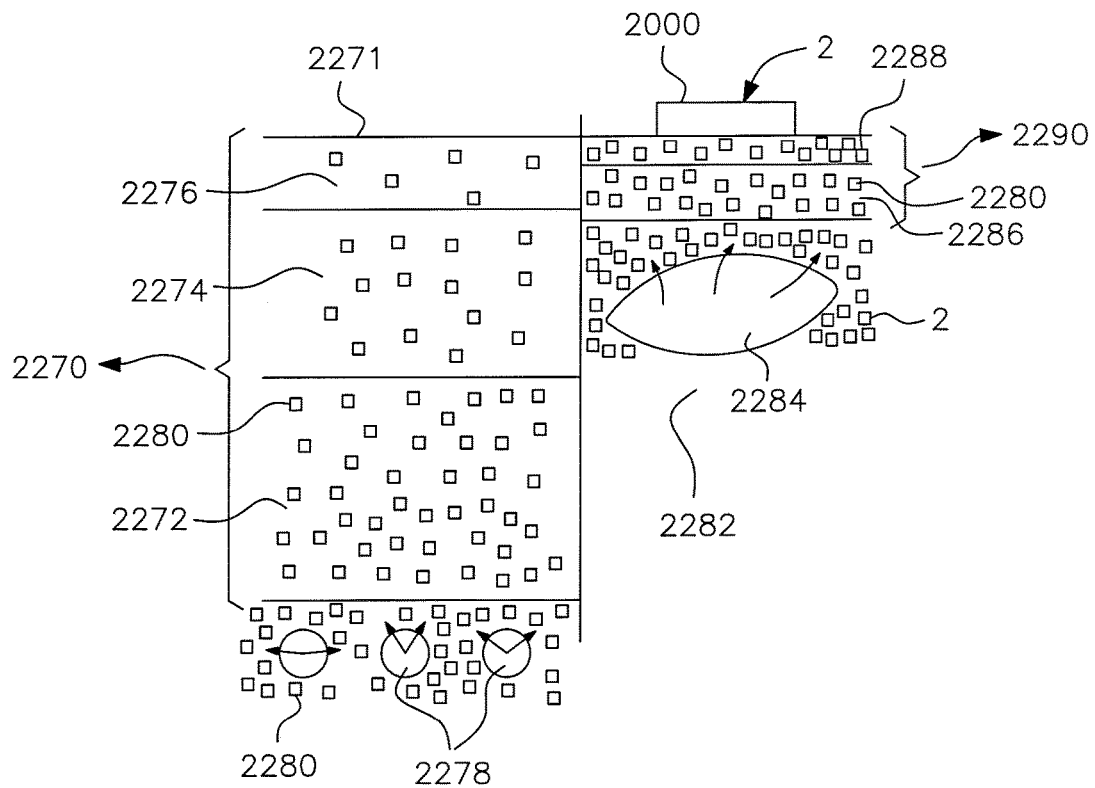
FIG. 2 schematically illustrates a comparison between trans-subcutaneous measurements of the arterial oxygen pressure as previously known and as measured by the present invention.

FIG. 2 illustrates a comparison between transcutaneous measurement of the arterial oxygen pressure in the prior art and the present invention. FIG. 2 shows the skin 2270 with its three thick layers, which is present in the whole body. Methods of the prior art use this skin 2270, which has several thick layers, namely subcutaneous tissue (fat tissue) 2272, thick dermis 2274, and thick epidermis 2276. Underneath this thick skin tissue 2270 there are small blood vessels 2278. Oxygen represented by small squares 2280 diffuses through the walls of the small blood vessels 2278, as indicated by the two small arrows in each blood vessel 2278. Contrary to the thick and multilayered skin 2270 present in other parts of the body, which comprised the method used by the prior art, the method and apparatus of the present invention uses specialized skin 2290 at the BT 2282, which has a large vascular bed 2284, no fat issue, a thin dermis 2286, and thin epidermis 2288. A large blood vessel and large vascular bed 2284 present in the brain tunnel provides more stable and more accurate level of molecules and substances such as oxygen level as well as the level of other blood substances such as glucose. Contrary to the method of the prior art which tried to measure substances in areas subject to vasoconstriction and subject to the effect of drugs, the present invention teaches device and methods using a vascular bed 2284 at the brain tunnel that is not subject to such vasoconstriction.

Skin 2270 of the prior art is thick and has a thick subcutaneous layer 2272 in comparison with the thin skin 2290 of the BT. In the method of the prior art, oxygen molecules 2280 from small blood vessel 2278, which is located deep in the body, have to cross thick layers of skin 21742 (fat tissue), 2174 (dermis), 2176 (epidermis and dead cells) present in said skin 2270 in order for said oxygen molecules 2280 to reach a conventional sensor of the prior art. Accordingly, in the method of the prior art the oxygen 2280 from vessel 2278 has a long path before reaching a sensor of the prior art. Oxygen 2280 diffuses through the wall of the small blood vessel 2278 and through the subcutaneous tissue 2272 to finally reach a thick dermis 2274 and a thick layer of dead cells 2276 at skin 2270, to only then reach conventional sensors of the prior art. As can be seen, the number of oxygen molecules 2280 drop drastically from around vessel 2278 to surface of skin 2271 as it moves along the long path of conventional thick skin 2270 present in the body.

Contrary to the prior art, the method and device of the present invention uses a specialized and extremely thin skin 2290 of the BT, in which oxygen molecules 2280 from vessel 2284 have an extremely short path to reach specialized sensor 2000 of the present invention. Oxygen molecule 2280 is right underneath the thin skin 2290 since terminal large vascular area 2284 lies just underneath the thin skin 2290, and thus oxygen 2280 rapidly and in an undisturbed fashion reaches specialized sensor 2000. This allows an undisturbed diffusion of oxygen from vessel 2284 to sensor 2000 without any drop of the partial oxygen pressure. Because the specialized skin 2290 of the BT produces a rapid and undisturbed diffusion of oxygen (and other blood gases) to the special sensor 2000 of the present invention and the area measured is characterized by a natural condition of hyperperfusion, the present invention results in more accurate measurement than previously available estimates of partial blood gas pressures.

An exemplary transcutaneous blood gas sensor of the present invention consists of a combined platinum and silver electrode covered by an oxygen-permeable hydrophobic membrane, with a reservoir of phosphate buffer and potassium chloride trapped inside the electrode. FIG. 2A shows a small heating element 2298, which is located inside the silver anode. Oxygen 2280 diffuses through the skin 2290 and reaches sensor 2292 wherein a reduction of oxygen occurs generating a current that is converted into partial pressure of oxygen. It is understood that other substances can be measured. Exemplarily, carbon dioxide can be measured with the invention, wherein carbon dioxide molecules diffuse across a permeable plastic membrane into the inner compartment of the electrode where the molecule reversibly reacts with a buffer solution altering the pH which produces a measurable signal, said signal corresponding to the amount of the substance or partial pressure of the gas. A processing circuit can be used to calculate the partial pressure of the substance based on predetermined calibration lines.

In reference to FIG. 2A, measuring portion 2006 of the sensor system is arranged on the skin 2290 at the BT 2282 and includes element 2294. The element 2294 can operate as a blood gas sensor, oxygen saturation sensor, glucose sensor, or any other sensor measuring blood substances or body tissue. Sensing element 2294 in this embodiment includes a Clark-type sensor 2292 for detecting oxygen molecule 2280 and a heating element 2298 which is adapted for periodical actuation for generating heat. Measuring portion 2006 includes a cell 2300 and a temperature sensor 2296. Cell 2300, which is the chemical sensing portion, includes sensor 2292 and heating element 2298. The maximum preferred length or diameter of cell 2300 is equal to or less than 2.5 cm, and preferably equal to or less than 1.5 cm and most preferably equal to or less than 1.0 cm as represented by line C to D. The sensing device 2000 is connected to a processing circuit 2302 and power supply circuit 2304 via a wire 2306. Measuring portion 2006 is secured onto the skin 2290 in a completely leak-free manner, to avoid oxygen from the air reaching the sensor 2292. Preferably, the surface 2308 of measuring portion 2006 is provided with an adhesive layer or other means for sealing. Surface 2310 of sensor 2292 is preferably permeable to oxygen, carbon dioxide, glucose and any other blood components depending on the analyte being measured. Measuring portion 2006 has a preferred maximum length or diameter of equal to or less than 4 cm, and preferably equal to or less than 2.5 mm and most preferably equal to or less than 1.5 cm, as represented by line A to B in FIG. 2A.

The skin 2290 at the BT 2282 is heated by heating source 2298 adjacent to the area of sensor 2292 with consequent increase in arterial blood flow. Electrodes and a voltage source in processing circuit 2302 provide a circuit in which the electrical current flow is dependent on the partial oxygen pressure at the sensor 2292.

Although a contact device and method was illustratively shown, it is understood that a non-contact method and device can be equally used in accordance with the invention. It is also understood that a variety of support structures, disclosed in the present invention, can be used for housing the elements of measuring portion 2006 including adhesive patches, head mounted gear such as eyewear and headbands, and the like. In addition to or as a substitute of wired transmission, the transmission of the signal can use a wireless transmitter and the sensor system of the invention can include a wireless transmitter.

FIG. 2B shows sensor system 2320 which includes an essentially convex sensing surface 2322. Although a convex surface is illustratively described, a flat surface can also be used. Sensor system 2320 is a reflectance sensor including a sensing portion comprised of two parts, the light emitter 2324, 2326 and the detector 2328, which receive the light emitted from light emitter 2324, 2326. Sensor system 2320 uses an infrared light source 2324, 2326 and detector 2328 in specialized pads that are fixed firmly to the skin 2290 of the BT 2282 to detect regional blood oxygen saturation. Sensing portion 2330 has a dimension from point C to point D which is preferably equal to or less than 2.1 cm, and more preferably equal to or less than 1.6 cm, and most preferably equal to or less than 1.1 cm. Sensor system 2320 includes a processing circuit 2332, said processing circuit 2332 including a processor which is coupled to a wireless transmitter 2334 for wirelessly transmitting data, preferably using Bluetooth™ technology. The light emitter can include a near-infrared emitter. Any near infrared radiation source can be used. Preferably radiation having wavelengths between 700 to 900 nm are used for measurement of oxygen and other substances. Radiation sources include near-infrared wavelength. It is understood that radiation source 2324, 2326 can also include mid-infrared wavelength. It is also understood that radiation source 2324, 2326 can also include far-infrared wavelength. It is also understood that radiation source 2324, 2326 can also include a combination of various wavelengths or any electromagnetic radiation. The region of the spectrum and wavelength used depend on the substance or analyte being measured. It is understood that a mid-infrared light source, having wavelength between 3,000 nm and 30,000 nm can also be used. The light source can further include visible light and fluorescent light depending on the analyte or tissue being evaluated.

FIG. 2C shows sensor 2340 which includes a specialized two plane surface formed by an essentially convex surface 2334 and a flat central surface 2336. The flat surface 2336 is preferably the sensing surface of sensor 2340. The two plane surface convex-flat-convex allows preferred apposition to the skin 2290 at the BT 2282. Measuring portion 2006 includes a reflectance sensor comprised of two parts, the light emitter 2338 and a detector 2342, which receive the light emitted from light emitter 2338. Measuring portion 2006 houses light emitter 2338, which uses near infrared light or mid-infrared light source, and a photodetector 2342, and a mechanical plunger 2344, which when powered through wire 2346 elicit a rhythmic motion, gently tapping the skin 2290 at the BT 2282, to increase perfusion in cases of hypoperfusion. Although a mechanical plunger is described, it is understood that any device or article that by motion compresses and decompresses the skin at the BTT will create increased perfusion and can be used in the invention as well as a suction cup and the like, all of which are within the scope of the invention. Dimensions of measuring portion 2006 from point A1 to point B1 have preferred maximum length or diameter of equal to or less than 3.1 cm, and preferably equal to or less than 2.1 cm and most preferably equal to or less than 1.6 cm.

Figure 3:
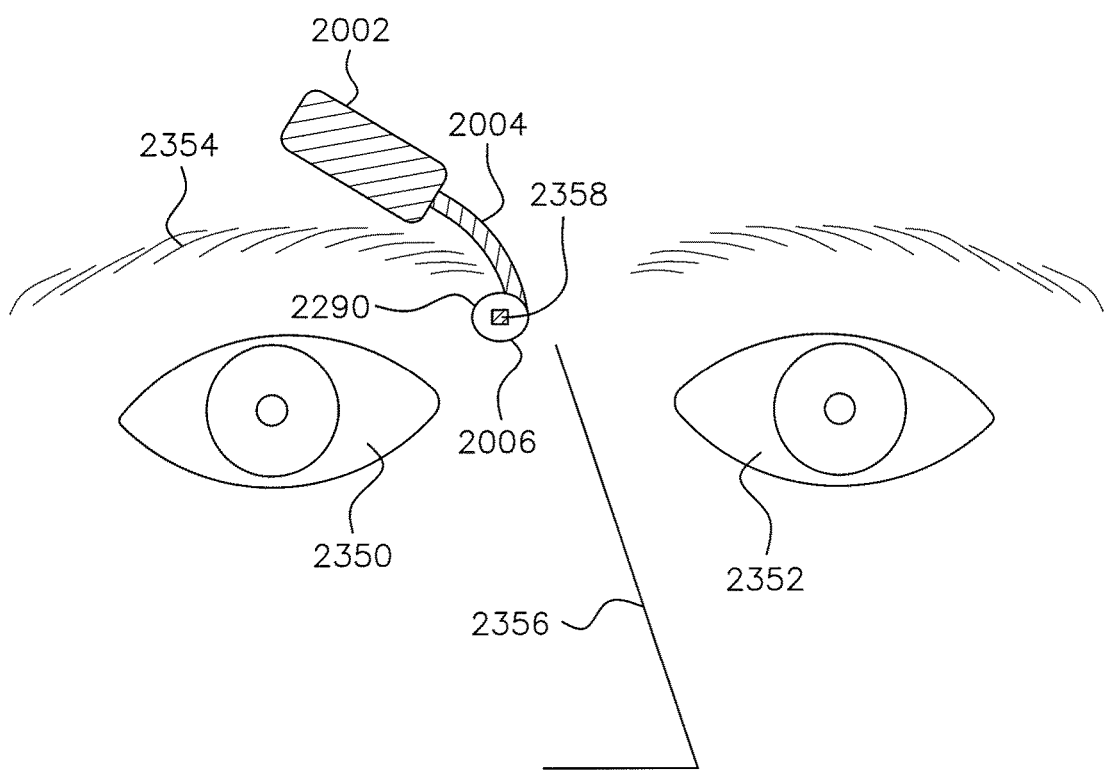
FIG. 3 schematically illustrates the placement of a sensor assembly and its support structure on the face of a wearer.

Since the skin at the BT is highly oxygenated and has a high blood flow, the heating element or any element to cause increase blood flow is not necessary in most patients. Accordingly, another preferred embodiment of the present invention is shown in FIG. 3, and said embodiment does not include a heating element. FIG. 3 shows a face with eyes 2350 and 2352, eyebrow 2354, and nose 2356, with sensing device 2000 including body 2002, arm 2004, and measuring portion 2006 with sensor 2358 secured to the skin above eye 2350 and below eyebrow 2354. By way of illustration, sensor 2358 works as a blood gas sensor previously described, said sensor 2358 positioned on the skin at the brain tunnel or adjacent to the skin 2290 at the brain tunnel, said sensor being in contact with the skin or spaced away from the skin at the brain tunnel during measurement.

The device of the present invention is adapted to measure any component present in the blood by utilizing a plurality of sensors adjacent to or in apposition to the skin of the BT and other physiologic and anatomic tunnels of the present invention. It is understood that an electrochemical sensor or optical sensor can be used to measure other blood components such as glucose, carbon dioxide, cholesterol, pH, electrolytes, lactate, hemoglobin, and any of the blood components.

The sensor system of the invention includes skin surface oxygen pressure measurement, carbon dioxide pressure measurement and measurement of the arterial partial pressure of oxygen or carbon dioxide by locally applying a specialized device on the skin at the BTT comprised by the various new and specialized supports structures. A processing circuit uses the skin surface oxygen or carbon dioxide pressure at the BTT and other tunnels of the invention to calculate the arterial partial pressure of oxygen or carbon dioxide. The processing circuit can be operatively coupled to a memory for correlating the acquired value with a stored value. A processing circuit can be further coupled to a display for visual or audible reporting of the values.

The present invention also discloses a method comprising the steps of applying a electrochemical sensor or an optical sensor or a radiation detector on or adjacent to the skin at the entrance of the BT and other tunnels, applying electrical energy, and measuring at least one analyte including at least one of glucose, oxygen, cholesterol, oxygen, and carbon dioxide. An alternative step includes increasing blood flow to the area by using at least one of heating, creating suction, mechanically tapping the area, using sound waves such as ultrasound, increasing BT skin permeability with laser light, increasing BT skin permeability with chemical substances, and the like.

Sensor 2358 can also work as an infrared detector for measurement of analytes such as glucose. Likewise sensor 2358 can operate as a light emitter-detector pair for measuring analytes. The noninvasive measurement methods of the present invention takes advantage that the BT is an ideal emitter of infrared radiation at precisely the right spectral radiation for measuring substances such as glucose. The emission from the BT works as a black body emission. The emission from the BT contains the radiation signature of analytes. Contrary to other parts of the body in which radiation is deep inside the body, the radiation at the BT is the closest to the surface of the body. A variety of cooling or heating elements can be incorporated to enhance measurement of glucose at the BT. Besides mid-infrared radiation, it is also understood that near-infrared spectroscopy can be used of the measurement of glucose at the BTT. It is also understood that mid-infrared spectroscopy can be used of the measurement of glucose at the BTT. It is also understood that far-infrared spectroscopy can be used of the measurement of glucose at the BTT.

Furthermore, techniques such as Raman spectroscopy can also be used for measuring the concentrations of blood analytes at the BTT and other tunnels of the present invention. Raman spectroscopy has sharp spectral features, which are characteristic for each molecule. This strength is ideally suited to blood analyte measurements, where there are many interfering spectra, many of which are much stronger that that of blood analytes. Accordingly, in the present invention Raman light is generated in the tissue at the BT and collected by a mirror secured to any of the support structures of the present invention such as the frame of eyeglasses, clips, adhesive patches attached to the skin, finger like structure with a plate and an arm, and the like. A fiber bundle in any of the support structures of the present invention guides the collected Raman light to a portable spectrograph and/or to a processor and a CCD. Since there are no interfering elements at the BT, the Raman's sharp spectral features enable accurate detection of blood analyte spectra including glucose, urea, triglyceride, total protein, albumin, hemoglobin and hematocrit.

A light source can illuminate the skin at the brain tunnel area and generate a detectable Raman spectrum for detecting analytes based on said spectrum. Accordingly, another embodiment of the present invention includes an apparatus and method for the non-invasive determination of an analyte comprising a light source for generating an excitation light directed into the brain tunnel and an optical system coupled with said excitation light, said optical system configured for directing the excitation light into the brain tunnel to generate a detectable Raman spectrum thereof, a light detector coupled with said optical system and configured to detect a Raman spectrum from the brain tunnel, a processor operatively coupled with said detector said processor including a processing circuit, said processing circuit having a computer readable medium having code for a computer readable program embodied therein for comparing Raman spectrum from the brain tunnel to a reference radiation corresponding to the concentration of an analyte, and a memory operatively coupled with said processor. The electrical signal corresponding to Raman spectrum from the brain tunnel is fed into the processing circuit and compared to Raman spectrum from the brain tunnel corresponding to the analyte concentration stored in the memory.

It is also understood that glucose at the BTT can be measured with enzymatic sensors such as glucose oxidase as well as artificial glucose receptors. Fluorescence techniques can also be used and include use of engineered molecules, which exhibit altered fluorescence intensity or spectral characteristics upon binding glucose, or use of competitive binding assays that employ two fluorescent molecules in the fluorescent resonance energy transfer technique. In addition, "reverse iontophoresis", with a device held in the specialized support structures of the invention such as eyeglasses can be used, and interstitial fluid from the BT area removed for analysis. Ultrasound applied to the BT and/or a low-level electrical current on the skin of the BT, by convective transport (electroosmosis) can also be used for moving glucose across the thin skin of the BT and other tunnels around the eye. In addition, light scattering and photoacoustic spectroscopy can be used to measure various substances such as glucose. Pulsed infrared light directed at the BT, when absorbed by molecules, produces detectable ultrasound waves from the BT, the intensity and patterns of which can be used to measure glucose levels. The apparatus and methods of the present invention then determines the concentration of an analyte using a processor that correlates signals from the brain tunnel with a reference table, said reference table having values of analytes corresponding to signals from the brain tunnel.

Furthermore, a detector having an ultrasound and a light source illuminates the skin at the rain tunnel area with a wavelength that is absorbed by the analyte being measured and generates a detectable ultrasound wave from the brain tunnel for detecting analytes based on said ultrasound wave and light absorption. Accordingly, another embodiment of the present invention includes an apparatus and method for the non-invasive determination of an analyte comprising a light source for generating light directed into the brain tunnel and an ultrasound configured to waves generated from the brain tunnel, a processor operatively coupled with said ultrasound said processor including a processing circuit, said processing circuit having a computer readable medium having code for a computer readable program embodied therein for comparing absorption of radiation from the brain tunnel based on the signal from the ultrasound to a reference radiation corresponding to the concentration of an analyte, and a memory operatively coupled with said processor. The electrical signal corresponding to the intensity of sound waves is used to determine radiation absorption of light from the brain tunnel, which is used to determine the concentration of the analyte, said signal being fed to the processing circuit and compared with the radiation absorption from the brain tunnel corresponding to the analyte concentration stored in the memory.

The present invention includes non-invasive optical methods and devices for measuring the concentration of an analyte present in the BT. A variety of optical approaches including infrared spectroscopy, fluorescent spectroscopy, and visible light can be used in the present invention to perform the measurements in the BT including transmission, reflectance, scattering measurement, frequency domain, or for example phase shift of modulated light transmitted through the substance of interest or reflected from the BT, or a combination thereof.

The present invention includes utilizing the radiation signature of the natural black-body radiation emission from the brain tunnel. Natural spectral emissions of infrared radiation from the BT and vessels of the BT include spectral information of blood components such as glucose. The radiation emitted by the BT as heat can be used as the source of infrared energy that can be correlated with the identification and measurement of the concentration of the substance of interest. Infrared emission in the BT traverses only an extremely small distance from the BT to the sensor which means no attenuation by interfering constituents. The devices and methods can include direct contact of the instrument with the skin surface at the BT or the devices of the invention can be spaced away from the BT during the measurements.

The methods, apparatus, and systems of the present invention can use spectroscopic analysis of the radiation from the BT to determine the concentration of chemical substances present in such BT while removing or reducing all actual or potential sources of errors, sources of interference, variability, and artifacts. The natural spectral emission from the BT changes according to the presence and concentration of a substance of interest. One of the methods and apparatus involves using a radiation source to direct electromagnetic radiation at the BT with said radiation interacting with the substance of interest and being collected by a detector. Another method and apparatus involves receiving electromagnetic radiation naturally emitted from the BT with said radiation interacting with the substance of interest and being collected by a detector. The data collected is then processed for obtaining a value indicative of the concentration of the substance of interest.

The infrared thermal radiation emitted from the brain tunnel follow Planck's Law, which can be used for determining the concentration of chemical substances. One embodiment includes determining the radiation signature of the substance being measured to calculate the concentration of the substance. Another embodiment includes using a reference intensity calculated by measuring thermal energy absorption outside the substance of interest band. The thermal energy absorption in the band of substance of interest can be determined via spectroscopic means by comparing the measured and predicted values at the BT. The signal is then converted to concentration of the substance of interest according to the amount of infrared energy absorbed.

The apparatus uses the steps of producing output electrical signals representative of the intensity of the radiation signature and sending the signal to a processor. The processor is adapted to provide the necessary analysis of the signal to determine the concentration of the substance of interest and is coupled to a display for displaying the concentration of the substance of interest, also referred to herein as analyte.

The analyte measured or detected can be any molecule, marker, compound, or substance that has a radiation signature. The radiation signature preferably includes a radiation signature in the infrared wavelength range including near-infrared, mid-infrared, and far-infrared. The analyte being measured can preferably have a radiation signature in the mid-infrared range or the near infrared range.

Infrared spectroscopy, as used in some embodiments of the present invention, is a technique based on the absorption of infrared radiation by substances with the identification of said substances according to its unique molecular oscillatory pattern depicted as specific resonance absorption peaks in the infrared region of the electromagnetic spectrum. Each chemical substance absorbs infrared radiation in a unique manner and has its own unique absorption spectra depending on its atomic and molecular arrangement and vibrational and rotational oscillatory pattern. This unique absorption spectra allows each chemical substance to basically have its own infrared spectrum, also referred as fingerprint or radiation signature which can be used to identify each of such substances.

In one embodiment radiation containing various infrared wavelengths is emitted at the substance or constituent to be measured, referred to herein as "substance of interest", in order to identify and quantify said substance according to its absorption spectra. The amount of absorption of radiation is dependent upon the concentration of said chemical substance being measured according to Beer-Lambert's Law.

One embodiment includes a method and apparatus for analyte measurement, such as blood glucose measurement, in the near infrared wavelength region between 750 and 3000 nm and preferably in the region where the highest absorption peaks are known to occur, such as the radiation absorption signature of the substance being measured. For glucose, for example, the near infrared region includes the region between 2080 to 2200 nm and for cholesterol the radiation signature is centered around 2300 nm. The spectral region can also include visible wavelength to detect other chemical substances including glucose or cholesterol.

The apparatus includes at least one radiation source from infrared to visible light which interacts with the substance of interest and is collected by a detector. The number and value of the interrogation wavelengths from the radiation source depends upon the chemical substance being measured and the degree of accuracy required. As the present invention provides reduction or elimination of sources of interference and errors, it is possible to reduce the number of wavelengths without sacrificing accuracy. Previously, the mid-infrared region has not been considered viable for measurement of analytes in humans because of the presence of fat tissue and the high water absorption that reduces penetration depths to microns. The present invention can use this mid-infrared region since the blood with the substance of interest is located very superficially in an area void of fat tissue which allows sufficient penetration of radiation to measure said substance of interest.

The present invention reduces variability due to tissue structure, interfering constituents, and noise contribution to the signal of the substance of interest, ultimately substantially reducing the number of variables and the complexity of data analysis, either by empirical or physical methods. The empirical methods including Partial Least Squares (PLS), principal component analysis, artificial neural networks, and the like while physical methods include chemometric techniques, mathematical models, and the like. Furthermore, algorithms were developed using in-vitro data which does not have extraneous tissue and interfering substances completely accounted for as occurs with measurement in deep tissues or with excess background noise such as in the skin with fat tissue. Conversely, standard algorithms for in-vitro testing correlates to the in vivo testing of the present invention since the structures of the brain tunnel approximates a Lambertian surface and the skin at the brain tunnel is a homogeneous structure that can fit with the light-transmission and light-scattering condition characterized by Beer-Lambert's law.

Spectral radiation of infrared energy from the brain tunnel can correspond to spectral information of the substance of interest or analyte. These thermal emissions irradiated as heat at 38 degrees Celsius can include the 3,000 nm to 30,000 nm wavelength range, and more precisely the 4,000 nm to 14,000 nm range. For example, glucose strongly absorbs light around the 9, 400 nm band, which corresponds to the radiation signature of glucose. When mid-infrared heat radiation is emitted by the brain tunnel, glucose will absorb part of the radiation corresponding to its band of absorption. Absorption of the thermal energy by glucose bands is related in a linear fashion to blood glucose concentration in the brain tunnel.

The infrared radiation emitted by the BTT contains the radiation signature of the substance being measured and the determination of the analyte concentration is done by correlating the spectral characteristics of the infrared radiation emitted from the brain tunnel to the analyte concentration for that radiation signature. The analyte concentration can be calculated from the detected intensity of the infrared radiation signature, said radiation signature generating an electrical signal by a detector, with said signal being fed into a microprocessor. The microprocessor can be coupled to a memory which stores the concentration of the analyte according to the intensity of the radiation signature of the analyte being measured. The processor calculates the concentration of the substance based on the stored value in the memory. The processor is operatively coupled with said detector, said processor including a processing circuit, said processing circuit having a computer readable medium having code for a computer readable program embodied therein for comparing infrared spectrum from the brain tunnel to a reference radiation corresponding to the concentration of an analyte, and a memory operatively coupled with said processor. The electrical signal corresponding to the infrared spectrum from the brain tunnel is fed into the processing circuit and compared to infrared spectrum from the brain tunnel corresponding to the analyte concentration stored in the memory. The infrared spectrum preferably includes near-infrared or mid-infrared radiation.

One embodiment includes a device and method for measuring an analyte concentration in the blood or tissue of the BT. One embodiment includes detecting the level of infrared radiation naturally emitted from the BT. One embodiment includes detecting the level of infrared radiation emitted from the BT after directing radiation at the BTT.

One embodiment includes a device which measures the level of mid-infrared radiation from the surface of a brain tunnel and determines the concentration of an analyte based on the analyte's infrared radiation signature. The radiation signature can be preferably in the infrared region of the spectrum including near-infrared or mid-infrared. The device can include a filter, a detector, a microprocessor and a display.

A detector having a light source can illuminate the skin at the brain tunnel area and generate a detectable infrared radiation for detecting analytes based on said infrared spectrum. The detectable infrared radiation from the brain tunnel contains the radiation signature of the analyte being measured. Accordingly, another embodiment of the present invention includes an apparatus and method for the non-invasive determination of an analyte comprising a light source for generating an infrared light directed into the brain tunnel and an infrared radiation detector configured to detect infrared radiation from the brain tunnel, a processor operatively coupled with said detector, said processor including a processing circuit, said processing circuit having a computer readable medium having code for a computer readable program embodied therein for comparing infrared radiation from the brain tunnel to a reference radiation corresponding to the concentration of an analyte, and a memory operatively coupled with said processor. The electrical signal corresponding to infrared radiation signature from the brain tunnel is fed into the processing circuit and compared to infrared radiation signature from the brain tunnel corresponding to the analyte concentration stored in the memory.

A variety of radiation sources can be used in the present invention including LEDs with or without a spectral filter, a variety of lasers including diode lasers, a Nernst glower broad band light emitting diode, narrow band light emitting diodes, NiChrome wire, halogen lights a Globar, and white light sources having maximum output power in the infrared region with or without a filter, and the like. The radiation sources have preferably enough power and wavelengths required for the measurements and a high spectral correlation with the substance of interest. The range of wavelengths chosen preferably corresponds to a known range and includes the band of absorption for the substance of interest or radiation signature of the substance. The instrument comprises a light source which may be any suitable infrared light source, including mid-infrared light source, near-infrared light source, far-infrared light source, fluorescent light source, visible light source, radio waves, and the like.

A light source can provide the bandwidth of interest with said light being directed at the substance of interest in the brain tunnel. A variety of filters can be used to selectively pass one or more wavelengths which highly correlate with the substance of interest. The filter can select the wavelength and includes bandpass filter, interference filter, absorption filter, monochromator, grating monochromator, prism monochromator, linear variable filter, circular variable filter, acousto-optic tunable filter, prism, and any wavelength dispersing device The radiation can be directly emitted from a light source and directly collected by a photodetector, or the radiation can be delivered and collected using optic fiber cables. An interface lens system can be used to convert the rays to spatial parallel rays, such as from an incident divergent beam to a spatially parallel beam.

The detector can include a liquid nitrogen cooled detector, a semiconductor photodiode with a 400 μm diameter photosensitive area coupled to an amplifier as an integrated circuit, and the like. The photodetector has spectral sensitivity in the range of the light transmitted. The photodetector receives an attenuated reflected radiation and converts the radiation into an electrical signal. The detector can also include a thermocouple, a thermistor, and a microbolometer.

Analyte as used herein describes any particular substance to be measured. Infrared radiation detector refers to any detector or sensor capable of registering infrared radiation. Examples of a suitable infrared radiation detectors, include but are not limited to, a microbolometer, a thermocouple, a thermistor, and the like. The combined detected infrared radiation may be correlated with wavelengths corresponding to analyte concentrations using means such as a Fourier transform.

The BT provides the mid-infrared radiation signature and the near-infrared radiation signatures of the analytes present therein. The infrared radiation signature from the BT is affected by the concentration of analytes in the BT. One of the molecules present in the BT is glucose, and the natural mid-infrared or near-infrared radiation signature of glucose contained within the brain tunnel's natural infrared radiation allows the non-invasive measurement of glucose. Changes in the concentration of certain analytes such as glucose, cholesterol, ethanol, and others, may cause an increase or change in the brain tunnel's natural emission of infrared radiation which can be used to measure the concentration of an analyte.

The BT emits electromagnetic radiation within the infrared radiation spectrum. The spectral characteristics of the infrared radiation emitted by the BT can be correlated with the concentration of analyte. For example, glucose absorbs mid-infrared radiation at wavelengths between about 8.0 microns to about 11.0 microns. If mid-infrared radiation passes through or reflects from the brain tunnel where glucose is present, a distinct radiation signature can be detected from the attenuated radiation or the remaining radiation that is not absorbed by the analyte. The absorption of some amount of the radiation that is applied to the brain tunnel (which contains the substance of interest), may result in a measurable decrease in the amount of radiation energy, which can be utilized to determine the concentration of an analyte.

One embodiment of the present invention provides a method and device for non-invasively measuring the analyte concentration in blood or other tissues, and includes the steps of detecting mid-infrared radiation naturally emitted by the brain tunnel, and determining the concentration of said analyte by correlating the spectral characteristics or radiation signature of the detected infrared radiation with a radiation signature that corresponds to the analyte concentration. The method can also include a filtering step before detection by filtering the naturally emitted infrared radiation from the brain tunnel. In the case of glucose measurement, filtering allows only wavelengths of about 8,000 nanometers to about 11,000 nanometers to pass through the filter. The method further includes a detecting step using an infrared radiation detector, which generates an electrical signal based on the radiation received and feeds the signal into a processor. A mid-infrared radiation detector can measure the naturally emitted mid-infrared radiation from the brain tunnel. A variety of detectors can be used including thermocouples, thermistors, microbolometers, liquid nitrogen cooled MTC such as by Nicolet, and the like. A processor can be used to analyze and correlate the spectral characteristics or radiation signature of the detected mid-infrared radiation with a radiation signature of an analyte. For glucose the generated radiation signature is within the wavelength between about 8,000 nm to about 11,000 nm. The method may include an analyzing step using algorithms based on Plank's law to correlate the radiation signature with glucose concentration. The method may further include a reporting step, such as a visual display or audio reporting.

Many illustrative embodiments for chemical sensing were provided, but it is understood that any other sensing system can be used in accordance to the invention. For example a transducer that uses fluorescence to measure oxygen partial pressure, carbon dioxide, pH, nitric oxide, lactate, and anesthetic gases can also be used as well as any other optical chemical sensor including absorbance, reflectance, luminescence, birefringence, and the like.

Figure 11H:
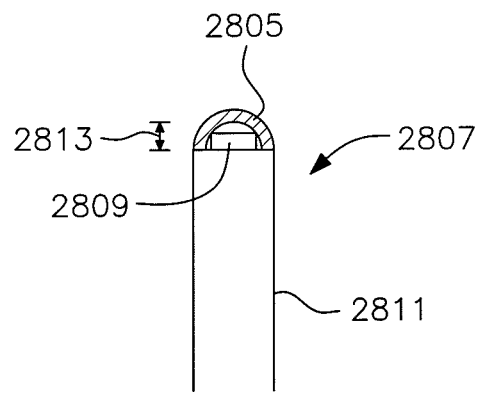
FIG. 11H illustrates a specialized end of a thermometer.
Figure 11J:
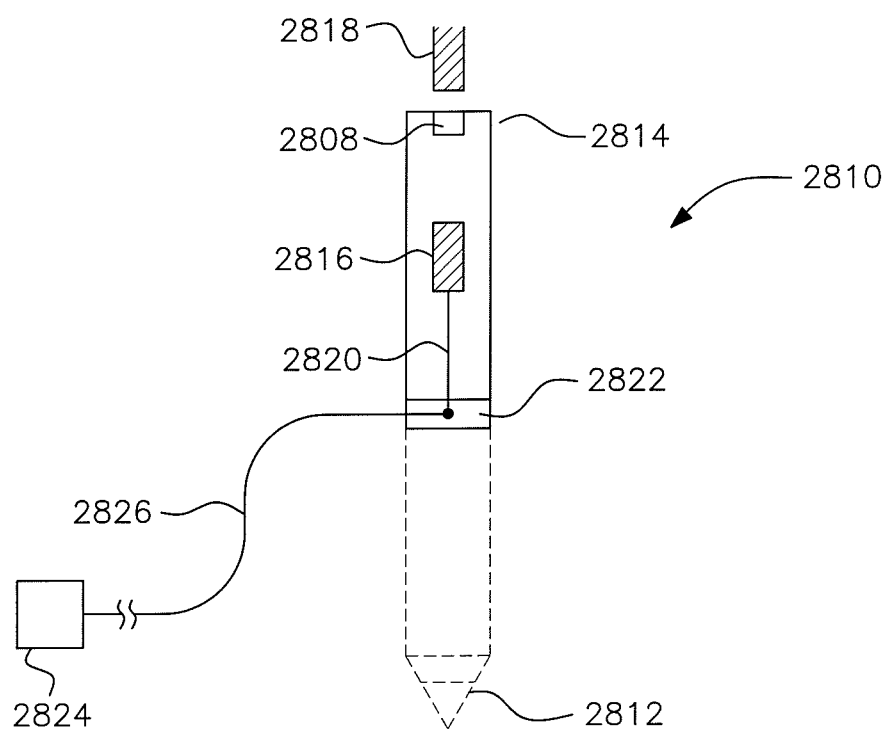
FIG. 11J illustrates a stylus having a touching end and a sensing end.
Figure 11K:
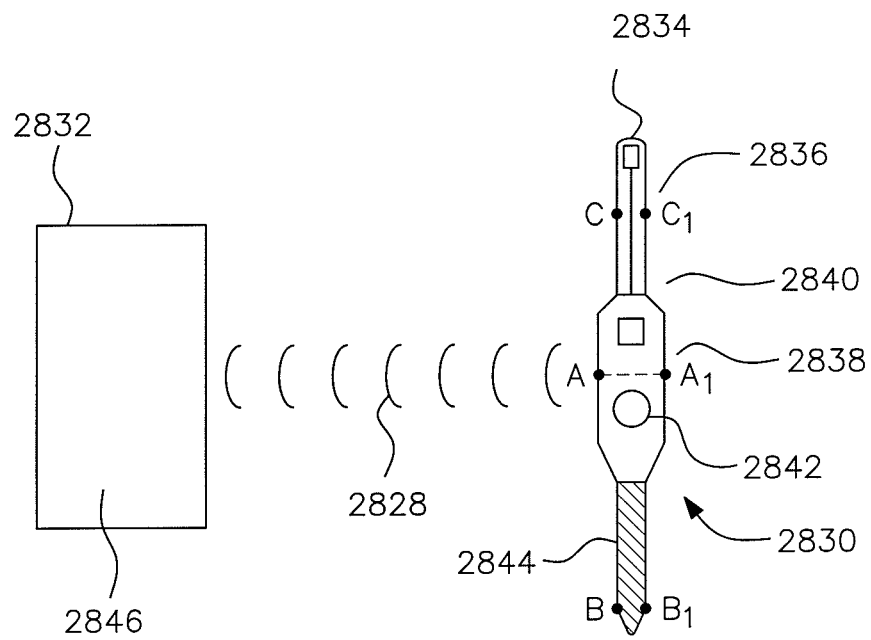
FIG. 11K illustrates a stylus connected by a wireless system with an electronic device.
Figure 11L:
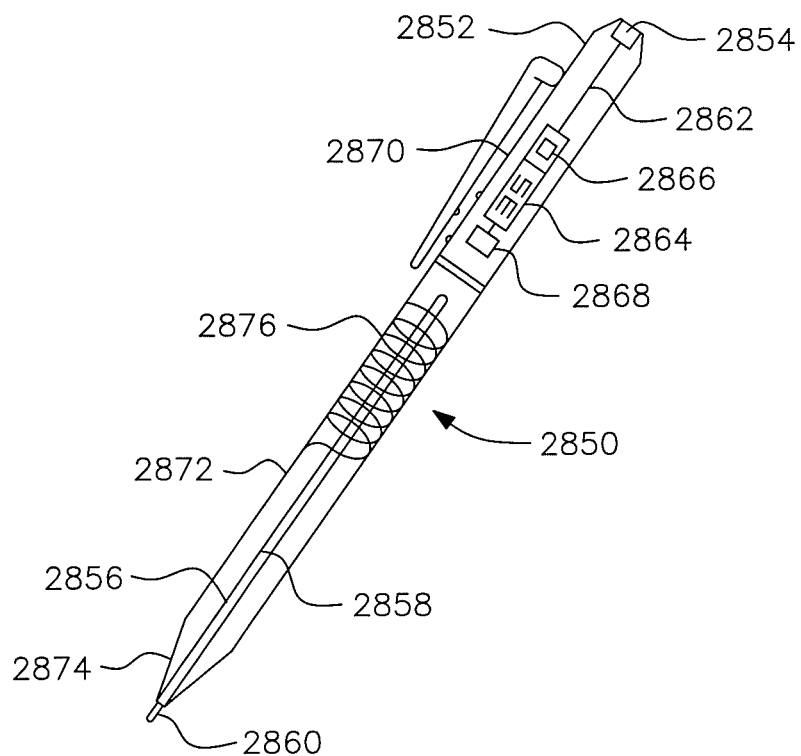
FIG. 11L illustrates a sensing-writing instrument.
Figure 11M:
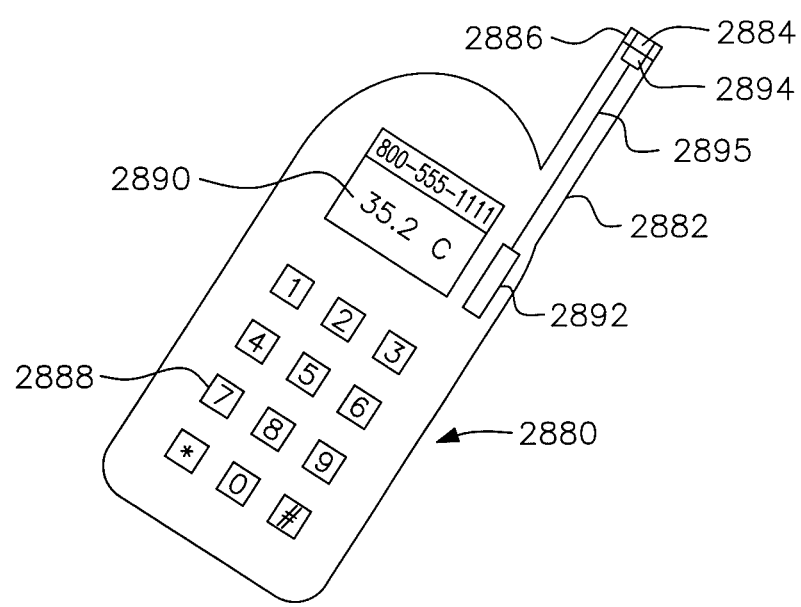
FIG. 11M illustrates a telephone having a sensing antenna.
Figure 11N:
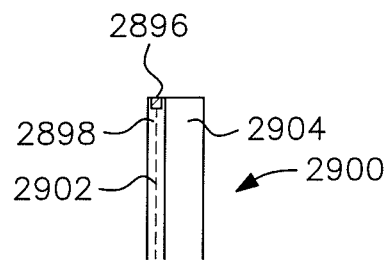
FIG. 11N illustrates a sensing antenna.
Figure 11P:
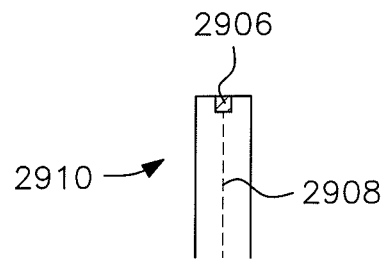
FIG. 11P illustrates a sensing antenna.
Figures 1, 11R:
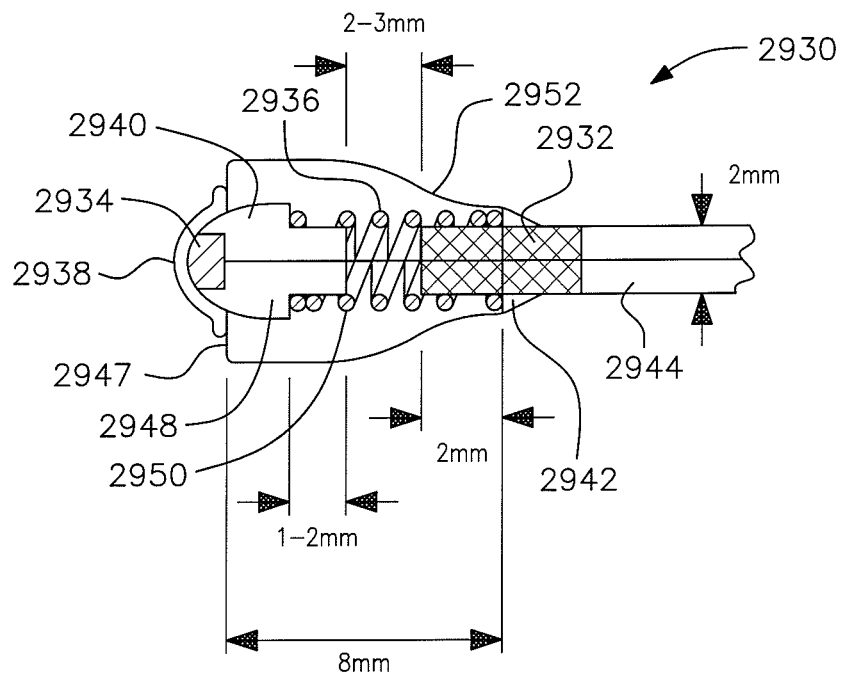
Figures 2, 11R:
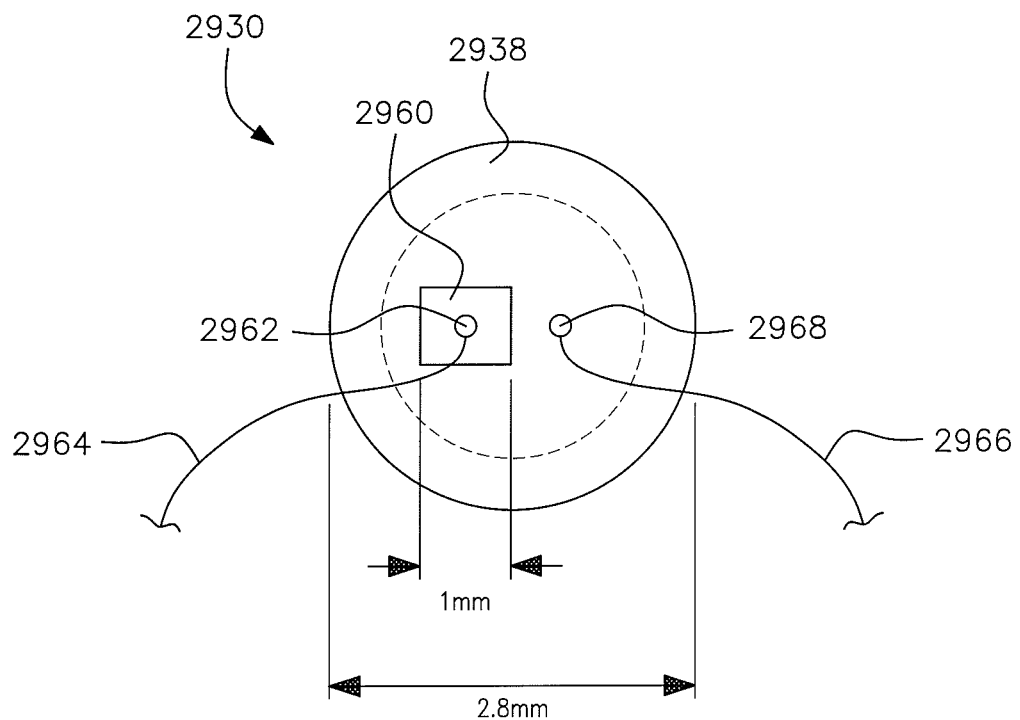
Figures 1, 11S:
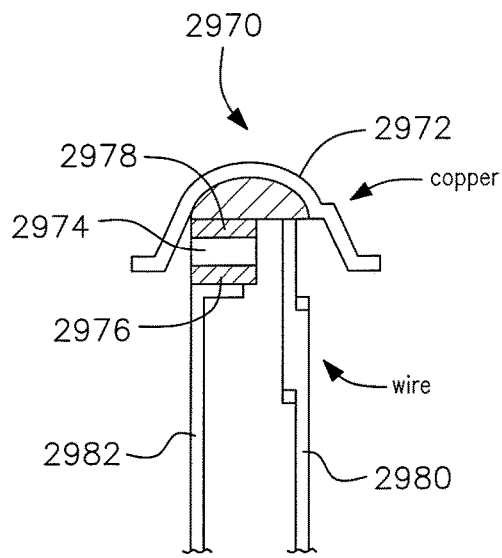
Figures 2, 11S:
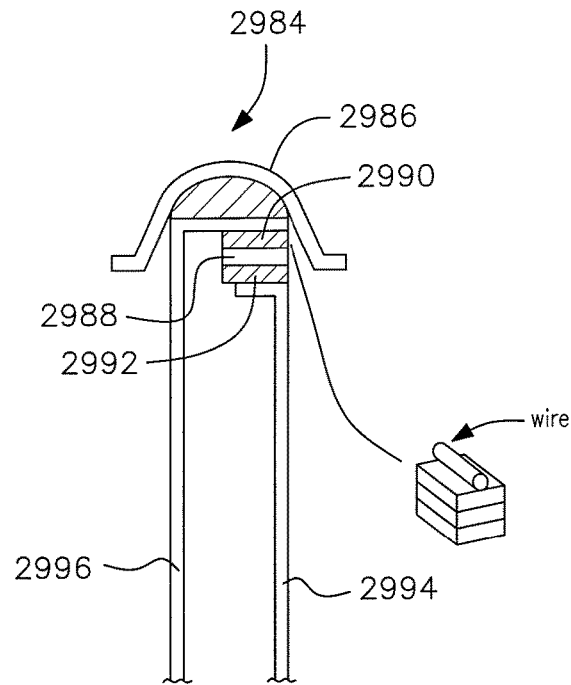
Figures 3, 11S:
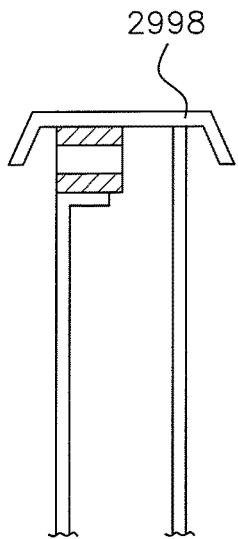
Figures 4, 11S:
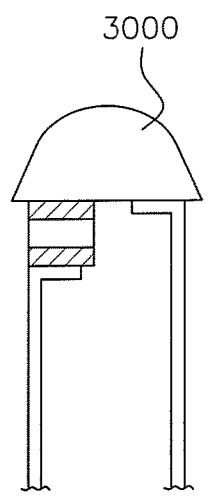

FIG. 4 is a diagrammatic perspective view of another preferred embodiment showing measuring portion 2006 comprised of a plurality of sensors and/or detectors. There is seen measuring portion 2006 having a light emitter-light detector pair 2360 and temperature sensor 2362 housed in said measuring portion 2006. The radiation source-detector pair 2360 is preferably housed in a plate 2364. Plate 2364 can have any shape, exemplarily and preferably plate 2364 has an essentially rectangular shape. Rectangular plate 2364 houses at least one light emitter 2366 in one side and at least one detector 2368 on the opposite side. Light emitter 2366 is connected to at least one wire 2372 and detector 2368 is connected to at least one wire 2374. Wire 2372, 2374 start at the light-emitter-light detector pair 2360, and run along measuring portion 2006, and terminate in multi-strand wire 2382 of arm 2004. Wire portion 2382 terminates in wire portion 2384 of body 2002. Temperature sensing part 2370 is essentially cylindrical and houses wire portion 2375 (shown as broken lines) in its body 2380 and temperature sensor 2362 located at the free end 2378 of temperature sensing part 2370. Temperature sensing part 2370 is disposed adjacent to light emitter-detector pair 2360, preferably next to light detector 2368, to avoid heat generated by light emitter 2366 to affect body temperature measurement. Wire 2372, 2374, and 2376 preferably form a single multi-strand wire 2385 which exit measuring portion 2006. Wire portion 2382 is disposed on or within arm 2004, and further disposed on or within body 2002. The free end 2378 of temperature sensing part 2370 housing temperature sensor 2362 preferably projects beyond the bottom plane 2386 of measuring portion 2006. The temperature sensing part 2370 of measuring portion 2006 can preferably comprise a soft and compressible material. Light emitter-detector pair 2360 can also project beyond bottom plane 2386. Wire portion 2384 may be connected to a processing circuit, memory, and display and/or a transmitter. Any combination of sensors, sensing molecules, and detectors can be housed in measuring portion 2006. Another embodiment includes a pulse sensor combined with a temperature sensor and a glucose sensor. The measuring portion 2006 can also further include an oxygen sensor, including an optical sensor for measuring oxygen saturation such as pulse oximetry and an electrochemical sensor for measuring partial pressure of oxygen. Any combination of any physical measurement including temperature, pressure and pulse with any chemical measurement or optical measurement can be used and are contemplated.

Figure 5A:
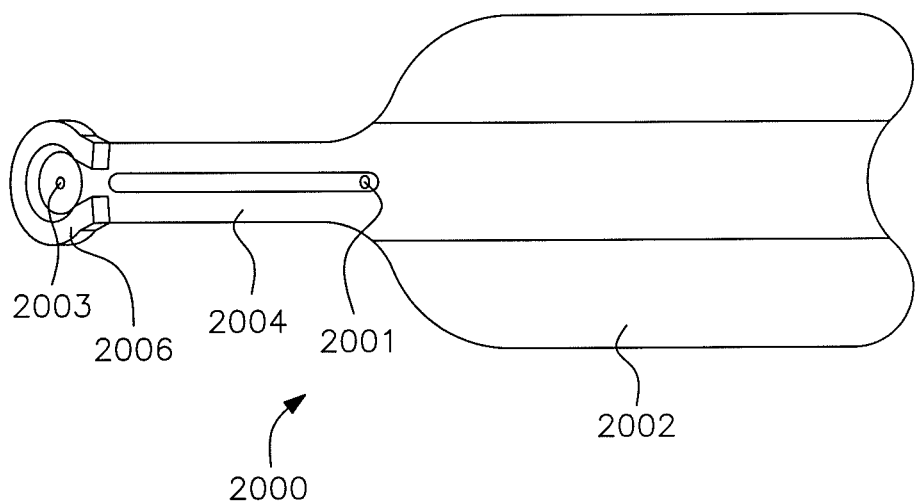
FIG. 5A illustrates a routing of a transmission wire through the support structure.

FIG. 5A is a perspective planar view of another embodiment showing sensing device 2000 comprised of body 2002, arm 2004 with hole 2001 for housing a wire, and measuring portion 2006 with hole 2003 for housing a wire.

Figure 5B:
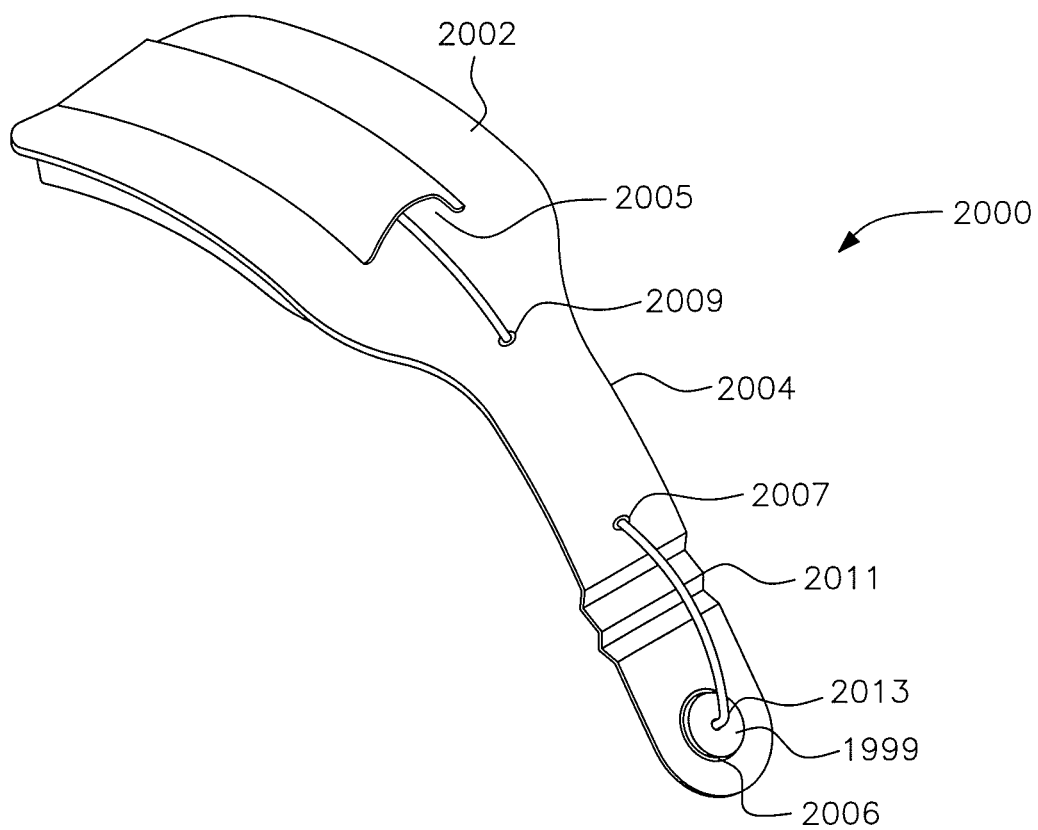
FIG. 5B is a perspective view illustrating the path of the wire through the support structure.

FIG. 5B is a perspective side top view of another embodiment of sensing device 2000 showing body 2002 having a tunnel structure 2005 for housing a wire, and arm 2004 with two holes 2007, 2009 for housing a wire, and an adjustably extendable neck portion 2011 such as an accordion portion for allowing better flexible bending and/or extending of arm 2004 for positioning a sensor at the BT area. Measuring portion 2006 comprises a cylinder 1999 with a wire 2013 entering said cylinder 1999 and said wire 2013 terminating in a sensor. Wire 2013 is preferably housed in a Teflon™ tube, said tube penetrating arm 2004 at hole 2007 adjacent to the accordion portion 2011 and exiting at the opposite end of arm 2004 at a second hole 2009.

Figure 5C:
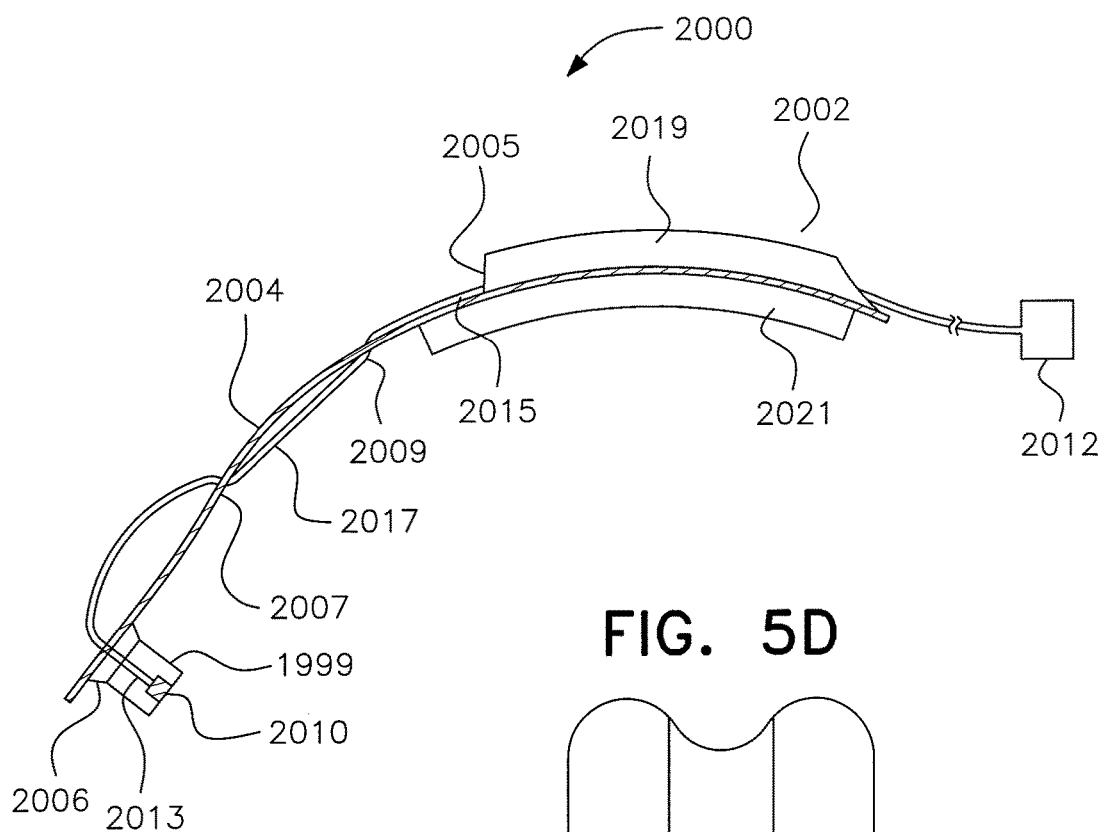
FIG. 5C is a side view illustrating the path of the transmission wire.

FIG. 5C is a side view of another embodiment of sensing device 2000 showing body 2002 having a tunnel structure 2005 for housing a wire portion 2015, and a thin metal sheet representing arm 2004 with said arm 2004 having two holes 2007, 2009 for housing a wire portion 2017. For temperature measurement, measuring portion 2006 comprises a cylinder 1999 of insulating material with a wire 2013 entering said cylinder 1999 and running along the center of said cylinder 1999, said wire 2013 terminating in a temperature sensor 2010. Wire 2017 is preferably housed in a Teflon™ tube, said tube penetrating arm 2004 in its mid portion and exiting at the end of arm 2004 at the junction with body 2002. Body 2002 has two portions, a semi-rigid upper part 2019, preferably metal or plastic, and a soft bottom part 2021 made with rubber, polyurethane, polymers, or any other soft material. Wire portion 2015 runs inside tunnel 2005 of body 2002 and terminates in processing and reading unit 2012.

Figure 5D:
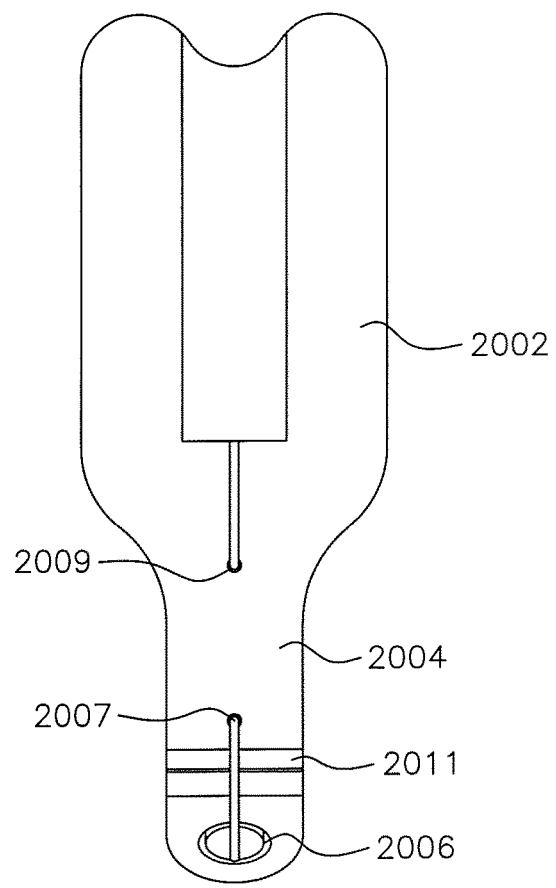
FIG. 5D is a top view illustrating the path of the transmission wire.

FIG. 5D is a planar view of sensing device 2000 of FIG. 5C showing body 2002, arm 2004 with holes 2007 and 2009 for housing a wire, said arm 2004 having an extendable portion 2011, and a measuring portion 2006.

Figure 5E:
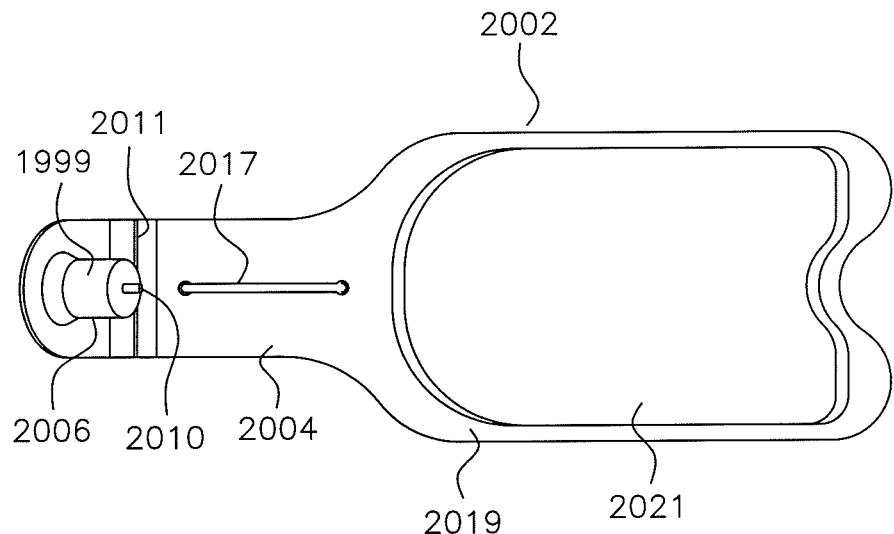
FIG. 5E illustrates a path of the transmission wire from a bottom view.

FIG. 5E is a planar bottom view of sensing device 2000 showing body 2002 having two portions, a semi-rigid upper part 2019, preferably a thin sheet of metal or plastic, and a soft bottom part 2021 made with rubber, polyurethane, polymers, or any other soft material. Wire portion 2017 is secured to arm 2004, said arm 2004 having an adjustably extendable portion 2011. Measuring portion 2006 comprises a holder 1999, represented by a cylinder with a sensor 2010 disposed at the end of the cylinder 1999.

Figure 5F:
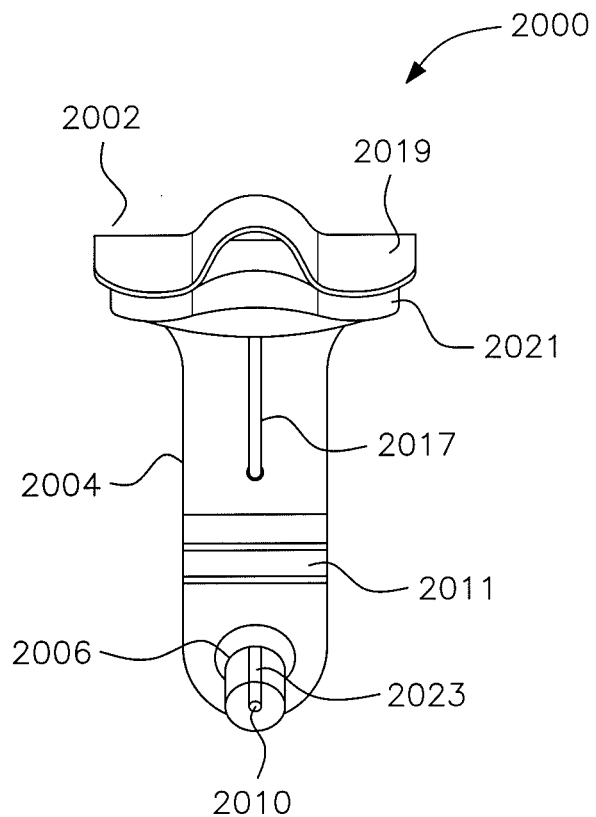
FIG. 5F illustrates the path of the wire from an end view.

FIG. 5F is a bottom view of sensing device 2000 showing body 2002 having two portions, a semi-rigid upper part 2019, preferably a thin sheet of metal, and a soft bottom part 2021 made with rubber, polyurethane, polymers, or any other soft material. Wire portion 2017 is secured to arm 2004, said arm 2004 having an adjustably extendable portion 2011. Measuring portion 2006 comprises a holder 1999 represented as a cylinder, said cylinder 1999 having a slit 2023 for facilitating securing wire 2013 to said cylinder 1999, with a sensor 2010 disposed at the end of the cylinder 1999.

Figure 5G:
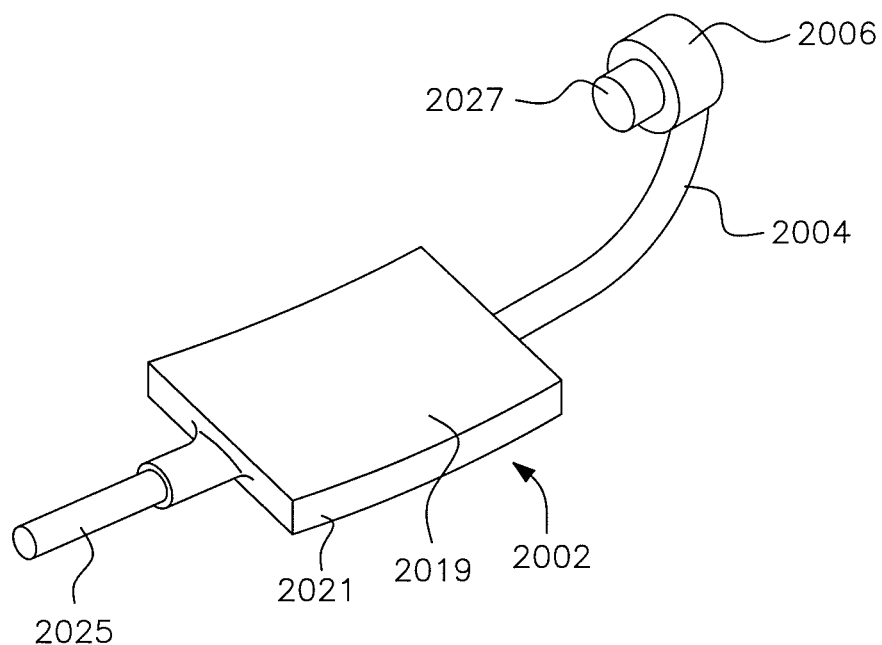
FIG. 5G illustrates a sensing device including its support body and sensor head.

FIG. 5G is illustrative of a bottom view of sensing device 2000 which shows body 2002, arm 2004 bent for use, and measuring portion 2006 having a two level insulating material 2027 of two different heights and a wire 2025 which exits body 2002. Wire in this embodiment is not exposed and is completely covered by insulating rubber in arm 2004, and by the polyurethane cylinder in measuring portion 2006, and being sandwiched between metal plate 2019 and soft cushion pad 2021 in body 2002.

Figure 5H:
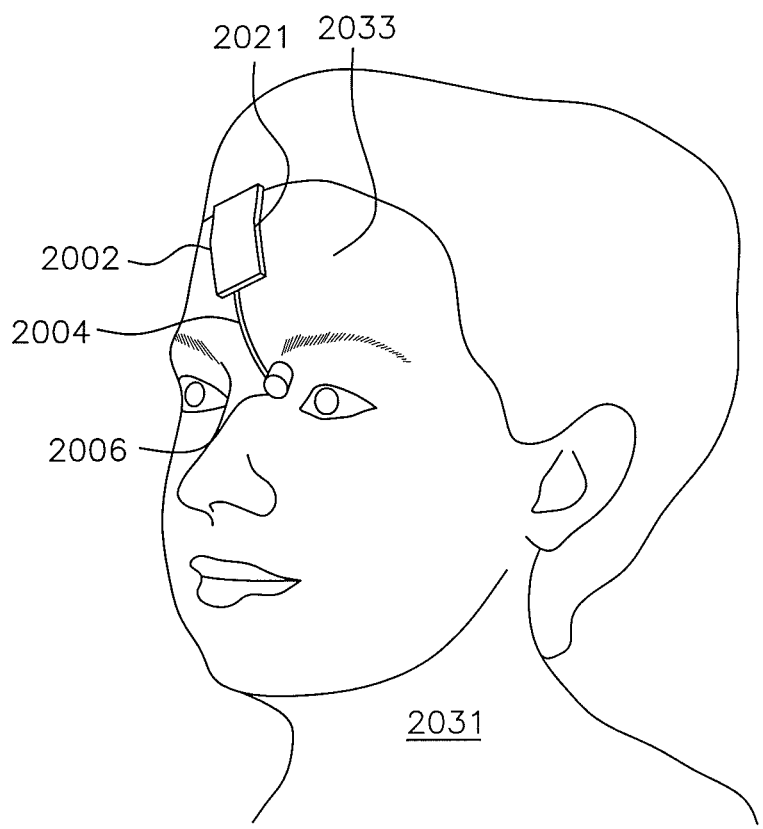
FIG. 5H illustrates the locating of the sensing assembly on the face of a wearer.

FIG. 5H shows sensing device 2000 when worn by a user 2031, with measuring portion 2006 positioned at the junction between nose and eyebrow. Body 2002 is connected to arm 2004, said body 2002 being secured to the forehead 2033 via adhesive soft surface 2021.

Figure 5I:
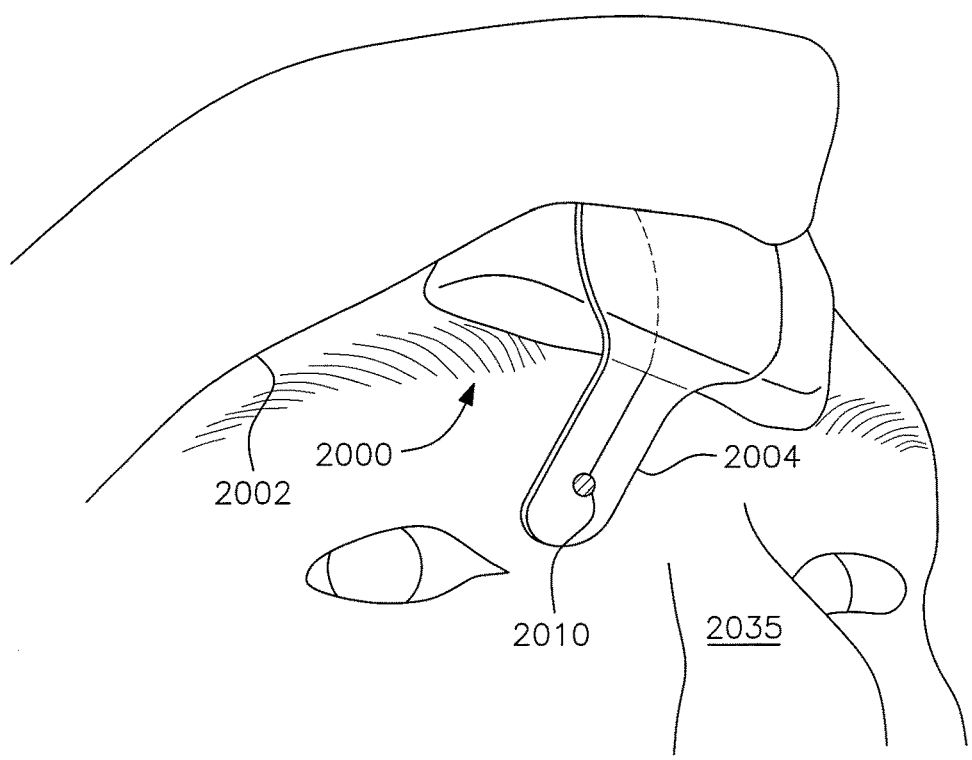
FIG. 5I illustrates a sensing device worn by a user and held in place by a headband.

FIG. 5I shows sensing device 2000 when worn by a user 2035, said sensing device comprised of a plastic arm 2004 with spring capabilities, said plastic arm 2004 having a sensor 2010 at its free end positioned at the junction between the nose and the eyebrow. Body 2002 comprises a headband which may house an electronic circuit, processing circuit, power source, and transmitter, as well as a display.

Figure 5J:
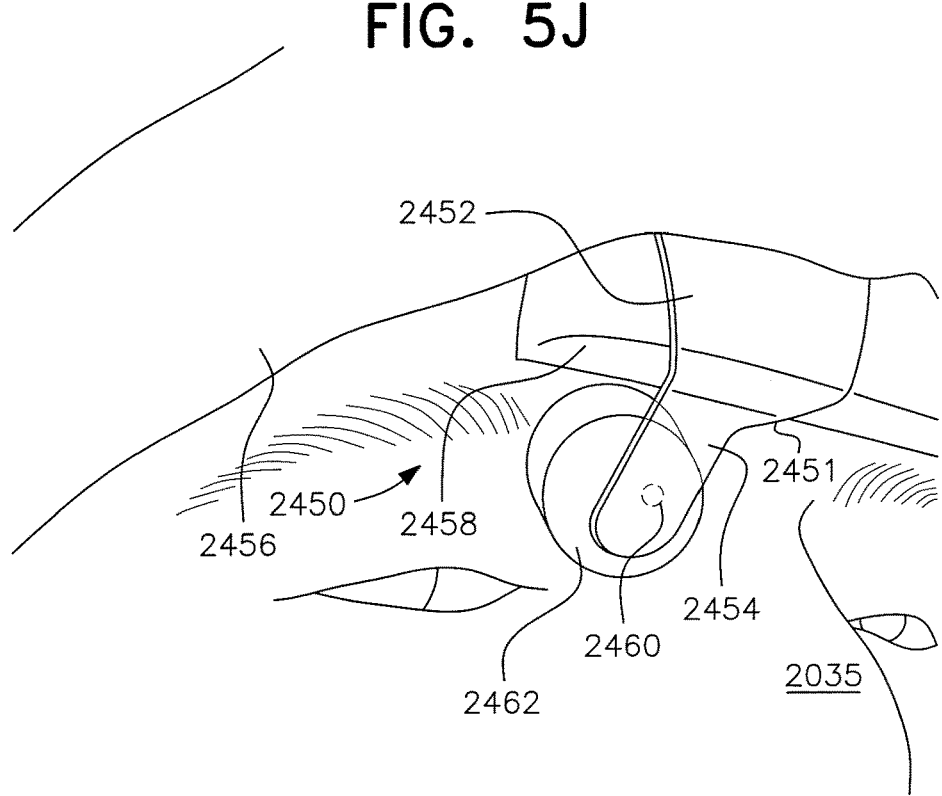
FIG. 5J illustrates a two part separable sensing device worn by a user and held in place by a headband.

FIG. 5J shows a two part, separable sensing device 2450 when worn by a user 2035, said two part, separable sensing device comprised of: (1) a holding device 2451 including plastic arm 2454 with spring capabilities, and (2) a patch 2462 housing a sensor 2460 with said plastic arm 2454 holding said patch 2462 in a stable position for measurement. To assure even better stability the patch 2462 may have an adhesive surface. Sensor 2460 can be placed centrically in patch 2462, and held in place by pressure applied by arm 2454. Arm 2454 is connected to body 2452, exemplarily shown mounted on a headband 2456, but any other structure such as a plate, frame of eyeglasses, head mounted gear, and the like as well as any support structures of the present invention can be used as body 2452 connected to arm 2454. In this embodiment sensor 2460 is located in patch 2462. Arm 2454 and body 2452 do not have any electrical parts or electronic parts, and serve as mechanical holder. Alternatively, arm 2454 and/or body 2452 may have an electrical connector for connecting with a wire from patch 2462. Dimensions of arm 2454 are similar in nature to the dimensions described for arm 2004 of sensing device 2000. Arm 2454 helps to position patch 2462 at the junction between nose and eyebrow. Body 2452 comprises a headband which may house electronic circuit, processing circuit, power source, and transmitter, as well as a display. A cushion pad 2458 can be coupled to arm 2454 for comfort.

Figure 6:
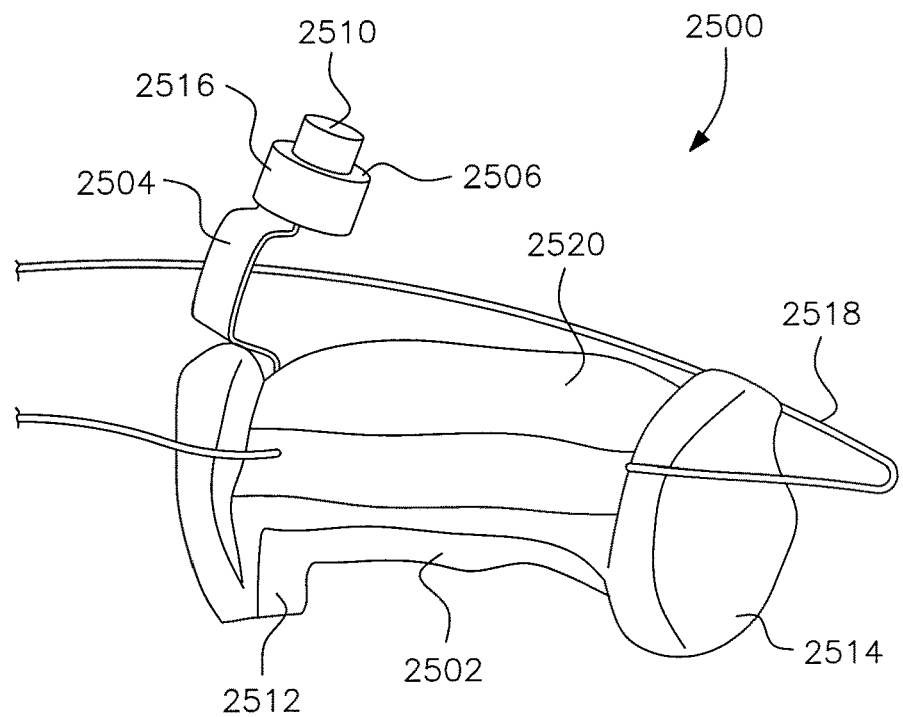
FIG. 6 illustrates a nose bridge and clip for mounting a sensing device.

FIG. 6 is another embodiment showing a nose bridge or clip sensing device 2500 comprised of a nose bridge piece 2502, adjustably positionable arm 2504 and measuring portion 2506. Nose bridge piece 2502 preferably includes two pads 2512 and 2514 and bridge 2520 connecting the two pads 2512, 2514, said pads preferably having an adhesive surface. Arm 2504 branches off the nose bridge piece 2502 and terminates in measuring portion 2506. Measuring portion 2506 illustratively is shown as a two level structure 2516 housing sensor 2510, such as a two level stepped "wedding cake" configuration. Arm 2504 is aimed upwards at the roof of the orbit for positioning sensor 2510 on or adjacent to the BT. A cord or strap 2518 may be secured to nose bridge piece 2502 for better stability and securing to the head.

FIG. 7A to 8A shows preferred embodiments for the sensing system 2400 of the present invention. Accordingly, in reference to FIG. 7A, the specialized support and sensing structure 2400 of the present invention includes a body 2402 (such as frame of sunglasses, a headband, a helmet, a cap, or the like), illustrated herein as the frame of eyeglasses, for securing sensing system 2400 to a body part such as the head (not shown). Sensing system 2400 includes an adjustably positionable arm 2404 preferably made with a shape memory alloy or any material that is deformable and has a memory, wherein the end of this arm 2404 terminates in a measuring portion 2406 which houses a sensor 2410 electrically connected to body 2402 via wire 2419. Wire portion 2418 in the measuring portion 2406 is surrounded by a compressible element 2422, preferably a spring. The spring 2422 is connected to sensor 2410. When in use the spring 2422 presses sensor 2410 against the skin creating a small indentation. Wire 2418 terminates in wire portion 2419, and preferably travels within arm 2404 and exits at the opposite end to connect to structure 2402, which houses circuit board 2420 including processing circuit 2422 and transmitter elements 2424 and power source 2421. Measuring portion 2406 preferably comprises an outer shell 2407, said outer shell preferably comprised of a rubber like material. Sensor 2410 can comprise a temperature sensor, said sensor preferably being covered by a metal sheet, said attachment being accomplished using a thermal transfer glue.

The eyeglasses of the present invention can include the use of a cantilever system. The present invention preferably includes an arm 2404 held rigidly at one end of the body 2402, represented by a frame of eyeglasses, said arm 2404 having a free end which includes a measuring portion 2406 with walls 2407 which houses sensor 2410. The end of arm 2404 can house any type of sensor or detector such as exemplarily a blood gas analyzer which includes not only a chemical sensor but also a temperature sensor as well as a heating element. It is understood that a variety of sensing systems such as optical sensing, fluorescent sensing, electrical sensing, ultrasound sensing, electrochemical sensing, chemical sensing, enzymatic sensing, piezoelectric, pressure sensing, pulse sensing, and the like can be housed at the end of arm 2404 in accordance to the present invention. Exemplarily, but not by way of limitation, a glucose sensing system comprised of photodetector, filters, and processor can be housed at the end of arm 2404 and operate as sensor 2410. Likewise a combination light emitter and photodetector diametrically opposed or side-by-side and housed at the end of arm 2404 to detect oxygen saturation, glucose or cholesterol by optical means and the like is within the scope of the present invention.

Figure 7A:
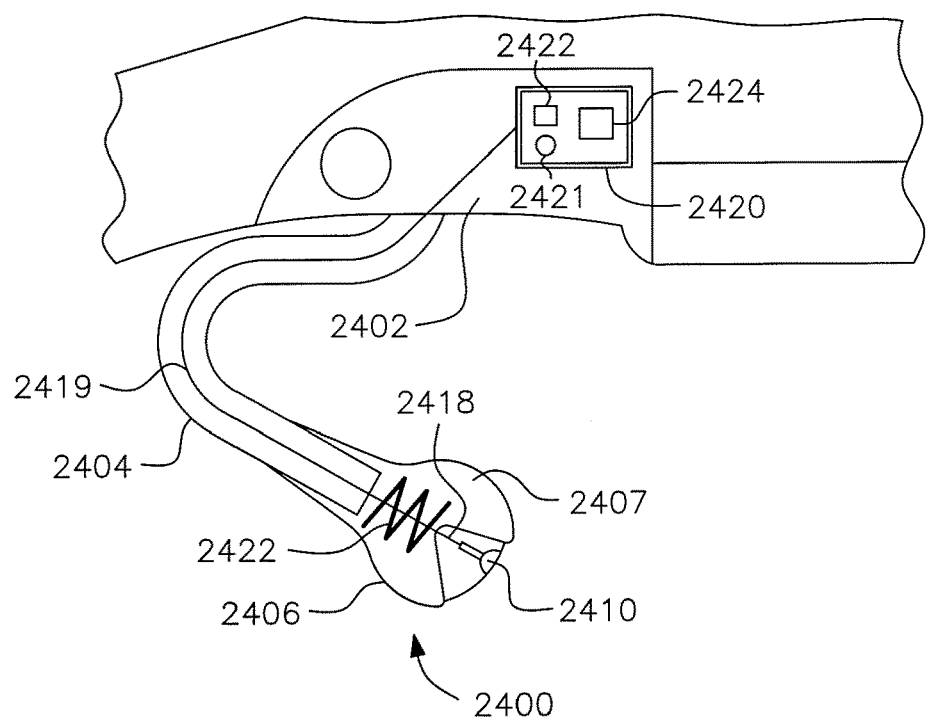
FIG. 7A illustrates a specialized support and sensing structure.
Figure 7B:
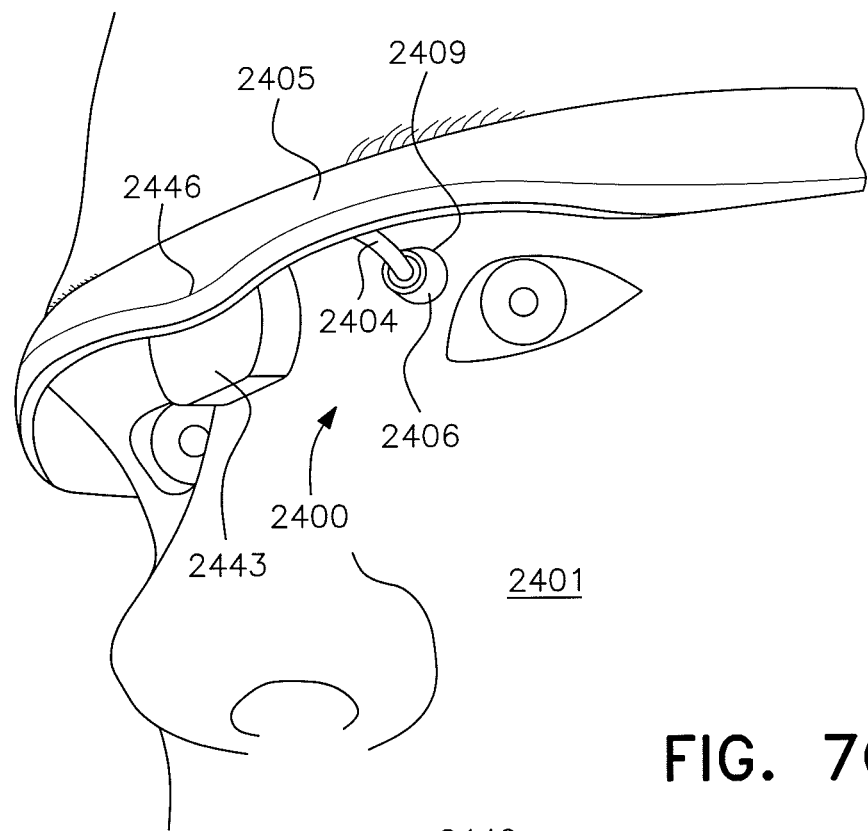
FIG. 7B illustrates a specialized support and sensing structure worn by a user.

FIG. 7B shows the specialized support and sensing structure 2400 of FIG. 7A when worn by a user 2401, and comprises measuring portion 2406 preferably having an essentially cone like structure positioned at the brain tunnel 2409 at the junction of eyebrow and nose, and below the eyebrow and above the eye. Measuring portion 2406 is connected to an adjustably positionable arm 2404 which is flexible and shown in a bent position, said arm 2404 being connected to a headband 2405, which operates as the body of sensing structure for securing measuring portion 2406 to a body part. The center 2446 of headband 2405 has an extension 2443 which houses electronic circuits, processor, power source, and wireless transmitter. Headband 2405 can function as a frame of eyeglasses with detachable lenses.

Figure 7C:
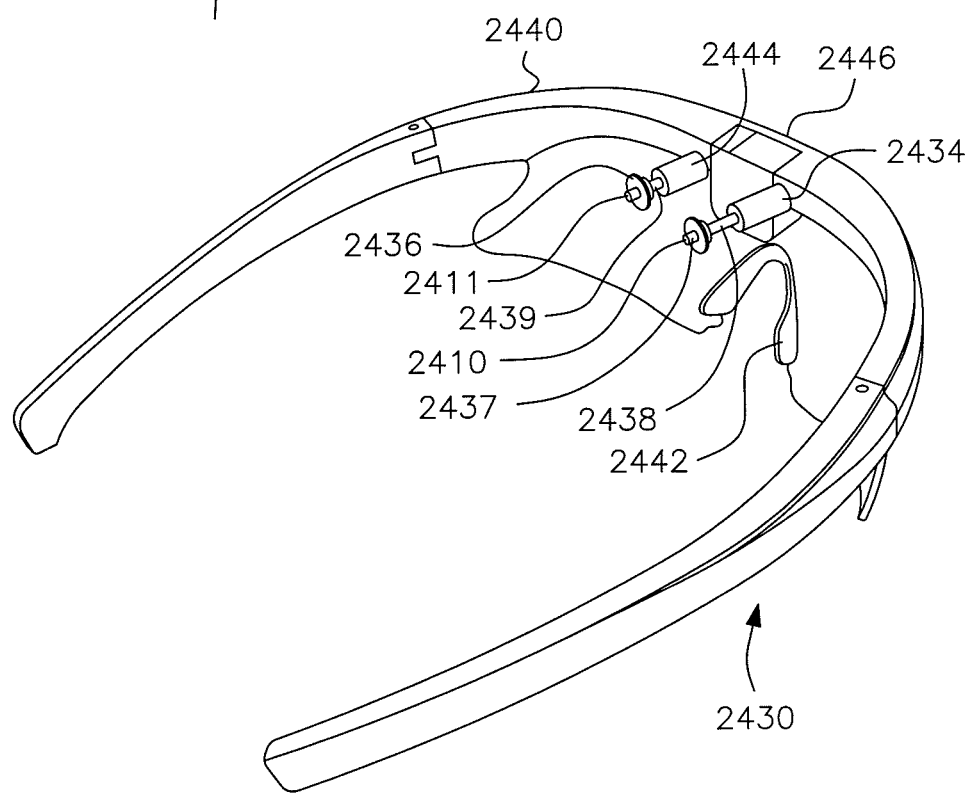
FIG. 7C illustrates the mounting of a specialized sensing device on eyeglasses.

FIG. 7C shows another embodiment of the specialized sensing eyeglasses 2430 of the present invention comprised of a dual sensing system with two arms 2434, 2444 which branch off the upper portion 2438 of frame of eyeglasses 2440, said arms 2434, 2444 extending from the middle portion 2446 of frame 2440 and being located above the nose pads 2442. Arms 2434, 2444 are located at about the middle of the frame of eyeglasses 2440. Arms 2434, 2444 may include an opening for housing rods 2438, 2439, said rods being connected to measuring portion 2436, 2437 and said rods 2438, 2439 being able to slide and move within said opening in arms 2434, 2444. Measuring portion 2436, 2437 houses sensor 2410, 2411 at its external end, exemplarily shown as a temperature measuring sensor 2410 and a pulse measuring sensor 2411. Middle portion of frame 2440 can have a receptacle area which houses power source, transmitter and processing circuit.

Figure 7D:
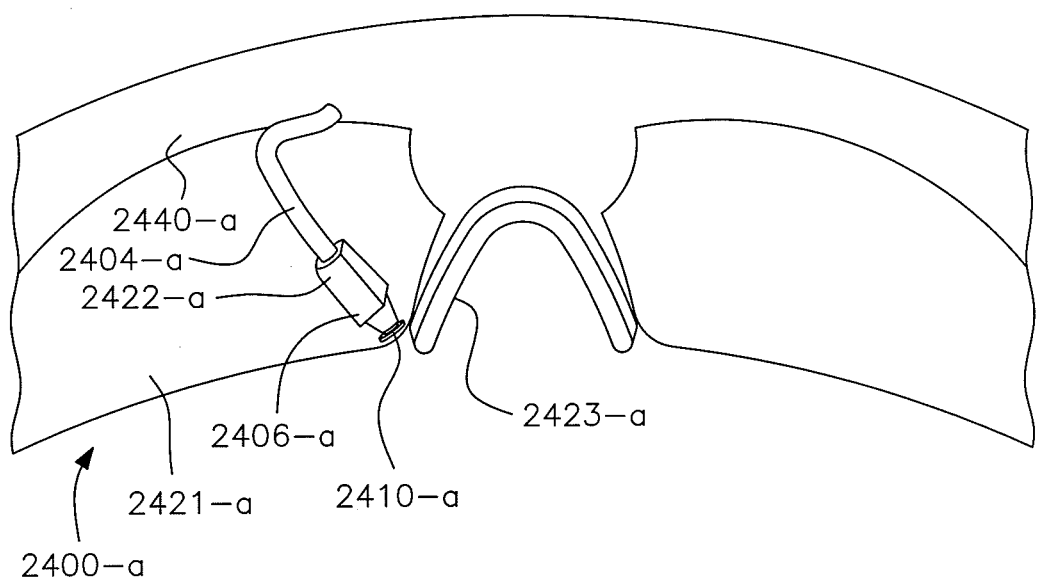
FIG. 7D illustrates the support and sensing structure mounted on a frame of eyeglasses.

FIG. 7D shows another embodiment of the specialized support and sensing structure 2400-*a* of the invention and comprises frame of eyeglasses 2440-*a*, lens 2421-*a*, nose pads 2423-*a*, adjustably positionable arm 2404-*a*, and measuring portion 2406-*a* preferably having an essentially cylindrical like structure said measuring portion 2406-*a* housing a spring 2422-*a* which is connected to sensor 2410-*a*. Measuring portion 2406-*a* is connected to arm 2404-*a*, said arm 2404-*a* being connected to the frame of eyeglasses 2440-*a*. Spring 2422-*a* projects sensor 2410-*a* beyond measuring portion 2406-*a*.

Figure 7E:
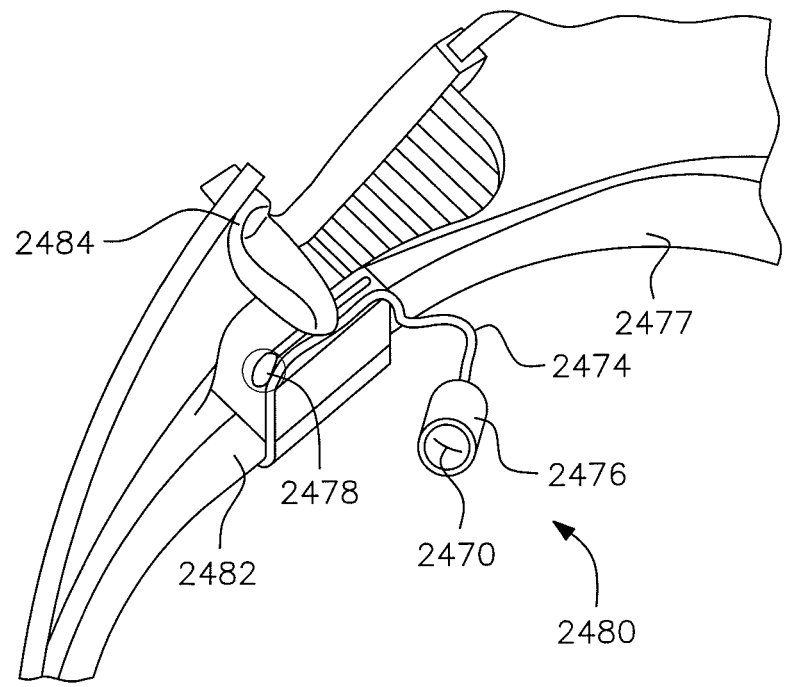
FIG. 7E illustrates a bottom view of an LED based sensing eyeglass.

FIG. 7E is a preferred embodiment showing a bottom view of LED-based sensing eyeglasses 2480 comprised of a sensor 2470 in holder 2476 representing a measuring portion of sensing eyeglasses 2480, an adjustable arm 2474 branching off the frame 2477 of sensing eyeglasses 2480, LED 2478, said LED 2478 being disposed along the lens rim 2482 and above nose pad 2484, and said LED 2478 being operatively connected to a processor housed in frame 2477, so as to activate said LED 2478 when the value of the biological parameter being measured falls outside the normal range.

Figure 7F:
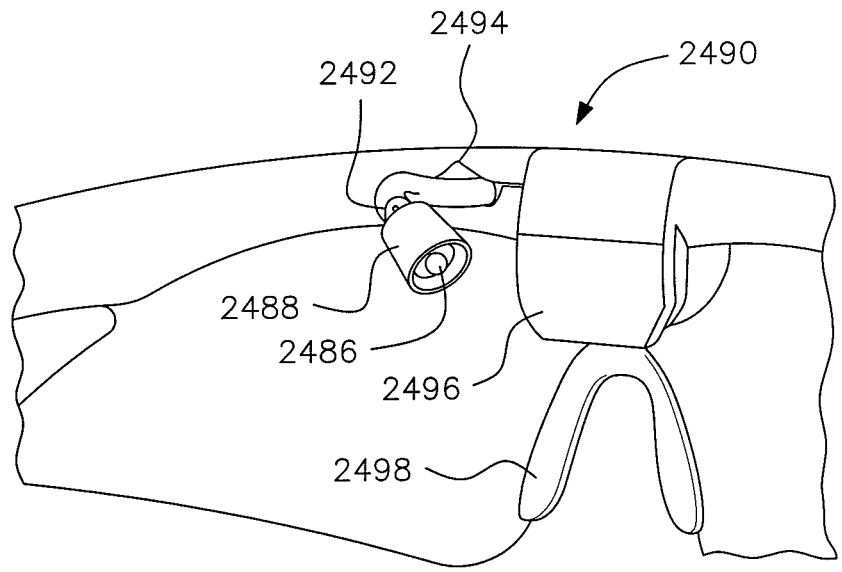
FIG. 7F illustrates a wireless based sensing pair of eyeglasses.

FIG. 7F is a preferred embodiment showing a wireless-based sensing eyeglasses 2490 comprised of a sensor 2486 in holder 2488 representing a measuring portion of the wireless sensing eyeglasses 2490, an adjustable arm 2492 branching off the frame 2494 of sensing eyeglasses 2490, a housing 2496, said housing 2496 extending from frame 2494 and above nose pad 2498. A processor, power source, and transmitter may be mounted inside said housing 2496 and be electrically connected to sensor 2486. A wireless signal corresponding to the biological parameter measured is transmitted by a transmitter in the housing 2496 to a receiver.

Figure 8A:
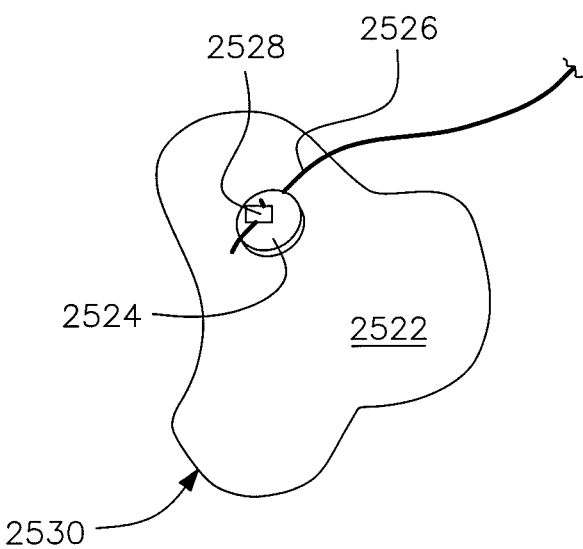
FIG. 8A illustrates a patch sensing system.

FIG. 8A shows another embodiment of the patch sensing system of the invention. Accordingly, FIG. 8A shows a clover-leaf patch 2530 comprised of two parts: (1) a thin and large flexible part in a clover-leaf shape 2522, and (2) a thicker round shaped part 2524, represented as a button, which secures a sensor 2528, said button 2524 being thicker than the large underlying clover-leaf shape part 2522. Button 2524 securing sensor 2528 is attached to a thinner and large part 2522. The large portion of the patch 2530 comprises the thin part 2522 and the portion of the patch 2530 holding the sensor 2528 comprises a part of smaller size as compared to the thin part 2522. The portion holding the sensor 2528 is smaller and thicker than the underlying portion of the patch 2530. Large part 2522 is thinner and larger in size than said portion holding the sensor 2500. The sensor 2528 is connected to a wire 2526 which has an approximate 90 degree bend between the side portion of button 2524 and the plane of the large portion 2522. Wire 2526 runs along the button 2524 and then runs along the thin portion 2522, and exits the thin portion 2522. The button 2524 holding the sensor 2528 projects beyond the surface of the thin portion 2522, said button 2524 being preferably eccentrically positioned on the thin underlying portion 2524 of patch 2530. Both the thin portion 2522 and the thick portion 2524 of patch 2530 may have an adhesive surface on the surface of the patch 2530 facing a body part.

Figure 9A:
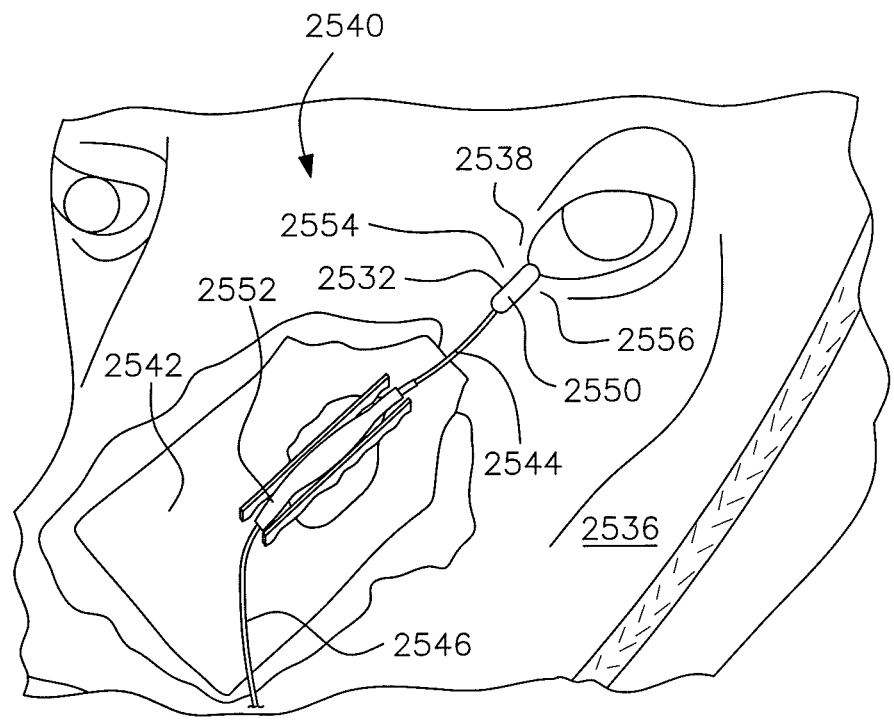
FIG. 9A illustrates a system for mounting a sensing device on an animal.
Figure 9B:
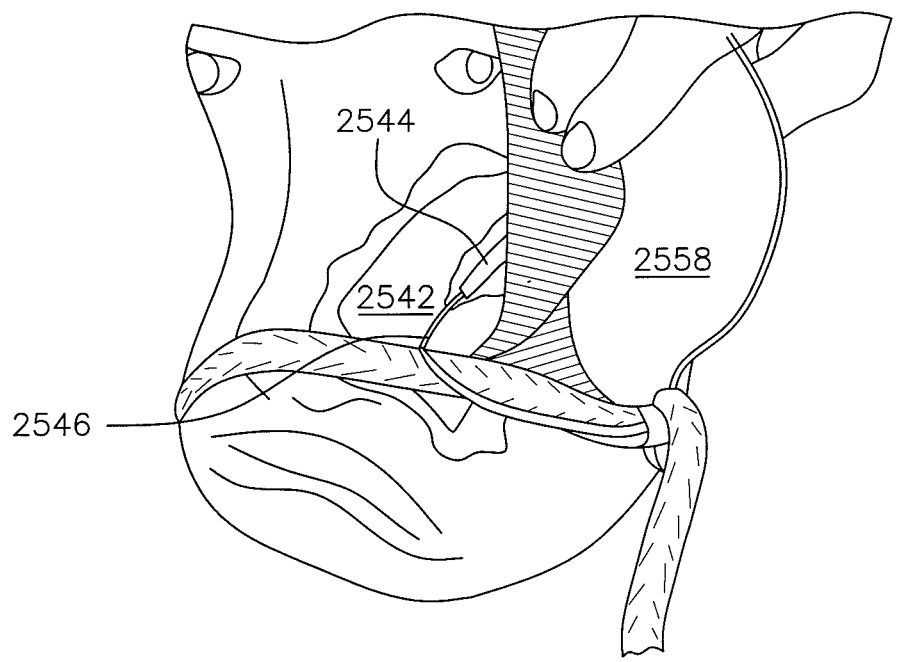
FIG. 9B illustrates a multilayer protection cover mounted on a sensing system for an animal.

FIG. 9A to 9B shows an illustration of another embodiment of the support structure or sensing system 2540 of the invention, for use in animals, with sensor 2550 placed on the eyelid area 2538 of an animal 2536 at the brain tunnel 2532. The animal BTT sensing device 2540 includes a body 2542, represented by a plate, an adjustably positionable elongated arm 2544 attached to said plate 2542, and a sensor 2550 disposed at the free end of said arm 2544. Arm 2544 is secured to plate 2542, said arm 2544 preferably having a sliding mechanism and plate 2542 preferably having a groove 2552, allowing thus arm 2544 to move in relation to plate 2542 so as to position sensor 2550 on the BTT area 2532 while plate 2542 is in a fixed position on the skin of animal 2536. Grooved mechanism 2552 has a plurality of locking positions, allowing arm 2544 to be locked in different positions. Arm 2544 is connected to a processing and transmitter unit (not shown) through wire 2546. Sensor 2550 has preferably an essentially rectangular shape. Preferably sensor 2550, or the material surrounding sensor 2550 such as epoxy, has a thickness between 1 mm and 6 mm, and most preferably a thickness between 2 mm and 4 mm, and most preferably a thickness between 1 mm and 3 mm. Sensor 2550 can be covered by insulating material or any material that presses the sensor 2550 leading the sensor to enter the brain tunnel, said other materials can thus increase the overall thickness of the sensor portion.

It is understood that plate 2542 can work as a circuit board and house a processor, wireless transmitter and power source. Alternatively, plate 2542 houses a transmitter and power source with signals being transmitted to a remote receiver for further processing and display of results, or plate 2542 holds an antenna for remote electromagnetic powering including passive devices. It is understood that the electronics, transmitter, processor and power source can be housed in a box for implantation under the skin of the animal. In this embodiment the plate 2542 is replaced by this box, and the method includes the step of creating an opening on the skin, and implanting the box under the skin or on top of the skin while arm 2544 preferably remains on top of the skin, and said box is anchored under the skin. A further step may include suturing the skin around the sensor 2550 in order to provide better stability and protection of the sensor, with said suture grasping the skin 2554 on the upper part of brain tunnel 2532 and the skin 2556 in the lower part of brain tunnel 2532, and applying a stitch on edge of each said skin 2554, 2556, said stitch located right above sensor 2550.

FIG. 9B shows another embodiment for animal sensing device 2540, comprised of a multi-layer protection cover 2558 which is mounted on top of the plate 2542 and the sensor (not shown since it is covered by layer 2558), said layer 2558 preferably having insulating properties, an arm 2544, and a wire 2546. Preferably a thick support such as hard piece of material such as wood in the shape of the sensor is placed on top of said sensor for creating better apposition between sensor and the skin at the BTT.

The method includes securing plate 2542 to the head of a mammal, preferably by gluing the internal surface of the plate 2542 to the skin of the animal using glue or an adhesive surface; positioning sensor 2550 on the BTT 2532 at the eyelid area 2538, said step preferably accomplished by sliding arm 2544 in a groove 2552 in plate 2542 until the sensor 2550 is on or adjacent to the BTT area 2532. A further step may include bending the free end of arm 2544 and applying pressure at the BTT 2532 by sensor 2550 and producing a signal by said sensor 2550. Further steps include applying an electrical current, and generating a signal by sensor 2550. Other steps may include processing and analyzing said signal, and reporting a value of said signal. Similar steps can be used when applying sensing device 2000, but preferably during human medical use positioning may not include a sliding step.

Now in reference to FIG. 10A, there is seen another method and apparatus of the invention, comprised of coupling signals from a physiological tunnel, such as for example, coupling the BTT signal with alert means mounted on apparel, such as clothing, or coupled with footwear. It should be understood that any article of footwear including sneakers, cleats, sports shoes, sandals, boots, and the like is considered within the scope of this invention as well as any type of apparel or clothing.

Prior art relied on numerical values for guiding a user about exercise intensity, such as looking at a wrist watch to see the value for heart rate from a chest strap monitoring heart beat. Looking at a number has several disadvantages including increasing stress and distraction, both of which can lead to reduced performance. In addition, the human brain is organized in a way to associate indicia such as numbers with a particular information or condition, and that may briefly reduce concentration in the exercise in order for the brain to finish the association, which in this case is for example number 100 beats per minute (bpm) means out of an optimal pulse zone for fitness or number 39.5 degrees Celsius meaning out of optimal thermal zone. Just holding the arm to look at a number may take away precious seconds of performance, since to see a number is necessary to use the ciliary muscle of the eye to focus and also to hold the display in a essentially motionless position such as holding the arm steady and aligned with the eye. In addition, a person older than 45 years of age may have presbyopia and thus have difficult seeing a numerical value unless using eyeglasses. Contrary to those disadvantages of the prior art, the present invention relies on reporting means which do not require using the ciliary muscle of the eye to focus such as in order to read a number. The present invention also is suitable for use by persons of all ages including people older than 45 years of age and with presbyopia and even cataract. In addition the present invention does not require holding a display in an essentially immobile position. Actually reporting means of the present invention are preferably in constant motion during the time of providing the information to the user. Furthermore there is no distraction as trying to read a number and associate that number with a biological condition. Furthermore there is no increased stress as occur when looking and seeing a numerical value, nor extra brain work to interpret a number. All of those advantages are accomplished by using a light source as the reporting means, as in accordance with this invention, said light source adapted to provide information according to the value of the biological parameter. In addition, a light source, such as in a shoe, is naturally present within the visual field of a human without said subject having to directly look or focus at the light. This allows the information to be naturally delivered and effortlessly received by the user. Furthermore the brain through the occipital cortex is better adapted to recognize a visual stimulus than a numerical stimulus and the brain is also better adapted to memorize visual stimuli such as a yellow LED to inform about potential danger than to memorize a number such as 147 bpm or 38.9 degrees Celsius. Furthermore, the information such as a light source is available immediately and without the need for association as occurs with numbers. In addition, the human brain is trained on a daily basis for recognizing and processing visual stimuli, such as green, yellow and red lights in a traffic light or the LED of an electronic device to indicate the device is turned on. Accordingly, the present invention couples the biological aspects related to visual stimuli with engineering and discloses such monitoring device, which preferable include LEDs mounted on or in a wearable article such as clothing, apparel accessories, or shoes as the reporting means instead of numerical values.

FIG. 10A illustrates coupling of physiological signals such as temperature and pulse with footwear, said footwear operating as a receiver for the signal and to alert the user of abnormal physiological values. This embodiment is directed to an article of footwear having one or a plurality of alert means such as light sources, represented by LEDs, vibration, buzzers, speakers and the like, which are activated according to the physiological value measured by a sensor. It is understood that any sound can be produced or any visual indicia can be used to effortlessly and naturally inform the user about the biological parameter level without the need to display any numerical value or requiring the user to look for the information such as for example looking at a watch. The information is acquired by the user in a passive and effortless manner. The visual field of a user allows receiving the visual stimulus without having to do any extra movement such as holding the arm to look at a watch. The actual numerical value during physical exercise is of secondary interest since the key aspect for evaluating exercise level is a range of values or threshold values, (such as too high or too low) which are represented by visual and sound stimuli, as per the present invention. By causing a light to be illuminated corresponding to the value of a biological parameter, the user is assisted in guiding the exercise level and remaining within safe zones, in an effortless way in which the user has immediate response without having to think about a number being displayed and then analyzing whether the number falls into a desired exercise level.

Besides temperature and pulse, any other signal can be used including oxygen level, blood pressure, glucose level, eye pressure, and the like as well as signals from other devices such as a pedometer and the like. In addition, the light-based reporting means of the invention can include activation of a light source, such as LED, to indicate the distance or in the case of speedometer to indicate the speed of the user. For example, a user can program the pedometer to activate a light every 1,000 steps or every mile for instance during a marathon. The program is also adapted to activate a LED when the user is running within a certain speed, said speed being predetermined by the user. In this embodiment for example, the pedometer has 3 LEDs blue, green, and red, which are programmed to be activated according to a predetermined speed or distance. For example, the blue LED is activated if the speed is less than 6 minutes per mile, the green LED is activated if the speed is between 6 and 7 miles per minute, and the red LED is activated if the speed is more than 7 miles per minute. The system may also include a global positioning system or other system to track speed and/or distance, with a light being activated when the desired speed or distance is achieved, or alternatively the light is activated when the programmed speed and/or distance is not achieved.

The alert means alert the user when the signals received from a sensor are within appropriate levels or alert the user when the signal is outside levels of safety. For example, alert means inform the user about said user being in an optimal thermal zone (OTZ), in which the body temperature is within ideal levels for example for stimulating formation of heat-shock proteins. The OTZ is considered an appropriate level for health and performance, such as a temperature range between 37.0 degrees C. and 39.4 degrees C., and most preferably around 38.0 degrees C., and even more preferably around 38.5 degrees, up to 39 degrees C., for stimulating formation of heat shock proteins. The OTZ indicates a range of temperature that is safe and that leads to the best performance without overheating. Different levels of OTZ can lead to burning fat efficiently, as burning generates heat which is reflected in an increase in body temperature. Likewise, an optimal pulse zone (OPZ) indicates the optimal range for improving heart fitness. A second zone OPZ-F indicates the range of pulse that can lead to burning fat. A variety of optimal zones can be used and programmed so as to activate the LEDs in accordance with the optimal zone of interest such as fitness, endurance, heart-lung exercise, improving cardiovascular fitness, burning fat, and the like.

The alert means of the footwear or clothing preferably includes a set of lights which are activated according to the level of a biological parameter, such as temperature zone or pulse of the user. One aspect of this invention includes providing an interactive footwear or apparel which helps the user maintain physical activity within an optimal range by visualizing lights and/or listening to sound from shoes and/or apparel. An array of LEDs are mounted on a portion of footwear or clothing which are easily visualized, such as for example the upper portion of a footwear or the portion of an apparel covering the chest or front part of the lower extremities. It is understood that any head mounted gear can also be used with the array of LEDs mounted on a location easily visualized during physical activity. The information about exercise level is then acquired in an effortless way and a natural way. A particular number is not necessary in the preferred embodiment, since the array of lights can indicate the level of exertion and whether the user is within an optimal zone for the planned activity. For example an array of LEDs mounted in the tongue of a shoe or upper portion of a shoe illuminates in a certain manner or flashes in a sequence to indicate the level of a biological parameter, such as pulse level, oxygen level, blood pressure level, or temperature level, or to identify the presence of a chemical substance such as drugs or any analyte present in the body.

In one embodiment an array of LEDs is mounted on the upper portion or tongue of the shoe, said LEDs being electrically connected to a processor which controls and drives the LED array based on an electrical signal, received from a transmitter coupled to a sensor monitoring a physiological parameter. The processor is operatively coupled to a receiver, said receiver receiving signals from said sensor monitoring a any parameter including physiological parameters or environmental parameters such as ambient temperature, humidity, wind and the like, said signals from said sensor preferably being wirelessly transmitted to the receiver in the footwear. In another embodiment the sensor is located in the shoe including sensors for physiological parameters such blood flow, temperature, pulse and any other physiological parameter and/or for detecting ambient conditions such as a ambient temperature, humidity, ultraviolet rays, wind, and the like. In those embodiments there is no need for signal transmission as with remotely placed sensors since the light source is also located in the shoe, and said light source can be integrated with the sensor. The processor is operative to illuminate the LED for a certain period of time preferably in accordance with the user being in the OTZ and/or OPZ, for example by illuminating a green LED. Alternatively, the processing circuit illuminates a red LED to inform the user that the temperature or pulse is too high, or a blue LED to inform that the temperature or pulse is too low, or any combination thereof involving any color or number of LEDs.

The signal from the transmitter coupled to the sensor is transmitted to the receiver in a shoe or clothing, said signal driving a LED or a speaker in said shoe or clothing. For example, when a human subject monitoring pulse and temperature with a BTT sunglasses sends a wireless signal from said BTT sunglasses to a receiver in a shoe worn by said user, and said signal corresponds to an optimal thermal zone and optimal pulse zone, then said signal causes two green LEDs to illuminate in the shoe to indicate that both temperature and pulse are within ideal levels, and causes the shoe to produce the sound "optimal zone". It is understood that any sound can be produced or any visual indicia can be used to effortlessly and naturally inform the user about the biological parameter level. Accordingly, if the signal received indicates the user is too hot or the pulse is too high, then an indicia representing a Coca-Cola™ logo or a Pepsi-Cola™ logo is illuminated indicating that the user should take some liquid and be hydrated, so as for example to avoid heat injury. Likewise, the signal indicating high temperature can cause the speaker in the shoe or apparel to produce the sound "water", "time for your Coke™", "time for your Pepsi™", and the like. Besides monitoring pulse with a BTT device, any other device for pulse detection including a conventional chest strap for pulse monitoring can be used, said monitoring devices transmitting a signal to a shoe or apparel to drive lights, speaker, and the like. It is also understood that any signal from any device monitoring physiological parameters can be used. Accordingly, a device monitoring glucose, eye pressure, drug levels, cholesterol, and the like can transmit the signal to a footwear or apparel, which cause for example a LED representing low glucose levels to illuminate, and the speaker to produce the sound "sugar low—drink a juice" or the name of a medication is illuminated in the shoe or apparel to indicate the physiological value. Thus when a diabetic is the user of the biological light-sound system of this invention and if the user is monitoring glucose and the word "insulin" is illuminated in the shoe, clothing, or accessories, then that user knows that sugar levels are too high.

It is understood that the housing, referred to herein as module or biological monitoring electronic-LED module, containing the RF receiver, power source, processor, LED, and speaker can be removably attached to the shoe or apparel or permanently mounted on the shoe or apparel. For example a pocket in the shoe or apparel such as a pocket in the tongue of the shoe can be used to house the biological monitoring electronic-LED module. Any pocket or other means to secure one or a plurality of modules to a shoe or apparel are contemplated and can be used. For example, two modules, one for monitoring temperature from a BTT sunglasses is secured by a hook and loop fastener (such as a Velcro™) to a shirt while a second module for monitoring pulse from a chest strap is placed in a pocket located in the tongue of a shoe. When the BTT sunglasses sends a temperature signal to inform the user of the temperature level the LED secured to the shirt illuminates. The same occurs with the LED in the shoe which is activated by a pulse signal from the chest strap.

Now referring to FIG. 10A, there is seen a shoe 2600 having an upper portion 2602 including a tongue 2604 having a housing 2606, such as a pocket, for housing module 2610, said module 2610 including a power source 2612, a wireless receiver circuit 2614, and at least one LED 2620 operatively coupled to the wireless receiver circuit 2614 functioning as a LED driver. Module 2610 can further include a processor 2616 and a speaker 2618. Module 2610 is preferably made of plastic or any water-proof material. Although module 2610 is shown mounted in a tongue 2604 of the shoe 2600, it is understood that module 2610 can be mounted on any part of any shoe and in any type of shoe. It is further understood that module 2610 can include electronics mounted in one location of the shoe connected to a fiber optic or LED mounted in a second location in the shoe. For example the battery, wireless receiver, and controller are housed in a cavity in the heel of the shoe, and said electronics and battery in the heel are connected through wires to a LED in the tongue of the shoe, or an electronic circuit in the sole of the shoe can be connected to fiber optics located in the front part of the shoe. Any type of light source can be used including LED, fiber optic, chemiluminescent sources such as a light stick, fluorescent light, and the like. The location of the light source and speakers include any portion of the apparel or shoe, preferably the light source is located within the natural visual field of a human. It is understood that all of the arrangements described for a shoe can be used for an apparel or clothing.

The module 2610 can include a switch 2622, which can be activated by application of pressure when the shoe is in use or the module 2610 can include a manually operated switch. Module 2610 can include any type of inertia-based switch to allow automated activation of a receiving system of module 2610. Accordingly, when the shoe is not in use or no pressure-based switch is activating the receiving system of the shoe it automatically shuts off. In addition, if the receiving system of the shoe does not receive any signal for a certain period of time, such as for example 10 minutes, then the receiving system of the shoe also automatically shuts off. Those arrangements for automatically turning the shoe on and/or off allows saving battery power and/or making the system of this invention easier to use. If the user wants to know an actual number for the biological parameter, a switch located in the monitoring device coupled to the sensor can be activated or a second switch on the shoe or apparel can be activated and a number can be displayed in the shoe or apparel, or in the monitoring device. In this embodiment, the shoe or apparel, or monitoring device can include a numerical display. For example, it is contemplated that the BTT sunglasses can be adapted to display a numerical value on the lens if requested by the user.

In FIG. 10B-1, a schematic illustration of this invention for pulse and temperature measurement is shown and includes a heart rate monitoring device 2624, represented by a chest strap for detecting a heart beat, a thermometer 2626, represented by eyeglasses for detecting body temperature, and a shoe, 2630, said shoe 2630 having a logo 2628 comprised of LEDs. Logo 2628 is seen in a magnified view in FIG. 10B-2, which shows one first LED 2632 and a second LED 2634 corresponding to a heart zone, said first LED 2632 being coupled to a signal representing a slow heart rate, and said second LED 2634 being coupled to a signal representing a fast heart rate. Besides LEDs 2632, 2634 coupled to a heart monitoring zone, a third LED 2636 corresponds to a body temperature zone, said LED 2636 being coupled to a signal representing an unsafe temperature level, such as a high body temperature.

Several exercise programs can be implemented with the invention. In order to achieve the proper exercise intensity, the user can use keypads or buttons to enter information into the monitoring device such as the eyeglasses or the chest strap device, or alternatively the user can enter the information in the shoe, said shoe being adapted to receive information and said information including age, body weight, height, exercise goals, and the like. A processor can then calculate the optimal temperature zone and optimal pulse zone for that particular exercise goal which will activate the LEDs in accordance with the signal received and exercise goal. For example, a user 40 years of age, 1.80 m tall, and weighing 95 kg, who wants to have a long workout (more than 45 min) with the objective of burning fat (weight loss), enters the information, which is fed into a processor. The processor is operatively coupled to a memory which stores the OTZ and OPZ associated with an exercise goal and user data. For example according to the user data, OTZ is between 38.1 degrees Celsius and 38.5 degrees Celsius and the OPZ is between 117 and 135 beats per minute (bpm), meaning optimal pulse is between 117 and 135 bpm. A preferred way to calculate the OPZ includes subtracting 220 from the age, which provides 180, and then calculating a percentage of the OPZ number (180) based on the user and exercise goals, which in this example is between 65% and 75%.

The processor is operatively coupled to the LEDs, and in the exemplary embodiment if the temperature signal from the thermometer eyeglasses 2626 corresponds to a temperature higher then 38.5 degrees then LED 2636 is illuminated to indicate the high temperature, translating for example into the need for hydration or reducing exercise intensity since the user is outside his/her OTZ. Likewise, if a pulse signal from heart monitoring device 2624 corresponds to a heart rate less than 117 beats per minute, which is the target for the slowest heart rate, then the processor activates LED 2632 which is illuminated and indicating therefore a slow heart rate for the exercise goal. If the signal received from heart monitoring device 2624 corresponds to a heart rate faster than 135 bpm, which is the target for the fastest heart rate, then LED 2636 is activated and illuminated.

Considering another embodiment with four LEDs comprised of two LEDs marked T and two LEDs marked P, if the temperature falls below 38.1 degrees Celsius a "yellow LED market T" is illuminated indicating low temperature for OTZ, and if above 38.5 degrees Celsius then a "red LED marked T" is illuminated. If pulse is slower than 117 bpm then "yellow LED marked P" is illuminated and if pulse is faster than 135 a "red LED marked P" is illuminated.

Figures 1, 10C:
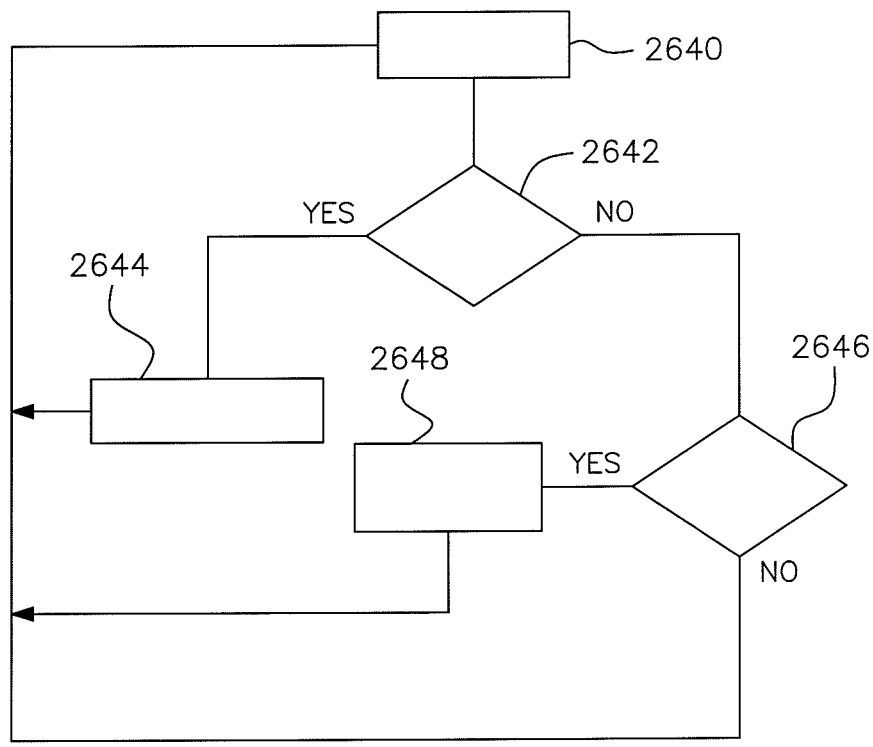
Figures 2, 10C:
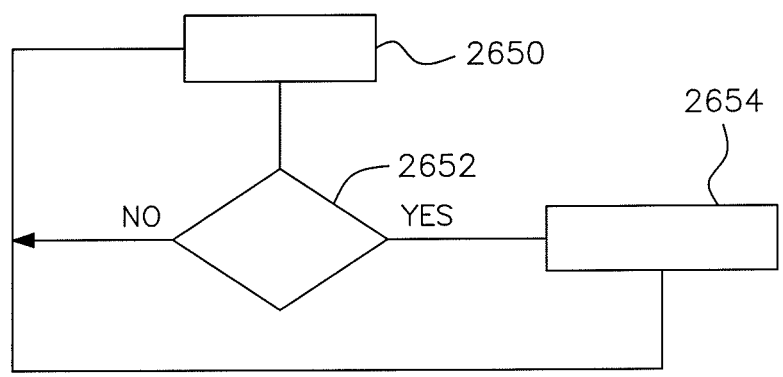

An exemplary algorithm for heart monitoring in accordance with this invention is seen in FIG. 10C-1 and includes step 2640 to "acquire heart rate signal', which is preferably received wirelessly from heart monitoring device 2624. Step 2642 then determines whether "heart rate is slower than the slowest target heart rate", illustrated in the embodiment as heart rate less than 117 bpm. If yes, then step 2644 activates LED 2632 to indicate slow heart rate, and then proceed with the program at step 2640 to acquire heart rate signal. If not, then step 2646 determines whether "heart rate is faster than the fastest target heart rate" illustrated in the embodiment as a heart rate faster than 135 bpm. If yes, then step 2648 activates LED 2634 to indicate a fast heart rate and then proceed to step 2640. If not, then processing continues and program proceeds to step 2640. Likewise, FIG. 10C-2 shows an algorithm for body temperature monitoring according to this invention. Step 2650 acquires body temperature level, and step 2652 determines whether "temperature is higher than the highest target temperature", illustrated in the embodiment as temperature more than 38.5 degrees C. If yes, then step 2654 activates LED 2636 to indicate a high temperature and then proceed to step 2650. If not, then program continues to step 2650 and processing continues.

The invention includes a method for detecting and transmitting a biological parameter, receiving the transmitted signal with a receiver connected to a shoe or apparel, processing the received signal, determining the value of the biological parameter, and activating a light source based on the value. Further step may include activating a speaker. Other steps may include displaying a numerical value and transmitting the signal to another device.

It is understood that the program can be done in sequence, and include other parameters such as oxygen level and uptake, glucose level, blood pressure, acid lactic level, heat shock protein, and any other biological parameter or environmental parameter such as ambient temperature, humidity, wind speed, and the like. All of those parameters are reported using the reporting means of the invention such as the LED system of the invention. Accordingly, in yet another embodiment of this invention, a plurality of array of LEDs are provided. For example a first array of LEDs detects one parameter (e.g. pulse), said array of LEDs separate from a second array of LED measuring a second parameter (e.g. temperature), and both the first and second array of LEDs being separate from a third array of LEDs which measure a third parameter (e.g. environmental humidity). Each group of LEDs can be activated by a signal from a separate transmitter connected to each specific array of LEDs.

It is also understood that each LED can be marked with indicia indicating the physiological condition. Accordingly, an LED can have for example wording "High Temp", and/or "Fast HR" and/or "Slow HR" in order to report the physiological condition. Furthermore, a speaker or speech synthesizer can be included and concomitantly activated to produce, for example, the sound "High Temp", and/or "Fast HR" and/or "Slow HR". It is also understood that LED of different colors to indicate different levels for biological parameters can be used. For example, a green LED represents heart rate less than 130 bpm, a yellow LED represents heart rate more than 130 but less than 170 bpm, and red LED represents heart rate more than 170 bpm. A series of bars can also be used, one bar illuminated indicating heart rate less than 130 bpm, two bars illuminated indicating heart rate less than 170 bpm, and three bars illuminated indicating heart rate more than 170 bpm. The invention further includes a kit containing a device to monitor biological parameter and a shoe or an apparel. The kit can further include instructions. The illuminating device, such as LED, can be also removable to permit interchangeable selectivity of the color of the illuminating light.

Figure 10D:
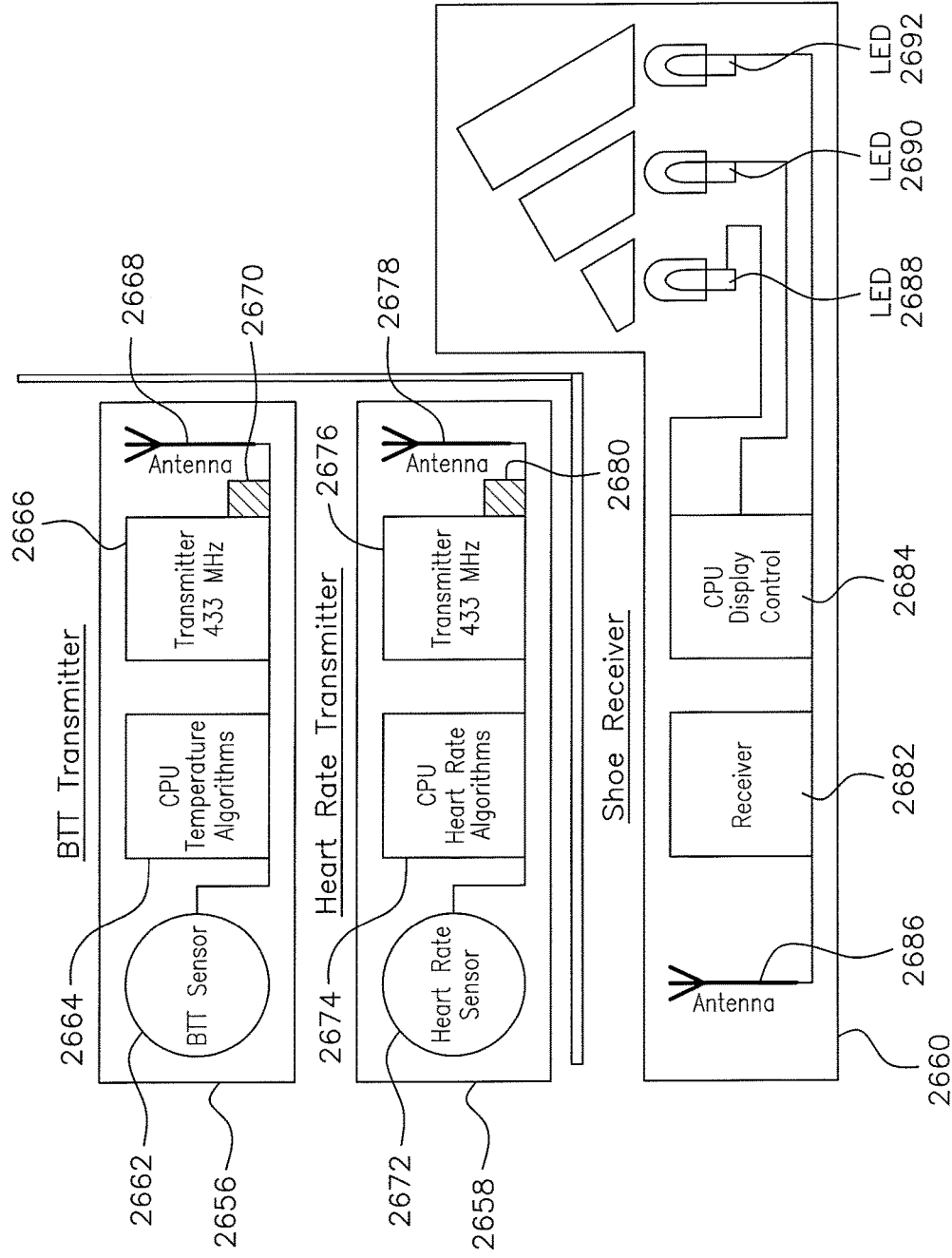
FIG. 10D schematically illustrates a brain temperature tunnel transmitting system, a heart rate transmitting system and a shoe receiving system.

Referring now to FIG. 10D, a block diagram is schematically illustrated, which includes a BTT transmitting system 2656, a heart rate transmitting system 2658, and shoe receiving system 2660. BTT transmitting system 2656 includes a BTT sensor 2662 (such as a temperature sensor), a processor and processing circuit 2664 including temperature algorithms, a transmitter 2666, an antenna 2668, and a battery 2670. Heart rate transmitting system 2658 includes a heart rate sensor 2672, a processor and processing circuit 2674 including heart rate algorithms, a transmitter 2676, an antenna 2678, and a battery 2680. Heart rate transmitting system 2658 can include a system comprised of electrodes and a transmitter attached to the body of the user, which can be housed for example in a chest strap. Heart rate monitoring system 2658 can also include a wrist band, headband, head mounted gear, or any other means to monitor pulse or gear adapted to detect a pulse of a user. Shoe receiving system 2660 includes a receiver 2682 a processor and display control circuit 2684, an antenna 2686, and LEDs 2688, 2690, 2692, said LEDs 2688, 2690, 2692, corresponding to a different physiological condition as previously described. Accordingly, LEDs 2688, 2690, 2692, can correspond to the functions of LEDs 2632, 2634, and 2636. It is understood that each of the systems 2656, 2658, 2660 can include switches, electrical connections, and other integrated circuits for performing the need functions. Sensors 2662, 2672 generate an electrical signal which is transmitted to shoe receiving system 2660. In response to the signal received from the transmitting systems 2666, 2676 the processor and display control circuit 2684 may activate one or more LEDs for a certain period of time including flashing. Essentially any combination of lighting sequences of the LEDs and flashing can be employed in response to a signal received. The system of the invention provides a novel way in which a biological parameter level is indicated through illuminating specific LEDs. By causing a light to be illuminated corresponding to the value of a biological parameter, the user is assisted in guiding the exercise level and remaining within safe zones, in an effortless way in which the user has immediate response without having to think about a number being displayed and then analyzing whether the number falls into a desired exercise level and/or safe level.

It is understood that other receiving devices are contemplated and can benefit from the present invention. For example, an exercise machine can receive the signal and an array of LEDs mounted in said machine indicate to the user the exercise condition and biological parameter values without the user having to rely on a numerical value. Other devices contemplated include a wrist band mounted with at least one LED which is activated based on the level of the biological parameter, said wrist band detecting the level and reporting the level through a least one LED. In this embodiment there is no need for wireless transmission since the wrist band can detect pulse and thus detecting and reporting function are accomplished in the same device. Likewise, a chest strap can have one or more light sources to indicate the pulse level, said chest strap preferably being part of a garment or being under a thin shirt to facilitate visualizing the flashing LEDs. In another embodiment the chest strap monitoring heart rate can include speaker for audio reporting of a numerical value or reporting an optimal zone for exercising such as OPZ or OTZ. It is also understood that a wrist watch can include a set of lights which are illuminated to indicate OPZ and OTZ, or any other optimal value of a biological parameter. Besides, a range and threshold, a mean value can also be calculated and an LED activated to indicate achieving that mean value, or being outside the mean value, such as for example a mean pulse value. It is understood that in addition to illuminating light for feedback, if the user chooses, real-time, spoken feedback can alert said user to milestones, such as number of miles, throughout a workout. It is also contemplated that the shoe or apparel may include a chip that recognizes module 2610, which can work as a removably attached module, so a user can remove module 2610 from one shoe and insert the same module 2610 in or on an apparel or in or on another shoe, so any shoe or apparel with the chip can use the module 2610.

There are basically two types of thermometer probes using contact sensors in the prior art: 1) one for measuring internal temperature such as food thermometers and body temperature such as oral thermometers, which are inserted inside the object being measured, and 2) a second one for measuring surface temperature, such as for instance measuring temperature of a grill. Contrary to the prior art this invention teaches a new method and apparatus which combines in the same thermometer probe features of both internal temperature measurement and surface temperature measurement, such arrangement being necessary for measuring temperature in the brain tunnel.

Thermometer probes for internal temperature measurement of the prior art, such as oral/rectal thermometers, have temperature sensors covered by a metal cap or by other materials which are good heat conductors. The tip of the thermometers of the prior art were made out of metal or other thermally conducting material such as ceramics and the like, including the temperature sensor on the tip being surrounded by a metallic cap. Contrary to the prior art, this invention teaches a thermometer in which the temperature sensor is surrounded by an insulating material. In distinction to the prior art, the thermometer of this invention comprises a tip in which there is no metal or any conducting material surrounding the temperature sensor. The sides of the tip of the thermometer of this invention comprise insulating material, and thus the sides of the tip have at least one insulating layer. In addition this invention couples specialized dimensions with a novel temperature sensing tip that includes an insulating tip instead of a metallic tip, said insulating tip housing the temperature sensor.

Thermometer probes measuring surface temperature are concerned only with the surface being measured and thus do not require insulation in a large area of the probe nor a metallic cover to increase heat transfer. Basically those surface thermometer probes of the prior art have a thermocouple at the end of the probe, said end being rigid and made with hard material.

The design of this invention allows both to be accomplished, measuring internal as well as surface temperature simultaneously. In order to achieve precise surface measurement the BTT sensor is completely surrounded by insulation at the end of the probe. In order to measure internal temperature, the sensor has to enter the tunnel which causes an indentation in the skin. When the probe is pushed into the tunnel because of the characteristics of the BTT area and of skin, there is a rather significant indentation, which leads the skin to encircle and surround the tip, which would lead to affecting the temperature of the thermal sensor since the skin is cold. To prevent that, the probe of the invention has a rather long area (length) of insulating material above the sensor, and no heat conducting material around the tip of the probe, besides the special dimensions previously described. In addition, to conform to the specialized geometry of the skin at the BTT, the insulating material of this invention comprises a soft and preferably compressible insulating material at the tip. Contrary to this invention, the prior art has used hard materials on the tip, since those probes are used for measuring hard and/or flat surfaces, and not irregular surfaces such as the skin at the BTT. In addition, since the BTT geometry is concave in nature, the preferred embodiment of the end of the probe of this invention is essentially convex. Furthermore, the tip of the probe may comprise one or more sensors, and preferably a plurality of sensors disposed in an essentially convex surface. Programming in the processor selects the highest temperature among all sensors facilitating reading the temperature at the main entry point of the tunnel, which has the highest temperature. Preferably, a tip of the probe or the measuring surface of the probe includes both sensor and insulating material in said surface, and said probe is essentially cylindrical. The sensor of this invention which is located at the tip of the probe is surrounded by insulating material, both on top of said sensor and around the sides of said sensor. The sensor of this invention is preferably exposed at the tip of the probe without any material covering said sensor. Contrary to hard insulating material of the prior art, the sensor of this invention is surrounded by soft insulating material. The probe preferably uses a rod and hand held configuration. Contrary to the prior art which uses hard material to support the tip of the probe, such as used in surface measuring thermometer, the present invention uses exclusively soft material around the thermal sensor in its entirety, and no metallic or hard material are adjacent to the sensor or located within 4 mm from the tip of the sensor, this material being illustratively represented in several embodiments including body 2020. The shape of the tip of the probe of this invention is designed to conform and take the shape of the area of the BTT below and adjacent to the eyebrow and the nose, and more specifically to match the roof of the orbit by the nose and eyelid area. The prior art has a very small amount of insulating material around the tip since it was not designed to measure internal temperature. Contrary to the prior art, this invention, by having the necessity of avoiding temperature of the skin that may encircle the probe during entry of the sensor into the tunnel affecting the measurement, a rather large amount of insulation is used. The preferred length of material at the tip of the probe, said insulating material facing the environment, is equal to or less than 3.5 mm, and preferably equal to or no greater than 5 mm, and most preferably equal to or no greater than 10 mm. The insulating material at the tip is preferably not covered by any other material. The thermometer probe of this invention uniquely has features of both types of thermometer, penetrating and surface measuring thermometers. The tip of the thermometer of this invention preferably uses deformable material and conforms to the surface being measured. The tip of the probe takes the contour of the area that is being measured so it seal off any ambient temperature, and prevent surrounding skin tissue around the tunnel from touching the temperature element. Preferably stand alone insulating material is what supports the tip of the probe, said material being preferably compressible material with some springing characteristics. Features mentioned herein have been described in several embodiments of this invention including measuring portion and FIG. 11V-1 to FIG. 12M-2.

In addition, the present invention discloses novel methods and apparatus for measuring biological parameters, such as temperature. Accordingly and in reference to FIG. 11, the present invention discloses an intelligent stylus 2700 associated with an electronic device 2702, such as a PDA, a hand held computerized device, a tablet computer, a notebook computer, or any electronic device which uses a rod (stylus) for touching the screen for performing a function. The device of the invention includes the intelligent stylus 2700 represented herein by a touch-screen stylus or any rod for touching the screen of the electronic device 2702. Stylus 2700 houses a sensor 2704 on one end 2706, said end being opposite to the end of the stylus adapted to touch the screen, with said end 2706 referred herein as the sensing end of stylus 2700, and further including an opposite end 2708, hereinafter referred to as the touching end of the stylus 2700. Stylus 2700 further includes wiring 2710 disposed on or inside stylus 2700, and preferably inside the body 2712 of the stylus 2700 for connecting said stylus 2700 with electronic device 2702. The free end of wire 2710 connects with sensor 2704 and the other end exits the stylus 2700, and connects with a thicker external wire portion 2714 which is connected to electronic device 2702. Wire 2710 preferably exits said stylus 2700 at the mid portion 2716. In the prior art, wires exit a rod through the end or the tip of said rod, and not through the mid-portion of the rod. This novel arrangement of the present invention which include the wire exiting in the middle portion of the rod, allows both ends, sensing end 2706 and touch screen end 2708 to be free, with the touching end 2708 for touching the screen 2718 of electronic device 2702 and sensing end 2706 housing sensor 2704 to touch the body for measurement.

The electronic device 2702 comprises a touch-screen 2718 which includes a display box 2720 for displaying the numerical value of the signal acquired by the sensor 2704, a second window 2722 to display stored values of the signal being measured, a wire 2714 for connecting the electronic device 2702 with the stylus 2700, and further preferably including a dialog box 2724 for displaying user information such as patient identification, in addition to a processor 2726, and power source 2728. If electronic device 2702 is arranged as a Personal Digital Assistant (PDA), it preferably includes a conventional key pad 2730 for PDAs.

FIG. 11A concerns Prior Art and shows a rod 2732 with a contact sensing tip 2734 for body temperature measuring device, such as internal thermometer, with said sensing tip 2734 comprised of metal or other material with high thermal conductive. Sensor 2745 in the tip 2734 of rod 2732 is covered by a high thermal conductivity material 2735. Tip 2734 of the prior art also comprises a hard material. In addition the tip of a thermometer of the prior art covered by metal or a thermally conductive material has a dimension equal to or more than 10 mm for said thermal conductive material.

In contrast to the Prior Art, FIG. 11B shows the specialized temperature measuring device 2760 of this invention, wherein a rod 2742 with a sensing tip 2740 housing a temperature sensor 2736 is surrounded by an insulating material 2738, said insulating material 2738 comprised of any material having low thermal conductivity. Rod 2742 is connected to a main body 2752, said body 2752 housing a printed circuit board with microprocessor 2754, battery 2756 and display 2758. The tip 2740 housing the temperature sensor comprises low thermal conductivity material 2738. The tip 2740 of the rod of the thermometer of this invention includes a combination of a temperature sensor 2736 and low thermal conductivity material 2738. Temperature sensor 2736 is surrounded by insulating material 2738, with only the sensing surface 2746 of said sensor 2736 not being covered by insulating material 2738. The external side surfaces 2744 of the tip 2740 comprise insulating material 2738. Temperature sensor 2736 is surrounded by the insulating material 2738. The insulating material 2738 has an external sensing surface 2748 which touches the body or skin during measurement and supports the sensor 2736, an external side surface 2744 which is essentially perpendicular to sensing surface 2748, and an internal surface 2750 which faces the inner portion of the rod 2742. FIG. 11-C is a schematic perspective view of the tip 2740 of the rod 2742 of FIG. 11-B showing sensor 2736 and the insulating material 2738, said insulating material 2738 having external sensing surface 2748 and side external face 2744. The preferred largest dimension for external sensing surface 2748 of insulating material 2738 is equal to or less than 20 mm, and preferably equal to or less than 15 mm, and most preferably equal to or less than 10 mm in its longest dimension, and even most preferably equal to or less than 8 mm. The preferred largest dimension of the temperature sensor 2736 is equal to or less than 6 mm, and preferably equal to or less than 4 mm, and most preferably equal to or less than 2 mm in its longest dimension, and even most preferably equal to or less than 1 mm, in accordance to the main entry point and general entry point, of the brain tunnel. The dimension for other sensors are similar, such as pressure, piezoelectric, and the like, and a pair light emitter-detector may include larger dimensions. Dimensions of and description of insulating material is applicable to any of the rod-like embodiments of this invention including intelligent stylus 2700, and any other rod-like sensing device such as a pen, an antenna, and any other stick-like structure. The tip housing for securing a temperature sensor of the prior art comprises an essentially hard tip. Contrary to the prior art, the tip of this invention housing or securing the temperature sensor is essentially soft. FIG. 11D shows another embodiment comprising a rod 2764 having a bulging sensor 2762 surrounded by insulating material 2766, which extends beyond the end of rod 2764.

The intelligent stylus of the invention can be used in the conventional manner with a metal cap, but contrary to the thermometers of prior art, the wire of the intelligent stylus of this invention exit said stylus in the mid-portion of the stylus. As seen in FIG. 11-E, which shows Prior Art, wire 2782 of the thermometer 2784 of the prior art exit the rod 2786 at the end 2788 of said rod 2786. Wire 2782 connect sensor 2790 to electronic device 2792. The thermometers of the Prior Art that includes a rod and a wire comprises one end having the sensor and the opposite end of the rod having the wire, such as found in Welch Allyn thermometers, Filac thermometers, and the like.

FIG. 11-F shows another embodiment according to the invention, wherein sensor 2770 is housed in the end of the stylus 2768, wherein sensor 2770 is covered with cap 2772 preferably made of metal, ceramic, or other thermally conductive material and most preferably made of a metal, said cap 2772 completely covering the end 2774 of the stylus 2768, and said sensor 2770 is connected to a wire 2778 which exits stylus 2768 in the mid-portion 2776 of said stylus 2768. The distance from the tip of the metal cap 2772 to the mid part 2776 of the stylus 2768, shown by arrow 2769, measures preferably at least 30 mm and less than 300 mm, and most preferably at least 30 mm and less than 200 mm, and even most preferably at least 20 mm and less than 40 mm. Wire 2778 which connects stylus 2768 to an electronic device 2780 uniquely exits stylus 2768 at a mid-portion 2776. Mid-portion or middle portion is referred in this invention as any portion which is located between the two ends of the stylus or any rod like structure.

FIG. 11-G1 shows another preferred embodiment, wherein a cap 2794 housing reagent 2796 such as glucose oxidase is adapted on top of the sensing end 2798 housing sensor 2800 of the stylus 2802. Cap 2794 has arms 2804 for securing cap 2794 on top of sensing end 2798. When blood containing glucose is deposited on top of cap 2794, reagent 2796 generates a reaction which is sensed by sensor 2800, such as an electrochemical or optical sensor, generating a signal that is translated into glucose level after standard processing. FIG. 11-G2 shows in more detail specialized cap 2794 of FIG. 11-G1, which is preferably essentially cylindrical, and houses reagent 2796. Cap further includes arms 2804 and extension 2806 for handling and placement purpose.

FIG. 11H shows a specialized end 2807 of the thermometer of this invention that includes a rod 2811 having a cap 2805 made of metal or thermally conductive material, said cap covering a temperature sensor 2809. Dimension "2813", represented by arrow 2813, said dimension going from the edge of the cap 2805 to the tip of the cap 2805 corresponds to the largest dimension of a metal cap of this invention. The preferred length of dimension 2813 is equal to or less than 3 mm, and preferably equal to or less than 2 mm, and more preferably equal to or less than 1.5 mm, and even more preferably equal to or less than 1 mm.

FIG. 11J is another embodiment, wherein the stylus 2810 includes a touching end 2812 and a sensing end 2814, said sensing end 2814 having a slot 2808, said slot adapted to receive a strip 2818 such as a strip reagent for a chemical reaction including glucose oxidase detection of glucose present in blood applied to said strip 2818. Stylus 2810 further includes a detecting area 2816 which is adapted to receive strip 2818 and detects the chemical reaction that occurred in said strip 2818, and produces a signal corresponding to the amount of a chemical substance or analyte present in strip 2818. Wire 2820 is connected in one to end to detecting area 2816 and exits stylus 2810 through the mid-portion 2822 of said stylus 2810. The external wire portion 2826 connects the stylus 2810 to a processing and display unit 2824. Touching end 2812 comprises an end adapted to touch a screen, or alternatively an end adapted for writing, such as a pen or pencil.

Although, a preferred embodiment includes a wired system, it is understood that the intelligent stylus of the invention also includes a wireless system. In this embodiment, as shown in FIG. 11K, stylus 2830 is connected by wireless wave 2828 with electronic wireless electronic device 2832. Stylus 2830 has three portions, sensing end 2836, touching end 2844, and middle portion 2838. The sensor 2834 is housed on the sensing end 2836 of the stylus 2830, and the mid portion 2838 of the stylus 2830 houses a printed circuit board 2840 which includes a wireless transmitter, and power source 2842. Mid-portion 2838 preferably has a larger dimension than the sensing end 2836 housing the sensor 2834 and larger than the touching end 2844. Dimension A-A1 of mid portion 2838 is preferably larger than dimension B-B1 of the touching end 2844 and larger than dimension C-C1 at the sensing end 2836.

The end opposite to sensing end 2836 preferably comprises touching end 2844, with said touching end 2844 of the stylus 2830 being preferably free of any sensors and used to touch a surface 2846 of wireless electronic device 2832. This arrangement keeps surface 2846 of wireless electronic device 2832 from being scratched or damaged if the touching end also would house a sensor. Likewise the arrangement prevents the sensor 2834 from being damaged by touching a surface, such as surface 2846.

In reference to FIG. 11-L, another preferred embodiment of the invention includes a sensing-writing instrument 2850 comprising preferably a rod-like shape article which comprises a sensing portion 2870 and a writing portion 2872. Sensing portion 2870 houses electronic parts 2864, 2866, and battery 2868 and includes a sensing end 2852 which houses a sensor 2854. Writing portion 2872 houses a writing element 2856 and includes a writing end 2874. Writing element 2856 contains ink 2858 said writing element 2856 having a distal end 2860 adapted to deliver said ink 2858. The sensing-writing device 2850 further includes a wire 2862 which connects sensor 2854 to electronics and display circuit 2864, which displays a value measured from sensor 2854, a printed circuit board/microchip 2866, which calculates the value based on signal from sensor 2854, and a power source 2868, all of which are preferably housed in the upper portion of the instrument 2850. It is understood that writing element 2856 can be mounted on a spring 2876. Sensing portion 2870 is preferably of larger diameter than the writing portion 2872. Although the preferred embodiment includes the sensor 2854 being housed in the end opposite to the writing end 2874, it is understood that the sensor 2854 can be housed in the writing end 2874, preferably having a rotating barrel and spring that includes the sensor 2854 and writing element 2856 sitting adjacent to each other in the barrel (not shown). Upon actuation the sensor end is exposed, and with further actuation the sensor end retracts and the writing end is exposed. Writing element 2856 can include a tube holding ink, and for the purposes of the description include any article that can deliver a substance that allows writing, drawing, painting, and the like and includes pens of any type, pencils of any type, wax-based writing instruments such as crayons, a paint brush, and the like.

It is understood that any electronic device such as an electronic device which recognizes alphabetical, numerical, drawing characters and the like is within the scope of the invention. An exemplary electronic device includes a device with an electronic surface that recognizes strokes by a writing instrument in which regular paper can be placed on top of said electronic surface for the purpose of writing and converting said writing into digital information by a variety of optical character recognition systems or similar systems, with said writing instrument housing a sensor in accordance with the present invention.

By way of illustration, but not of limitation, exemplary sensors and systems for the intelligent stylus will now be described. The sensor can comprise at least one of or a combination of temperature sensor, electrochemical sensor (such as a blood gas sensor for measuring oxygen), an enzymatic sensor (such as glucose oxidase sensor for measuring glucose), a fluorescent sensor, and an infrared sensing system including a light emitter and a photodetector adapted side-by-side, and using preferably reflectance for measuring the level of a substance, such as glucose or oxygen saturation.

A plurality of sensing and detecting systems are contemplated including an intelligent stylus comprising a microphone and a pressure sensor for measurement of pulse and blood pressure. The end of the stylus preferably houses a piezoelectric sensor to detect sound, and a mechanism to apply pressure, such a blood pressure cuff, in order to change the blood flow and elicit a change in sound. The blood pressure cuff has a wireless pressure transmitter that transmits the pressure information to the electronic device, such as a PDA. When the piezoelectric or microphone of the stylus detects a change in sound it sends a signal to the PDA, which then stores the pressure transmitted by the pressure cuff, creating thus a coupling between the pressure being measured by the cuff and the change in sound detected by the stylus. It is understood that the stylus can include a pressure sensor coupled to a mechanical pressure means that apply pressure in the blood vessel for detection of the mean arterial pressure, and the change in pressure corresponding to the arterial pressure. It is also understood that the end of the stylus of the invention can house a fiberoptic system or other optical system such as system for measuring fluorescent light, and for illuminating the area being measured and identifying the arterial pulse.

Another preferred embodiment includes an antenna with sensing capabilities, the sensing-antenna article comprises preferably a rod-like antenna including a whip antenna and wire antenna which houses in its free end a sensor and the opposite end is void of any sensor and connected to conventional radio electronics or communications electronics and ground plane such as antennas found in cellular phones and radios. Although the sensor is preferably located at the end of the antenna, it is understood that the sensor can be housed adjacent to the free end of the antenna. A preferred embodiment includes a cellular phone housing a temperature sensor at the free end of the antenna, with said cell phone comprising electronic means to convert the sensor signal into a temperature signal, and further means to display by visual, audio, or other indicator the temperature measured. The radio or cell phone of the present invention is adapted to generate and process the signal of a biological parameter being measured with the antenna, thus the cell phone, radio, or other device with an antenna can then function as a thermometer for measuring body temperature using a sensor housed in the antenna. Besides measuring body temperature, the antenna can be adapted to measure temperature in general such as liquids and also for measuring ambient temperature.

Accordingly, FIG. 11-M is another preferred embodiment showing a telephone 2880 including a dial pad 2888, a display 2890, electronics 2892 and a sensing antenna 2882 having a sensor 2884 in its free end 2886. Sensor 2884 is connected to ground plane and electronics 2894 through wire 2895.

FIG. 11-N and FIG. 11-P show in detail exemplary arrangements of the antenna with sensing capabilities of this invention. FIG. 11-N shows sensing antenna 2900 having two compartments, one compartment 2898 housing sensor 2896 and wire 2902, and a second compartment comprised of the antenna 2904 for transmitting and receiving electromagnetic waves. Sensor 2896 can be positioned on the top part or the side part of the compartment 2898. FIG. 11-P shows antenna 2910 having a sensor 2906 and a wire 2908 inside the antenna 2910. The method includes the step of positioning the free end of the antenna housing a sensor in apposition to the area being measured, such as the skin of the BT; generating an electrical signal based on the value of the biological parameter being measured, and reporting the value of the biological parameter such as displaying a numerical value. It is understood that any contact and non-contact sensor or detector, can be housed in or on the antenna.

The system can further include a system for measuring wind effect. In this embodiment the temperature sensor is a thermistor. Upon actuation electronics in the cell phone apply current to the thermistor in order to increase the temperature of said thermistor. Since the antenna is exposed to air, the rate of increase of temperature of the thermistor is inversely proportional to the wind speed. With higher wind speed, there is proportionally a need to increase in energy in order to maintain the temperature of the sensor constant. Software can be adapted to identify wind speed, and thus heat or cold index, based on the ambient temperature and the change in temperature of the thermistor being heated up.

It is understood that the sensor at the end of the sensing-antenna or at the end of the sensing-writing instruments can also include a probe cover to avoid cross-contamination when touching a body part, or when touching a drink to measure the temperature of such a drink. It is yet understood that software can be adapted to allow subtle changes in temperature corresponding to ovulation or pre-ovulation to be detected, with said cell phone or radio having means to identify such changes and indicators to display the information about ovulation.

It is understood that a variety of sensing and detecting arrangements are contemplated as shown from FIG. 11-Q1 to FIG. 11-Q4. FIG. 11-Q1 is a planar view of a rod-like sensing device such as a thermometer, a stylus, a writing instrument, an antenna, and the like showing the sensing surface 2912 of a rod-like sensing device having a sensor 2914. Sensing surface 2912 can comprise entirely of a sensor or detector. The preferred largest dimension of sensing surface 2912 is equal to or less than 21 mm, and preferably equal to or less than 15 mm, and most preferably equal to or less than 10 mm. Considering sensor 2914 as a single sensor, the preferred largest dimension of sensor 2914 is equal to or less than 15 mm, and preferably equal to or less than 10 mm, and most preferably equal to or less than 5 mm. FIG. 11-Q2 is a side view of another preferred embodiment showing rod-like structure 2916 having an infrared radiation detector 2918 and sensing surface 2920. FIG. 11Q-3 shows a pair light emitter-light detector 2922 mounted in a rod-like structure 2924, said sensor being disposed flush in relation to the end of said rod 2924. FIG. 11Q-4 shows a bulging light emitter-light detector pair 2926 of a rod-like sensing structure 2928.

FIG. 11R-1 is another preferred embodiment showing a spring-based measuring portion 2930 including a hollow rod 2932 that works as a tunnel, an adjustably positionable arm 2944, a spring 2936, and a sensor 2934, said sensor 2934 being secured to a sensing support structure 2940 and covered by a cap 2938. Spring 2936 is covered by an essentially cylindrical-like structure 2952 which has free end 2946 and has a second end 2942 attached to rod 2932 and/or arm 2944. Sensing support structure 2940 includes preferably two portions, a distal portion 2948 housing sensor 2934, and a proximal part 2950 comprised of a rod-like portion, said portion being adapted to secure one end of the spring 2936. The spring 2936 is connected to the proximal part 2950 of the support structure 2940 in one end and is connected to rod 2932 at the opposite end. Any attachment means such as glue, heat, and the like can be used to attach spring 2936 to support structure 2940 and rod 2932. The preferred length of the proximal part 2950, in which spring 2936 is attached to, is equal to or less than 7 mm, and preferably equal to or less than 3 mm, and most preferably equal or less than 2 mm. The preferred length of the rod 2932, in which spring 2936 is attached to, is equal to or less than 7 mm, and preferably equal to or less than 3 mm, and most preferably equal to or less than 2 mm. Rod 2932 terminates in adjustably positionable arm, 2944, which is preferably hollow and has flexible characteristics and memory, and is similar to arm 2004 which has been previously described. The preferred length from the edge of the proximal part 2950 and the edge of the rod 2932, which corresponds to the length in which spring 2936 is not in contact with any structure, is equal to or less than 9 mm, and preferably equal to or less than 4 mm, and most preferably equal to or less than 3 mm. The preferred diameter of spring 2936 is equal to or less than 10 mm, and preferably equal to or less than 4 mm, and most preferably equal to or less than 2 mm. The preferred diameter of rod 2932 is equal to or less than 10 mm, and preferably equal to or less than 4 mm, and most preferably equal to or less than 2 mm. Sensor 2934 is connected to wire 2947 which is disposed inside the spring 2936, and inside rod 2932 and arm 2944. The preferred length from the edge of cap 2938 to part 2932 is equal to or less than 14 mm, and preferably equal to or less than 11 mm, and most preferably equal to or less than 8 mm. The preferred largest dimension of sensor 2934 is equal to or less than 14 mm, and preferably equal to or less than 10 mm, and most preferably equal to or less than 5 mm, and even more preferably equal to or less than 2 mm. The embodiment of FIG. 11R-1 can be used with any support structure including those of the embodiments of FIG. 1A, FIG. 6, FIG. 7A, FIG. 7B and FIG. 7D as well as FIGS. 15A to 15Z, said FIG. 7D showing by way of example the embodiment of FIG. 11R-1 integrated into eyewear.

FIG. 11R-2 is a planar view of the spring-based measuring portion 2930 showing the surface of cap 2938 showing an exemplary sensor chip 2960 disposed under said cap 2938, said cap 2938 preferably being made of metal or other heat conducting material. A soldering joint 2962 connects sensor chip 2960 to a wire 2964, and a second wire 2966 is connected to the cap 2938 through solder joint 2968. The preferred diameter of cap 2938 is equal to or less than 14.8 mm, and preferably equal to or less than 10.8 mm, and most preferably equal to or less than 5.8 mm, and even more preferably equal to or less than 2.8 mm.

FIG. 11S-1 to 11S-4 shows an exemplary embodiment for a measuring portion of this invention. FIG. 11S-1 shows measuring portion 2970 comprised of a convex cap 2972 made preferably of copper, and includes a sensor arrangement disposed under said cap 2972, said arrangement comprised of sensor chip 2974 sandwiched between electrode 2976 and electrode 2978 and connected to wire 2982, and includes a second wire 2980 connected to cap 2972. FIG. 11S-2 shows measuring portion 2984 comprised of a convex cap 2986, and includes a sensor arrangement disposed under said cap 2986, said arrangement comprised of sensor chip 2988 sandwiched between electrode 2990 and electrode 2992. Wire 2994 is soldered with electrode 2992 and wire 2996 is disposed between electrode 2990 and cap 2986. FIG. 11S-3 shows the embodiment of FIG. 11S-1 in which convex cap 2972 is replaced by a flat cap 2998. This preferred embodiment provides the least amount of heat loss. FIG. 11S-4 shows the embodiment of FIG. 11S-1 in which flat copper cap 2998 is replaced by a solid metal cap 3000.

Figures 1, 11T:
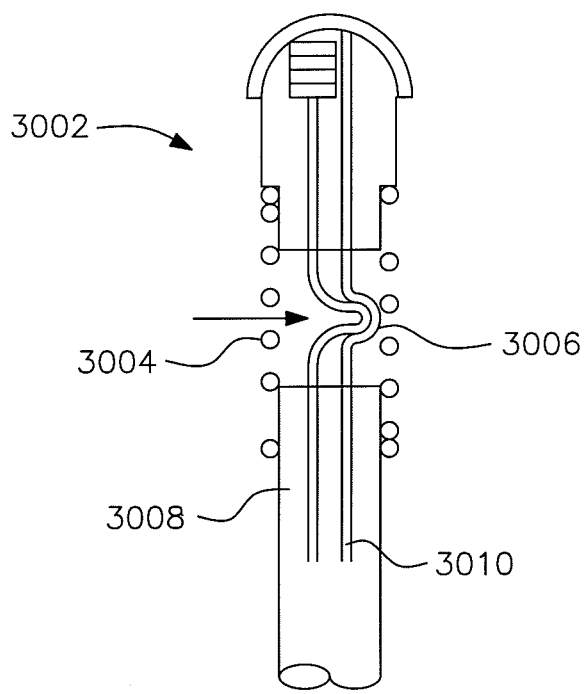
Figures 2, 11T:
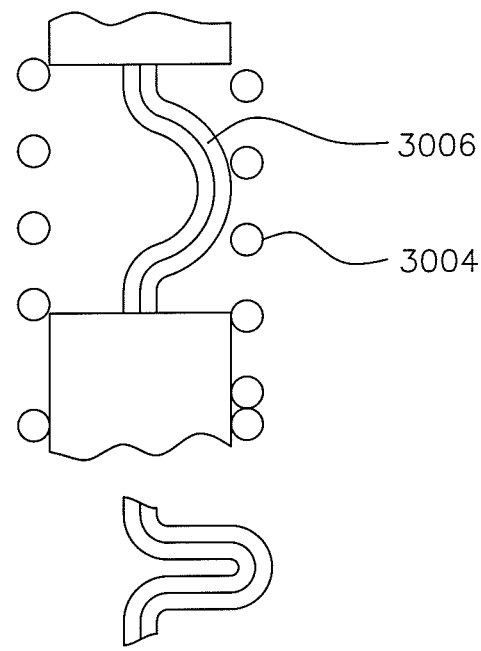

FIG. 11T-1 shows measuring portion 3002 including the sensor arrangement of the embodiment of FIG. 11S-3, in addition to spring 3004 seen in a cross sectional view, said spring 3004 being adjacent to wire portion 3006, which is shown in its bent position (by small arrow) after compression of spring 3004, said wire portion 3006 being adapted for bending upon compression of spring 3004, and further including rod 3008 which is attached to spring 3004 and houses wire portion 3010, said wire portion 3010 being unable to move or slide. FIG. 11T-2 shows detail of the wire portion 3006 forming a curve upon pressing of spring 3004. The curve formed by wire 3006 upon compression is limited by the diameter of the spring. It is understood that the method includes the step of positioning the sensor, compressing the spring, and generating an electrical signal from said sensor. The dimension of the wire curve is adjusted to fit within the diameter of the spring.

Figure 11U:
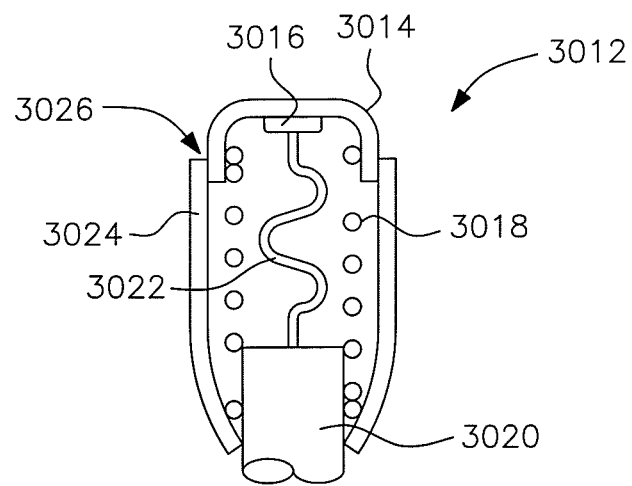
FIG. 11U is a sectional view of a measuring portion or sensing assembly.

FIG. 11U is a cross sectional diagrammatic view of a preferred embodiment of the measuring portion or sensing assembly 3012 of this invention, and includes a flat cap 3014. Preferred thickness of cap 3014 from the edge of said cap 3014 to the tip of said cap 3014 is equal to or less than 2 mm, and the preferred diameter of said cap 3014 is equal to or less than 2 mm. Those dimensions are preferably used for measurement of temperature or pulse. Cap 3014 is attached to sensor 3016, said cap 3014 covering sensor 3016. Spring 3018 is connected in one end to cap 3014 and in the opposite end to rod 3020. A wire 3022 connected to sensor 3016 is seen in a bent position and inside an area comprised by the spring 3018. Spring 3018 is attached to cap 3014 in one end and to rod 3020 at the other end. Wire 3022 is affixed to sensor 3016 in one end and to rod 3020 in the other end in order to allow said wire 3022 to bend and extend upon compression and decompression of spring 3018. Measuring portion 3012 is covered by a structure 3024 made preferably of a soft plastic and adapted to protect the spring 3018 and associated components such as wire 3022, said structure 3024 preferably shaped as a cylinder in which the distal end 3026 is open, allowing thus unobstructed movement of cap 3014 and sensor 3016. It is understood that any material that works as a spring or which has compression and decompression capabilities can be used in a similar manner as spring 3018. Any foam, gels, or compressible material with spring capabilities can be used. It is also understood that any sensor or sensor system can be used and replace cap 3014 including enzymatic sensors, optical sensors, fluorescent light, a pair light emitter-light detector, a radiation detector including infrared radiation detector, and the like. It is also understood that preferred dimensions are chosen according to the type of sensor being used.

Figures 3, 11V:
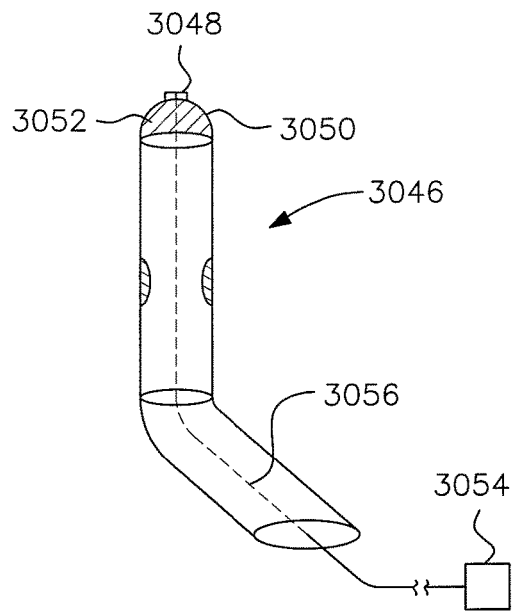
Figures 4, 11V:
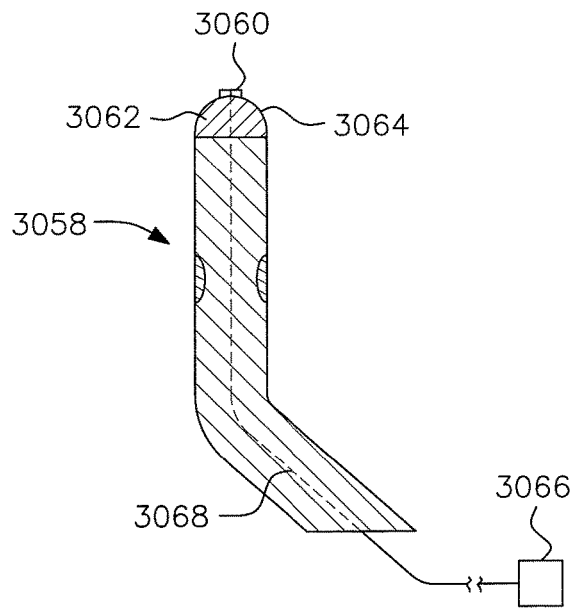

FIG. 11V-1 is another embodiment showing another handheld device for measuring biological parameters, and illustratively shows the illustration of a hand held device 3030 including a body 3032 divided in two parts, one straight part 3036 and a bent part 3034, said straight part 3036 being of large diameter than bent part 3034, and said straight part 3036 terminating in a wire 3042, and further including a sensing tip 3038, which secures sensor 3044 and includes an insulating material 3040 surrounding sensor 3044. FIG. 11V-2 is a planar view of the hand held device 3030 showing sensing tip 3038 and sensor 3044 positioned on the center of sensing tip 3038 and surrounded by insulating material 3040.

Figures 5, 11V:
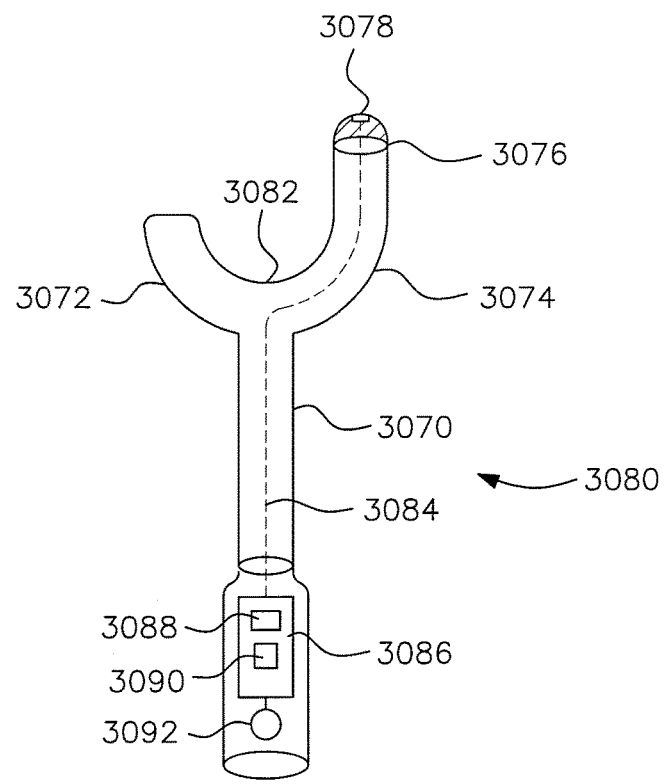

FIG. 11V-3 is diagrammatic perspective view of a hand-held probe 3046 including a sensing tip 3050, said tip 3050 being essentially convex, and a sensor 3048 disposed at the end of said probe 3046. Sensing tip 3050 includes sensor 3048 and support structure 3052 which supports and insulates said sensor 3048, said structure 3052 being preferably comprised of soft insulating material. Sensor 3048 is connected to a processing and display unit 3054 through wire 3056 disposed preferably inside probe 3046. FIG. 11V-4 is a diagrammatic perspective view of a hand-held probe 3058 having a pair light emitter-detector 3060 in the sensing tip 3062, said sensing tip 3062 having support structure 3064 which preferably includes material that creates a barrier to infrared light. The radiation emitter-detector 3060 is connected to a processing and display unit 3066 through wire 3068. FIG. 11V-5 is another embodiment showing a J-shape configuration of probe 3070 of hand held measuring device 3080, said probe 3070 including two arms, 3074, 3072 said two arms 3074, 3072 being of dissimilar length. Arm 3074 terminates in sensing tip 3076, said tip 3076 securing sensor 3078. Arm 3074 is longer than the opposite arm 3072. Curve 3082 between two arms 3074 and 3072 is adapted to be positioned over the nose, with arm 3074 being positioned in a manner so as to position sensor 3078 on or adjacent to a brain tunnel. Sensor 3078 is connected through wire 3084 to a printed circuit board 3086 which houses processor 3088 and display 3090, said printed circuit board being connected to a power source 3092. Sensor 3078 includes contact and non-contact sensors and detectors such as a stand alone infrared radiation detector, said sensor being spaced from the site being measured or resting on the site being measured.

Figure 12A:
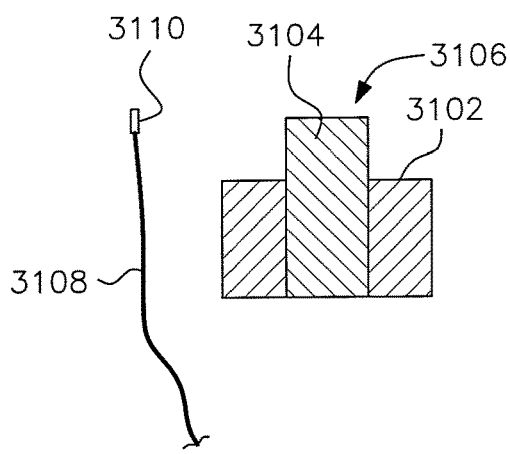
FIG. 12A illustrates a measuring portion in a sensor connected to a wire.
Figure 12B:
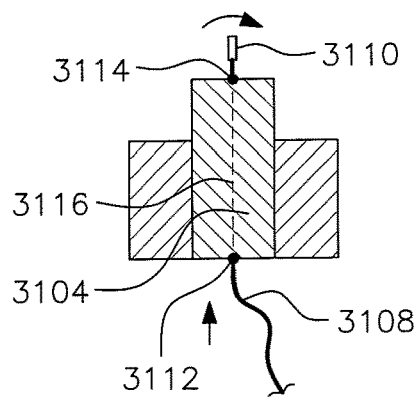
FIG. 12B illustrates a passageway for a sensor and for a wire.
Figure 12C:
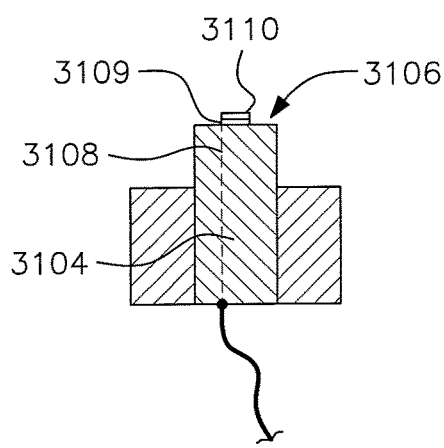
FIG. 12C illustrates a bending of the end of the wire of the sensor.
Figure 12D:
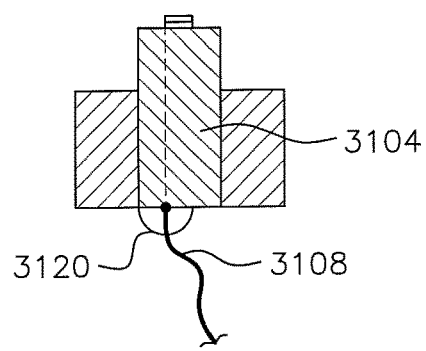
FIG. 12D illustrates securing of the wire.
Figure 12H:
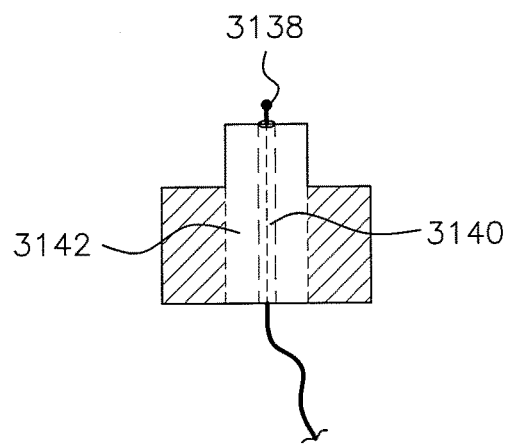
FIG. 12H shows an enlarged sensor and wire inserted through a passageway.
Figure 12E:
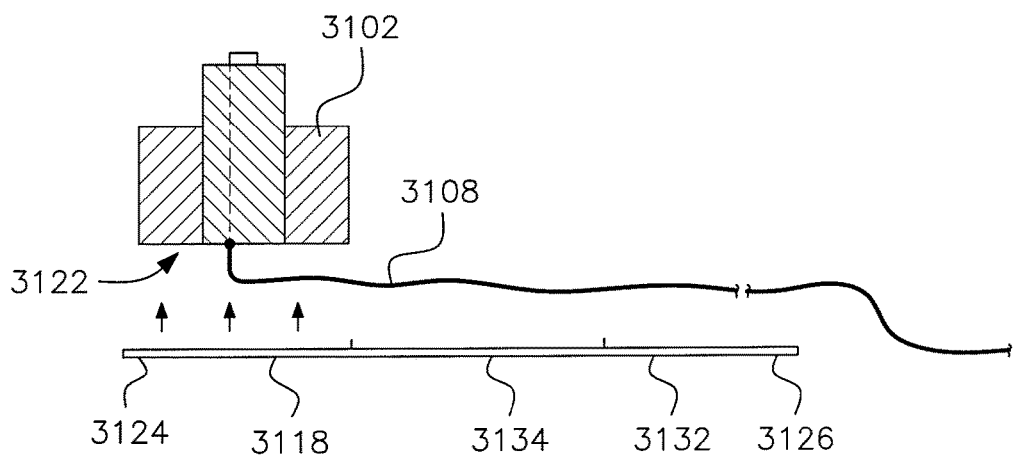
FIG. 12E illustrates a plate disposed along the lower portion of a measuring portion.
Figure 12F:
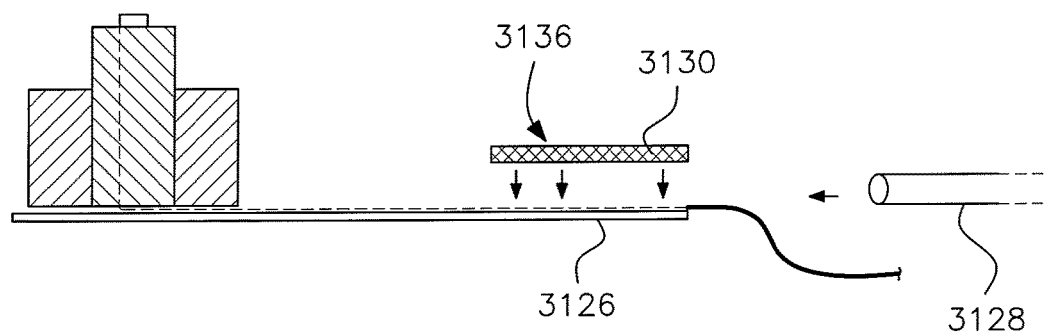
FIG. 12F illustrates insertion of a rubberized sleeve and subsequent heat shrinking of the sleeve.
Figure 12G:
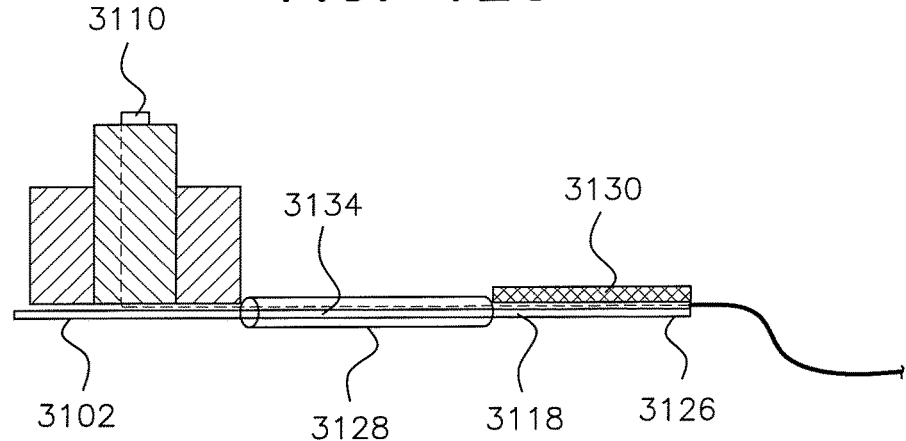
FIG. 12G illustrates a finished sensing device.

FIG. 12A to 12G shows exemplary manufacturing steps of a sensing device in accordance with this invention. FIG. 12A shows an exemplary measuring portion 3102 and a sensor 3110 connected to a wire 3108. Measuring portion 3102 includes insulating material 3104 disposed in a manner to create a two level sensing tip 3106. The first manufacturing step includes creating a passage 3116 in material 3104 to accommodate sensor 3110 and wire 3108. FIG. 12B shows material 3104 with passage 3116 and two holes 3112 and 3114 at the ends of passage 3116. Sensor 3110 and wire 3108 are inserted through material 3104. FIG. 12C shows an optional next step and includes bending the end 3109 of wire 3108 of the sensor 3110. Passage 3116 is made preferably eccentrically to allow sensor 3110 to be in the geometric center of sensing tip 3106 after being bent. This step of bending the wire of a long rectangular sensor, such as the thermistor of this invention, allows passage 3116 through material 3104 to be of small dimensions. Manufacturing may include a step of securing wire 3108 to material 3104 as shown in FIG. 12D, for example using a piece of glue 3120 or other attachment means. FIG. 12E shows plate 3118 being disposed along the lower portion 3122 of measuring portion 3102. Plate 3118 is preferably made of a thin metallic sheet, said plate 3118 having two ends 3124, 3126 and forming the arm and body of sensing device of this invention, said arm represented by portion 3134 of plate 3118 and body represented by portion 3132 of plate 3118. One end 3124 of plate 3118 is attached the lower portion 3122, sandwiching wire 3108 between end 3124 of plate 3118 and measuring portion 3102. Next step, as shown in FIG. 12F, may include inserting a rubberized sleeve 3128 including heat shrinking tube into plate 3118, but said step may also occur before attaching plate 3118 to measuring portion 3102, which is preferably used if end 3126 of plate 3118 is of larger dimension than end 3124. It is also shown in FIG. 12F the step comprised of attaching a soft plate 3130 to end 3126, said soft plate 3130 having preferably an adhesive surface 3136. FIG. 12G shows the finished sensing device 3100 including rubberized sleeve 3128 covering portion 3134 corresponding to the arm of sensing device 3100, soft plate 3130 being attached to end 3126 of plate 3118 corresponding to the body of sensing device 3100, and measuring portion 3102 with sensor 3110. It should be noted that, as in accordance to this invention, the sensor shown in FIGS. 12A to 12M-2 is supported and surrounded by the insulating material only and no other material, said insulating material being essentially soft.

FIG. 12H shows a larger sensor 3138 with wire 3142 being inserted through passage 3140. In this embodiment manufacturing step does not include bending the wire. A larger passage 3140 is made for inserting through material 3142 a sensor 3138, including a bead thermistor, a sensor covered by a cap, a thermopile, a radiation detector, and the like.

Figure 12J:
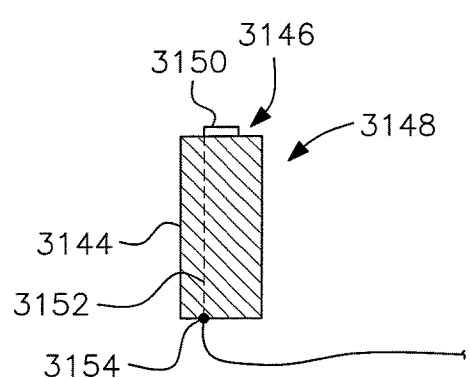
FIG. 12J illustrates a measuring portion of a sensing assembly.
Figures 1, 12K:
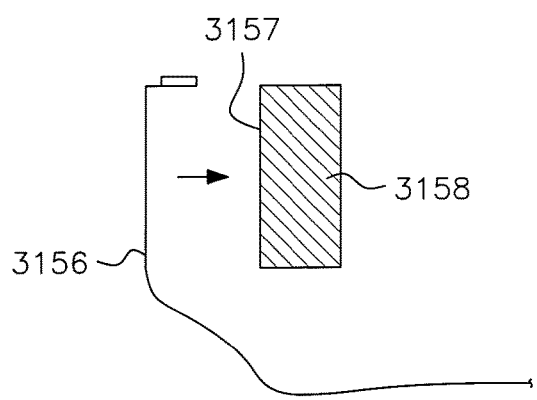
Figures 2, 12K:
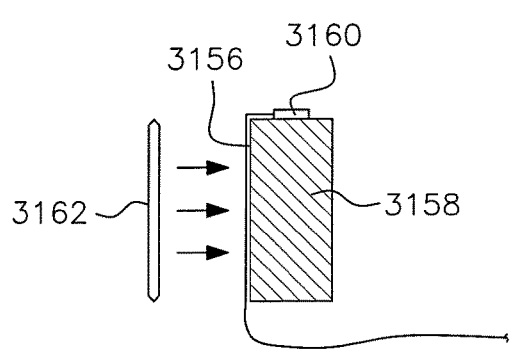
Figure 12L:
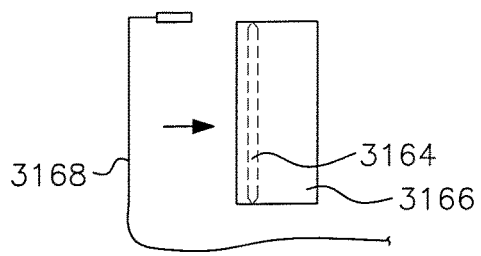
FIG. 12L illustrates passing a wire through a slit in a support structure.

FIG. 12J shows another preferred embodiment of a measuring portion according to this invention. FIG. 12J shows support structure 3144 of a measuring portion 3148 comprised of a one level sensing tip 3146, said sensing tip 3146 securing a sensor 3150. Wire 3152 is inserted through hole 3154 into the support structure 3144 and disposed within support structure 3144 of measuring portion 3148. Wire 3152 is connected to sensor 3150 in one end and to a processing unit (not shown) at the other end. FIG. 12K-1 is another embodiment showing wire 3156 disposed on the external surface 3157 of support structure 3158 of a measuring portion. In this embodiment there is no hole in the support structure 3158 and the manufacturing step includes placing wire 3156 on the surface 3157 of structure 3158. As shown in FIG. 12K-2, manufacturing may include the step of attaching or securing wire 3156 and/or sensor 3160 to structure 3158 using glue or adhesive material represented by material 3162. FIG. 12L is another embodiment showing a slit 3164 being cut through support structure 3166, and wire 3168 being disposed along slit 3164 and secured to said slit 3164. Manufacturing may further include the steps described in FIGS. 12E and 12F.

Figures 1, 12M:
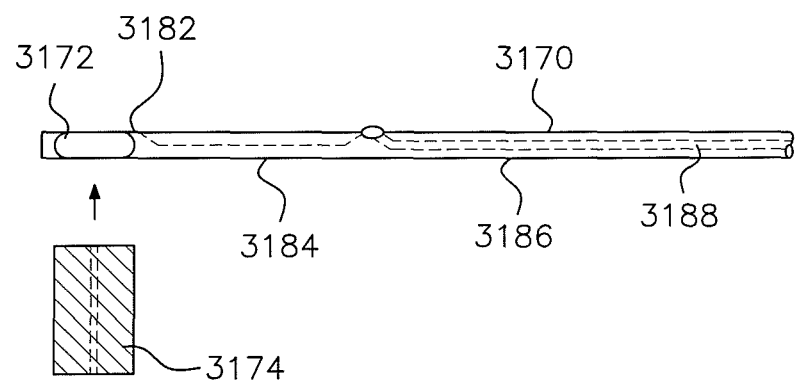
Figures 2, 12M:
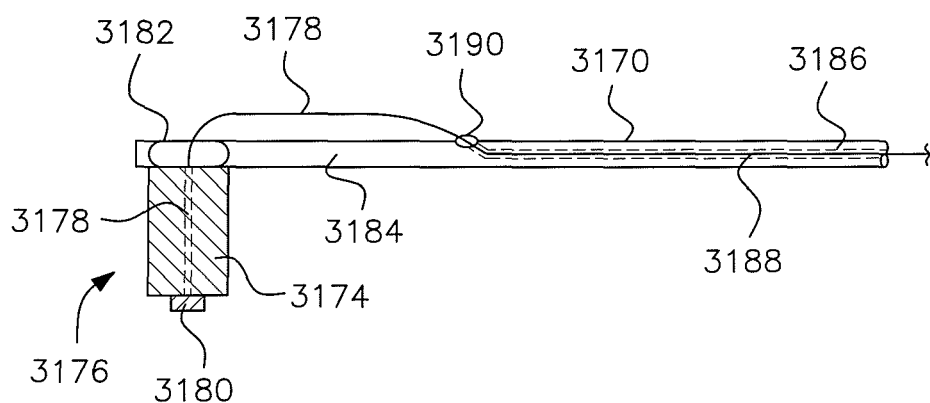

FIG. 12M-1 is another embodiment showing a perforated plate 3170 having in one end 3182 an opening 3172 for receiving a measuring portion represented herein by structure 3174 which is adapted to secure a sensor. Perforated plate is divided in arm 3184 and body 3186, said body having a tunnel-like structure 3188. The step of a perforated plate receiving a measuring portion which holds a sensor may be followed by inserting a wire through the perforation in the plate. Accordingly, FIG. 12M-2 shows measuring portion 3176 comprised of a structure 3174, wire 3178 and sensor 3180, said measuring portion 3176 being attached to perforated plate 3170 at the end 3182. Sensor 3180 is connected by a wire 3178 which goes through structure 3174 and run on the surface of arm 3184 and then enters body 3186 through a hole 3190 and run inside tunnel 3188 of body 3186. Any of the measuring portions described in this invention can be used in a hand held device and be disposed at the end of a probe.

This embodiment of the present invention includes apparatus and methods for measuring brain temperature and detecting analytes in blood vessels directly from the brain by detecting infrared radiation from a brain tunnel. As previously taught the brain tunnel allows direct communication with the physiology and physics of the brain. Blood vessel of the brain tunnel remains open despite circulatory changes and/or vasoconstriction in other parts of the body and/or head.

The most representative and clinically significant representation of the thermal status of the body is brain temperature, and in particular the temperature of the hypothalamic thermoregulatory center. This invention identified a central thermal storage area in the brain around the hypothalamic thermoregulatory center and disclosed the pathway of least thermal resistance to the surface of the body, called Brain Temperature Tunnel because of its ability to work as a physiologic tunnel in which thermal and biological events in one end of the tunnel can be reproduced in an undisturbed manner at the other end of the tunnel. The BTT is an undisturbed and direct thermal connection between this thermal storage area in the brain and a specialized thermoconductive peri-orbital skin.

This central thermal storage area is represented by the cavernous sinus (CS). CS is an endothelium-lined system of venous channels at the base of the skull creating a cavity working as a pool of venous blood adjacent to the hypothalamic thermoregulatory center. Venous blood in the CS is slow moving which creates a homogenous distribution of thermal energy. Venous blood is the blood type more representative of brain temperature. From a physical standpoint the slower moving blood will generate a lesser thermal gradient between the two ends of a vessel. Arterial blood, such as used in the prior art including temporal artery thermometer, is a fast moving blood which generates a significant thermal gradient and thus void the ability to reproduce accurately core temperature or brain temperature.

This invention identifies unique thermal characteristics only found in the CS. The CS collects and stores thermal energy from the various parts of the brain carried by slow moving deoxygenated blood that is in thermal equilibrium with the brain tissue, namely blood from the cerebral veins, meningeal veins, the sphenopalatine sinus, the superior petrosal sinus, the inferior petrosal sinus, and pterygoid venous plexus. By collecting blood from various parts of the brain, being located in the vicinity of the hypothalamic thermoregulatory center, and having slow moving blood, which allows thermal equilibrium with surrounding tissue and reduced heat loss, the CS functions as a central thermal storage area. While uniquely thermally communicating with various parts of the brain and being located adjacent to the thermoregulatory center, this invention identifies that the CS thermally communicates in an undisturbed manner to the surface of the body through a path of minimal thermal resistance represented by the superior ophthalmic vein (SOV).

To examine the thermal path from brain to skin and create a function for determining the temperature of brain tissue, this invention examined from a thermal standpoint each biological layer between the brain and the skin at the brain tunnel and gave a thermal resistance value to each structure. The temperature gradient between the brain and the skin at the brain tunnel is the summation of the individual temperature gradients across each structure. The lower the thermal resistance between the brain and the measuring site, the less the temperature difference.

Since according to the second law of thermodynamics heat will automatically flow from points of higher temperature to points of lower temperature, heat flow will be positive when the temperature gradient is negative. The metabolism taking place within the brain generates a considerable amount of heat, which the brain must dissipate in order to maintain a consistent and safe operating temperature within the skull. This generates a positive heat flow. When the temperature of the skin area of the brain tunnel and the temperature of the air around the skin of the brain tunnel is greater than the heat produced by the brain there will be a reduction of the positive heat flow up to a point of equilibrium between the brain and the skin area of the brain tunnel.

Most of the heat dissipation is accomplished by direct conduction through the circulatory system. However, the structure which encloses the brain providing physical protection also causes thermal isolation. As can be seen, these two requirements are in opposition to each other. Multiple layers of protection (1. thick skin, 2. subcutaneous tissue, 3. connective tissue aponeurosis (epicraninum), 4. loose areolar tissue, 5. pericranium, 6. cranial bone, 7 dura matter, and 8 cerebral spinal fluid) also represent multiple layers of thermal insulation. Those insulating layers are represented by thermal resistance TR1, TR2, TR3, TR4, TR5, TR6, TR7 and TR8).

This invention identifies that with the exception of the thermal path through the BTT, heat energy flowing from within the brain to the external environment, including the forehead, must pass through about 8 insulating structures, and there is a temperature drop associated with each layer TR1 to TR8. As the heat flows in the direction of the cooler environment outside the body, we traced its path through multiple resistance layers which gives rise to a considerable temperature drop at the surface of the skin in all areas of the body including the head. The outer layer, especially, with a thick skin, fat tissue, and sweat glands (about 5 mm thick) contribute heavily to the thermal resistance equation. The variability resulting from those layers will lead to inconsistent measurements which occur in any skin area in the whole body outside the BTT, which were observed during testing and showed that skin areas outside the BTT area have 1.8 to 7.5 degrees centigrade difference between core temperature and skin temperature in skin areas outside the BTT.

Analysis of the pathway of least thermal resistance from the brain to the surface of the body was performed and the functional and anatomical architecture of the pathway characterized. A model for brain temperature and the thermal resistance pathway was done. The model includes the relationship for heat transfer by conduction proposed by the French scientist, J. J. Fourier, in 1822. It states that the rate of heat flow in a material is equal to the product of the following three quantities:
1. k, the thermal conductivity of the material.
2. A, the area of the section through which the heat flows by conduction.
3. dT/dx, the temperature gradient at the section, i.e., the rate of change of temperature T with respect to distance in the direction of heat flow x.

The fundamentals of heat transfer for conduction show that the greater the thermal conductivity, the less is the temperature drop or loss for a given quantity of heat flow. Conversely, the greater the thermal resistance in the heat flow path, the greater the temperature drop. The flow of heat through a thermal resistance is analogous to the flow of direct current through an electrical resistance because both types of flow obey similar equations.

The thermal circuit:

$$q = \Delta T/R \qquad \text{Equation 1-1}$$

q=thermal energy flow,
$\Delta T$=the temperature difference between two points,
R=the thermal resistance separating the two measuring points The electrical circuit:

$$i = \Delta E/Re \qquad \text{Equation 1-2}$$

i=the flow rate of electricity, i.e., the current
$\Delta E$=voltage difference
Re=electrical resistance The thermal resistance of the various insulating layers surrounding the brain was represented with resistors to evaluate the relative degree of resistance between different possible thermal paths from the brain to the skin. Heat flux sensors were constructed to measure true surface temperature. This is a special temperature probe with two sensors. A thin insulator is placed between the two temperature sensors. One sensor (S1) contacts the surface whose temperature is to be measured (BTT), the other sensor (S2) is on the opposite side of the insulator (facing away from the measurement site). If there is no net heat flow through the insulation layer (Q=0 in equation 1-1), there can be no temperature difference ($\Delta T$ in Equation 1-1 must=0) between the two sensors. The control circuit of the heat flux temperature probe provides just enough power to a small heating element next to sensor S2 to equalize or bring to zero the difference in temperature between S1 and S2. By eliminating the heat flow to the external environment we minimize, if not totally cancel, the heat flow from the superior ophthalmic vein to the skin surface under S1. This allows for a very accurate measurement of surface temperature (if Q=0 there is no temperature difference between the vein and skin). By comparing temperature measurements made with the heat flux temperature probe at the BTT site to those made with a miniature temperature probe (very low mass, 38 gauge connecting wires, and well insulated), it was possible to compute the temperature of the heat source (represented by the CS) within the body.

One embodiment includes acquiring radiation emitted from a brain tunnel. Preferably, radiation is acquired using the region between the eye and the eyebrow including scanning and/or positioning a radiation detector over the brain tunnel. Preferably, the brain tunnel area is scanned for about 5 to 10 seconds and the highest peak of infrared radiation from the brain tunnel is acquired, which reflects the peak temperature of the brain tunnel area. Every time a higher temperature is detected a beep or sound is produced, thus when no more beeps are produced the user knows that the peak temperature was acquired. The temperature acquired is representative of brain temperature reflected by blood from the brain. To acquire the core temperature of the brain, a specialized processing is used. The processing may take into account the thermal resistance (TR) of the path between the skin of the brain tunnel and the brain, which can be simplified by using the two main thermal resistances, namely TRB1 (representing thermal resistance due to skin) and TRB2, (representing thermal resistance due to the vascular wall and associated structures). Another factor in the calculation of core temperature may include the thermal gradient between the two ends of the tunnel. Through our experiments including using our fabricated heat flux sensors it was determined that the thermal resistance by TRB1 and TRB2 accounts for up to 0.65 degrees Celsius. Hence in order to determine the core temperature of the brain this invention includes apparatus and methods adapted to perform processing for determining internal body temperature, represented by the core temperature of the brain, illustrated by the equation:

$$T_b = T_{bt} + TR \qquad \text{(Equation 1-3)}$$

where $T_b$ is the core temperature of the brain, $T_{bt}$ is the peak temperature of the skin of the brain tunnel as acquired by the radiation detector, and TR is an empirically determined factor which includes the thermal resistance between the skin of the brain tunnel and the brain.

The processing includes a sum of thermal resistances between the source of thermal energy inside the body plus the temperature of the skin area being measured. Specifically, the core temperature of the brain includes the temperature of the skin at the brain tunnel plus the sum of the thermal resistances of the structures between the skin of the brain tunnel and the brain. More specifically, the preferred processing circuit and processing includes the peak temperature of the skin area of the brain tunnel plus the sum of the thermal resistances between the skin of the brain tunnel and the brain, said thermal resistance comprised of a factor equal to or less than 0.20 degrees Celsius and equal to or more than 0.05 degrees Celsius. Preferably, processing circuit and processing includes the peak temperature of the skin area of the brain tunnel plus the sum of the thermal resistances between the skin of the brain tunnel and the brain, said thermal resistance comprised of a factor equal to or less than 0.30 degrees Celsius and more than 0.20 degrees Celsius. Most preferably, the processing circuit and processing includes the peak temperature of the skin area of the brain tunnel plus the sum of the thermal resistances between the skin of the brain tunnel and the brain, said thermal resistance comprised of a factor equal to or less than 0.65 degrees Celsius and more than 0.30 degrees Celsius. The radiation detector includes a processor and processing circuit having a computer readable medium having code for a computer readable program embodied therein for performing the calculations for determining core temperature, and may further include a memory operatively coupled with said processor, and a display, audio or visual, for reporting a value. Another embodiment includes a further step for determining the brain tissue temperature using the temperature of the skin of brain tunnel that includes a factor pertaining to heat flow and environment temperature around the brain tunnel. To acquire the temperature of the brain tissue (parenchymal temperature), a function taught by the present invention can be used and includes processing in the device to compute the brain tissue temperature based on thermal resistance and the environment temperature around the brain tunnel. The apparatus and methods includes a processing circuit that computes the brain temperature as a function of the temperature of the skin at the end of the brain tunnel and a factor related to the temperature of air within a 90 cm radius from the entrance of the brain tunnel at the skin, described herein as BT-ET300 (brain tunnel Environmental Temperature at 300 cm radius), also referred to herein as BT-300. The BT-300 factor varies with the environment temperature around the area being measured and is based on heat flow. It is understood that this function that includes a factor for each range of environment temperature can be used in other parts of the body beside the brain tunnel.

The BT-300 varies according to the environment temperature around the brain tunnel, or the skin target area being measured. If there is negative heat flow, then the value of the BT-300 is equal to zero in Equation 1-4 below, and equal to 1 (one) in Equation 1-5. If there is positive heat flow from brain to the environment of 0.1 degree Celsius, then BT-300 factor is equal to 1.003. Illustratively, if there is positive heat flow from brain to the environment with a difference of 0.2 degree Celsius, then BT-300 factor is equal to 1.006. If there is positive heat flow from brain to the environment with a difference of 0.3 degree Celsius, then BT-300 factor is equal to 1.009. If there is positive heat flow from brain to the environment with a difference of 0.5 degree Celsius, then BT-300 factor is equal to 1.012. If there is positive heat flow from brain to the environment with a difference of 0.5 degree Celsius, then BT-300 factor is equal to 1.015. If there is positive heat flow from brain to the environment with a difference of 0.6 degree Celsius, then BT-300 factor is equal to 1.018. If there is positive heat flow from brain to the environment with a difference of 0.7 degree Celsius, then BT-300 factor is equal to 1.021. If there is positive heat flow from brain to the environment with a difference of 0.8 degree Celsius, then BT-300 factor is equal to 1.024. If there is positive heat flow from brain to the environment with a difference of 0.9 degree Celsius, then BT-300 factor is equal to 1.027. If there is positive heat flow from brain to the environment with a difference of 1.0 degree Celsius, then the BT-300 factor is equal to 1.030. If there is positive heat flow from brain to the environment with a difference of equal to or more than 1.0 degree Celsius and less than 1.5 degrees Celsius, then the BT-300 factor is equal to 1.045. If there is positive heat flow from brain to the environment with a difference of equal to or more than 1.5 degrees Celsius and less than 2.0 degrees Celsius, then the BT-300 factor is equal to 1.060. If there is positive heat flow from brain to the environment with a difference of equal to or more than 2.0 degree Celsius, then the BT-300 factor is equal to 1.090. Therefore, equation 1-4 provides a method to calculate the corrected brain temperature.

$$T_{bc}=T_{bt}*\text{BT-300} \qquad \text{(Equation 1-4)}$$

where $T_{bc}$ is the core temperature of the brain corrected for heat flow from the brain, $T_{bt}$ is the peak temperature of the skin of the brain tunnel as acquired by the radiation detector, and BT-300 is a factor based on the heat flow.

Using equation 1-4, the corrected temperature of brain tissue can be determined with the following equation:

$$T_{ct}=TR+(T_{bt}*\text{BT-300}) \qquad \text{(Equation 1-5)}$$

where $T_{ct}$ is the corrected core temperature of the brain tissue, $T_{bt}$ is again the peak temperature of the skin of the brain tunnel as acquired by the radiation detector, TR is an empirically determined factor which includes the thermal resistance between the skin of the brain tunnel and the brain, and BT-300 is a factor based on the heat flow.

Figure 13A:
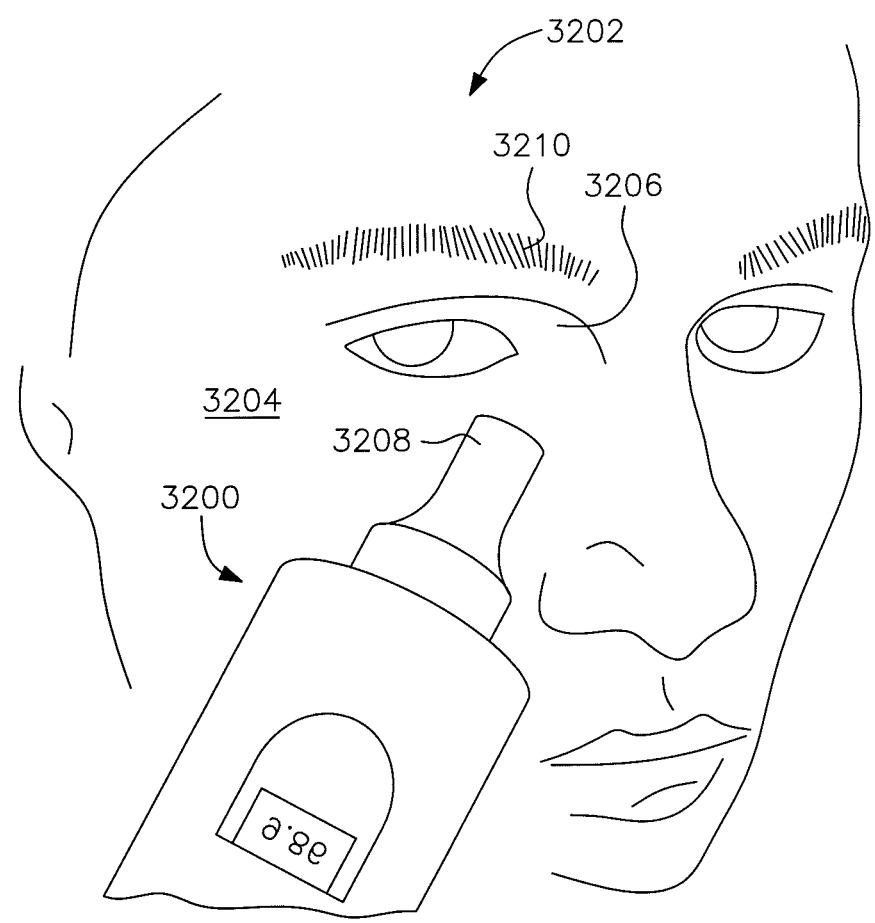
FIG. 13A illustrates a handheld radiation detector approaching the face of a user.

FIG. 13A is another embodiment of the apparatus and method of this invention showing a hand-held radiation detector 3200 held by the hand of a subject 3202 and positioned in a preferred diagonal position in relation to the plane of the face 3204. The preferred method includes positioning the end 3208 of an infrared detector 3200, or alternatively the tip of an infrared detector, in any area below the eyebrow 3210, with the infrared sensor having a view of the brain tunnel area 3206. The preferred method includes positioning an infrared detector with an angle between 15 and 75 degrees in relation to the plane of the face, and preferably between 30 and 60 degrees, and most preferably between 40 and 50 degrees, and even most preferably at a 45 degree angle with respect to the x, y and z axes. The tip of the infrared detector is positioned in a manner that the infrared sensor has an optimal view of the brain tunnel area. The infrared detector such as a thermopile is pointed at the roof of the orbit adjacent to and below the eyebrow. Preferably the sensor is pointed to the area of the tunnel next to the nose. Preferably the sensor is pointed to an area between the eye and the eyebrow. It is understood that the plane of the face can include the plane of the forehead, surface of the face or the forehead, or similar anatomic structure. The reference point for determining angle of the method can also include the floor or similar physical structure when the head is held straight. Although the infrared detector can be positioned perpendicular to the face with the sensor viewing the brain tunnel area from this perpendicular position, the optimal position is diagonal and preferably in a tri-dimensional manner the Z axis has an angle between 15 and 75 degrees, and preferably between 30 and 60 degrees, and most preferably between 40 and 50 degrees, and even most preferably at a 45 degree angle.

The method includes the steps of positioning an infrared detector in a diagonal position aiming at the brain tunnel from below the eyebrow, receiving infrared radiation from the brain tunnel, and generating an electrical signal based on the received infrared radiation. The brain tunnel may include an area between the eye and the eyebrow. Further step may include generating radiation or directing radiation by the detector prior to the step of receiving radiation form the brain tunnel. A further steps include processing the signal and determining the body temperature or concentration of a chemical substance or analyte. The body temperature in accordance with this invention ranges preferably from 15 degrees Celsius to 45 degrees Celsius.

Another embodiment of this invention includes a device for removably mounting sensors on spectacles and more particularly to a clip for mounting a sensor on spectacles which includes a spring or a tension ring which provides the force to clamp the spectacles and an adjustably positionable sensor anchored to the clip. The mounting sensing device may further include electronics such as a processor and reporting means such as a LED and/or a wireless transmitter to report the value of a biological parameter. It is understood that a clamp for removably mounting sensors can be adapted for clamping any head mounted gear such as spectacles, headbands, caps, helmets, hats, sleeping masks, and the like.

The invention includes sensors, sensing systems, or detectors including infrared detectors adapted to removably clip onto spectacles in a manner which permits the sensors to be positioned on or adjacent to a brain tunnel. The sensor is more preferably adjustably positionable, and most preferably positioned at the roof of the orbit and between the eye and the eyebrow. The present invention is designed to removably mount sensors or detectors of any type including optical sensors, pressure sensors, pulse sensors, fluorescent elements, and the like onto spectacles or head mounted gear. It is understood that the clip of this invention can be adapted to hold any therapeutic system including drug delivery systems such as for example iontophoresis-based systems, thermal energy delivery devices such as for example thermo-voltaic systems including Peltier systems and gels which change the temperature of the area such as polypropyleneglycol. Any head mounted gear of this invention can hold or house a physical element, electrical device, substances, Peltier devices, resistors, cooling elements, heating elements in a manner so as to position those cooling or heating elements on the brain tunnel area in order to change the temperature of the brain tunnel, and consequently the temperature of the brain. Thus, this embodiment can be useful for therapy of heatstroke and hypothermia.

In accordance with this invention, a clip is provided for mounting sensors on spectacles. Preferably a spring is used to retain the front portion and back portion of the clip together and to provide the necessary force to clamp the frame of spectacles or head mounted gear. Preferably the front portion houses power source and electronics while the back portion houses the sensor. The clip includes electronic housing means, support means, sensor attaching means movably mounted relative to the support means, spectacle clamping means movably mounted relative to the support means and clamping means such as a spring or tension ring.

Figure 14A:
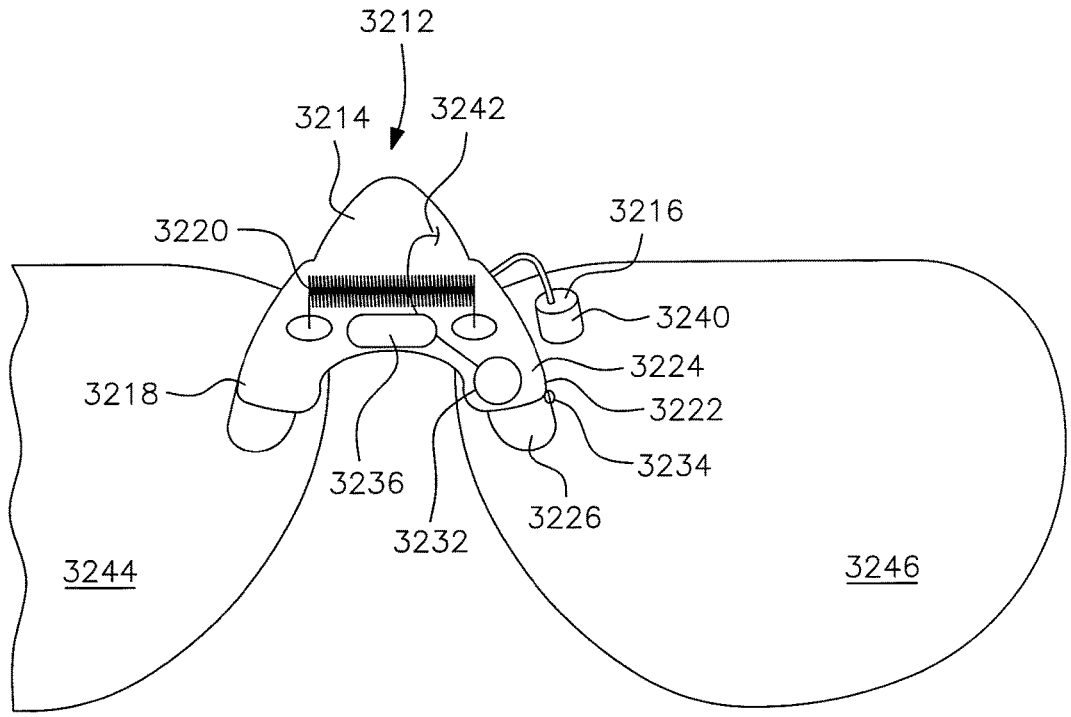
FIG. 14A illustrates a sensing clip for mounting on a pair of eyeglasses.

FIG. 14A is a frontal diagrammatic view of a sensing clip 3212 of the invention mounted on a spectacle illustrated by right lens 3244 and left lens 3246. The sensing clip 3212 comprises support means 3214, sensing means 3216, right clamping system 3218 and left clamping systems 3222, and clamping means 3220 such as pressure applying means represented herein by a spring, which is preferably housed in the centrally located support means 3214. Right and left clamping systems 3218, 3222 each comprise a front and back clamping elements, which are essentially similar and therefore only one side is illustrated. In this exemplary embodiment the left side is the sensing side and therefore the left clamping system 3222 is the side illustrated herein, said left clamping system 3222 is comprised of left front clamp element 3224 and left back clamp element 3226. Spring 3220 allows the force for right and left clamping systems 3218, 3222 to clasp a spectacle or a portion of a head mounted gear. Sensing means 3216 includes sensor 3240 and can comprise any sensor or detector mentioned or described in the present invention. The sensing means 3216 preferably branches off from the top of the support structure 3214 or alternatively sensor 3240 is built-in in the top part of the support structure 3214.

Support portion 3214 is centrally located and connects the right clamping system 3218 and left clamp system 3222, said support portion 3214 shown housing microprocessor 3236. Left front clamp element 3224 preferably houses power source 3232 and left back clamp element 3226, in the vicinity of the skin preferably houses a light source such as LED 3234. It is understood however, that the LED 3234 can be housed in the left front clamp element 3224, and in this embodiment, LED 3234 may be covering an element such as plastic, said plastic having a logo or other indicia which is illuminated upon activation of LED 3234, which allows viewing of the logo by an external observer. Wire 3242 connects electronic circuit 3236 and power source 3232 to light source 3234 and sensor 3240.

Right and left clamping systems 3218, 3222 are preferably positioned on either side of the nose of the wearer. Front clamping elements 3224 and back clamping element 3226 extend downwardly from a central support portion 3214 and are adapted for clamping a structure such as lenses and frames of spectacles and head mounted gear. Front clamping element 3224 and back clamping element 3226 may operate as legs which are aligned with each other in order to clamp a structure such as spectacles or any head mounted gear. Spring means 3220 is preferably housed in central support portion 3214 and serves to connect the right and left clamping systems 3218, 3222 and to provide the necessary forces for clamping a spectacles frame and for maintaining a stable position for the sensing clip 3212.

Figure 14B:
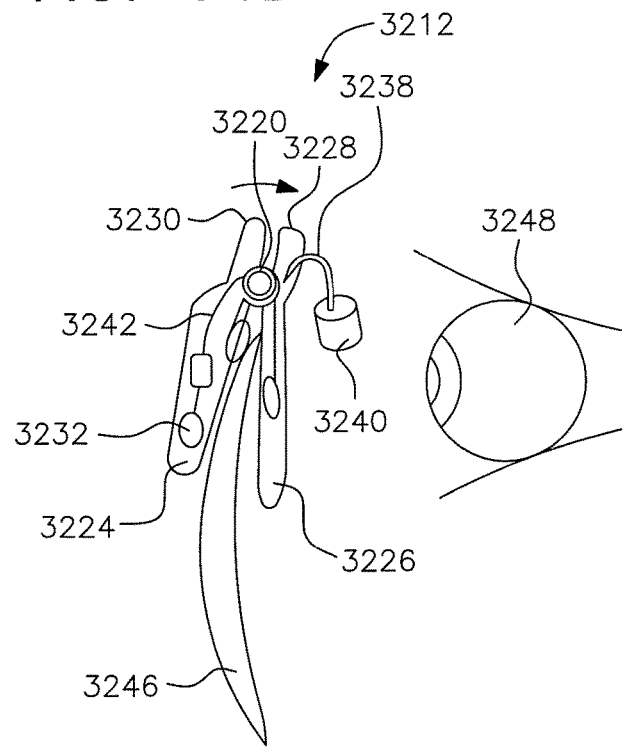
FIG. 14B is a side view of the mounting clip shown on FIG. 14A.

FIG. 14B is a side view of embodiment of FIG. 14A showing sensing clip 3212 mounted on top of left lens 3246. The sensing clip 3212 has preferably a front portion and a back portion in each side, right and left. The left front and back portion is similar to the right front and back portion, and therefore only the left side will be illustrated. The left side is illustrated herein as left back portion 3228 and left front portion 3230, said front portion 3230 and back portion 3228 being joined together by spring 3220. Back portion 3228 and front portion 3230 includes in its end the back clamping element and front clamping element respectively, illustrated herein as left front clamp element 3224 and left back clamp element 3226. The left back clamping element 3226 is located adjacent to the eye 3248. Battery 3232 is preferably housed in the left front portion clamp 3230, and more specifically in the front clamp element 3224. LED 3234 is preferably housed in the back clamp element 3226. Wire 3242 connects the components of the front portion 3230 to components of the back portion 3228 including sensor 3240. It is understood that battery, microchip, and light source can also be housed in the central support portion 3214 or in the back portion 3228.

The sensor 3240 is preferably disposed along the back portion 3228 adjacent to the skin or on the skin. Sensor 3240 preferably has an arm 3238 for adjustably positioning said sensor 3240. It is also understood that sensor 3240 may include any other structure adapted for adjustably positioning a sensor or detector such as infrared detector on or adjacent to a target area for measuring a parameter. Any of the sensors or detectors described in this invention can operate as sensor 3240. Wire 3242 connects electronics, light source and power source in the front portion 3230 to a sensing system in the back portion 3228.

Arm 3238 may house a wire and may also have a light source disposed in its surface. It is understood that sensing means 3216 does not require an arm to be operative. The sensing means of this invention can include a built-in sensor with no arm, said built-in sensor housed in support portion 3214 or any of the clamping elements of this invention. A variety of clip-on and clamping systems can have a sensor and be used to measure a parameter according to this invention including clip-on affixed with lenses which when in an operative position a lens intersect the visual axis and when in an inoperative position said lens is located away from the visual axis of the wearer.

Upon actuation and pressing the clamps, the upper end of the front portion 3230 and the upper end of the back portion 3228 are brought closed together, causing the front clamping element 3224 and back clamping element 3226 to move away from each other creating an opening for receiving a structure such as spectacles. Upon release of the upper end front portion 3230 and the upper end of the back portion 3228 spring 3220 causes front clamping element 3224 and back clamping element 3226 to be brought together causing clamping of the spectacles or any head mounted gear by virtue of the clamping elements 3224 and 3226.

In another preferred embodiment, as shown in FIG. 14C, there is seen a frontal view of a sensing clip 3250, said sensing clip including two main component parts, a clip 3252 and sensing means 3260 including sensor 3261. The clip 3252 includes the central portion 3258, which houses a spring 3262, and right and left clamping systems 3264 and 3266. Right clamping system 3264 has a front clamp and a back clamp and left clamping system 3266 has a front clamp and a back clamp, illustrated herein as left front clamp 3270 and a left back clamp 3256. The sensor 3260 is secured to a back clamp element 3256 of clip 3252 by arm 3254. The left back clamping element and right back clamping element have preferably a pad, illustrated herein as left pad 3268 for firmly clamping eyeglasses between said back clamp 3256 and a front clamp 3270.

FIG. 14D is a side view of an embodiment of a sensing clip 3272 in a resting position showing front clamp 3274 and back clamp 3276. The back clamp leg 3276 preferably has a pad 3278 and houses sensor 3280. Although an arm attached to a sensor has been described, it is understood that a sensor can be secured or be part of a sensing clip in a variety of ways. Accordingly, in this embodiment of FIG. 14D the sensor 3280 is integrally molded in unitary construction with the back clamp 3276. In the resting position front clamp 3274 rests against back clamp 3276. Preferably front clamp element 3274 is longer than back clamp element 3276, said front clamp 3274 being located on the front of a lens facing the environment and said back clamp 3276 located adjacent to the skin and/or the eye. FIG. 14E shows the sensing clip 3272 in an open position with pad 3278 of back clamp 3276 located away from front clamp 3274, for receiving a structure such as frame of eyeglasses or any head mounted gear.

It is contemplated that any other assembly for clamping, grasping, or attaching a sensing device to eyeglasses or head mounted gear can be used including clamping assembly without a spring. Accordingly, by way of example, FIG. 14F shows the frontal view of a sensing device 3280 that includes a central portion 3286 housing a right and left tension bar 3282, 3284, right and left clamping systems 3294, 3296, right and left pad 3288 and 3290 coupled to the tension bar 3282, 3284, and arm 3292 connecting sensor 3294 to back clamp element 3298, said back clamp 3298 having a LED 3300. FIG. 14G is a side view of sensing device 3280 of FIG. 14F showing tension bar 3282 in a resting position, in which left pad 3290 rests against a left back clamp element 3300. FIG. 14H is a side view of sensing device 3280 showing tension bar 3282 in an open position. In this embodiment the frame of the eyeglasses or any structure can push the pad 3290 away from back clamp 3298 and place the tension bar 3282 in an open position for securing eyeglasses.

Figure 14J:
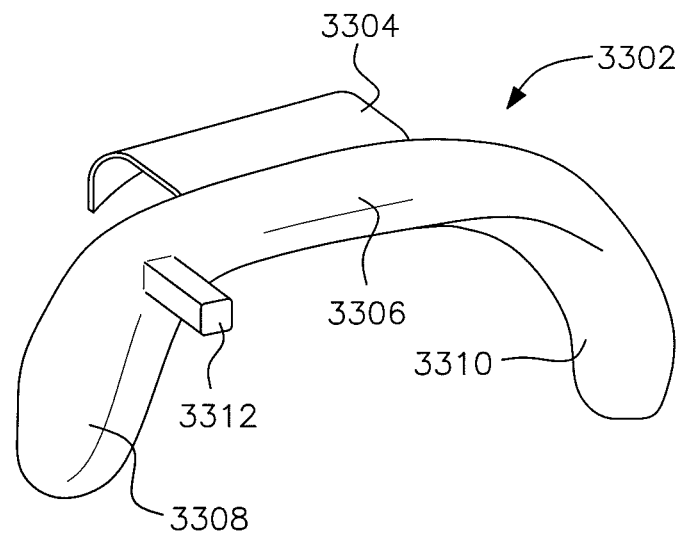
FIG. 14C illustrates a sensing clip including a sensor.
FIG. 14D is a side view of the sensing clip shown in FIG. 14C.
FIG. 14E illustrates the sensing clip in an open position.

Any attachment means with a sensor for attaching to eyeglasses or head mounted gear is contemplated or any sensing device adapted to be secured to eyeglasses or head mounted gear. Accordingly, FIG. 14J shows sensing device 3302 adapted to be secured to the frame of eyeglasses by a hook-like structure 3304 which branches off from the main support portion 3306 and includes sensor 3312. The main support portion 3306 has a U configuration with two legs 3308, 3310 which houses electronics, light source, and power source (not shown).

Figure 14K:
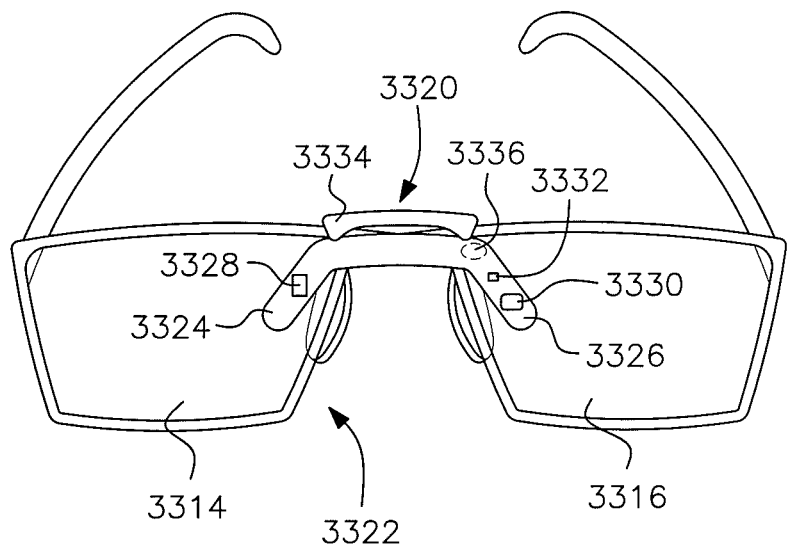

FIG. 14K shows a sensing device 3320 mounted on spectacles 3322 having right lens 3314 and left lens 3316. The sensing device 3320 includes a hook 3334 and is adapted to be supported by the frame of spectacles and includes right leg 3324 and left leg 3326. The right leg 3324 houses electronic processing circuit 3328 and left leg 3326 houses power source 3330 and light source 3332. The right leg 3324 and left leg 3326 face the environment and are disposed in front of the lens 3316. A sensor 3336 on the opposite side of lens 3316 is facing the face of the user.

Figure 14L:
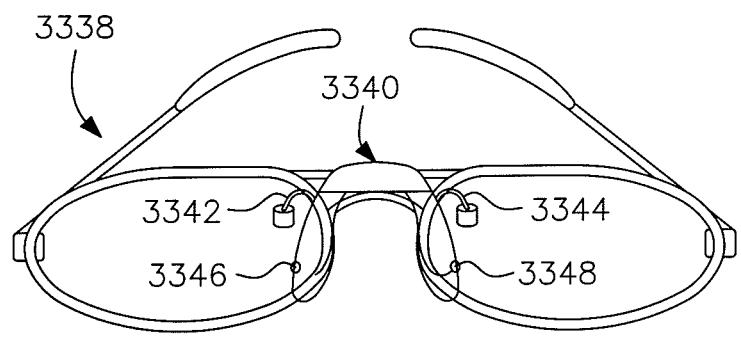

FIG. 14L shows sensing device 3340 clipped to eyeglasses 3338 said sensing device 3340 including a dual sensing system, exemplarily illustrated as right sensing system 3342 detecting pulse and left sensing system 3344 detecting temperature. The structure of sensing device 3340 is similar to the structure described for sensing devices of FIGS. 14A to 14K. Sensing device 3340 has a dual reporting system, illustrated herein as right LED 3346 and left LED 3348.

Figure 14M:
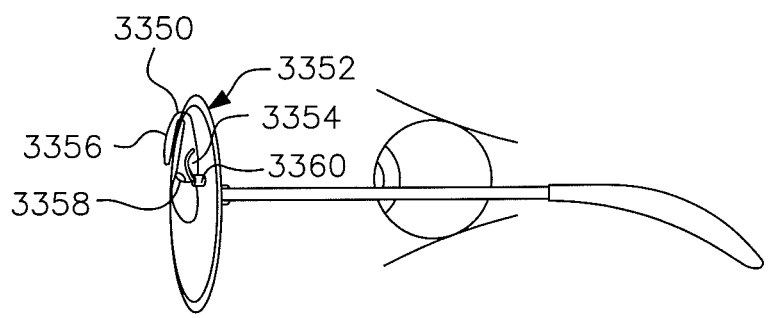

FIG. 14M is a side view of an exemplary embodiment of sensing device 3350 having back portion 3354 and front portion 3356 and being secured to the frame of eyeglasses 3352, shown as ghost image. A sensor 3360 is secured to the back portion 3354 and a LED 3358 is positioned in alignment with the visual axis of user 3362.

Figures 1, 14N:
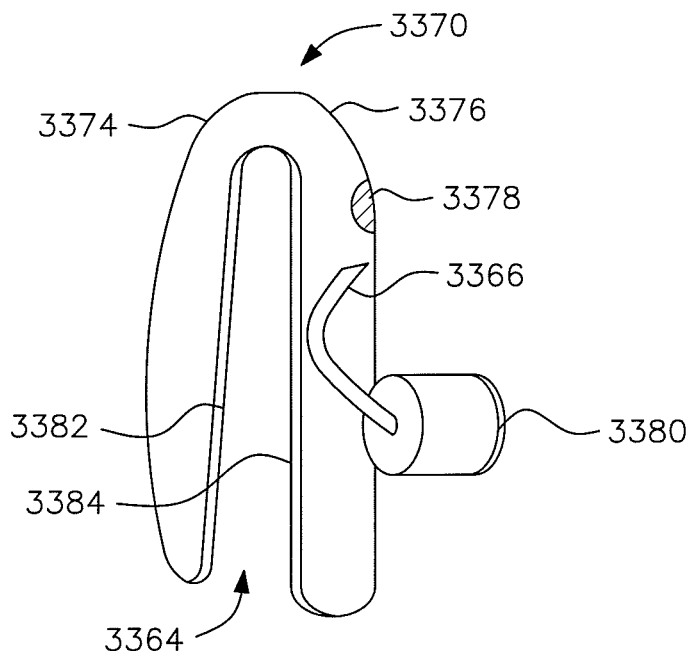
Figures 2, 14N:
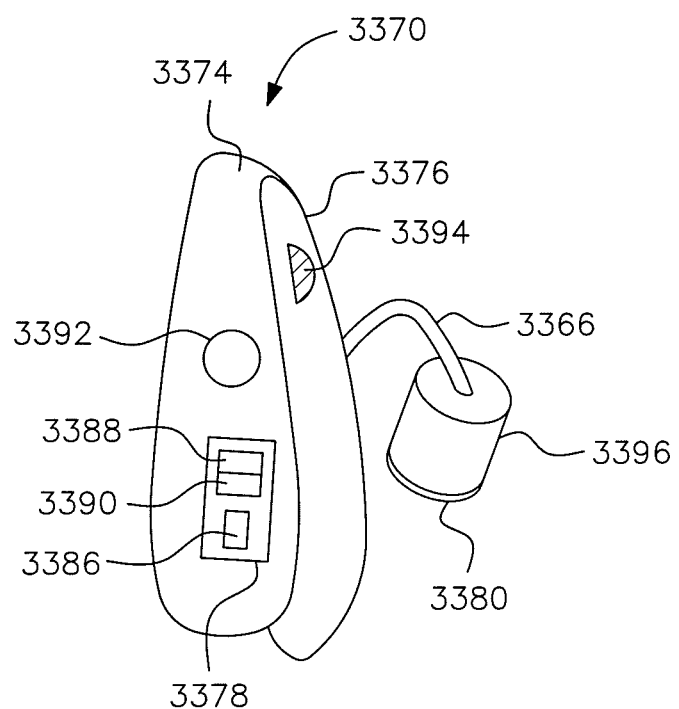
Figures 3, 14N:
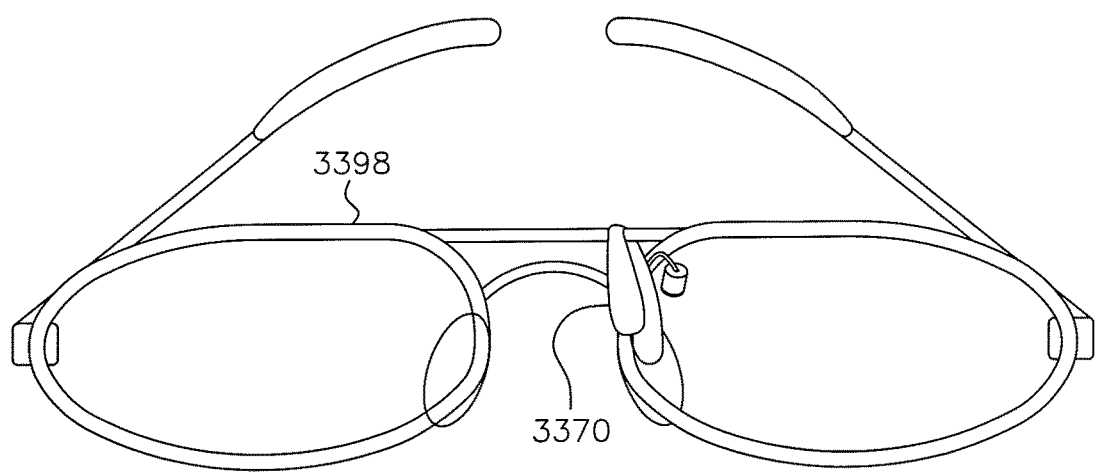

In another preferred embodiment, as shown in FIG. 14N-1, there is seen a side view of a sensing device 3370, which has an opening 3364 and an inverted U shape configuration for receiving a frame of eyeglasses or a head mounted gear. Sensing device 3370 has a front portion 3374 and a back portion 3376 and is preferably made of plastic or polymer that has a memory or any shape memory alloy. Preferably internal surfaces 3382 and 3384 have a gripping surface or are rubberized for securing a structure such as frame of eyeglasses. A sensor 3380 is attached to the back portion 3376 preferably by adjustably positionable arm 3366. Back portion 3376 house LED 3378, which is operatively connected to sensor 3380. In this embodiment there is no spring, tension bar, clamping element, and the like. A stable position is achieved by virtue of the U shape configuration.

FIG. 14N-2 is a front view of the sensing clip device 3370 of FIG. 14N-1 showing front portion 3374 having a printed circuit board 3378 and memory area 3386, wireless transmitter 3388, and processor 3390. A battery 3392 is housed in front portion 3374. Battery 3392 can be permanently attached to sensing clip 3370 or be removably secured to said sensing clip 3370. Back portion 3376 houses LED 3394 and sensing means comprised of a sensor holder 3396 holding a sensor 3380, said sensor holder 3396 being connected by arm 3366 to sensing clip 3370. FIG. 14N-3 is a frontal schematic view of the sensing clip 3370 of FIG. 14N-1 mounted on eyeglasses 3398, shown as a ghost image.

Figure 14P:
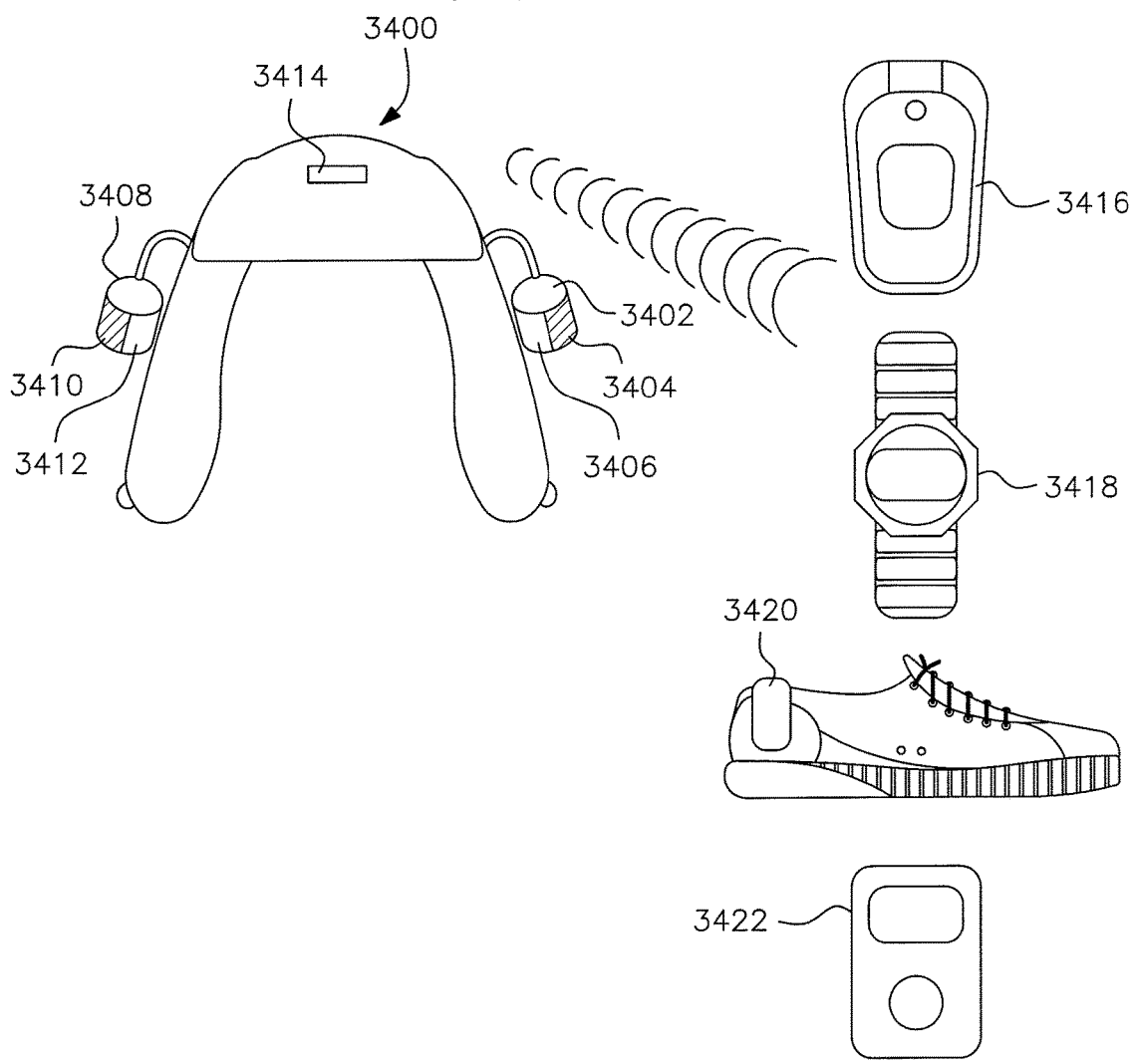

FIG. 14P is a frontal view of dual sensing clip 3400, illustratively shown as a pair light emitter-light detector 3402, illustrated on the left side, including radiation emitter 3404 and radiation detector 3406, for detecting glucose, and a second pair light emitter-light detector 3408 located on the opposite side including radiation emitter 3410 and radiation detector 3412 for detecting oxygen and pulse oximetry. Besides, a temperature sensor or any other sensor can be used as a substitute or in addition to the pair light emitter-detector. Sensing clip 3400 is adapted for performing measurements and detecting analytes by touching the area being measured or by being spaced away from the area being measured. Wireless transmitter 3414 is adapted for transmitting a wireless signal to a remotely placed device including a telephone 3416, watch 3418, shoe 3420, and a digital device 3422 such as a music player or computing device.

In addition, a sensing device can have arms which wrap around or that are attached to the temples of eyeglasses or to a portion of a head mounted gear. The sensing means may branch off from the sensing device, which is adapted to position a sensor on or adjacent to a target area, such as a brain tunnel. It is also contemplated that any flip sunshades or any type of clip-on sunshades can include sensors for measuring a parameter.

The present invention teaches a modular construction of head mounted gear for measuring biological parameters. Accordingly, FIG. 15A is a perspective diagrammatic view of another support structure comprised of a specialized headband 3430 including a recess 3432 for receiving a housing 3434, said housing being preferably a module removably attached to said headband 3430 and includes right arm 3436 and left arm 3438. Arms 3436 and 3438 terminate in right and left sensing portion 3440, 3442. Housing 3434 can comprise a box housing wires from sensors 3440, 3442, and further include wire 3444 which exits box 3434 and is disposed along the surface 3446 of headband 3430, and more particularly disposed on a groove 3448. Groove 3448 is adapted for being covered by a strip 3450 attached to headband 3430. The strip 3450 is preferably made of fabric and has a hinge mechanism, said strip 3450 being positioned over the groove 3448 for securing wire 3444 to headband 3430. Edge 3456 of strip 3450 comprises preferably a hook and loop material which matches a hook and loop material 3454 secured to headband 3430. Wire 3444 terminates in connector 3452, for connecting with a processor and display unit (not shown).

FIG. 15B shows in more detail the BTT temperature module 3460 which includes a housing 3434 and a steel rod 3458 shaped as an inverted U and secured to the housing 3434. Wire 3462 runs along or in the right rod 3466, and connects sensor 3470 to PCB 3464 and processor 3478. Wire 3472 runs along or in the left rod 3474 and connects sensor 3468 to PCB 3464 and processor 3478. Processor 3478 selects the best signal, illustrated herein as selecting the highest of the two temperature signals being measured at the right and left side, illustrated herein by sensors 3470 and 3468. Processor 3478 can be operatively coupled to a memory 3476 and is connected with a display by wire 3482, said wire 3482 exiting housing 3434 and terminating in an electrical connector 3484. Sensor portion 3468 and 3470 can have any of the configurations described herein, and in particular the configuration and dimensions of measuring portion 2006. Right rod 3466 and left rod 3474 can have any of the configurations described herein, and in particular the configuration and dimensions of arm 2004. The thickness of said arm 2004 can be converted to a diameter of said arm 2004 since rods 3466, 3474 are essentially cylindrical in nature and may function as arm 2004.

FIG. 15C is a frontal perspective view of another embodiment of a sensing modular headband 3500 of this invention when worn by a user 3486 and includes a headband 3480 having an area 3488 for receiving BTT temperature module 3490, said area 3488 having an electrical connector 3492 for electrically connecting module 3490 to headband 3480. Temperature module 3490 includes processor 3494, memory 3496, and arms 3498 and 3502, said arms 3498 and 3502 terminating in measuring portion 3504 and 3506 respectively. Measuring portions 3504 and 3506 are disposed on or adjacent to the brain tunnel area 3508 and 3510, and located below the eyebrows 3512 and 3514. Electrical connector 3492 can function as an electrical pad and is connected to wire 3516 disposed along the surface or within headband 3480.

FIG. 15D is a side view of another sensing modular headband 3520 of this invention when worn by a user (as ghost image) and including four different biologic parameter modules, namely a BTT temperature module 3522, an ear temperature module 3524, an infrared detection module 3526 illustrated herein as pulse oximetry module, and a behind the ear temperature module 3528. BTT temperature module 3522 is disposed on the surface 3580 of sensing modular headband 3520 facing away from the skin 3536 and includes adjustably positionable arm 3530 and measuring portion 3532 positioned below and adjacent to the eyebrow 3534. Ear temperature module 3524 may include a removably attached module secured by a clip 3538 to the edge of headband 3520. Module 3524 may further include a retractable cord spool 3540 securing cord 3542 which terminates in sensing probe 3544 which rests in the ear canal, said probe 3544 including at least one of an infrared detector, a pair infrared emitter-infrared detector, a temperature sensor such as a thermistor, RTD, and thermocouple, and the like. Module 3524 also receives electrical input from behind the ear temperature module 3528, which measures temperature behind the ear and more specifically at the lower part of the ear 3546 and/or around the ear lobe 3548. Behind the ear temperature module 3528 can be removably attached to headband 3520 by fastening structure 3556, such as a hook or loop, and includes a C-shape housing 3550 and a sensor 3552, said sensor 3552 being connected to module 3524 by wire 3554 which is disposed on or along the C-shape housing 3550 and terminates in said ear temperature module 3524.

Pulse oximetry module 3526 is located right above the eyebrow 3534 and disposed in the internal face of headband 3520 adjacent to the skin 3536 and includes a pair light emitter-light detector 3582 housed in an adhesive patch 3558 and further includes a wire 3560 which runs on the external surface 3562 of headband 3520 after going through hole 3564 located in headband 3520. Wire 3566 of ear temperature module 3524, wire 3568 of BTT module 3522, and wire 3560 of pulse oximetry module 3526, all run along the external surface 3562 and more specifically sandwiched between a movable lip 3570 which covers the wires 3566, 3568, 3560 and the external surface 3562 of headband 3520. Wires 3566, 3568, 3560 exit headband 3520 and connect to display and processing unit 3572 through connectors 3574, 3576, and 3578.

FIG. 15E is a frontal perspective view of another sensing modular headband 3590 of this invention when worn by a user 3592 and including two different biologic parameter modules, namely a BTT temperature module 3594 and an ear monitoring module 3596, said modules 3594 and 3596 including any sensor described in this invention and any temperature sensors such as infrared radiation and thermistors. BTT temperature module 3594 is disposed on the surface 3598 of sensing modular headband 3590 and includes adjustably positionable arms 3600, 3602 and measuring portion 3604, 3608 positioned below and adjacent to the eyebrow 3606, 3610, and further including wire 3612 which exits headband 3590 and run behind the ear 3628 terminating in connector 3614 which connects to wire 3616, said wire 3616 being connected to a display and interface 3618. Ear monitoring module 3596 includes a wireless transmitter 3620 wirelessly connected to receiver and display 3622, and further including wire 3624 which terminates in ear probe 3626.

FIG. 15F is a diagrammatic view of another sensing modular headband 3630 of this invention with eyes 3674, 3678 and nose 3680 seen below, said headband 3630 including eight different biologic parameter modules, namely a Brain Tunnel module 3632 illustrated by a radiation detector 3634 on the left and a radiation emitter-detector pair 3636 on the right, an ear temperature module 3638, an infrared detection module 3640 illustrated herein as pulse oximetry module, pulse detection module 3642, a blood pressure detection module 3644, a brain monitoring module such as a digitized EEG (electroencephalogram) module illustrated herein by three electrodes 3648, 3650, 3652, a skin temperature module 3654, preferably using a sensor over the temporal artery, and a medical device holding module 3656, illustrated herein by a nasal canula module. Brain tunnel module 3632 includes adjustably positionable arm 3660 terminating in measuring portion 3636 illustrated herein by an infrared pair emitter-detector for analyte detection such as glucose and an adjustably positionable arm 3662 terminating in measuring portion 3634 illustrated by an infrared detector positioned on or adjacent to the brain tunnel next to the bridge of the nose and/or on the eyelid.

Pulse oximetry module 3640 is disposed on cavity or recess 3666 on the internal face of headband 3630 and includes a pair light emitter-light detector 3664. Ear temperature module 3638 may include a cord 3646 that terminates in sensing probe 3658 which rests in the ear canal 3668 and receive radiation 3670 from said ear canal. Pulse detection module 3642 and a blood pressure detection module 3644 can include any pressure sensing device, piezoelectric devices, and the like. Brain monitoring module allows directly monitoring of a patient's level of consciousness to help determine and administer the precise amount of drug to meet the needs of each individual patient and to avoid intraoperative awareness. Brain monitoring module works by using a sensor that is placed on the patient's forehead to measure electrical activity in the brain from the EEG and the activity is digitized and displayed as a numerical value. Brain monitoring module allows customized amount of anesthetic and sedative medication to be delivered to the patient and therefore ensure that they are unconscious and free of pain, yet able to wake-up quickly and experience minimal side-effects from anesthesia and sedation. Brain monitoring module 3646 is illustrated herein by three electrodes 3648, 3650, and 3652. The information from the electrodes 3648, 3650, 3652 is processed and a number achieved which provides a direct measure of the patient's level of consciousness allowing clinicians to determine the most effective anesthetic and sedative mix, consequently patients have faster, more predictable wake-ups and higher-quality recoveries with less nausea and vomiting. The brain monitoring module may include an external monitor that analyzes and displays EEG signals, and then converts EEG signals to digital data, and then transfers the data to the external monitor for processing, analysis, and display. Nasal canula module includes a canula that goes up over the nose, and preferably not to the sides as per prior art. Modular nasal canula 3672 is secured by fastening means such as hooks and/or VELCRO and disposed on the surface of the headband 3630. The apparatus and method for supporting the nasal canula includes a plurality of hooks in the head mounted gear such as a headband of FIG. 15F or the frame of FIG. 15X, suspending thus the canula and supporting the canula along the surface of the head mounted gear, prevented from shifting during sleep and transport.

FIG. 15G is a diagrammatic cross sectional view of a sensing modular headband 3680 of this invention showing the disposition of the modules in the internal surface 3682 facing the skin 3684 and the external surface 3686 of headband 3680 facing away from the skin 3684. Strap 3688 is adapted to be secured to skin 3684 as pointed by large arrows, said strap 3688 having an area and/or recess 3690 on the external surface 3686 for receiving a brain tunnel module 3692, said area or recess 3690 preferably made of a thin sheet of plastic or other polymer adapted to give stability to the module; and two areas or recesses 3694, 3696 on the internal surface 3682 for receiving an infrared module 3698 and a skin temperature module 3700. The Brain Tunnel includes two areas 3702, 3704 indicating the junction of right and left adjustable arms (not shown in cross sectional view) to the housing 3730, with wires 3706, 3708 connecting wires from adjustable arms to a processor 3712. Wire 3710 connects processor 3712 with a display unit (not shown), said wire 3710 being disposed between the external surface 3686 and a lip 3714, made preferably of fabric or any pliable material. Area 3690 has preferably two plugs 3716, 3718 for fastening and securing a module such as a snap-on action to secure the module to the recess or cavity. Plugs 3716, 3718 can also work as electrical connectors.

Pulse oximetry module 3698 is disposed on cavity or recess 3696 on the internal face 3682 of strap 3688 and includes a pair light emitter-light detector 3720. Wire 3722 connects pair 3720 with a display unit (not shown), said wire 3722 being disposed between the external surface 3686 and a lip 3714 after said wire 3722 goes through a hole 3724. Skin temperature sensor module 3700 is disposed on cavity or recess 3694 on the internal face 3682 of strap 3688 and includes a sensor 3726. Wire 3728 connects sensor 3726 with a display and processing unit (not shown), said wire 3728 being disposed along the internal surface 3682 facing the skin 3684. There is also shown the flap 3714, also referred as lip, being connected to external surface 3686 by a hook and loop fastener Wire 3710 connects processor 3712 with a display unit (not shown), said wire 3710 being disposed between the external surface 3686 and a lip 3714, made preferably of fabric or any pliable material.

FIG. 15H is a diagrammatic planar view of the sensing modular headband 3680 showing the external surface 3686 of strap 3688, said external surface 3686 having area or recess 3690 for receiving a brain tunnel module 3692. Area 3690 has preferably two snap-on plugs 3716, 3718 for fastening and securing a module. There is also seen the hole 3724 and the impression of plastic sheet of area 3696 on the external surface 3686, which secures an infrared detection module. There is also shown the flap 3714, also referred as lip, being connected to external surface 3686 by a hook and loop fastener 3732.

FIG. 15J is a diagrammatic cross sectional view of a sensing modular headband 3740 of this invention showing the disposition of the modules on external surface 3742 of headband 3740 facing away from the skin 3744. Strap 3746 is adapted to be secured to skin 3744 as pointed by large arrow, said strap 3746 having an area and/or recess 3750 on the external surface 3742 for receiving a brain tunnel module 3744, said area, cavity, or recess 3750 preferably made of a thin sheet of plastic or other polymer adapted to give stability to the module; and another specialized area or recesses 3752 for receiving an infrared module 3754. Wire 3756 connects brain tunnel module 3744 with a display and processing unit (not shown), said wire 3756 being disposed between the external surface 3742 and a flap 3758. Area 3750 has preferably two plugs 3760, 3762 for fastening and securing a module.

Pulse oximetry module 3754 is disposed on the cavity or recess 3752 on the external surface 3742, said pulse oximetry module 3754 including a pair light emitter-light detector 3756. Area, recess, or cavity 3752 of strap 3746 has preferably two openings 3758, 3748 for respectively receiving light emitter 3770 and light detector 3772. Light emitter 3770 and light detector 3772 are preferably disposed in a manner to press such emitter 3770 and detector 3772 against skin 3744 and create an indentation. Openings 3758 allow light to be directed at the skin 3744 by emitter 3770 and light to be received by detector 3772 through opening 3748. Plugs 3764 and 3766 are disposed on the bottom of recess 3752 for fastening and firmly securing the module 3754 to strap 3746. Wire 3768 connects pulse oximetry module 3754 with a display and processing unit (not shown), said wire 3768 being disposed between the external surface 3742 and a flap 3758. Internal surface 3778 of strap 3746 may include a peel-back adhesive 3776, which exposes an adhesive surface for more stable securing strap 3746 to a body part. The oxymetry module is preferably located in the headband portion that is above the eye, said oximetry module being next to the module for temperature measurement.

All the modules described herein preferably physically conform to a body portion of a patient, such as a forehead, and provide a firm pressing engagement between the sensors and the living creature's body portion. The pair light emitter-detector may include a flexible structure such as a flexible patch, which is physically conformable and attachable to the subject's body portion. The pair light emitter-detector includes a light source assembly for illuminating the patient's body portion, and a light detector assembly for measuring reflected light. When the pair light emitter-detector is conformably applied to the recess or cavity of the sensing headband, preferably using the snap-on plugs of said headband, localized pressure is exerted on the body portion at the points of contact with the light source and light detector assemblies, and/or the electrodes, and/or the temperature sensors and/or the pressure sensors and pulse sensors, and any of the sensors of this invention.

As in conventional pulse oximetry sensors, the light emitter or light source may include two light-emitting diodes emitting light at red and infrared wavelengths, and the light detector assembly may include a corresponding two or more photodetectors. It is understood that a single light detector can be used to detect light at both wavelengths. The electric signals are carried to and from the light source and light detector assemblies by an electric cable which terminates at an electrical connector, said connector being connected to control and processing circuitry and display.

The present invention teaches a method and apparatus for reusing expensive parts while making the least expensive part, the only disposable part. Electronics and medical sensors are expensive and due to the arrangement of the invention, those expensive parts do not remain in contact with the skin and do not have adhesive surfaces adhering to the skin. The modular construction in which an optical sensor is the only portion touching the skin surface, allows easy cleaning of said optical sensor and reutilization, such as for pulse oximetry. For temperature measurement a very low cost disposable cover is the only disposable material, which is required for covering the sensor that rests on the BTT. Since in the arrangement of the invention, preferably, the electronics, sensors, and other expensive parts do not touch the skin, said parts can be reused. Since the arrangement is done in a manner in which only the forehead material touches the body, and the forehead material is the least expensive of the material sitting on the forehead, and actually really low cost. The device of the invention includes reusable parts and disposable parts.

FIG. 15K is a diagrammatic planar view of the external surface of the sensing modular headband 3740 showing the external surface 3742 of strap 3746, said external surface 3742 having area or recess 3750 for receiving a brain tunnel module 3744; and area or recess 3752 for receiving a pulse oximetry module 3754. Area 3750 has preferably two snap-on plugs 3760, 3762 for fastening and securing a module. Area 3752 has preferably two snap-on plugs 3764, 3766 for fastening and securing an infrared module, and openings 3758, 3748 for allowing passage of light to/from the skin to light emitter-detector pair 3756. There is also shown the flap 3758, also to referred as a lip, being connected to external surface 3742 by a hook and loop fastener 3774.

FIG. 15L is a diagrammatic planar view of the internal surface 3778 of the sensing modular headband 3740 showing the adhesive surface 3780 exposed after removing the backing 3776. Method includes using straps that have adhesive surface in different locations, allowing thus the skin to breathe more properly. Accordingly, a first strap has adhesive surface in the center, said strap is used for 3 days for example. After the 3 days, a new strap is applied, namely a second strap which has adhesive only on the side parts but not the central part as with the first strap, thus allowing area covered by adhesive to breathe since the area will not be covered consecutively with adhesives.

FIG. 15M is a diagrammatic planar view of an exemplary cavity or recess 3782 for receiving a module 3784 for monitoring biological parameters. Cavity 3782 may include an adjacent housing for housing electronic circuit and printed circuit board 3786 in addition to a processor 3788, wireless transmitter 3790, and display 3792.

FIG. 15N is a diagrammatic side view of another embodiment comprised of a head mounted gear 3800, illustrated herein by a cap worn by a user, and including arm 3796 terminating in measuring portion 3794, said arm 3796 being secured to the cap 3800 and further including a wire 3798 disposed along the cap 3800 and connected to a processing and reporting unit 3802. The reporting unit 3802 may audibly report the value of a parameter being measured, and further include an ear bud assembly 3804 connected by wire 3806 to processing and reporting unit 3802.

FIG. 15P is a diagrammatic perspective view of another embodiment comprised of a head mounted gear 3804, illustrated herein by a cap worn by a user 3822, and including arm 3806 terminating in measuring portion 3808, said arm 3806 being secured to the cap 3804, and further including a wire 3810 disposed along the cap 3804 and connected to a second measuring portion 3812, said measuring portion 3812 having a housing 3816 and a sensor 3814. The measuring portion 3812 is disposed under the brim of the cap 3804, with said measuring portion 3812 having a housing 3816 which is secured to the cap 3804. Sensor 3814 is pressed against the skin by housing 3816, said sensor comprising any of the sensors, or pair light emitter-detector, or infrared detector of this invention. Wire 3818 connects measuring portions 3808 and 3812 to processing, transmitting, and reporting unit 3820 disposed in the back of the user 3822.

FIG. 15Q is a diagrammatic perspective view of another embodiment comprised of a head mounted gear 3824, illustrated herein by a cap, and including measuring portion 3828 and 3826 housing respectively an infrared detecting system 3830 and piezoelectric system 3832 being secured to the cap 3824, and further including a groove 3826. Measuring portions 3828 and 3826 are movable and may slide on a groove shown by arrow, and illustrated herein as groove 3840 for proper positioning of sensor 3830. Wire 3834 and wire 3836 join at the back of the cap 3824 and form a single wire 3838 that connects to a processing and reporting unit (not shown). It is understood that the measuring portions can be constructed as removably attached modules as previously described for headbands.

FIG. 15R is a diagrammatic perspective view of another embodiment comprised of a head mounted gear 3842, illustrated herein by a burette worn by a user 3844, and including arm 3846 terminating in measuring portion 3848, which is disposed on or adjacent to a physiologic tunnel 3850 between the eye 3866 and the eyebrow 3868 next to the nose 3852, said arm 3846 being secured to the burette 3842, and further including a wire portion 3854 disposed along the burette 3842 and connected to a processing and transmitting unit 3856. A second arm 3858 terminates in a second measuring portion 3860, which is disposed on or adjacent to a second physiologic tunnel 3862 between the eye 3866 and the eyebrow 3868 next to the ear 3864, said arm 3858 being secured to the burette 3842, and further including a wire portion 3870 disposed along the burette 3842 and connected to a processing and transmitting unit 3856. A third arm 3872 terminates in a third measuring portion 3874, which is disposed on or adjacent to a third physiologic tunnel 3876 behind the ear 3864, said arm 3872 being secured to the burette 3842, and further including a wire portion 3878 disposed along the burette 3842 and connected to a processing and transmitting unit 3856. It is understood that any of the arms of this invention may be adjustably positionable and extendable according to the application.

FIG. 15S is a diagrammatic perspective view of another embodiment comprised of a head mounted gear 3880, illustrated herein by a light source worn by a user 3882, and including arm 3884 terminating in measuring portion 3886, which is disposed on or adjacent to a physiologic tunnel 3888 adjacent to the eyebrow 3890, said arm 3884 being secured to the sensing head light 3880, and further including a wire portion 3892 disposed on or within the head light 3880 and connected to a processing and transmitting unit 3894. Head light 3880 has an arm 3896 for securing said head light 3880 to the head 3898 of the user 3882, said arm 3896 having a housing that includes an oxygen or analyte measuring device 3900, illustrated herein by a pair radiation emitter-radiation detector 3902, which is connected by wire 3904 to a processing and transmitting unit 3894.

FIG. 15T is a diagrammatic perspective view of another embodiment comprised of a head mounted gear 3910, illustrated herein by a sensing visor worn by a user 3912, and including arm 3914 terminating in measuring portion 3916, and terminating in a second measuring portion 3918 measuring a second parameter, said arm 3914 being secured to the sensing visor 3910 by fastening means 3920 such as a loop anchored to said sensing visor 3910. Sensing visor 3910 may include a microphone 3928 disposed along the side of the face and connected to a processing, transmitting, and reporting circuit 3922 via stalk 3930, and may further include a display 3924 for visual display of data or information connected to a processing, transmitting, and reporting circuit 3922 via wire 3932. Sensing visor 3910 may include an ear bud assembly 3926 connected to a processing, transmitting, and reporting circuit 3922 via wire 3934. This embodiment includes athletic applications in which an athlete wants to report to a coach a value of biological value or other information. Accordingly, the user receives the information audibly by the ear bud assembly 3926 or visually by display 3924, and then communicates the relevant information via microphone 3928.

FIG. 15U is a diagrammatic perspective view of another embodiment comprised of apparel or clothing 3940, illustrated herein by a sensing-enabled shirt worn by a user 3942, and including a moldable wire 3944 preferably with memory for more stability and being supported by the ear or other fasteners (not shown). Wire 3944 terminates in an adjustably positionable arm 3946, which further terminates in measuring portion 3948. Arm 3946 further includes a measuring portion having a sensing system 3958 contained in an adhesive patch 3956 and applied to the forehead of user 3942. Wire 3944 terminates in a support structure 3950 secured to the collar 3952 of sensing shirt 3940, said support structure 3950 being electrically connected via wire 3960 to a reporting and display unit 3954 preferably secured to a piece of clothing.

FIG. 15V is a diagrammatic perspective view of another embodiment comprised of head mounted gear 3962, illustrated herein by a helmet, and including arm 3964 terminating in measuring portion 3966 comprised of a temperature sensor, said arm 3964 being disposed on or within helmet 3962 and being connected to a processing, transmitting, and reporting circuit 3968 via wire 3970. Sensing-enabled helmet 3962 may include an ear bud assembly 3972 connected to a processing, transmitting, and reporting circuit 3968 via wire 3976. Sensing-enabled helmet 3962 may also include a second sensor 3974 for measuring pulse and disposed along the side of the head, said sensor 3974 being connected to a processing, transmitting, and reporting unit 3974 via wire 3978. Unit 3974 may further include a music player, which adjusts to a lower volume in case the value of biological parameter is audibly transmitted.

FIG. 15X is a diagrammatic view of another sensing frame 3980 of this invention, said frame 3980 including seven different biologic parameter modules, namely a Brain Tunnel module 3982 illustrated by a radiation emitter-detector 3984 on the left and a radiation emitter-detector pair 3986 on the right; an ear monitoring module 3988, an infrared detection module 3990 illustrated herein as pulse oximetry module, pulse detection module 3992, a behind the ear detection module 3994, a skin temperature module 3996, preferably using a sensor over the temporal artery, and a medical device holding module 3998, illustrated herein by a nasal canula module. It is understood that although removably attached modules are described, the invention includes modules being permanently attached and the frame working as an integral one piece construction, or alternatively some devices are removably attached and some are permanently affixed to the head mounted gear or eyeglasses, and those configurations apply to all devices described in this application.

Brain tunnel module 3982 includes adjustably positionable arm 3400 terminating in measuring portion 3984 illustrated herein by an infrared pair emitter-detector for analyte detection such as glucose and an adjustably positionable arm 3402 terminating in measuring portion 3986 illustrated by an infrared emitter-detector positioned on or adjacent to the brain tunnel next to the bridge of the nose and/or on the eyelid and detecting pulse and oxygen. The housing 3414 of the pulse oximetry module 3990 branches off from the frame 3980 and it is seen located on the right side of frame 3980 with the pair emitter-detector located above the eyebrow 3404. Ear monitoring module 3988 may include a cord 3406, with or without a retractable cable, from the frame 3980, said cord 3406 terminating in sensing probe 3408 which rests in the ear canal and receive radiation from said ear canal. Pulse detection module 3992 branches off the frame 3980 and is adapted to detect pulsation of a blood vessel using a sensor 3416 disposed in said module 3992, said sensor 3416 being located above the eyebrow 3410 and including any pressure sensing device, piezoelectric devices, tonometric device, and the like. Skin temperature module 3996 branches off the frame 3980 includes a temperature sensor 3412 preferably positioned over the temporal artery or in the vicinity of the temporal artery. Behind the ear monitoring module 3994 includes a sensor 3420 located in frame 3980, and more specifically at the end of the temples 3418, and even more specifically at the free end 3422 of the temples 3418. Nasal canula module 3998 includes a canula 3999 that goes up over the nose, and preferably not to the sides as per prior art. Modular nasal canula 3998 is secured by fastening means such as hooks and/or loops disposed along the frame 3980 and illustrated herein by hook-loop 3424, 3426, 3428, on the left side and one hook 3430 illustrated on the right side of frame 3980. By way of illustration nasal canula is shown on the left side as broken down lines along the frame 3980, but it is understood that said nasal canula is disposed in the same manner on the right side. Any fastening means to secure a nasal canula to the frame of eyeglasses can be used.

Wire 3432 connects infrared module 3390 to a processing and display circuit 3434 through electrical connector 3436. Wire 3438 connects ear monitoring module 3988 to the processing and display circuit 3434 through electrical connector 3436. Wire 3440 connects behind the ear monitoring module 3994 to the processing and display circuit 3434 through electrical connector 3436. Brain Tunnel module 3982, pulse detection module 3992, and skin temperature module 3996 connect to a processing and display circuit 3442 through wire 3446 and electrical connector 3444.

FIG. 15Y is a diagrammatic side view of another embodiment showing sensing frame 3450 worn by a user 3448, and including: a behind the ear monitoring portion 3452 comprised of a chemical sensor 3456 and temperature sensor 3458, said monitoring portion 3452 being integral with frame 3450; a skin temperature portion 3454 comprised of a temperature sensor 3460 being integral with frame 3450; an infrared emitter-detector 3462 located along the lens rim 3464; and a radiation detector 3466 held by an adjustably positionable arm 3468 for detecting radiation naturally emitted from the brain tunnel. Chemical sensor 3456 can include sensors for analyzing sweat such as glucose sensors, electrolyte sensors, protein sensors, and any analyte present in sweat or on the surface of the body.

FIG. 15Z is a diagrammatic planar view of another embodiment showing specialized sensing frame 3470 comprised of an essentially round frame for adjusting said frame 3470 to the head of a user and having temples 3472, 3474 which are adapted for securing the frame 3470 to head of the user by pressure means. Contrary to prior art the sensing frame of this invention does not have hinges. There is also seen a dual temperature sensor 3476, 3478 held by arms 3480, 3482, nose pad 3484 for nose support, and processing circuit 3488. Wire 3486 connecting sensors 3476, 3478 are disposed on or within frame 3470. Processing circuit 3488 is adapted to select the highest temperature from sensors 3476 and 3478 and report said highest value, or alternatively processing circuit 3488 is adapted to select the most stable signal from sensors 3476 and 3478, and report said value.

Another embodiment includes methods and apparatus for determining and preventing intraoperative awareness and detecting brain activity based on body temperature, more specifically temperature from the BTT.

The method and apparatus includes automated feed back control of an infusion pump based on the BTT temperature for automated and precise adjustment of infusion rate of drugs, such as anesthetics or sedatives, based on body temperature, and more particular core-brain temperature.

A first step determines the body temperature, and a second step determines if the temperature is increased. If yes then increase infusion rate by the pump. With an increased core temperature during anesthesia there will be increased drug metabolism, in which drugs are consumed faster, thus requiring increased infusion rate. With a decreased core temperature during anesthesia there will be reduced drug metabolism, in which drugs are consumed slower, thus requiring decreased infusion rate.

In the Intensive Care Unit, the apparatus and methods adjust rate of infusion of drugs, such as vasoactive drugs, based on the body temperature. With decreased core temperature patient requires warming, which may lead to vasodilation if done in excess leading to hypotension, which then requires administration of costly and dangerous drugs such as vasoconstrictors as epinephrine. Thus, with the present invention by carefully and precisely titrating the warming or cooling of the body based on the core temperature all of those issues can be avoided.

In addition, this invention provides a method and apparatus to determine brain awareness and detect risk of intraoperative awareness. If there is increased temperature during surgery, leading to increased drug metabolism, leading to a more superficial level of anesthesia and risk of intraoperative awareness, thus the method and apparatus of the invention adjusts the rate of infusion and increase the rate of infusion. With increased brain temperature there is an increase in blood flow to the brain, which increases the risk of intraoperative awareness, thus the method and apparatus of the invention adjusts the rate of infusion and increase the rate of infusion. If there is decreased temperature during surgery, leads to decreased drug metabolism, leading to more anesthetic drugs being available, which places the patient at a deeper level of anesthesia, and which can cause complications and death besides increased hospital stay and time for recovery. Thus, with the present invention, the level of anesthetic is precisely titrated and if there is lower core temperature, there is a consequent adjustment of the infusion rate with reduction of the infusion rate. With decreased temperature there is also reduced blood flow to the brain, which decreases the risk of intraoperative awareness, thus the method and apparatus of the invention adjusts the rate of infusion and decreases the rate of infusion. Integration of any pump drug with BTT signal can benefit adjustment of infusion rate of some of the most common surgical procedures including cardiac and cardiothoracic, trauma, neurosurgical, long surgeries, and high risk surgeries and surgeries in which vasodilators cannot be used, or patents with predisposition to shock or hypotension.

There are many clinical benefits due to integration of a BTT signal with a pump, including:

1) Automated and more precise adjustment of flow rate
2) To achieve better depth of anesthesia
3) To reduce risk of intraoperative awareness (increased brain temperature associated with risk of intraoperative awareness)
4) Eliminate/reduce the potential for both under- and overdosing
5) Maintenance of drug levels within a desired range
6) Optimal administration of drugs
7) Reduced drug use
8) Reduced surgical time
9) Reduced assisted ventilation time
10) Reduced ICU time
11) Faster post-operative recovery
12) Reduced hospitalization time
13) Reduced rate of complications intraoperative 14) Reduced rate of complications postoperative
15) Improved and expedited wake-up time from surgery
16) Reduced rate of complications due to hypothermia and hyperthermia
17) Reduced health care cost
18) Improved patient outcome Integration of infusion pump with BTT continuous signal can benefit adjustment of infusion rate of some of the most common drugs including all injectable anesthetics, propofol, phentanyl, midazolam and other benzodiazepines, insulin, and vasoactive drugs such as nytric oxide and all vasodilators, phenylephrine and all vasoconstrictors. The level of core temperature can also be used to identify effect of drugs and the diagnosis and prognosis of diseases such as Parkinson's, Alzheimer's, and depression. Accordingly FIG. 16 is a diagrammatic view of an infusion pump 3500 connected to a temperature monitoring system 3502, said temperature monitoring system secured to a living creature 3504. Pump 3500 receives signal from the temperature monitoring system 3502, and said pump 3500 includes an assembly 3506 for delivering drugs to a living creature 3504.

FIG. 17 shows an exemplary portable remote powering device 3510 coupled to a BTT passive sensing device 3516. The device 3150 includes a screen 3528 and antenna 3532, seen held by the hand of a subject and positioned to power the BTT sensing device 3516 located above the eye 3522. BTT sensing device 3516 includes a sensor 3520 and an antenna 3518 for emitting electromagnetic energy. Device 3510 powers passive device 3516 with electromagnetic energy 3514, and receives a reflected energy back represented as wave 3524 which contains the identification of the subject being measured and the level of the biologic parameter being measured. By way of illustration, temperature is measured and the level is displayed on screen 3528. Device 3510 is adapted to provide feed back information based on the signal received and the level of the biological parameter. In this embodiment the temperature is elevated, causing device 3510 to display information for fever, such as antibiotics and anti-fever medications shown in dialog box 3526 of screen 3528. In addition, the signal causes the device 3510 to produce a dialogue box 3530 for names of pharmacies and doctors associated with the patient identified by the signal received.

FIG. 18A is a diagrammatic view of another embodiment of a sensing device 3540 including a measuring portion 3550 and an arm 3554. The end 3552 of arm 3554 ends in holder 3550 and the opposite end 3564 ends in a body of sensing device (not shown). The measuring portion 3550 includes a structure 3542 comprised of a soft compressible insulating material such as polyurethane. Body 3542 has an opening 3544 that houses a wire portion 3548 that terminates in wire 3556 of arm 3544. Body 3542, represented herein by material 3542, has an exposed bottom surface 3560 and an exposed side surface shown as 3562. A holder 3550 surrounds material 3542 and connects with arm 3554. The edge 3558 of the holder 3550 is preferably located at a distance equal to or no greater than 2 mm from the surface 3560, and most preferably equal to or no greater than 4 mm from the surface 3560, and even most preferably equal to or no greater than 6 mm from the surface 3560, said distance represented by a dimension shown as 3562. Surface 3560 includes sensor 3546. Thus surface 3560 has a combination of a thermistor represented herein by sensor 3546 and insulating material such as polyurethane represented by body 3542.

FIG. 18B is a diagrammatic view of a probe cover 3570 for a measuring portion and/or an arm of a sensing device of this invention, such as measuring portions and arms of the embodiments of FIG. 86A to FIG. 18A. The probe cover of this invention is essentially soft and thin and it is adapted to fit the dimensions of the sensing devices and support structures of this present invention. The probe cover 3570 has one body 3576 and two ends 3574 and 3572; one end 3574 is open and adapted to receive a measuring portion and an opposite end 3572 is closed and adapted to fit a sensor. The open end 3574 has an adhesive surface 3578 which is disposed adjacent to the open end 3574, said adhesive surface forming an extension of the distal end 3580 of body 3576. The adhesive surface may include a peel back cover in an extension of body 3576, and when in use the peel back cover is removed exposing the adhesive surface. The adhesive surface 3578 attaches the probe cover to a body of a sensing device such as body 2002, frame of eyeglasses, headband, and the like. Any means to attach or firmly secure probe cover to an arm or body of a sensing device can be used. If the measuring portion is of larger dimension than arm, the probe cover is adapted to cover and fit both parts including the measuring portion.

It is understood that any sensor system of the invention can be coupled with finger-like structure, nose bridge, and other structures described in FIGS. 1A to 6 or coupled to frames of eyeglasses and head mounted gear described in FIGS. 7 to 15. It is also understood that the eyeglasses of this invention can comprise two separate parts, preferably with a removably detachable sensor, which becomes the disposable part. The tip of a rod thermometer or rod pulse detection can also house an identification chip or Radio Frequency identification (RF ID), said tip being reusable but only for one patient who is identified by the RF ID or the ID chip, allowing thus full traceability (of humans and animals) and portability of the sensing device. It is also understood that other embodiments include using a variety of detecting means housed in the sensing devices of this invention, including evaluating blood flow by conventional means and determining analyte concentration such as by using laser Doppler positioned at the brain tunnel for determining the concentration of analytes including glucose. It is also understood that any of the sensing devices and sensors of this invention can be powered by solar power or other renewable energy source.

Another embodiment includes stethoscope connected to a PDA, said stethoscope listening to body sounds such as heart and lung sounds and the PDA recording on digital file the heart or lung sound, and then comparing the sound captured with sounds stored in the PDA memory for determining the diagnosis of the condition.

The invention also includes methods for determining the usable life or function of a sensor based on the thickness of a coating applied to that sensor. Sensor can be covered in parylene and the thickness of the covering used for determining the life of the device. By way of example, a temperature sensor is covered with 100 microns thick layer of parylene which keeps the sensor functioning for X number of days. A 200 microns thick layer of parylene keeps then the sensor functioning for 2X number of days (twice as much) and a 50 microns layer keeps the sensor functioning for ½X (half). As the sensor continues to be used the layer of coating gradually dissolves until total dissolution of the coating exposes the sensor making said sensor inoperative. For example, a temperature sensor ceases to work properly as water and salt from the body reach the sensor and change the resistance after the parylene coating is removed.

Another embodiment includes methods and apparatus for detecting blood flow and diagnosing diseases. The embodiment further includes identifying changes in blood flow of the brain tunnel area after applying drugs locally at the brain tunnel area or systemically by oral or invasive means. The method includes applying, for example, a patch with acetylcholine to identify autonomic dysfunction and the diagnosis of diabetes, heart disease, vascular disorders and the like. Steps include measuring blood flow, applying or delivering a drug, and measuring the blood flow at the same location, such as the brain tunnel area. If there is a sustained change in blood flow at the brain tunnel area, then it is determined that function is normal. If after applying a drug the change in blood flow is not sustained it then indicates autonomic dysfunction.

Another embodiment includes therapy and/or prevention of obesity and reduction of weight through cooling the brain and monitoring the temperature at the BTT. Placing the subject under anesthesia, which reduces core temperature, lowers the temperature of the brain. A preferred step prior to anesthesia is an imaging study such as Magnetic Resonance Imaging to map and quantify the neuronal activity in the hunger center of the brain or other brain areas. Cooling of the body and of the brain is performed in order to cool the hunger center, and therefore reducing neuronal firing in the hunger center, and thus naturally reducing appetite. After the baseline activity is determined, the cooling is performed until core-brain temperature reaches 34 degrees Celsius. When the signal from the temperature sensor, such as the BTT, indicates that level of temperature or other predetermined level, an alarm sounds indicating that target temperature was achieved. Depending on the level of firing of neurons, and the baseline, the anesthesia continues on, with extended periods of anesthesia for people with severe obesity so as to shut down the hunger center and appetite, which can even last 6 months or more. The method and device can include using the area of the BTT between the eye and eyebrow and to cool this area in order to directly reduce brain activity. If a center is hyperactive, then cooling can help stabilize firing of neurons. The method and apparatus can also be used for therapy of a variety of neuro-disorders including stroke, Alzheimer, Parkinson, depression, and the like.

The invention further includes a memory chip housed in the device with a predetermined amount of memory, which correlates to the life of the device. Thus, a chip with capacity for 100 hours of measurements fills the chip memory in 100 hours, and after that occurs the sensing device does not work, and preferably a light on the device, such as body 2002 or an alarm on the screen of the reading unit informs the user that the life of the device has expired.

FIG. 19-A is another embodiment showing a diagrammatic view of a specialized noninvasive internal surface temperature measurement probe 3590. The sensor head 3594 of probe 3590 has features of both surface temperature measurement and internal temperature measurement. By being able to detect internal temperature through the sensor head 3594 penetrating into the brain tunnel through indenting the skin, the probe 3590 measures internal temperature. By touching the surface of the skin with a non-thermally conductive tip, the sensor head 3594 functions as a surface temperature measuring probe. The probe 3590 is of use only in specialized areas such as the BTT, which has a concave shape but of irregular geometry and with some anatomic variations as to the main entry point of tunnel. There is seen in FIG. 19-A probe 3590 including multi-sensor head 3594, straight handle 3600, and curved handle 3606. Sensor head 3594 for temperature measurement comprises an insulating material 3596 populated with a plurality of thermal sensors 3598, such as thermistors, thermocouples, silicone, and the like. The insulating material works as a support structure holding sensors 3598. Preferably thermal sensors 3598 comprise thermistors as per preferred embodiments of this invention. An array of thermal sensors 3598 is disposed on the surface of insulating material 3596 of the multi-sensor head 3594. The multi-sensor head has preferably a convex configuration and special dimensions. The distance from the tip 3592 of sensor head 3594 to the inferior edge 3602 of the sensor head 3594 is preferably equal to or no greater than 2.5 mm, and most preferably equal to or no greater than 4.5 mm, and even most preferably equal to or no greater than 6.5 mm, and even much more preferably is a distance equal to or no greater than 5 mm. Sensor head 3594 has one or more thermal sensors, and preferably an array of sensors 3598, each sensor connected with a respective wire represented as wire 3604. At the transition between straight handle 3600 and curved handle 3606, all wires form the sensors represented herein as wire 3604 join to from a multistrand cable which terminates in wire portion 3610, said wire portion 3610 being connected to a processing and display circuit 3612.

FIG. 19-B is a planar view of sensor head 3594 showing insulating structure 3596 populated by an array of sensors 3598. Sensor head 3594 has an essentially circular shape. Preferred diameter of sensor head 3594 is equal to or no greater than 5.0 mm, and most preferably equal to or no greater than 8.0 mm, and even most preferably equal to or no greater than 12 mm, and even much more preferably equal to or no greater than 20 mm. FIG. 19-C is a diagrammatic view of an embodiment of hand held portable sensing probe 3620 comprised of an essentially flat sensor head 3616. Probe 3620 includes three parts, a flat sensing tip 3634, also referred to as sensor head; a handle 3630 housing wires 3604 and multistrand wire 3618; and electronic and display part 3628 which houses chip 3624, battery 3626, and display 3622. Sensor head 3634 includes a sensing surface 3616, said sensing surface including an insulating material 3632 and one or more sensors 3614 disposed along the surface, and having a similar configuration as embodiment of FIG. 19-A.

As seen in FIG. 19-C handle 3630 has preferably a smaller diameter than sensor head 3634. The distance from the tip 3616 of sensor head 3634 to the inferior edge 3602 of the sensor head 3634 is preferably equal to or no greater than 2.0 mm, and most preferably equal to or no greater than 4.0 mm, and even most preferably equal to or no greater than 7.0 mm, and even much more preferably is a distance equal to or no greater than 5.0 mm.

FIG. 19-D is a side perspective view of a boomerang sensor probe 3640 including boomerang sensor head 3656 and handle 3650. It is understood that handle 3650 can be replaced by arm 2004 or other arms described in this invention, and any of the sensors heads described herein can be used in a measuring portion of other embodiments. Boomerang sensor head 3656 includes two wings 3642 and 3644, but contrary to the conventional boomerang shape which is essentially flat, the wings 3642 and 3644 have a bulging and essentially convex surface in order to fit with the anatomy of the brain tunnel entry point. Boomerang sensor head 3656 further includes a connecting portion 3658 connecting the two wings 3642 and 3644, said connecting portion having an essentially bulging and convex surface 3648, said convex surface 3648 having a much smaller radius than the radius of convex surface of wings 3642 and 3644, thus connecting portion 3658 is much more bulging than wings 3642 and 3644. Connecting portion 3658 has an essentially protruding configuration and houses at least one sensor 3646, but preferably houses a plurality of sensors along its surface, said sensors preferably having also a bulging configuration. The sensors are represented herein as small dots, but to avoid excessive repetition only one number 3646 is used for describing the plurality of sensors. Sensors 3646 are illustrated as one type of sensor, such as a thermal sensor, but it is understood that sensors measuring different parameters can be used, and any combination of sensors are contemplated, for example a sensor head comprising oxygen saturation infrared sensors, electrochemical gas sensors, thermal sensors, and pulse sensors. Each sensor 3646 connects with handle 3650, illustrated herein as wired communication, using wires 3652, which preferably become a multistrand cable 3654 in handle 3650. Handle 3650 is attached to sensor head 3656 through connecting points 3660 and 3662, located at the end of said handle 3650. Preferred dimensions of probe 3640 are consistent with the dimensions and shape of a brain tunnel area, and more particular the geometry of the area between the eye and the eyebrow on the upper eyelid and roof of the orbit.

FIG. 19-E is a planar perspective view of a boomerang sensor probe 3640 showing the sensing surface 3664 of sensor head 3656, which is the surface that touches the skin during contact measurements or the surface that is viewing the skin for non-contact measurements. The sensing surface 3664 comprises the connecting bulging portion 3658, and the wings 3642 and 3644, said sensing surface 3662 having one or more sensor 3646 on its surface. Connecting points 3660 and 3662 which connect a handle to the sensor head 3656 are seen as broken lines.

FIG. 19-F is a planar diagrammatic view of boomerang sensor head 3656, and its relation to anatomic structures such as the nose 3672, eyebrow 3666, and eye 3674. Wing 3642 which is located below the eyebrow 3666 is preferably longer than wing 3644 which rests adjacent to the nose 3672. There is also seen the essentially centrally located bulging connecting portion 3658, and its center point 3668, and the impression of the handle connecting points 3660 and 3662. The boomerang probe 3640 of this invention has preferably a tighter angle as compared to a conventional boomerang configuration. Accordingly the preferred angle 3670 between wings 3642 and 3644 is equal to or less than 45 degrees, and preferably equal to or less than 65 degrees, and most preferably equal to or less than 90 degrees. Preferred length of the wing running along the eyebrow 3666, illustrated herein as wing 3642, is equal to or less than 35 mm, and preferably equal to or less than 25 mm, and most preferably equal to or less than 20 mm, and even most preferably equal to or less than 14 mm, said length going from point 3668 to the edge 3676 of the wing 3642. Preferred width of wing 3642 is equal to or less than 30 mm, and preferably equal to or less than 20 mm, and most preferably equal to or less than 15 mm, and even most preferably equal to or less than 10 mm. Preferred thickness of wing 3642 is equal to or less than 25 mm, and preferably equal to or less than 20 mm, and most preferably equal to or less than 15 mm, and even most preferably equal to or less than 10 mm.

Preferred length of the wing running along the nose 3672, illustrated herein as wing 3644, is equal to or less than 33 mm, and preferably equal to or less than 23 mm, and most preferably equal to or less than 18 mm, and even most preferably equal to or less than 12 mm, said length going from point 3668 to the edge 3678 of the wing 3644. Preferred width of wing 3644 is equal to or less than 30 mm, and preferably equal to or less than 20 mm, and most preferably equal to or less than 15 mm, and even most preferably equal to or less than 10 mm. Preferred thickness of wing 3644 is equal to or less than 25 mm, and preferably equal to or less than 20 mm, and most preferably equal to or less than 15 mm, and even most preferably equal to or less than 10 mm.

The bulging connecting portion 3658 is the portion adapted to best fit with the main entry point of the tunnel and is located adjacent to the junction of the eyebrow 3666 with the bridge of the nose 3672. Preferred dimension or diameter of the bulging connecting portion 3658 is equal to or less than 30 mm, and preferably equal to or less than 25 mm, and most preferably equal to or less than 20 mm, and even most preferably equal to or less than 15 mm. Preferred thickness of portion 3658 is equal to or less than 30 mm, and preferably equal to or less than 20 mm, and most preferably equal to or less than 15 mm, and even most preferably equal to or less than 10 mm.

Processing circuit, such as processor 3624, screens and selects the most optimal signal, depending on the application, from the plurality of signals received from the plurality of sensors. In the case of thermal sensors, processing continuously screens and then selects the highest temperature, which is then reported. One or multiple sensing points can be checked periodically and one or more signals can be selected and displayed. For temperature measurement the thermal sensors are imbedded in an insulated material shaped to fit into the anatomical and thermal characteristics of the BTT pocket for easy placement and optimal heat transfer. Thermal sensor is preferably encapsulated and surrounded with a soft thick, non-conductive, insulating material that will take the contour/shape of the irregular skin surface to completely seal off any external ambient temperature and also to prevent any skin or tissues outside the BTT entrance site from touching the sensor.

Since folds of skin can touch the tip of the sensor head when is pressed against the BTT, the sensor head has a unique and specialized dimension of insulating material surrounding the sensor, which is preferably between 3 mm and 5 mm, and most preferably between 2 mm and 7 mm, and even most preferably between 1.5 mm and 10 mm as seen in FIG. 19-G and FIG. 19-H. FIG. 19-G shows a sensor head 3680 and handle 3682. The sensor head 3680 has three thermal sensors 3684, 3686 and 3688. The sensor head 3680 comprises the insulating material 3690 and the three thermal sensors 3684, 3686 and 3688, which are disposed along the surface of the insulating material 3690. All surfaces of the sensors 3684, 3686 and 3688 are surrounded by the insulating material 3690, with the exception of the surface of the sensor exposed to the environment. The dimension of insulating material 3690 is based on the position of a thermal sensor closest to the non-insulating part 3692, illustrated as a part which is made of thermally conductive material or metal such as a handle 3682. Since sensors 3688 is lower as compared to sensors 3684 and 3686, the starting point to determine length or dimension 3694 of insulating material 3690 is based on said sensor 3688, the dimension 3694 starting at sensor 3688 and ending at non-insulating material 3692.

FIG. 19-H shows a bulging sensor 3696 on the surface of an insulating material 3690, which terminates in a thermally conductive material 3692. All surfaces of the sensor 3696 is surrounded by the insulating material 3690, with the exception of the surface of the sensor exposed to the environment or the target area being measured. The dimension of insulating material 3690 is based on the position of a thermal sensor closest to the non-insulating part 3692. Since sensors 3696 is the only thermal sensor, said sensor 3696 determines the dimension of the insulating material 3690, the dimension 3694 starting at sensor 3696 and ending at non-insulating material 3692. The dimension 3694 is the same for both embodiments, shown in FIG. 19-G and FIG. 19-H. The sensor insulation needs to have the described thickness, unlike conventional surface temperature probes of the prior art, which needs to be thin. The reason is because the BTT sensor is pushed into the BTT tunnel opening and the thicker insulation material prevents external ambient influences and tissues to come in contact with the integrity of the temperature sensor measuring the opening surface area of the BTT. Insulation material and dimension or length of insulating material as per the present invention includes any insulating material around a sensor head or measuring portion, including an insulating holder such as insulating holder 3550 as shown in FIG. 18A.

The sensing systems of this invention measures, records and/or processes feedback information for a closed loop system and controlling a second device, such as the infusion pump of FIG. 16 and thus allowing for therapeutic applications, such as cooling or heating the brain based on the signal received, or increasing oxygen delivered based on the signal of an oxygen sensor, or increasing the flow of glucose or insulin based on the signal from a glucose sensor.

It is understood that other configurations of the modular design of the invention would be apparent to one of ordinary skill in the art. Other configurations using other head mounted gear such as a cap, eyewear, and the like are contemplated. Those head mounted gear positions and secures the sensor assembly as a docking device and can measure, record, feedback multiple parameters in a modular design such as pulse oxymetry, heart rate, temperature, and the like.

FIG. 20 illustrates the maintaining of a sensor on the BTT by adhesive applied to the body of the support structure. The support structure is applied on the cheek of the user.

It should be noted that this invention provides not only measurement, recording and processing of a biological parameter such as temperature but also includes a device that will house the therapy. By way of illustration, the modular forehead docking system of this invention can include a mechanical holding and positioning structure for a cold or hot element or substance that is placed on the BTT site for cooling or heating the brain including a thermovoltaic device such as a Peltier device, serpentine for circulating fluids, and the like. The head mounted gear such as the head band of this invention can also be an electronics structure positioning, powering, and controlling device to heat or cool the BTT site. The module of the sensing head band includes controlling/processing circuit that can work as a close loop device itself for therapy, by having one side a BTT thermometer and the other side the cold/hot device on the BTT site, providing thus an independent medical close loop monitoring, controlling and cooling/heating device.

The module of the sensing head band box is also designed to analyze a temperature signal or other biological signal and correlate it to other patient data and display other parameters either on the sensing head band device or transmit the information via wire or wireless means to another host monitor or device. The parameters that the system correlate/calculate/analyze include sleep disorder patterns, Alzheimer syndromes, obesity parameters, calorie burns for weight control, fatigue/drowsiness, ECG/EKG, brain wave patterns, and the like.

I claim:

1. A thermal sensing support structure comprising:
headwear having a head engaging portion;
an arm secured at one end to the headwear at said head engaging portion;
a free end of the arm being located opposite to the one end of the arm;
a sensor located at the free end of the arm, said arm being configured to place the sensor at the brain temperature tunnel area for measuring temperature at the brain temperature tunnel area;
said sensor being at least a thermal sensor; said thermal sensor being partially surrounded by insulation to leave an exposed portion of the thermal sensor, said insulation having a thermally insulating surface, said thermally insulating surface being exposed for the thermally insulting surface to directly contact the skin at the brain temperature tunnel area, and the exposed portion of the thermal sensor receiving thermal energy from said skin surface.

2. The thermal sensing support structure according to claim 1, wherein the exposed portion of the thermal sensor is located at a free end of a cylindrical sensor holder.

3. The thermal sensing support structure according to claim 1, wherein the head engaging portion is a plate.

4. The thermal sensing support structure according to claim 3, wherein the plate is flexible.

5. The thermal sensing support structure according to claim 1, wherein the arm is curved.

6. The thermal sensing support structure according to claim 1, wherein the arm is flexible.

7. The thermal sensing support structure according to claim 1, wherein the arm is movably mounted on the head engaging portion.

8. The thermal sensing support structure according to claim 7, wherein the arm is pivoted with respect to the head engaging portion.

9. The thermal sensing support structure according to claim 1, wherein the sensor is a contact or a non-contact sensor.

10. The thermal sensing support structure according to claim 1, wherein the arm is a shape memory alloy.

11. The thermal sensing support structure according to claim 1, wherein the head engaging portion is wider than said arm.

12. The thermal sensing support structure according to claim 1, wherein the arm has a length of less than 15 cm.

13. The thermal sensing support structure according to claim 1, wherein a thickness of the arm is less than or equal to 2.5 cm.

14. A sensing support structure comprising
headwear having a head engaging portion,
an arm secured at one end to the headwear at said head engaging portion,
a free end of the arm being located opposite to the one end of the arm,
a sensor located at the free end of the arm, said arm being configured to place the sensor adjacent to a brain temperature tunnel area for measuring radiation emitted from the brain temperature area,
said sensor being spaced forwardly of the headwear so as to measure naturally emitted radiation projected away from an individual from the brain tunnel area.

15. The sensing support structure according to claim 14, wherein said sensor is a radiation detector held by the arm.

16. The sensing support structure according the claim 15, wherein the arm is adjustably positionable with respect to the brain tunnel area.

17. The thermal sensing support structure according to claim 14, wherein the head engaging portion is a plate.

18. The thermal sensing support structure according to claim 17, wherein the plate is flexible.

19. The thermal sensing support structure according to claim 14, wherein the arm is curved.

20. The thermal sensing support structure according to claim 14, wherein the sensor is a contact or a non-contact sensor.

21. The thermal sensing support structure according to claim 14, wherein the arm is a shape memory alloy.

22. The thermal sensing support structure according to claim 14, wherein the head engaging portion is wider than said arm.

23. The thermal sensing support structure according to claim 14, wherein the arm has a length of less than 15 cm.

24. The thermal sensing support structure according to claim 14, wherein a thickness of the arm is less than or equal to 2.5 cm.

* * * * *